United States Patent
Wrobleski et al.

(10) Patent No.: US 9,221,826 B2
(45) Date of Patent: Dec. 29, 2015

(54) PYRROLOPYRIDAZINE JAK3 INHIBITORS AND THEIR USE FOR THE TREATMENT OF INFLAMMATORY AND AUTOIMMUNE DISEASES

(75) Inventors: Stephen T. Wrobleski, Flemington, NJ (US); Jagabandhu Das, Mercerville, NJ (US); Lidia M. Doweyko, Vero Beach, FL (US); Junqing Guo, Princeton, NJ (US); John Hynes, Washington Crossing, PA (US); Bin Jiang, Norristown, PA (US); James Kempson, Princeton, NJ (US); Shuqun Lin, Newtown, PA (US); Steven H. Spergel, Warrington, PA (US); John S. Tokarski, Princeton, NJ (US); Hong Wu, New Hope, PA (US); Bingwei Vera Yang, Belle Mead, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/005,572

(22) PCT Filed: Mar. 16, 2012

(86) PCT No.: PCT/US2012/029337
§ 371 (c)(1),
(2), (4) Date: Sep. 17, 2013

(87) PCT Pub. No.: WO2012/125887
PCT Pub. Date: Sep. 20, 2012

(65) Prior Publication Data
US 2014/0005146 A1 Jan. 2, 2014

Related U.S. Application Data

(60) Provisional application No. 61/453,620, filed on Mar. 17, 2011.

(51) Int. Cl.
*A61K 31/5025* (2006.01)
*A61K 31/675* (2006.01)
*C07D 487/04* (2006.01)
*C07F 9/6561* (2006.01)

(52) U.S. Cl.
CPC .......... *C07D 487/04* (2013.01); *C07F 9/6561* (2013.01)

(58) Field of Classification Search
None
See application file for complete search history.

(56) References Cited

FOREIGN PATENT DOCUMENTS

WO WO 2004/099204 11/2004
WO WO 2011/014817 2/2011

OTHER PUBLICATIONS

Legendre, Transplantation Research 2013, 2(Suppl 1):S6 pp. 1-5.*
Sandborn et al. N Engl J Med 2012;367:pp. 616-624.*
Coombs, J.H. et al., "Improved pain, physical functioning and health status in patients with rheumatoid arthritis treated with CP-690,550, an orally active Janus kinase (JAK) inhibitor: results from a randomised, double-blind, placebo-controlled trial", Ann. Rheum. Dis., vol. 69, pp. 413-416 (2010).
Ghoreschi, K. et al., "Modulation of Innate and Adaptive Immune Responses by Tofacitinib (CP-690,550)", The Journal of Immunology, vol. 186, pp. 4234-4243 (2011).
Milici, A.J. et al., "Cartilage preservation by inhibition of Janus kinase 3 in two rodent models of rheumatoid arthritis", Arthritis Research & Therapy, vol. 10, R14 (2008).
O'Shea, J.J. et al., A New Modality for Immunosuppression: Targeting the JAK/STAT Pathway, Nature Reviews: Drug Discovery, vol. 3, pp. 555-564 (2004).
Pesu, M. et al., "Jak3, severe combined immunodeficiency, and a new class of immunosuppressive drugs", Immunological Reviews, vol. 203, pp. 127-142 (2005).
Shi, M. et al., "Janus-Kinase-3-Dependent Signals Induce Chromatin Remodeling at the *Ifng* Locus during T Helper 1 Cell Differentiation", Immunity, vol. 28, pp. 763-773 (2008).

* cited by examiner

*Primary Examiner* — Emily Bernhardt

(57) ABSTRACT

Disclosed are compounds of formula (I) and pharmaceutically acceptable salts thereof. The compounds of formula (I) inhibit tyrosine kinase activity of JAK3, thereby making them useful for the treatment of inflammatory and autoimmune diseases.

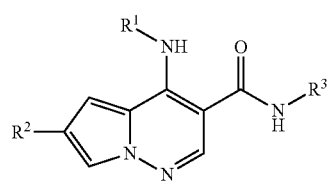

10 Claims, No Drawings

PYRROLOPYRIDAZINE JAK3 INHIBITORS AND THEIR USE FOR THE TREATMENT OF INFLAMMATORY AND AUTOIMMUNE DISEASES

This application is a 371 application of PCT/US2012/125887 filed Mar. 16, 2012 which claims priority from U.S. Provisional Application Ser. No. 61/453,620 filed Mar. 17, 2011 which are incorporated by reference herein in their entirety.

FIELD OF THE INVENTION

This invention relates to novel pyrrolopyridazine compounds that are useful as inhibitors of Janus kinases (JAKs), more particularly JAK3. This invention also relates to a method of using the compounds in the treatment of inflammatory and autoimmune diseases, and to pharmaceutical compositions containing the compounds.

BACKGROUND OF THE INVENTION

The present invention relates to pyrrolopyridazine compounds, the methods of preparation of these compounds, and their use in the treatment of conditions in which selective modulation of the JAK signaling pathway via inhibition of the Janus kinases (JAKs) kinases, particularly JAK3 kinase, may be therapeutically beneficial.

The Janus kinases (JAKs) belong to the non-receptor protein tyrosine kinase family and are known to be critical intracellular regulators of cytokine signaling via modulation of the JAK-STAT pathway (see, Murray, P. J. *Immunity*, 2008, 28, 763). There are four known mammalian JAK isoforms which include JAK1, JAK2, JAK3 and TYK2.

JAK3 has been shown to play a specific role in the signaling of a subset of cytokines known as the gamma common chain cytokine family which includes the interleukins IL-2, IL-4, IL-7, IL-9, IL-15, and IL-21. Deficiency of JAK3 in rodents and humans results in a severe combined immunodeficient (SCID) phenotype (see, Pesu, M. et al *Immunol. Rev.* 2005, 203, 127). Furthermore, JAK3 is known to have limited expression in hematopoeitic cells whereas JAK1, JAK2 and TYK2 have been shown to be more ubiquitously expressed. As a result of its specific role in regulating the immune response and its localized expression in lymphoid cells, inhibition of JAK3 has been recognized as a promising strategy for development of novel and selective immunosuppressive agents useful for transplant rejection prevention and in the treatment of autoimmune and inflammatory diseases such as psoriasis, rheumatoid arthritis, psoriatic arthritis, multiple sclerosis, inflammatory bowel diosease, and lupus (see, O'Shea J. J. et al, *Nat. Rev. Drug Discov.* 2004, 3(7), 555). Moreover, the reported JAK inhibitor CP-690,550 which potently inhibits JAK3 has been shown to be effective in the treatment arthritis in rodent models as well as in patients with rheumatoid arthritis (see, Milici, A. J. et.al. *Arthritis Res. & Therapy*, 2008, R14 and Coombs, J. H. et al *Ann. Rheum. Dis.* 2010, 69, 413). It has been suggested that the clinical efficacy of CP-690,550 (Tofacitinib) may be related to its ability to inhibit other JAK family members (see Ghoreschi, K et al, *J. Immunol.* 2011, 186, 4234). While JAK3 and JAK1 are both capable of modulating gamma common chain induce phosphorylation of STAT signalling, JAK1 inhibition can also decrease non-gamma common chain cytokine signalling (e.g. IL-6 signalling). As such, orally available compounds that inhibit JAK3 and/or JAK1 may be useful for the treatment of inflammatory and autoimmune diseases.

Accordingly, novel compounds which inhibit the JAK/STAT pathway, more particularly via selective inhibition of JAK3 and/or JAK1, may be therapeutically useful. The closely related isoform JAK2 is classically associated with interferon-γ production through the IL-12 pathway, but it also mediates the signaling of important hematopoietic growth factors such as erythropoietin (EPO), thromobopoetin (TPO) and granulocyte macrophage-stimulating factor (GM-CSF). As a result, inhibition of JAK2 may result in adverse hematopoietic effects such as anemia, thrombocytopenia and generalized leukopenia. As such, novel compounds which selectively inhibit JAK3 and/or JAK1 over JAK2 may be especially desirable in the safe treatment of chronic inflammatory and automimmune diseases.

DETAILED DESCRIPTION OF THE INVENTION

The present invention provides for compounds of formula I, pharmaceutical compositions employing such compounds and for methods of using such compounds.

In accordance with the present invention, there are disclosed compounds of formula I:

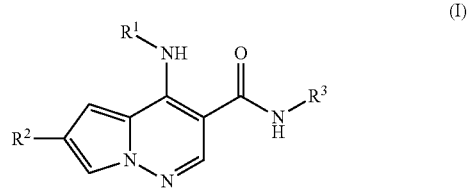

or salts, stereoisomers, or prodrugs thereof, wherein:

$R^1$ is $C_{1-6}$ alkyl substituted with 0-2 $R^{1a}$, wherein the alkyl is optionally further substituted with 0-1 $R^{1b}$;

$R^{1a}$ is halogen, $-(CH_2)_rC(O)NR^cR^c$, $-OH$, $-(CH_2)_rC(O)OR^b$, $C_{1-6}$ alkyl substituted with 0-4 $R^a$, $C_{1-6}$ haloalkyl, $C_{2-6}$ alkenyl substituted with 0-3 $R^a$, $C_{2-6}$ alkynyl substituted with 0-3 $R^a$, $C_{3-10}$ cycloalkyl substituted with 0-4 $R^a$, $C_{6-10}$ aryl substituted with 0-3 $R^a$, or a 5-10 membered heterocycle containing 1-4 heteroatoms selected from N, O, and S, substituted with 0-3 $R^a$;

$R^{1b}$ is hydrogen, $=O$, F, Cl, Br, $-OCF_3$, $-CF_3$, $-CHF_2$, $-CN$, $-NO_2$, $-(CH_2)_rOR^b$, $-(CH_2)_rSR^b$, $-(CH_2)_rC(O)R^b$, $-(CH_2)_rC(O)OR^b$, $-(CH_2)_rOC(O)R^b$, $-(CH_2)_rNR^cR^c$, $-(CH_2)_rC(O)NR^cR^c$, $-(CH_2)_rNR^bC(O)R^c$, $-(CH_2)_rNR^bC(O)OR^c$, $-NR^bC(O)NR^cR^c$, $-S(O)_2NR^cR^c$, $-NR^bS(O)_2R^c$, $-S(O)R^c$, $-S(O)_2R^c$, $(CH_2)_rNH(C=NCN)NHR^c$, $C_{1-6}$ alkyl substituted with 0-1 $R^a$, $C_{1-6}$ haloalkyl, $-(CH_2)_r$-3-14 membered carbocycle substituted with 0-1 $R^a$, or $-(CH_2)_r$-5-7 membered heterocycle comprising carbon atoms and 1-4 heteroatoms selected from N, O, and $S(O)_p$ substituted with 0-1 $R^d$, alternatively two $R^a$ on adjacent or the same carbon atom form a cyclic acetal of the formula $-O-$, $(CH_2)_n-O-$, or $-O-CF_2-O-$, wherein n is selected from 1 or 2;

$R^2$ is $-NR^bC(O)NR^{11}R^{11}$, $-NR^bC(O)R^{2b}$, $-NR^bC(O)OR^{2d}$, $-NR^bS(O)_2R^{2b}$, $-(CH_2)_r-C_{6-10}$ aryl substituted with 0-3 $R^{2a}$, or $-(CH_2)_r$-4-10 membered heterocycle containing 1-4 heteroatoms selected from N, O, and S substituted with 0-3 $R^{2a}$;

$R^{2a}$ is $=O$, F, Cl, Br, $OCF_3$, $CF_3$, CN, $NO_2$, $-(CH_2)_rOR^b$, $-(CH_2)_rSR^b$, $-(CH_2)_rC(O)R^b$, $-(CH_2)_rC(O)OR^b$, $-(CH_2)_rOC(O)R^b$, $-(CH_2)_rNR^{11}R^{11}$, $-(CH_2)_rC(O)NR^{11}R^{11}$, $-(CH_2)_rNR^bC(O)R^{2b}$, $-(CH_2)_rNR^bC(O)OR^c$, $-NR^bC(O)NR^{11}R^{11}$, $-S(O)_2NR^{11}R^{11}$, $-NR^bS(O)_2R^c$,

—S(O)R$^c$, —S(O)$_2$R$^c$, (CH$_2$)$_r$NH(C=NCN)NHR$^{11}$, C$_{1-6}$ alkyl substituted with 0-2 R$^a$, C$_{2-6}$ alkenyl, C$_{1-6}$ haloalkyl, —(CH$_2$)$_r$-3-14 membered carbocycle substituted with 0-1 R$^a$, or —(CH$_2$)$_r$-5-7 membered heterocycle comprising carbon atoms and 1-4 heteroatoms selected from N, O, and S(O)$_p$ substituted with 0-1 R$^a$;

R$^{2b}$ is hydrogen, C$_{1-6}$ alkyl substituted with 0-2 R$^a$, C$_{1-6}$ haloalkyl, C$_{3-6}$ cycloalkyl substituted with 0-2 R$^a$, or (CH$_2$)$_r$-phenyl substituted with 0-2 R$^a$, or —(CH$_2$)$_r$-5-10 membered heterocycle comprising carbon atoms and 1-4 heteroatoms selected from N, O, and S(O)$_p$ substituted with 0-1 R$^a$; R$^{2d}$ is C$_{1-6}$ alkyl substituted with 0-2 R$^a$, C$_{1-6}$ haloalkyl, C$_{3-6}$ cycloalkyl substituted with 0-2 R$^a$, or (CH$_2$)$_r$-phenyl substituted with 0-2 R$^a$, or —(CH$_2$)$_r$-5-10 membered heterocycle comprising carbon atoms and 1-4 heteroatoms selected from N, O, and S(O)$_p$ substituted with 0-1 R$^a$;

R$^3$ is hydrogen, C$_{1-6}$ alkyl substituted with 0-1 R$^a$, phenyl substituted with 0-1 R$^a$, or C$_{3-6}$ cycloalkyl substituted with 0-1 R$^a$;

R$^{11}$ is independently hydrogen or C$_{1-4}$ alkyl substituted with 0-1 R$^a$, —(CH$_2$)$_r$-3-6 membered carbocycle substituted with 0-1 R$^a$, or —(CH$_2$)$_r$-5-7 membered heterocycle comprising carbon atoms and 1-4 heteroatoms selected from N, O, and S(O)$_p$;

R$^a$ is hydrogen, =O, F, Cl, Br, —OCF$_3$, —CF$_3$, —CHF$_2$, —CN, —NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^c$R$^c$, —(CH$_2$)$_r$C(O)NR$^c$R$^c$, —(CH$_2$)$_r$NR$^b$C(O)R$^c$, —(CH$_2$)$_r$NR$^b$C(O)OR$^c$, —NR$^b$C(O)NR$^c$R$^c$, —S(O)$_2$NR$^c$R$^c$, —NR$^b$S(O)$_2$R$^c$, —S(O)R$^c$, —S(O)$_2$R$^c$, —(CH$_2$)$_r$NH(C=NCN)NHR$^c$, C$_{1-6}$ alkyl substituted with 0-1 R$^d$, C$_{2-6}$ alkenyl substituted with 0-1 R$^f$, C$_{1-6}$ haloalkyl, —(CH$_2$)$_r$-3-14 membered carbocycle substituted with 0-1 R$^d$, or —(CH$_2$)$_r$-5-7 membered heterocycle comprising carbon atoms and 1-4 heteroatoms selected from N, O, and S(O)$_p$ substituted with 0-1 R$^d$, alternatively two R$^a$ on adjacent or the same carbon atom form a cyclic acetal of the formula —O—(CH$_2$)$_n$—O—, or —O—CF$_2$—O—, wherein n is selected from 1 or 2;

R$^b$ is hydrogen, C$_{1-6}$ alkyl substituted with 0-2 R$^d$, C$_{1-6}$ haloalkyl, C$_{3-6}$ cycloalkyl substituted with 0-2 R$^d$, or (CH$_2$)$_r$-phenyl substituted with 0-2 R$^d$, or —(CH$_2$)$_r$-5-7 membered heterocycle comprising carbon atoms and 1-4 heteroatoms selected from S, and S(O)$_p$ substituted with 0-1 R$^d$, R$^c$ is C$_{1-6}$ alkyl substituted with 0-1 R$^f$, —CF$_3$, —CH$_2$CF$_3$, C$_{3-6}$ cycloalkyl, or —(CH$_2$)$_r$-phenyl substituted with 0-1 R$^f$;

R$^d$ is hydrogen, F, Cl, Br, —OCF$_3$, —CF$_3$, —CN, —NO$_2$, —OR$^e$, —SR$^e$, —(CH$_2$)$_r$C(O)R$^e$, —NR$^e$R$^e$, —NR$^e$C(O)OR$^e$, —NR$^e$C(O)R$^e$, —C(O)N(R$^e$)$_2$, —C(O)OR$^e$, —SO$_2$N(R$^e$)$_2$, —SO$_2$R$^e$, C$_{1-6}$ alkyl, or —(CH$_2$)$_r$-phenyl substituted with 0-1R$^f$; or —(CH$_2$)$_r$-pyridyl;

R$^e$ is hydrogen, C$_{1-6}$ alkyl, C$_{3-6}$ cycloalkyl, or —(CH$_2$)$_r$-phenyl substituted with 0-1R$^f$;

R$^f$ is hydrogen, halo, CN, —S(O)$_2$(methyl), phenyl, —NH$_2$, —NHC(O)(methyl), —OH, or —OCH$_3$;

r is 0, 1, 2, 3, or 4; and p is 0, 1, or 2.

In one embodiment, there are provided compounds of Formula (I) or salts, stereoisomers, or prodrugs thereof, wherein R$^3$ is hydrogen. The compounds of this embodiment have the structure of Formula (II):

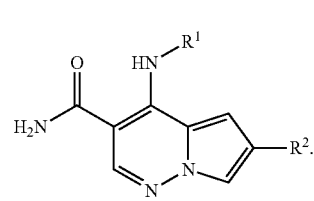

In one embodiment, there are provided compounds of Formula (II) or salts, stereoisomers, or prodrugs thereof, wherein:

R$^1$ is C$_{1-6}$ alkyl substituted with zero to 3 substituent groups independently selected from F, —OH, —CF$_3$, —NH$_2$, —C(O)OH, —C(O)OCH$_3$, —C(O)NH$_2$, —C(O)NHCH$_2$CN, —C(O)NH(phenyl), —NHC(O)CH$_2$CN, —NHS(O)$_2$CH$_3$, —OP(O)(OH)$_2$, phenyl, fluorophenyl, oxazolyl substituted with —C(O)NH$_2$; and/or two substituent groups along with the carbon atom to which they are attached, form a cyclopropyl ring;

R$^2$ is -L-R$^x$ or R$^y$;

L is —NHC(O)—, —NHC(O)O—, —NHS(O)$_2$—, —NHC(O)NH—, —NHC(O)O—, or —C(O)NH—;

R$^x$ is C$_{1-6}$ alkyl, C$_{3-6}$ cycloalkyl, C$_{1-4}$ fluoroalkyl, and a cyclic group selected from 5-membered heterocyclyl having at least one oxygen heteroatom, 5-membered heteroaryl having at least one nitrogen heteroatom, or phenyl, each cyclic group substituted with zero to 2 substituents independently selected from F, Cl, —OH, —CN, C$_{1-3}$ alkyl, C$_{1-3}$ alkoxy, —C(O)OH, and/or —NH$_2$; and R$^y$ is:

a) phenyl substituted with zero to 2 substituents independently selected from i) F, Cl, —CN, C$_{1-4}$ alkyl, —O(C$_{1-3}$ alkyl), —C(O)OH, —NH$_2$, —NH(C$_{1-3}$ alkyl), —N(C$_{1-3}$ alkyl)$_2$, C$_{3-6}$ cycloalkyl, and/or C$_{2-4}$ alkenyl;

ii) C$_{1-4}$ alkyl substituted with —CN, —OH, —NH$_2$, —NH(CH$_3$), —N(CH$_3$)$_2$, C$_{3-6}$ cycloalkyl, morpholinyl, piperidinyl substituted with methoxyphenyl, —NHC(O)R$^m$, —NHC(O)NHR$^n$, —NHCH(=N—CN)NH(C$_{1-3}$ alkyl), and/or —NHS(O)$_2$(C$_{1-3}$ alkyl); wherein R$^m$ is C$_{1-4}$ alkyl, C$_{3-6}$ cycloalkyl, hydroxy (C$_{3-6}$ cycloalkyl), C$_{1-3}$ cyanoalkyl, C$_{1-4}$ hydroxyalkyl, —CH$_2$NH$_2$, —CH$_2$H(CH$_3$), —CH$_2$N(CH$_3$)$_2$, phenyl, phenyl-S(O)$_2$NH$_2$, phenyl-NHC(O)CH$_3$, pyrrolidinyl, furanyl, pyridinyl, —CH$_2$OC(O)(C$_{1-3}$ alkyl), —CH$_2$(morpholinyl), or —CH$_2$NHS(O)$_2$(methylphenyl); and R$^n$ is H, C$_{1-3}$ alkyl, C$_{3-6}$ cycloalkyl, or C$_{1-4}$ hydroxyalkyl;

iii) —C(O)NR$^i$R$^j$ wherein R$^i$ is H or —CH$_3$, and R$^j$ is C$_{1-3}$ alkyl, C$_{3-6}$ cycloalkyl, —CH$_2$C(O)NH$_2$, —CH$_2$C(O)NH(CH$_3$), —CH$_2$C(O)N(CH$_3$)$_2$, or —CH$_2$CH$_2$N(CH$_3$)$_2$;

iv) —OC(O)(C$_{1-3}$ alkyl) and/or —C(O)(N-methyl morpholinyl);

v) —NHC(O)R$^k$ wherein R$^k$ is H, C$_{1-3}$ alkyl, or C$_{3-6}$ cycloalkyl;

vi) —S(O)$_2$(C$_{1-3}$ alkyl), —NHS(O)$_2$(C$_{1-3}$ alkyl), —S(O)$_2$NH$_2$, and/or —S(O)$_2$N(CH$_3$)$_2$;

vii) thiophenyl, morpholinonyl, imidazolyl, oxazolyl, and/or imidazolidine-2,4-dionyl, each substituted with zero to 1 substituent selected from —CH$_3$, —C(O)O(C$_{1-3}$ alkyl), and dimethylaminophenyl;

b) heterocycle selected from azetidinonyl, pyrrolidinonyl, morpholinonyl, pyridinonyl, imidazolidinonyl, oxazolidinonyl, propane-1,3-sultam, butane-1,4-sultam, 5-thioxo-4,5-dihydro-1,3,4-oxadiazoly-2-yl, and 5-methylthio-1,3,4-oxadiazoly-2-yl, wherein said heterocycle is substituted with zero to 1 substituent selected from $C_{1-4}$ alkyl, $C_{1-3}$ fluoroalkyl, —NHC(O)O($C_{1-4}$ alkyl), and phenyl; or c) heteroaryl selected from pyrrolyl, pyrazolyl, thiazolyl, oxadiazolyl, pyridinyl, pyrimidinyl, pyrazinyl, indolyl, quinolinyl, 3,4-dihydroisoquinolin-1(2H)-onyl, benzo[d][1,3]dioxolyl, quinolin-2(1H)-onyl, benzothiazolyl, 1H-benzo[d]imidazol-2(3H)-onyl, wherein said heteroaryl is substituted with zero to 3 substituents independently selected from F, Cl, —OH, —CN, $C_{1-4}$ alkyl, $C_{1-3}$ fluoroalkyl, —O($C_{1-4}$ alkyl), —NH$_2$, —NH($C_{1-3}$ alkyl), —N($C_{1-3}$ alkyl)$_2$, —C(O)NH$_2$, —C(O)NH($C_{1-3}$ alkyl), —C(O)N($C_{1-3}$ alkyl)$_2$, —S(O)$_2$($C_{1-3}$ alkyl), —NHCH$_2$CH$_2$N($C_{1-2}$ alkyl)$_2$, —N(CH$_3$)CH$_2$CH$_2$N($C_{1-2}$ alkyl)$_2$, —NHCH$_2$CH$_2$(morpholinyl), piperidinyl, piperazinyl, phenyl, chlorophenyl, methoxyphenyl, dimethylaminophenyl, pyridinyl, morpholinyl, N-methyl piperazinyl, and/or piperazinyl(C(O)O(t-butyl)).

In one embodiment, there are provided compounds of Formula (II) or salts, stereoisomers, or prodrugs thereof, wherein:

$R^1$ is $C_{1-6}$ alkyl substituted with zero to 3 substituent groups independently selected from F, —OH, —CF$_3$, —NH$_2$, —C(O)OH, —C(O)OCH$_3$, —C(O)NH$_2$, —C(O)NHCH$_2$CN, —C(O)NH(phenyl), —NHC(O)CH$_2$CN, —NHS(O)$_2$CH$_3$, —OP(O)(OH)$_2$, phenyl, fluorophenyl, oxazolyl substituted with —C(O)NH$_2$; and/or two substituent groups along with the carbon atom to which they are attached, form a cyclopropyl ring;

$R^2$ is -L-$R^x$ or $R^y$;

L is —NHC(O)—, —NHC(O)O—, —NHS(O)$_2$—, —NHC(O)NH—, or —NHC(O)O—;

$R^x$ is $C_{1-6}$ alkyl, $C_{3-6}$ cycloalkyl, $C_{1-4}$ fluoroalkyl, and a cyclic group selected from 5-membered heterocyclyl having at least one oxygen heteroatom, 5-membered heteroaryl having at least one nitrogen heteroatom, or phenyl, each cyclic group substituted with zero to 2 substituents independently selected from F, Cl, —OH, —CN, $C_{1-3}$ alkyl, $C_{1-3}$ alkoxy, —C(O)OH, and/or —NH$_2$; and $R^y$ is:

a) phenyl substituted with zero to 2 substituents independently selected from
  i) F, Cl, —CN, $C_{1-3}$ alkyl, —O($C_{1-3}$ alkyl), —C(O)OH, —NH$_2$, —NH($C_{1-3}$ alkyl), —N($C_{1-3}$ alkyl)$_2$, $C_{3-6}$ cycloalkyl, and/or $C_{2-4}$ alkenyl;
  ii) $C_{1-4}$ alkyl substituted with —CN, —OH, —NH$_2$, —NH(CH$_3$), —N(CH$_3$)$_2$, $C_{3-6}$ cycloalkyl, morpholinyl, piperidinyl substituted with methoxyphenyl, —NHC(O)R'", —NHC(O)NHR", —NHCH(=N—CN)NH($C_{1-3}$ alkyl), and/or —NHS(O)$_2$($C_{1-3}$ alkyl); wherein R'" is $C_{1-4}$ alkyl, $C_{3-6}$ cycloalkyl, hydroxy($C_{3-6}$ cycloalkyl), $C_{1-3}$ cyanoalkyl, $C_{1-4}$ hydroxyalkyl, —CH$_2$NH$_2$, —CH$_2$H(CH$_3$), —CH$_2$N(CH$_3$)$_2$, phenyl, phenyl-S(O)$_2$NH$_2$, phenyl-NHC(O)CH$_3$, pyrrolidinyl, furanyl, pyridinyl, —CH$_2$OC(O)($C_{1-3}$ alkyl), —CH$_2$(morpholinyl), or —CH$_2$NHS(O)$_2$(methylphenyl); and R" is H, $C_{1-3}$ alkyl, $C_{3-6}$ cycloalkyl, or $C_{1-4}$ hydroxyalkyl;
  iii) —C(O)NR$^i$R$^j$ wherein R$^i$ is H or —CH$_3$, and R$^j$ is $C_{1-3}$ alkyl, $C_{3-6}$ cycloalkyl, —CH$_2$C(O)NH$_2$, —CH$_2$C(O)NH(CH$_3$), —CH$_2$C(O)N(CH$_3$)$_2$, or —CH$_2$CH$_2$N(CH$_3$)$_2$;
  iv) —OC(O)($C_{1-3}$ alkyl) and/or —C(O)(N-methyl morpholinyl);
  v) —NHC(O)R$^k$ wherein R$^k$ is H, $C_{1-3}$ alkyl, or $C_{3-6}$ cycloalkyl;
  vi) —S(O)$_2$($C_{1-3}$ alkyl), —NHS(O)$_2$($C_{1-3}$ alkyl), —S(O)$_2$NH$_2$, and/or —S(O)$_2$N(CH$_3$)$_2$;
  vii) thiophenyl, morpholinonyl, imidazolyl, oxazolyl, and/or imidazolidine-2,4-dionyl, each substituted with zero to 1 substituent selected from —CH$_3$, —C(O)O($C_{1-3}$ alkyl), and dimethylaminophenyl;

b) heterocycle selected from propane-1,3-sultam, butane-1,4-sultam, 5-thioxo-4,5-dihydro-1,3,4-oxadiazoly-2-yl, and 5-methylthio-1,3,4-oxadiazoly-2-yl, wherein said heterocycle is substituted with zero to 1 substituent selected from $C_{1-4}$ alkyl, $C_{1-3}$ fluoroalkyl, —NHC(O)O($C_{1-4}$ alkyl), and phenyl; or c) heteroaryl selected from pyrrolyl, pyrazolyl, thiazolyl, oxadiazolyl, pyridinyl, pyrimidinyl, pyrazinyl, indolyl, quinolinyl, 3,4-dihydroisoquinolin-1(2H)-onyl, benzo[d][1,3]dioxolyl, quinolin-2(1H)-onyl, benzothiazolyl, 1H-benzo[d]imidazol-2(3H)-onyl, wherein said heteroaryl is substituted with zero to 3 substituents independently selected from F, Cl, —OH, —CN, $C_{1-4}$ alkyl, $C_{1-3}$ fluoroalkyl, —O($C_{1-4}$ alkyl), —NH$_2$, —NH($C_{1-3}$ alkyl), —N($C_{1-3}$ alkyl)$_2$, —C(O)NH$_2$, —C(O)NH($C_{1-3}$ alkyl), —C(O)N($C_{1-3}$ alkyl)$_2$, —S(O)$_2$($C_{1-3}$ alkyl), —NHCH$_2$CH$_2$N($C_{1-2}$ alkyl)$_2$, —N(CH$_3$)CH$_2$CH$_2$N($C_{1-2}$ alkyl)$_2$, —NHCH$_2$CH$_2$(morpholinyl), piperidinyl, piperazinyl, phenyl, chlorophenyl, methoxyphenyl, dimethylaminophenyl, pyridinyl, morpholinyl, N-methyl piperazinyl, and/or piperazinyl(C(O)O(t-butyl)).

In one embodiment, there are provided compounds of Formula (II) or salts, stereoisomers, or prodrugs thereof, wherein:

$R^1$ is $C_{1-6}$ alkyl substituted with zero to 3 substituent groups independently selected from F, —OH, —CF$_3$, —NH$_2$, —C(O)OH, —C(O)OCH$_3$, —C(O)NH$_2$, —C(O)NHCH$_2$CN, —C(O)NH(phenyl), —NHC(O)CH$_2$CN, —NHS(O)$_2$CH$_3$, —OP(O)(OH)$_2$, phenyl, fluorophenyl, oxazolyl substituted with —C(O)NH$_2$; and/or 2 substituents along with the carbon atom to which they are attached, form a cyclopropyl ring;

$R^2$ is -L-$R^x$ or $R^y$;

L is —NHC(O)—, —NHC(O)O—, or —NHS(O)$_2$—;

$R^x$ is $C_{1-4}$ alkyl, $C_{3-6}$ cycloalkyl, $C_{1-3}$ fluoroalkyl, and a cyclic group selected from 5-membered heteroaryl having 1 to 2 nitrogen heteroatoms, tetrahydrofuranyl, tetrahydropyranyl, or phenyl, each cyclic group substituted with zero to 2 substituents independently selected from F, —CN, —CH$_3$, —OCH$_3$, —C(O)OH, and/or —NH$_2$; and $R^y$ is:

a) phenyl substituted with zero to 2 substituents independently selected from
  i) F, —CN, $C_{1-3}$ alkyl, —OCH$_3$, —C(O)OH, —N(CH$_3$)$_2$, cyclohexyl, and/or —CH=CH$_2$;
  ii) $C_{1-3}$ alkyl substituted with —CN, —OH, —NH$_2$, —N(CH$_3$)$_2$, cyclopentyl, morpholinyl, piperidinyl substituted with methoxyphenyl, —NHC(O)R'", —NHC(O)NHR", —NHCH(=N—CN)NH($C_{1-3}$ alkyl), and/or —NHS(O)$_2$($C_{1-3}$ alkyl); wherein R'" is $C_{1-4}$ alkyl, cyclopropyl, hydroxycyclopropyl, —CH$_2$CN, $C_{1-3}$ hydroxyalkyl, —CH$_2$N(CH$_3$)$_2$, phenyl, phenyl-S(O)$_2$NH$_2$, phenyl-NHC(O)CH$_3$, pyrrolidinyl, furanyl, pyridinyl, —CH$_2$OC(O)CH$_3$, —CH$_2$(morpholinyl), or CH$_2$NHS(O)$_2$(methylphenyl); and R" is H, $C_{1-3}$ alkyl, cyclopropyl, or $C_{1-3}$ hydroxyalkyl;
  iii) —C(O)NR$^i$R$^j$ wherein R$^i$ is H or —CH$_3$, and R$^j$ is $C_{1-3}$ alkyl, cyclopropyl, —CH$_2$C(O)NH$_2$, or —CH$_2$CH$_2$N(CH$_3$)$_2$;

iv) —OC(O)CH₃ and/or —C(O)(N-methyl morpholinyl);
v) —NHC(O)R$^k$ wherein R$^k$ is H, —CH₃, or cyclopropyl;
vi) —S(O)₂(C$_{1-2}$ alkyl), —NHS(O)₂(C$_{1-2}$ alkyl), —S(O)₂NH₂, and/or —S(O)₂N(CH₃)₂;
and/or
vii) thiophenyl, morpholinonyl, imidazolyl, oxazolyl, and/or imidazolidine-2,4-dionyl, each substituted with zero to 1 substituent selected from —CH₃, —C(O)O(C$_{1-3}$ alkyl), and dimethylaminophenyl;
b) heterocycle selected from azetidinonyl, pyrrolidinonyl, morpholinonyl, pyridinonyl, imidazolidinonyl, oxazolidinonyl, propane-1,3-sultam, butane-1,4-sultam, 5-thioxo-4,5-dihydro-1,3,4-oxadiazoly-2-yl, and 5-methylthio-1,3,4-oxadiazoly-2-yl, wherein said heterocycle is substituted with zero to 1 substituent selected from C$_{1-3}$ alkyl, C$_{1-2}$ fluoroalkyl, —NHC(O)O(C$_{1-2}$ alkyl), and phenyl; or
c) heteroaryl selected from pyrrolyl, pyrazolyl, thiazolyl, oxadiazolyl, pyridinyl, pyrimidinyl, pyrazinyl, indolyl, quinolinyl, 3,4-dihydroisoquinolin-1(2H)-onyl, benzo[d][1,3]dioxolyl, quinolin-2(1H)-onyl, benzothiazolyl, 1H-benzo[d]imidazol-2(3H)-onyl, wherein said heteroaryl is substituted with zero to 3 substituents independently selected from F, Cl, —OH, —CN, C$_{1-3}$ alkyl, C$_{1-2}$ fluoroalkyl, —O(C$_{1-3}$ alkyl), —NH₂, —NH(C$_{1-3}$ alkyl), —C(O)NH(C$_{1-3}$ alkyl), —S(O)₂(C$_{1-3}$ alkyl), —NHCH₂CH₂N(C$_{1-2}$ alkyl)₂, —N(CH₃)CH₂CH₂N(C$_{1-2}$ alkyl)₂, —NHCH₂CH₂(morpholinyl), piperidinyl, piperazinyl, phenyl, chlorophenyl, methoxyphenyl, dimethylaminophenyl, pyridinyl, morpholinyl, N-methyl piperazinyl, and/or piperazinyl(C(O)O(t-butyl)).

In one embodiment, there are provided compounds of Formula (II) or salts, stereoisomers, or prodrugs thereof, wherein:
R¹ is C$_{1-6}$ alkyl substituted with zero to 3 substituent groups independently selected from F, —OH, —CF₃, —NH₂, —C(O)OH, —C(O)OCH₃, —C(O)NH₂, —C(O)NHCH₂CN, —C(O)NH(phenyl), —NHC(O)CH₂CN, —NHS(O)₂CH₃, —OP(O)(OH)₂, phenyl, fluorophenyl, oxazolyl substituted with —C(O)NH₂; and/or 2 substituents along with the carbon atom to which they are attached, form a cyclopropyl ring;
R² is -L-R$^x$ or R$^y$;
L is —NHC(O)—, —NHC(O)O—, or —NHS(O)₂—;
R$^x$ is C$_{1-4}$ alkyl, C$_{3-6}$ cycloalkyl, C$_{1-3}$ fluoroalkyl, and a cyclic group selected from 5-membered heteroaryl having 1 to 2 nitrogen heteroatoms, tetrahydrofuranyl, tetrahydropyranyl, or phenyl, each cyclic group substituted with zero to 2 substituents independently selected from F, —CN, —CH₃, —OCH₃, —C(O)OH, and/or —NH₂; and
R$^y$ is:
a) phenyl substituted with zero to 2 substituents independently selected from
i) F, —CN, C$_{1-3}$ alkyl, —OCH₃, —C(O)OH, —N(CH₃)₂, cyclohexyl, and/or —CH═CH₂;
ii) C$_{1-3}$ alkyl substituted with —CN, —OH, —NH₂, —N(CH₃)₂, cyclopentyl, morpholinyl, piperidinyl substituted with methoxyphenyl, —NHC(O)R$^m$, —NHC(O)NHR$^n$, —NHCH(═N—CN)NH(C$_{1-3}$ alkyl), and/or —NHS(O)₂(C$_{1-3}$ alkyl); wherein R$^m$ is C$_{1-4}$ alkyl, cyclopropyl, hydroxycyclopropyl, —CH₂CN, C$_{1-3}$ hydroxyalkyl, —CH₂N(CH₃)₂, phenyl, phenyl-S(O)₂NH₂, phenyl-NHC(O)CH₃, pyrrolidinyl, furanyl, pyridinyl, —CH₂OC(O)CH₃, —CH₂(morpholinyl), or CH₂NHS(O)₂(methylphenyl); and R$^n$ is H, C$_{1-3}$ alkyl, cyclopropyl, or C$_{1-3}$ hydroxyalkyl;
iii) —C(O)NR$^i$R$^j$ wherein R$^i$ is H or —CH₃, and R$^j$ is C$_{1-3}$ alkyl, cyclopropyl, —CH₂C(O)NH₂, or —CH₂CH₂N(CH₃)₂;
iv) —OC(O)CH₃ and/or —C(O)(N-methyl morpholinyl);
v) —NHC(O)R$^k$ wherein R$^k$ is H, —CH₃, or cyclopropyl;
vi) —S(O)₂(C$_{1-2}$ alkyl), —NHS(O)₂(C$_{1-2}$ alkyl), —S(O)₂NH₂, and/or —S(O)₂N(CH₃)₂;
and/or
vii) thiophenyl, morpholinonyl, imidazolyl, oxazolyl, and/or imidazolidine-2,4-dionyl, each substituted with zero to 1 substituent selected from —CH₃, —C(O)O(C$_{1-3}$ alkyl), and dimethylaminophenyl;
b) heterocycle selected from propane-1,3-sultam, butane-1,4-sultam, 5-thioxo-4,5-dihydro-1,3,4-oxadiazoly-2-yl, and 5-methylthio-1,3,4-oxadiazoly-2-yl, wherein said heterocycle is substituted with zero to 1 substituent selected from C$_{1-3}$ alkyl, C$_{1-2}$ fluoroalkyl, —NHC(O)O(C$_{1-2}$ alkyl), and phenyl; or
c) heteroaryl selected from pyrrolyl, pyrazolyl, thiazolyl, oxadiazolyl, pyridinyl, pyrimidinyl, pyrazinyl, indolyl, quinolinyl, 3,4-dihydroisoquinolin-1(2H)-onyl, benzo[d][1,3]dioxolyl, quinolin-2(1H)-onyl, benzothiazolyl, 1H-benzo[d]imidazol-2(3H)-onyl, wherein said heteroaryl is substituted with zero to 3 substituents independently selected from F, Cl, —OH, —CN, C$_{1-3}$ alkyl, C$_{1-2}$ fluoroalkyl, —O(C$_{1-3}$ alkyl), —NH₂, —NH(C$_{1-3}$ alkyl), —C(O)NH(C$_{1-3}$ alkyl), —S(O)₂(C$_{1-3}$ alkyl), —NHCH₂CH₂N(C$_{1-2}$ alkyl)₂, —N(CH₃)CH₂CH₂N(C$_{1-2}$ alkyl)₂, —NHCH₂CH₂(morpholinyl), piperidinyl, piperazinyl, phenyl, chlorophenyl, methoxyphenyl, dimethylaminophenyl, pyridinyl, morpholinyl, N-methyl piperazinyl, and/or piperazinyl(C(O)O(t-butyl)).

In one embodiment, there are provided compounds of Formula (II) or salts, stereoisomers, or prodrugs thereof, wherein:
R¹ is: —CH₃, —CH₂CH₂CH₃, —CH(CH₃)₂,

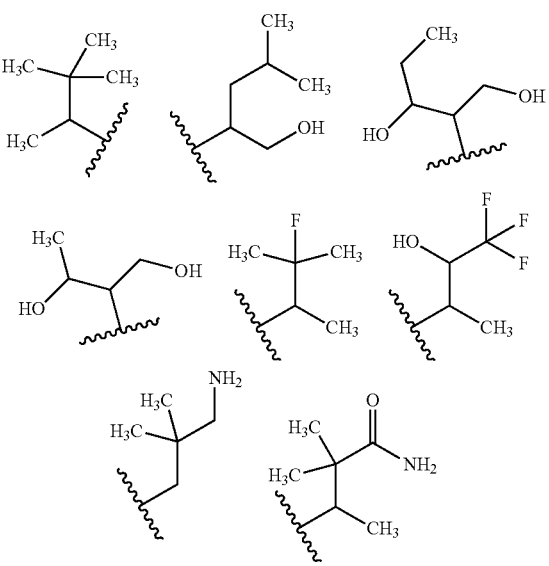

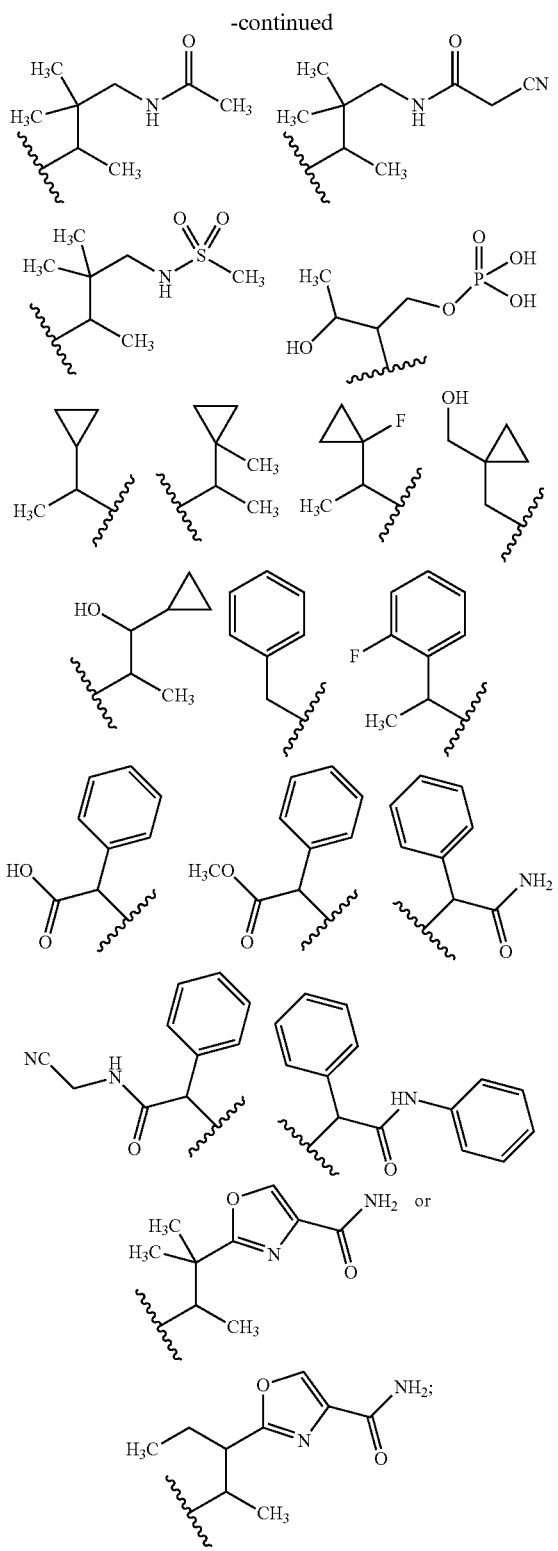

R² is -L-Rˣ or Rʸ;
L is —NHC(O)—, —NHC(O)O—, or —NHS(O)₂—;
Rˣ is $C_{1-4}$ alkyl, $C_{3-6}$ cycloalkyl, —CHF₂, —CF₃, pyridinyl, tetrahydropyranyl, or methoxyphenyl; and
Rʸ is:
a) phenyl substituted with zero to 2 substituents independently selected from F, —CN, —OCH₃, —C(O)OH, cyclohexyl, —CH=CH₂, —CH₂CN, —CH₂OH, —CH₂NH₂, —CH₂N(CH₃)₂, —CH₂(morpholinyl), —CH(OH)CH₂OH, —CH(CH₃)₂CN, —CH₂CH₂(piperidinyl)-(methoxyphenyl), —C(O)NH₂, —C(O)NH(cyclopropyl), —C(O)N(CH₃)₂, —C(O)NHCH(CH₃)₂, —C(O)NHCH₂C(O)NH₂, —C(O)N(CH₃)CH₂C(O)NH₂, —C(O)NHCH₂CH₂N(CH₃)₂, —OC(O)CH₃, —C(O)(N-methyl morpholinyl), —N(CH₃)₂, —NHC(O)H, —NHC(O)CH₃, —NHC(O)(cyclopropyl), —CH(NH₂)CH₃, —CH(cyclopentyl)NH(C(O)CH₃, —CH₂NHC(O)CH₃, —CH₂NHC(O)CH(CH₃)₂, —CH₂NHC(O)(t-butyl), —CH₂NHC(O)(cyclopropyl), —CH₂NHC(O)(hydroxycyclopropyl), —CH₂NHC(O)CH₂CN, —CH₂NHC(O)CH₂OH, —CH₂NHC(O)C(CH₃)₂OH, —CH₂NHC(O)(phenyl), —CH₂NHC(O)(phenyl-S(O)₂NH₂), —CH₂NHC(O)(phenyl-NHC(O)CH₃), —CH₂NHC(O)(pyrrolidinyl), —CH₂NHC(O)(furanyl), —CH₂NHC(O)(pyridinyl), —CH₂NHC(O)CH₂OC(O)CH₃, —CH₂NHC(O)CH₂(morpholinyl), —CH₂NHC(O)NH₂, —CH₂NHC(O)NHCH(CH₃)₂, —CH₂NHC(O)NH(cyclopropyl), —CH₂NHC(O)NH(CH₂CH₂OH), —CH₂NHCH(=N—CN)NHCH(CH₃)₂, —CH₂NHS(O)₂CH₃, —CH₂NHC(O)CH₂N(CH₃)₂, —CH₂NHC(O)CH₂NHS(O)₂(methylphenyl), —S(O)₂CH₃, —NHS(O)₂CH₃, —S(O)₂NH₂, —S(O)₂N(CH₃)₂, thiophenyl, methylthiophenyl, morpholinonyl, imidazolyl substituted with methyl and —C(O)O(ethyl), oxazolyl substituted with dimethylaminophenyl, and/or imidazolidine-2,4-dionyl;
b) heterocycle selected from azetidinonyl, pyrrolidinonyl, morpholinonyl, pyridinonyl, imidazolidinonyl, oxazolidinonyl, propane-1,3-sultam, butane-1,4-sultam, 5-thioxo-4,5-dihydro-1,3,4-oxadiazoly-2-yl, and 5-methylthio-1,3,4-oxadiazoly-2-yl, wherein said heterocycle is substituted with zero to 1 substituent selected from —CH₃, —CH(CH₃)₂, —CF₃, —NHC(O)O(t-butyl), and phenyl; or
c) heteroaryl selected from pyrrolyl, pyrazolyl, thiazolyl, oxadiazolyl, pyridinyl, pyrimidinyl, pyrazinyl, indolyl, quinolinyl, 3,4-dihydroisoquinolin-1(2H)-onyl, benzo[d][1,3]dioxolyl, quinolin-2(1H)-onyl, benzothiazolyl, 1H-benzo[d]imidazol-2(3H)-onyl, wherein said heteroaryl is substituted with zero to 3 substituents independently selected from F, Cl, —OH, —CN, $C_{1-2}$ alkyl —CF₃, —OCH₃, —NH₂, —NH(CH₃), —C(O)NH(CH₃), —S(O)₂CH₃, —NHCH₂CH₂N(CH₃)₂, —N(CH₃)CH₂CH₂N(CH₃)₂, —NHCH₂CH₂(morpholinyl), piperidinyl, piperazinyl, phenyl, chlorophenyl, methoxyphenyl, dimethylaminophenyl, pyridinyl, morpholinyl, N-methyl piperazinyl, and/or piperazinyl (C(O)O(t-butyl)).

In one embodiment, there are provided compounds of Formula (II) or salts, stereoisomers, or prodrugs thereof, wherein:
R¹ is: —CH₃, —CH₂CH₂CH₃, —CH(CH₃)₂,

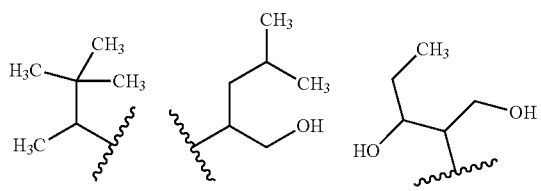

-continued

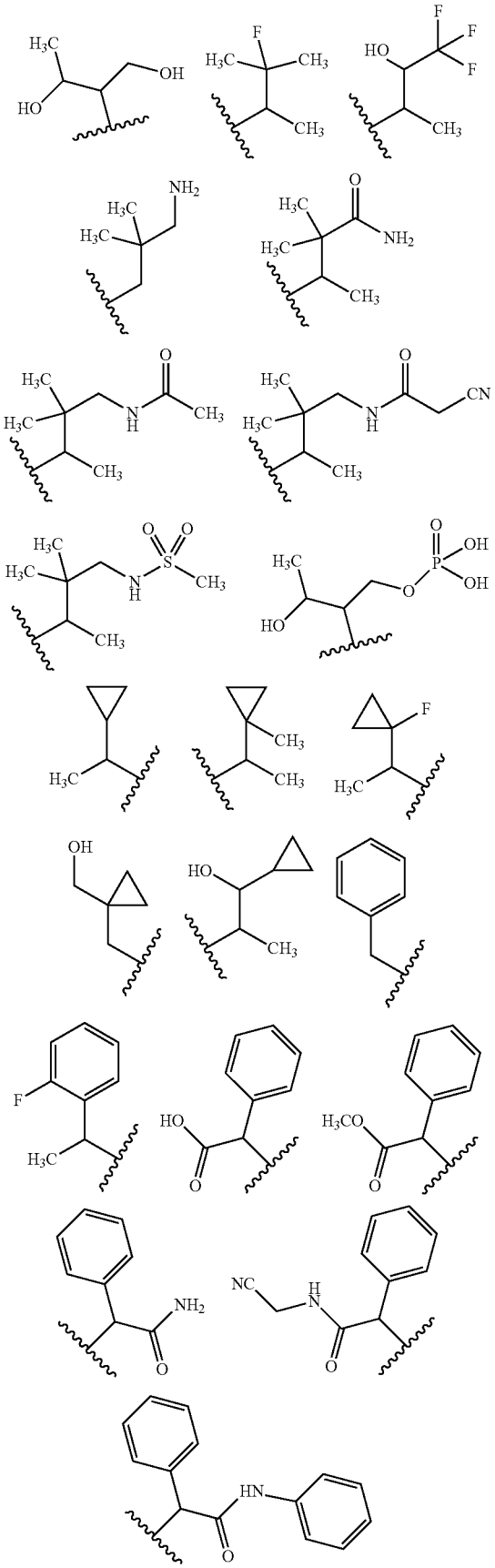

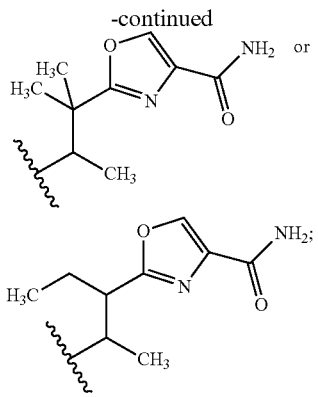

R² is -L-Rˣ or Rʸ;
L is —NHC(O)—, —NHC(O)O—, or —NHS(O)₂—;
Rˣ is $C_{1-4}$ alkyl, $C_{3-6}$ cycloalkyl, —CHF, —CF₃, pyridinyl, tetrahydropyranyl, or methoxyphenyl; and
Rʸ is:
  a) phenyl substituted with zero to 2 substituents independently selected from F, —CN, —OCH₃, —C(O)OH, cyclohexyl, —CH=CH₂, —CH₂CN, —CH₂OH, —CH₂NH₂, —CH₂N(CH₃)₂, —CH₂(morpholinyl), —CH(OH)CH₂OH, —CH(CH₃)₂CN, —CH₂CH₂(piperidinyl)-(methoxyphenyl), —C(O)NH₂, —C(O)NH(cyclopropyl), —C(O)N(CH₃)₂, —C(O)NHCH(CH₃)₂, —C(O)NHCH₂C(O)NH₂, —C(O)N(CH₃)CH₂C(O)NH₂, —C(O)NHCH₂CH₂N(CH₃)₂, —OC(O)CH₃, —C(O)(N-methyl morpholinyl), —N(CH₃)₂, —NHC(O)H, —NHC(O)CH₃, —NHC(O)(cyclopropyl), —CH(NH₂)CH₃, —CH(cyclopentyl)NH(C(O)CH₃, —CH₂NHC(O)CH₃, —CH₂NHC(O)CH(CH₃)₂, —CH₂NHC(O)(t-butyl), —CH₂NHC(O)(cyclopropyl), —CH₂NHC(O)(hydroxycyclopropyl), —CH₂NHC(O)CH₂CN, —CH₂NHC(O)CH₂OH, —CH₂NHC(O)C(CH₃)₂OH, —CH₂NHC(O)(phenyl), —CH₂NHC(O)(phenyl-S(O)₂NH₂), —CH₂NHC(O)(phenyl-NHC(O)CH₃), —CH₂NHC(O)(pyrrolidinyl), —CH₂NHC(O)(furanyl), —CH₂NHC(O)(pyridinyl), —CH₂NHC(O)CH₂OC(O)CH₃, —CH₂NHC(O)CH₂(morpholinyl), —CH₂NHC(O)NH₂, —CH₂NHC(O)NHCH(CH₃)₂, —CH₂NHC(O)NH(cyclopropyl), —CH₂NHC(O)NH(CH₂CH₂OH), —CH₂NHCH(=N—CN)NHCH(CH₃)₂, —CH₂NHS(O)₂CH₃, —CH₂NHC(O)CH₂N(CH₃)₂, —CH₂NHC(O)CH₂NHS(O)₂(methylphenyl), —S(O)₂CH₃, —NHS(O)₂CH₃, —S(O)₂NH₂, —S(O)₂N(CH₃)₂, thiophenyl, methylthiophenyl, morpholinonyl, imidazolyl substituted with methyl and —C(O)O(ethyl), oxazolyl substituted with dimethylaminophenyl, and/or imidazolidine-2,4-dionyl;
  b) heterocycle selected from propane-1,3-sultam, butane-1,4-sultam, 5-thioxo-4,5-dihydro-1,3,4-oxadiazoly-2-yl, and 5-methylthio-1,3,4-oxadiazoly-2-yl, wherein said heterocycle is substituted with zero to 1 substituent selected from —CH₃, —CH(CH₃)₂, —CF₃, —NHC(O)O(t-butyl), and phenyl; or
  c) heteroaryl selected from pyrrolyl, pyrazolyl, thiazolyl, oxadiazolyl, pyridinyl, pyrimidinyl, pyrazinyl, indolyl, quinolinyl, 3,4-dihydroisoquinolin-1(2H)-onyl, benzo[d][1,3]dioxolyl, quinolin-2(1H)-onyl, benzothiazolyl, 1H-benzo[d]imidazol-2(3H)-onyl, wherein said heteroaryl is substituted with zero to 3 substituents independently selected from F, Cl, —OH, —CN, $C_{1-2}$ alkyl —CF₃, —OCH₃, —NH₂, —NH(CH₃), —C(O)NH (CH$_3$), —S(O)$_2$CH$_3$, —NHCH$_2$CH$_2$N(CH$_3$)$_2$, —N(CH$_3$)CH$_2$CH$_2$N(CH$_3$)$_2$, —NHCH$_2$CH$_2$(morpholinyl), piperidinyl, piperazinyl, phenyl, chlorophenyl, methoxyphenyl, dimethylaminophenyl, pyridinyl, morpholinyl, N-methyl piperazinyl, and/or piperazinyl (C(O)O(t-butyl)).

In one embodiment, there are provided compounds of Formula (II) or salts, stereoisomers, or prodrugs thereof, wherein:

R$^1$ is: —CH$_3$, —CH$_2$CH$_2$CH$_3$, —CH(CH$_3$)$_2$,

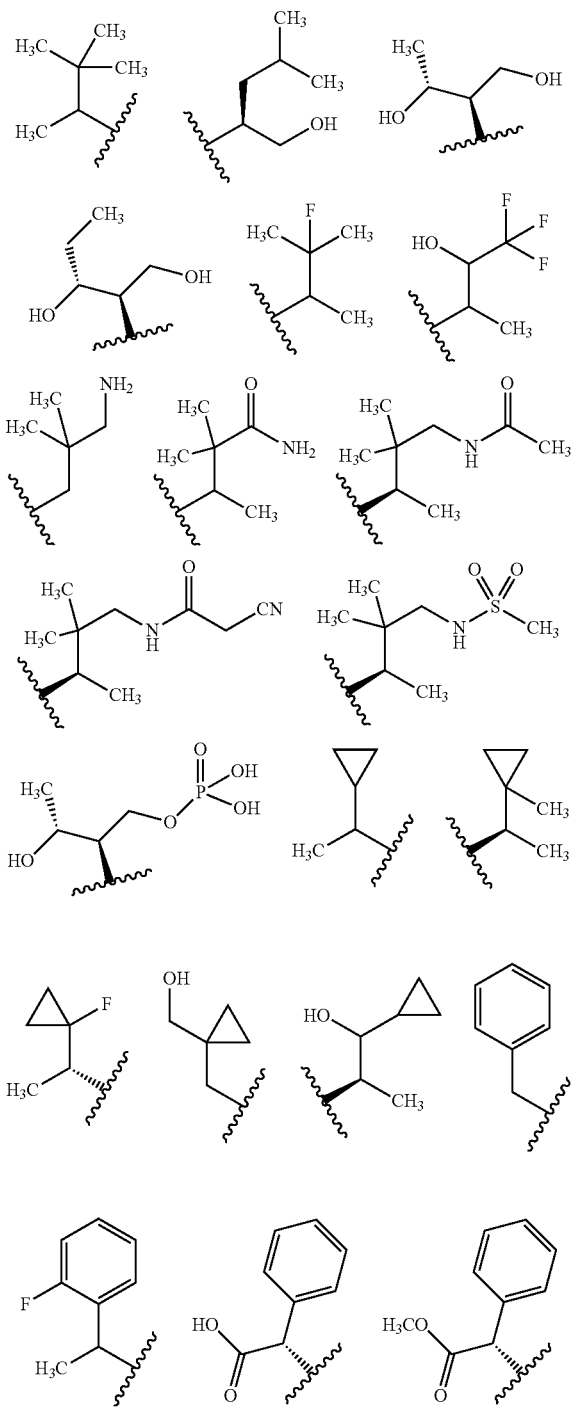

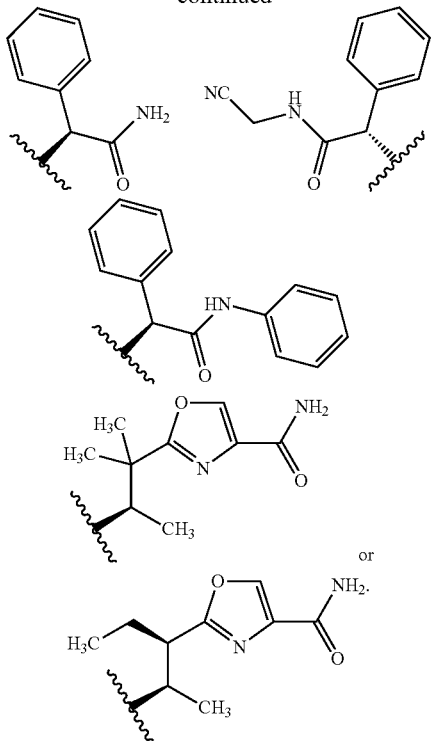

In one embodiment, there are provided compounds of Formula (II) or salts, stereoisomers, or prodrugs thereof, wherein R$^1$ is C$_{1-6}$ alkyl. Included in this embodiment are compounds in which R$^1$ is: —CH$_3$, —CH$_2$CH$_2$CH$_3$, —CH(CH$_3$)$_2$, or —CH(CH$_3$)C(CH$_3$)$_3$.

In one embodiment, there are provided compounds of Formula (II) or salts, stereoisomers, or prodrugs thereof, wherein R$^1$ is C$_{1-6}$ alkyl substituted with 1 or 2 hydroxyl groups. Included in this embodiment are compounds in which R$^1$ is C$_{3-6}$ alkyl substituted with 1 or 2 hydroxyl groups, and compounds in which R$^1$ is C$_{4-6}$ alkyl substituted with 1 or 2 hydroxyl groups. Examples of this embodiment include compounds in which R$^1$ is:

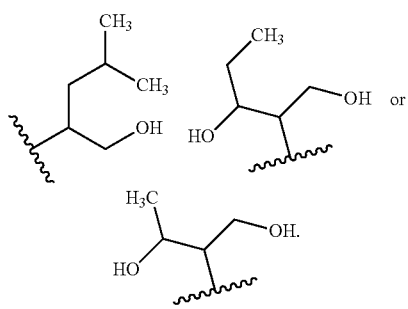

In one embodiment, there are provided compounds of Formula (II) or salts, stereoisomers, or prodrugs thereof, wherein R$^1$ is C$_{1-6}$ alkyl substituted with 1 to 2 substituents selected from F and —CF$_3$ and zero to 1 substituent selected from —OH. Included in this embodiment are compounds in which R$^1$ is C$_{3-6}$ alkyl substituted with substituted with 1 to 2 substituents selected from F and —CF$_3$ and zero to 1 substituent selected from —OH, and compounds in which R$^1$ is C$_{3-5}$ alkyl substituted with 1 to 2 substituents selected from F and —CF$_3$ and zero to 1 substituent selected from —OH. Examples of this embodiment include compounds in which R$^1$ is:

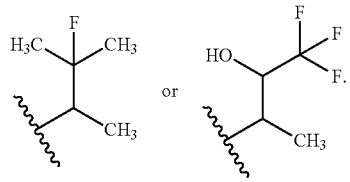

In one embodiment, there are provided compounds of Formula (II) or salts, stereoisomers, or prodrugs thereof, wherein R$^1$ is C$_{1-6}$ alkyl substituted with —NH$_2$. Included in this embodiment are compounds in which R$^1$ is C$_{3-6}$ alkyl substituted with —NH$_2$, and compounds in which R$^1$ is C$_{4-6}$ alkyl substituted —NH$_2$. Examples of this embodiment include compounds in which R$^1$ is:

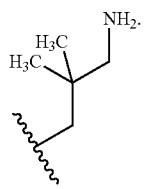

In one embodiment, there are provided compounds of Formula (II) or salts, stereoisomers, or prodrugs thereof, wherein R$^1$ is C$_{1-6}$ alkyl substituted with —C(O)NH$_2$. Included in this embodiment are compounds in which R$^1$ is C$_{3-6}$ alkyl substituted with —C(O)NH$_2$, and compounds in which R$^1$ is C$_{4-6}$ alkyl substituted —C(O)NH$_2$. Examples of this embodiment include compounds in which R$^1$ is:

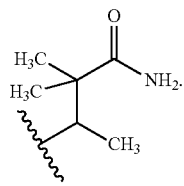

In one embodiment, there are provided compounds of Formula (II) or salts, stereoisomers, or prodrugs thereof, wherein R$^1$ is C$_{1-6}$ alkyl substituted with —NH$_2$C(O)CH$_3$ or —NH$_2$C(O)CH$_2$CN. Included in this embodiment are compounds in which R$^1$ is C$_{4-6}$ alkyl substituted with —NH$_2$C(O)CH$_3$ or —NH$_2$C(O)CH$_2$CN, and compounds in which R$^1$ is C$_{5-6}$ alkyl substituted —NH$_2$C(O)CH$_3$ or —NH$_2$C(O)CH$_2$CN. Examples of this embodiment include compounds in which R$^1$ is:

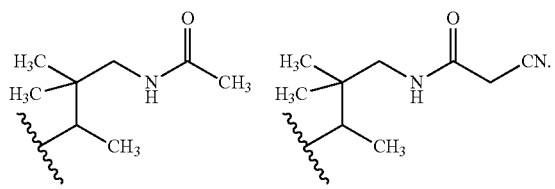 [SMILES: *C(C)C(C)(C)CNC(C)=O ; *C(C)C(C)(C)CNC(=O)CC#N]

In one embodiment, there are provided compounds of Formula (II) or salts, stereoisomers, or prodrugs thereof, wherein R$^1$ is C$_{1-6}$ alkyl substituted with —NH$_2$S(O)$_2$CH$_3$. Included in this embodiment are compounds in which R$^1$ is C$_{3-6}$ alkyl substituted with —NH$_2$S(O)$_2$CH$_3$, and compounds in which R$^1$ is C$_{4-6}$ alkyl substituted NH$_2$S(O)$_2$CH$_3$. Examples of this embodiment include compounds in which R$^1$ is:

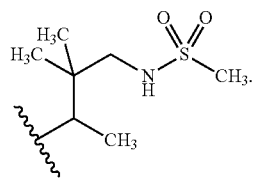

In one embodiment, there are provided compounds of Formula (II) or salts, stereoisomers, or prodrugs thereof, wherein R$^1$ is C$_{1-6}$ alkyl substituted with —OP(O)(OH)$_2$ and zero to 1 hydroxyl group. Included in this embodiment are compounds in which R$^1$ is C$_{3-6}$ alkyl substituted with —OP(O)(OH)$_2$ and zero to 1 hydroxyl group, and compounds in which R$^1$ is C$_{4-6}$ alkyl substituted with —OP(O)(OH)$_2$ and zero to 1 hydroxyl group. Examples of this embodiment include compounds in which R$^1$ is:

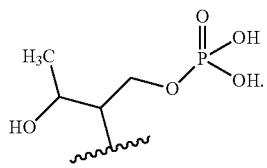

In one embodiment, there are provided compounds of Formula (II) or salts, stereoisomers, or prodrugs thereof, wherein R$^1$ is C$_{1-6}$ alkyl substituted with a cyclopropyl group and zero to 1 substituent selected from F and —OH. The cyclopropyl group may be pendant to the alkyl chain or may be formed to include a carbon atom of the alkyl group. Included in this embodiment are compounds in which R$^1$ is C$_{2-6}$ alkyl substituted with cyclopropyl and zero to 1 substituent selected from F and —OH, and C$_{2-5}$ alkyl substituted with cyclopropyl and zero to 1 substituent selected from F and —OH. Examples of this embodiment include compounds in which R$^1$ is:

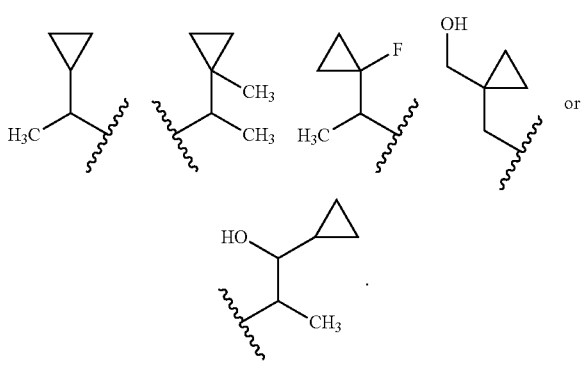

In one embodiment, there are provided compounds of Formula (II) or salts, stereoisomers, or prodrugs thereof, wherein R$^1$ is C$_{1-6}$ alkyl substituted with phenyl or fluorophenyl and zero to 1 substituent groups selected from —C(O)OH, —C(O)OCH₃, —C(O)NH₂, —C(O)NHCH₂CN, or —C(O)NH(phenyl). Included in this embodiment are compounds in which $R^1$ is $C_{1-4}$ alkyl substituted with phenyl or fluorophenyl and zero to 1 substituent groups selected from —C(O)OH, —C(O)OCH₃, —C(O)NH₂, —C(O)NHCH₂CN, or —C(O)NH(phenyl). Also included in this embodiment are compounds in which $R^1$ is $C_{1-2}$ alkyl substituted with phenyl or fluorophenyl and zero to 1 substituent groups selected from —C(O)OH, —C(O)OCH₃, —C(O)NH₂, —C(O)NHCH₂CN, or —C(O)NH(phenyl). Examples of this embodiment include compounds in which $R^1$ is:

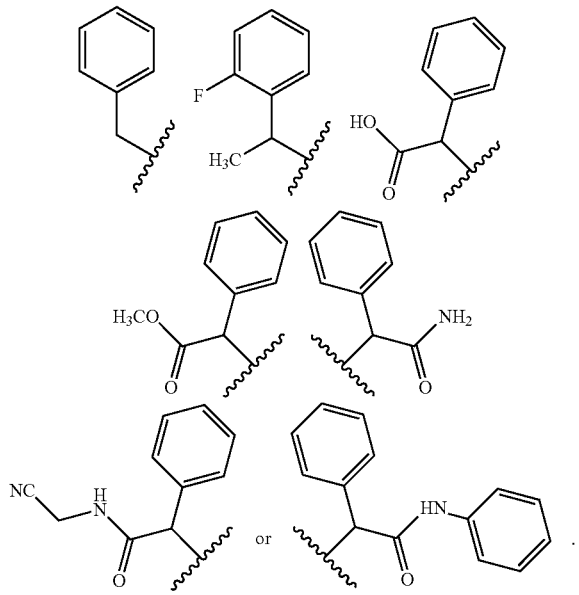

In one embodiment, there are provided compounds of Formula (II) or salts, stereoisomers, or prodrugs thereof, wherein $R^1$ is $C_{1-6}$ alkyl substituted with oxazolyl substituted with zero or 1 substituent group selected from —C(O)NH₂. Included in this embodiment are compounds in which $R^1$ is $C_{3-6}$ alkyl substituted with oxazolyl substituted with —C(O)NH₂, and $R^1$ is $C_{4-5}$ alkyl substituted with oxazolyl substituted with —C(O)NH₂. Examples of this embodiment include compounds in which $R^1$ is:

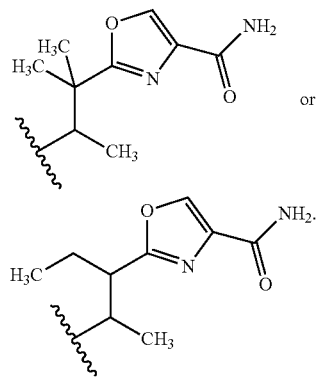

In one embodiment, there are provided compounds of Formula (II) or salts, stereoisomers, or prodrugs thereof, wherein $R^2$ is -L-$R^x$; L is —NHC(O)—, —NHC(O)O—, —NHS(O)₂—, —NHC(O)NH—, —NHC(O)O—, or —C(O)NH—; and $R^x$ is $C_{1-4}$ alkyl, $C_{3-6}$ cycloalkyl, $C_{1-3}$ fluoroalkyl, and a cyclic group selected from 5-membered heteroaryl having 1 to 2 nitrogen heteroatoms, tetrahydrofuranyl, tetrahydropyranyl, or phenyl, each cyclic group substituted with zero to 2 substituents independently selected from F, —CN, —CH₃, —OCH₃, —C(O)OH, and/or —NH₂. Included in this embodiment are compounds in which L is —NHC(O)—, —NHC(O)O—, —NHS(O)₂—, —NHC(O)NH—, or —NHC(O)O—.

In one embodiment, there are provided compounds of Formula (II) or salts, stereoisomers, or prodrugs thereof, wherein $R^2$ is -L-$R^x$; L is —NHC(O)—, —NHC(O)O—, —NHS(O)₂—, —NHC(O)NH—, —NHC(O)O—, or —C(O)NH—; and $R^x$ is $C_{1-4}$ alkyl, $C_{3-6}$ cycloalkyl, —CHF₂, —CF₃, pyridinyl, tetrahydropyranyl, or methoxyphenyl. Included in this embodiment are compounds in which L is —NHC(O)—, —NHC(O)O—, —NHS(O)₂—, —NHC(O)NH—, or —NHC(O)O—.

In one embodiment, there are provided compounds of Formula (II) or salts, stereoisomers, or prodrugs thereof, wherein $R^2$ is -L-$R^x$; L is —NHC(O)—, —NHC(O)O—, or —NHS(O)₂—; and $R^x$ is $C_{1-6}$ alkyl, $C_{3-6}$ cycloalkyl, $C_{1-4}$ fluoroalkyl, and a cyclic group selected from 5-membered heterocyclyl having at least one oxygen heteroatom, 5-membered heteroaryl having at least one nitrogen heteroatom, or phenyl, each cyclic group substituted with zero to 2 substituents independently selected from F, Cl, —OH, —CN, $C_{1-3}$ alkyl, $C_{1-3}$ alkoxy, —C(O)OH, and/or —NH₂.

In one embodiment, there are provided compounds of Formula (II) or salts, stereoisomers, or prodrugs thereof, wherein $R^2$ is -L-$R^x$; L is —NHC(O)—, —NHC(O)O—, or —NHS(O)₂—; and $R^x$ is $C_{1-4}$ alkyl, $C_{3-6}$ cycloalkyl, $C_{1-3}$ fluoroalkyl, and a cyclic group selected from 5-membered heteroaryl having 1 to 2 nitrogen heteroatoms, tetrahydrofuranyl, tetrahydropyranyl, or phenyl, each cyclic group substituted with zero to 2 substituents independently selected from F, —CN, —CH₃, —OCH₃, —C(O)OH, and/or —NH₂.

In one embodiment, there are provided compounds of Formula (II) or salts, stereoisomers, or prodrugs thereof, wherein $R^2$ is -L-$R^x$; L is —NHC(O)—, —NHC(O)O—, or —NHS(O)₂—; and $R^x$ is $C_{1-4}$ alkyl, $C_{3-6}$ cycloalkyl, —CHF₂, —CF₃, pyridinyl, tetrahydropyranyl, or methoxyphenyl.

In one embodiment, there are provided compounds of Formula (II) or salts, stereoisomers, or prodrugs thereof, wherein $R^2$ is $R^y$; and $R^y$ is phenyl substituted with zero to 2 substituents independently selected from F, —CN, —OCH₃, —C(O)OH, cyclohexyl, —CH=CH₂, —CH₂CN, —CH₂OH, —CH₂NH₂, —CH₂N(CH₃)₂, —CH₂(morpholinyl), —CH(OH)CH₂OH, —CH(CH₃)₂CN, —CH₂CH₂(piperidinyl)-(methoxyphenyl), —C(O)NH₂, —C(O)NH(cyclopropyl), —C(O)N(CH₃)₂, —C(O)NHCH(CH₃)₂, —C(O)NHCH₂C(O)NH₂, —C(O)N(CH₃)CH₂C(O)NH₂, —C(O)NHCH₂CH₂N(CH₃)₂, —OC(O)CH₃, —C(O)(N-methyl morpholinyl), —N(CH₃)₂, —NHC(O)H, —NHC(O)CH₃, —NHC(O)(cyclopropyl), —CH(NH₂)CH₃, —CH(cyclopentyl)NHC(O)CH₃, —CH₂NHC(O)CH₃, —CH₂NHC(O)CH(CH₃)₂, —CH₂NHC(O)(t-butyl), —CH₂NHC(O)(cyclopropyl), —CH₂NHC(O)(hydroxycyclopropyl), —CH₂NHC(O)CH₂CN, —CH₂NHC(O)CH₂OH, —CH₂NHC(O)C(CH₃)₂OH, —CH₂NHC(O)(phenyl), —CH₂NHC(O)(phenyl-S(O)₂NH₂), —CH₂NHC(O)(phenyl-NHC(O)CH₃), —CH₂NHC(O)(pyrrolidinyl), —CH₂NHC(O)(furanyl), —CH₂NHC(O)(pyridinyl), —CH₂NHC(O)CH₂OC(O)CH₃, —CH₂NHC(O)CH₂(morpholinyl), —CH₂NHC(O)NH₂, —CH₂NHC(O)NHCH(CH₃)₂, —CH₂NHC(O)NH(cyclopropyl), —CH₂NHC(O)NH(CH₂CH₂OH), —CH₂NHCH(=N—CN)NHCH(CH₃)₂, —CH₂NHS(O)₂CH₃, —CH₂NHC(O)CH₂N(CH₃)₂, —CH₂NHC(O)CH₂NHS(O)₂ (methylphenyl), —S(O)₂CH₃, —NHS(O)₂CH₃, —S(O)₂NH₂, —S(O)₂N(CH₃)₂, thiophenyl, methylthiophenyl, morpholinonyl, imidazolyl substituted with methyl and —C(O)O(ethyl), oxazolyl substituted with dimethylaminophenyl, and/or imidazolidine-2,4-dionyl.

In one embodiment, there are provided compounds of Formula (II) or salts, stereoisomers, or prodrugs thereof, wherein $R^2$ is $R^y$; and $R^y$ is phenyl substituted with zero to 2 substituents independently selected from F, —CN, —OCH₃, —C(O)OH, —N(CH₃)₂, cyclohexyl, and/or —CH=CH₂.

In one embodiment, there are provided compounds of Formula (II) or salts, stereoisomers, or prodrugs thereof, wherein $R^2$ is $R^y$; and $R^y$ is phenyl substituted with zero to 1 substituent selected from $C_{1-3}$ alkyl substituted with —CN, —OH, —NH₂, —N(CH₃)₂, cyclopentyl, morpholinyl, piperidinyl substituted with methoxyphenyl, —NHC(O)R'''', —NHC(O)NHR'''', —NHCH(=N—CN)NH(C_{1-3} alkyl), and/or —NHS(O)₂(C_{1-3} alkyl); wherein R'''' is $C_{1-4}$ alkyl, cyclopropyl, hydroxycyclopropyl, —CH₂CN, $C_{1-3}$ hydroxyalkyl, —CH₂N(CH₃)₂, phenyl, phenyl-S(O)₂NH₂, phenyl-NHC(O)CH₃, pyrrolidinyl, furanyl, pyridinyl, —CH₂OC(O)CH₃, —CH₂(morpholinyl), or CH₂NHS(O)₂(methylphenyl); and R'''' is H, $C_{1-3}$ alkyl, cyclopropyl, or $C_{1-3}$ hydroxyalkyl.

In one embodiment, there are provided compounds of Formula (II) or salts, stereoisomers, or prodrugs thereof, wherein $R^2$ is $R^y$; and $R^y$ is phenyl substituted with zero to 1 substituent selected from —C(O)NR'R^j wherein R^i is H or —CH₃, and R^j is $C_{1-3}$ alkyl, cyclopropyl, —CH₂C(O)NH₂, or —CH₂CH₂N(CH₃)₂.

In one embodiment, there are provided compounds of Formula (II) or salts, stereoisomers, or prodrugs thereof, wherein $R^2$ is $R^y$; and $R^y$ is phenyl substituted with zero to 1 substituent selected from —OC(O)CH₃ and/or —C(O)(N-methyl morpholinyl).

In one embodiment, there are provided compounds of Formula (II) or salts, stereoisomers, or prodrugs thereof, wherein $R^2$ is $R^y$; and $R^y$ is phenyl substituted with zero to 1 substituent selected from —NHC(O)R^k wherein R^k is H, —CH₃, or cyclopropyl.

In one embodiment, there are provided compounds of Formula (II) or salts, stereoisomers, or prodrugs thereof, wherein $R^2$ is $R^y$; and $R^y$ is phenyl substituted with zero to 1 substituent selected from —S(O)₂(C_{1-2} alkyl), —NHS(O)₂(C_{1-2} alkyl), —S(O)₂NH₂, and/or —S(O)₂N(CH₃)₂.

In one embodiment, there are provided compounds of Formula (II) or salts, stereoisomers, or prodrugs thereof, wherein $R^2$ is $R^y$; and $R^y$ is phenyl substituted with zero to 1 substituent selected from thiophenyl, morpholinonyl, imidazolyl, oxazolyl, and/or imidazolidine-2,4-dionyl, each substituted with zero to 1 substituent selected from —CH₃, —C(O)O(C_{1-3} alkyl), and dimethylaminophenyl.

In one embodiment, there are provided compounds of Formula (II) or salts, stereoisomers, or prodrugs thereof, wherein $R^2$ is $R^y$; and $R^y$ is heterocycle selected from azetidinonyl, pyrrolidinonyl, morpholinonyl, pyridinonyl, imidazolidinonyl, oxazolidinonyl, propane-1,3-sultam, butane-1,4-sultam, 5-thioxo-4,5-dihydro-1,3,4-oxadiazoly-2-yl, and 5-methylthio-1,3,4-oxadiazoly-2-yl, wherein said heterocycle is substituted with zero to 1 substituent selected from —CH₃, —CH(CH₃)₂, —CF₃, —NHC(O)O(t-butyl), and phenyl.

In one embodiment, there are provided compounds of Formula (II) or salts, stereoisomers, or prodrugs thereof, wherein $R^2$ is $R^y$; and $R^y$ is heterocycle selected from propane-1,3-sultam, butane-1,4-sultam, 5-thioxo-4,5-dihydro-1,3,4-oxadiazoly-2-yl, and 5-methylthio-1,3,4-oxadiazoly-2-yl, wherein said heterocycle is substituted with zero to 1 substituent selected from —CH₃, —CH(CH₃)₂, —CF₃, —NHC(O)O(t-butyl), and phenyl.

In one embodiment, there are provided compounds of Formula (II) or salts, stereoisomers, or prodrugs thereof, wherein $R^2$ is $R^y$; and $R^y$ is heteroaryl selected from pyrrolyl, pyrazolyl, thiazolyl, oxadiazolyl, pyridinyl, pyrimidinyl, pyrazinyl, indolyl, quinolinyl, 3,4-dihydroisoquinolin-1(2H)-onyl, benzo[d][1,3]dioxolyl, quinolin-2(1H)-onyl, benzothiazolyl, 1H-benzo[d]imidazol-2(3H)-onyl, wherein said heteroaryl is substituted with zero to 3 substituents independently selected from F, Cl, —OH, —CN, $C_{1-2}$ alkyl —CF₃, —OCH₃, —NH₂, —NH(CH₃), —C(O)NH(CH₃), —S(O)₂CH₃, —NHCH₂CH₂N(CH₃)₂, —N(CH₃)CH₂CH₂N(CH₃)₂, —NHCH₂CH₂(morpholinyl), piperidinyl, piperazinyl, phenyl, chlorophenyl, methoxyphenyl, dimethylaminophenyl, pyridinyl, morpholinyl, N-methyl piperazinyl, and/or piperazinyl(C(O)O(t-butyl)).

In one embodiment, there are provided compounds of Formula (II) or salts, stereoisomers, or prodrugs thereof, wherein $R^2$ is $R^y$; and $R^y$ is a heteroaryl selected from pyrazolyl, pyridinyl, pyrimidinyl, and pyrazinyl wherein said heteroaryl is substituted with zero to 3 substituents independently selected from F, Cl, —CN, $C_{1-2}$ alkyl —CF₃, —OCH₃, —NH₂, —NH(CH₃), —C(O)NH(CH₃), —S(O)₂CH₃, —NHCH₂CH₂N(CH₃)₂, —N(CH₃)CH₂CH₂N(CH₃)₂, —NHCH₂CH₂(morpholinyl), piperidinyl, piperazinyl, phenyl, chlorophenyl, methoxyphenyl, pyridinyl, and/or piperazinyl(C(O)O(t-butyl)).

In one embodiment, there are provided compounds of Formula (II) or salts, stereoisomers, or prodrugs thereof, wherein $R^2$ is $R^y$; and $R^y$ is oxadiazolyl substituted with zero to 1 substituent selected from —SH, —NH(CH₃), N-methylpiperazinyl, and —NHCH₂CH₂(morpholinyl).

One embodiment provides a compound of Formula (II) selected from: 6-(3-oxo-4-morpholinyl)-4-(((1R)-1,2,2-trimethylpropyl)amino)pyrrolo[1,2-b]pyridazine-3-carboxamide (1); (R)-4-(1-cyclopropylethylamino)-6-(2-oxopyrrolidin-1-yl)pyrrolo[1,2-b]pyridazine-3-carboxamide (185); and (R)-4-(1-cyclopropylethylamino)-6-(5-thioxo-4,5-dihydro-1,3,4-oxadiazol-2-yl)pyrrolo[1,2-b]pyridazine-3-carboxamide (126), or salts, stereoisomers, or prodrugs thereof.

One embodiment provides a compound of Formula (II) selected from: 4-(((1R)-2-fluoro-1,2-dimethylpropyl)amino)-6-phenylpyrrolo[1,2-b]pyridazine-3-carboxamide (32); 6-(3-(aminomethyl)phenyl)-4-(1R)-2-fluoro-1,2-dimethylpropyl)amino)pyrrolo[1,2-b]pyridazine-3-carboxamide (68); 6-(3-(((cyclopropylcarbonyl)amino)methyl)phenyl)-4-(((1R)-2-fluoro-1,2-dimethylpropyl)amino)pyrrolo[1,2-b]pyridazine-3-carboxamide (69); 6-(3-(((cyclopropylcarbamoyl)amino)methyl)phenyl)-4-(1R)-2-fluoro-1,2-dimethylpropyl)amino)pyrrolo[1,2-b]pyridazine-3-carboxamide (70); 4-(((1R)-1-cyclopropylethyl)amino)-6-phenylpyrrolo[1,2-b]pyridazine-3-carboxamide (73); (R)-6-(3-(aminomethyl)phenyl)-4-(1R)-1-cyclopropylethyl)amino)pyrrolo[1,2-b]pyridazine-3-carboxamide (87); (R)-4-(1-cyclopropylethylamino)-6-(3-(isobutyramidomethyl)phenyl)pyrrolo[1,2-b]pyridazine-3-carboxamide (88); 4-(((1R)-1-cyclopropylethyl)amino)-6-(3-(dimethylcarbamoyl) phenyl)pyrrolo[1,2-b]pyridazine-3-carboxamide (116); 4-(((1R)-1-(1-fluorocyclopropyl)ethyl)amino)-6-phenylpyrrolo[1,2-b]pyridazine-3-carboxamide (120); (S)-methyl 2-(3-carbamoyl-6-phenylpyrrolo[1,2-b]pyridazin-4-ylamino)-2-phenylacetate (121); (S)-2-(3-carbamoyl-6-phenylpyrrolo[1,2-b]pyridazin-4-ylamino)-2-phenylacetic acid (122); 4-(((1S)-2-((cyanomethyl)amino)-2-oxo-1-phenylethyl)amino)-6-phenylpyrrolo[1,2-b]pyridazine-3-carboxamide (123); 4-(((1R,3S)-3-amino-2,2,3-trimethylcyclopentyl)amino)-6-(4-(3-oxo-4-morpholinyl) phenyl)pyrrolo[1,2-b]pyridazine-3-carboxamide (144); 4-(((1R)-1-(2-fluorophenyl) ethyl)amino)-6-phenylpyrrolo[1,2-b] pyridazine-3-carboxamide (178); 4-(((1R)-1-(2-fluorophenyl)ethyl)amino)-6-(4-(isopropylcarbamoyl) phenyl)pyrrolo[1,2-b]pyridazine-3-carboxamide (182); 6-phenyl-4-(propylamino)pyrrolo[1,2-b]pyridazine-3-carboxamide (183); 4-(benzylamino)-6-phenylpyrrolo[1,2-b]pyridazine-3-carboxamide (184); (R)-4-(1-cyclopropylethylamino)-6-(3-vinylphenyl)pyrrolo[1,2-b]pyridazine-3-carboxamide (186); (R)-4-(1-cyclopropylethylamino)-6-(3-(1,2-dihydroxyethyl)phenyl)pyrrolo[1,2-b]-pyridazine-3-carboxamide (187); 4-((1-(hydroxymethyl)cyclopropyl) methylamino)-6-phenylpyrrolo[1,2-b]pyridazine-3-carboxamide (189); 6-(3-(acetamidomethyl)phenyl)-4((1-(hydroxymethyl)cyclopropyl)methylamino)pyrrolo[1,2-b] pyridazine-3-carboxamide (190); 6-(3-(cyanomethyl) phenyl)-4-(methylamino)pyrrolo[1,2-b]pyridazine-3-carboxamide (191); (+/-)-4-(4-amino-3,3-dimethyl-4-oxobutan-2-ylamino)-6-phenylpyrrolo[1,2-b]-pyridazine-3-carboxamide (193); (R)-4-(4-amino-3,3-dimethyl-4-oxobutan-2-ylamino)-6-phenylpyrrolo[1,2-b]-pyridazine-3-carboxamide (194); 4-((2R,3R)-1,3-dihydroxybutan-2-ylamino)-6-phenylpyrrolo[1,2-b]pyridazine-3-carboxamide (196); 4-((R)-1-cyclopropylethylamino)-6-(3-(1,2-dihydroxyethyl)phenyl)pyrrolo[1,2-b]pyridazine-3-carboxamide (197); (S)-6-(3-(dimethylamino)phenyl)-4-(1-hydroxy-4-methylpentan-2-ylamino)pyrrolo[1,2-b]pyridazine-3-carboxamide (207); 4-(3-amino-2,2-dimethylpropylamino)-6-(4-cyanophenyl)pyrrolo[1,2-b]pyridazine-3-carboxamide (208); 4-(((2R,3R)-1,3-dihydroxypentan-2-yl)amino)-6-(4-methoxyphenyl)pyrrolo[1,2-b]pyridazine-3-carboxamide (227); (R)-4-((4-amino-3,3-dimethyl-4-oxobutan-2-yl)amino)-6-(4-methoxyphenyl)pyrrolo[1,2-b]pyridazine-3-carboxamide (236); and (2R,3R)-2-((3-carbamoyl-6-phenylpyrrolo[1,2-b]pyridazin-4-yl)amino)-3-hydroxybutyl dihydrogen phosphate, disodium (240); or salts, stereoisomers, or prodrugs thereof.

One embodiment provides a compound of Formula (II) selected from: (R)-4-(1-cyclopropylethylamino)-6-(5-(methylthio)-1,3,4-oxadiazol-2-yl)pyrrolo[1,2-b]pyridazine-3-carboxamide (127); 4-(((1R)-1-cyclopropylethyl)amino)-6-(5-(4-morpholinyl)-1,3,4-oxadiazol-2-yl)pyrrolo[1,2-b]pyridazine-3-carboxamide (128); (R)-4-(1-cyclopropylethylamino)-6-(5-(methylamino)-1,3,4-oxadiazol-2-yl)pyrrolo[1,2-b]pyridazine-3-carboxamide (195); (R)-4-((1-(1-methylcyclopropyl)ethyl)amino)-6-(5-(4-methylpiperazin-1-yl)-1,3,4-oxadiazol-2-yl)pyrrolo[1,2-b]pyridazine-3-carboxamide (241); (R)-4-((1-(1-methylcyclopropyl)ethyl)amino)-6-(5-((2-morpholinoethyl)amino)-1,3,4-oxadiazol-2-yl)pyrrolo[1,2-b]pyridazine-3-carboxamide (242); and 4-(((2R,3R)-1,3-dihydroxybutan-2-yl)amino)-6-(1-methyl-1H-indol-5-yl)pyrrolo[1,2-b]pyridazine-3-carboxamide (231); or salts, stereoisomers, or prodrugs thereof.

One embodiment provides a compound of Formula (II) selected from: 4-(((1R)-1-(2-fluorophenyl)ethyl)amino)-6-(4-pyridinyl)pyrrolo[1,2-b]pyridazine-3-carboxamide (179); 4-(((1R)-1-(2-fluorophenyl)ethyl)amino)-6-(6-methoxy-3-pyridinyl)pyrrolo[1,2-b]pyridazine-3-carboxamide (180); (+/-)-4-((1-(2,5-difluorophenyl)ethyl)amino)-6-(4-pyridinyl)pyrrolo[1,2-b]pyridazine-3-carboxamide (181); (+/-)-4-(1-cyclopropylethylamino)-6-(pyridin-2-yl)pyrrolo[1,2-b]pyridazine-3-carboxamide (188); 6-(6-methoxypyridin-3-yl)-4-((4,4,4-trifluoro-3-hydroxybutan-2-yl)amino)pyrrolo[1,2-b]pyridazine-3-carboxamide (209); (R)-4-(1-cyclopropyl-1-hydroxypropan-2-ylamino)-6-(6-methoxypyridin-3-yl)pyrrolo[1,2-b]pyridazine-3-carboxamide (210); (R)-2-(3-((3-carbamoyl-6-(6-methylpyridin-3-yl)pyrrolo[1,2-b] pyridazin-4-yl)amino)-2-methylbutan-2-yl)oxazole-4-carboxamide (218); 2-((2R,3R)-2-((3-carbamoyl-6-(6-methoxypyridin-3-yl)pyrrolo[1,2-b]pyridazin-4-yl)amino) pentan-3-yl)oxazole-4-carboxamide (224); (R)-4-((3,3-dimethyl-4-(methylsulfonamido)butan-2-yl)amino)-6-(6-methoxypyridin-3-yl)pyrrolo[1,2-b]pyridazine-3-carboxamide (232); and (R)-6-(2-aminopyrimidin-5-yl)-4-(1-cyclopropylethylamino)pyrrolo[1,2-b]pyridazine-3-carboxamide (192); or salts, stereoisomers, or prodrugs thereof.

In another embodiment are compounds of Formula (I), wherein: the compound of formula (I) is selected from an Example herein.

In another embodiment the present invention provides a pharmaceutical composition comprising a pharmaceutically acceptable carrier and at least one of the compounds of the present invention or a stereoisomer, tautomer, pharmaceutically acceptable salt, solvate, or prodrug thereof.

In another embodiment, the present invention provides a pharmaceutical composition comprising a compound of Formula (I) or pharmaceutically acceptable salt thereof and a pharmaceutically acceptable carrier.

In another embodiment, the present invention provides a pharmaceutical composition, comprising: a pharmaceutically acceptable carrier and a therapeutically effective amount of at least one of the compounds of the present invention or a stereoisomer, tautomer, pharmaceutically acceptable salt, solvate or prodrug thereof.

In another embodiment, the present invention provides a method for treating inflammatory or autoimmune disease: administering to a patient in need of such treatment a therapeutically effective amount of at least one of the compounds of the present invention or a stereoisomer, tautomer, pharmaceutically acceptable salt, solvate or prodrug thereof, in combination with at least one other therapeutic agent, or a stereoisomer, tautomer, pharmaceutically acceptable salt, solvate or prodrug thereof.

In another embodiment, the present invention provides a method for treating inflammatory and/or autoimmune diseases comprising: administering to a patient in need of such treatment a therapeutically effective amount of at least one of the compounds of the present invention or a stereoisomer, tautomer, pharmaceutically acceptable salt, solvate or prodrug thereof.

In another embodiment, the present invention provides a method of treating a patient in need of inflammatory and/or autoimmune diseases treatment, comprising: administering a compound of the present invention or a stereoisomer, tautomer, pharmaceutically acceptable salt, solvate, or prodrug form thereof in an amount effective to treat the inflammatory and/or autoimmune diseases.

In another embodiment, the present invention provides a method of treating inflammatory or autoimmune diseases, wherein the inflammatory or autoimmune diseases is selected from Crohn's, ulcerative colitis, asthma, Graves' disease, rheumatoid arthritis, systemic lupus erythematosis, psoriasis, dry eye, multiple sclerosis, psoriatic arthritis and ankylosing spondylitis, solid organ transplant rejection, islet cell transplant rejection and graft vs. host disease.

In another embodiment, the present invention provides a novel method, comprising: administering a compound of the present invention or a stereoisomer, tautomer, pharmaceutically acceptable salt, solvate, or prodrug form thereof in an amount effective to treat an inflammatory and/or autoimmune diseases.

In another embodiment, the present invention provides a method for treating inflammatory and/or autoimmune diseases comprising: administering to a patient in need of such treatment a therapeutically effective amount of a compound of formula (I) or a stereoisomer, tautomer, pharmaceutically acceptable salt, solvate or prodrug thereof, in combination with at least one other anti-cancer agent or antiproliferative agent and/or another agent, or a stereoisomer, tautomer, pharmaceutically acceptable salt, solvate or prodrug thereof.

In another embodiment, the present invention provides a method for treating inflammatory and/or autoimmune diseases comprising: administering to a patient in need of such treatment a therapeutically effective amount of at least one of the compounds of the present invention or a stereoisomer, tautomer, pharmaceutically acceptable salt, solvate or prodrug thereof, in combination with at least one other therapeutic agent, or a stereoisomer, tautomer, pharmaceutically acceptable salt, solvate or prodrug thereof.

In another embodiment, the present invention provides a compound of the present invention for use in therapy.

In another embodiment, the present invention provides a compound of the present invention for use in therapy for treating an inflammatory and/or autoimmune disease.

In another embodiment, the present invention also provides the use of a compound of formula I of the present invention for the manufacture of a medicament for the treatment of an inflammatory and/or autoimmune disease.

The present invention may be embodied in other specific forms without departing from the spirit or essential attributes thereof. This invention encompasses all combinations of preferred aspects and/or embodiments of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

DEFINITIONS

The following are definitions of terms that may be used in the present specification. The initial definition provided for a group or term herein applies to that group or term throughout the present specification individually or as part of another group, unless otherwise indicated.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N).

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_{1-6}$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

"Halo" or "halogen" includes fluoro, chloro, bromo, and iodo.

The term "cycloalkyl" refers to cyclized alkyl groups, including mono-, bi- or poly-cyclic ring systems. $C_{3-10}$ cycloalkyl is intended to include $C_2$, $C_3$, $C_4$, $C_5$, $C_6$, and $C_7$, $C_8$, $C_9$, and $C_{10}$) cycloalkyl groups. Example cycloalkyl groups include, but are not limited to, cyclopropyl, cyclobutyl, cyclopentyl, cyclohexyl, norbornyl, and the like. As used herein, "carbocycle" or "carbocyclic residue" is intended to mean any stable 3, 4, 5, 6, or 7-membered monocyclic or bicyclic or 7, 8, 9, or 10-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

The definition of carbocycle as used within the definition is limited to saturated and partially saturated structures and does not included substitution which would join to form a heterocyclic ring.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "substituted aryl" refers to an aryl group substituted by, for example, one to four substituents such as alkyl, substituted alkyl, alkenyl, substituted alkenyl, alkynyl, substituted alkynyl, aryl, substituted aryl, arylalkyl, halo, trifluoromethoxy, trifluoromethyl, hydroxy, alkoxy, alkanoyl, alkanoyloxy, aryloxy, arylalkyloxy, amino, alkylamino, arylamino, arylalkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, halo, alkyl, alkoxy, alkenyl, alkynyl, aryl or arylalkyl.

The term "heteroaryl" refers to an optionally substituted, aromatic group for example, which is a 4 to 7 membered monocyclic, 7 to 11 membered bicyclic, or 10 to 15 membered tricyclic ring system, which has at least one heteroatom and at least one carbon atom-containing ring, for example, pyridine, tetrazole, indazole.

As used herein, the term "heterocycle", "heterocyclyl", "heterocyclic system" or "heterocyclic group" is intended to mean a stable 5, 6, or 7-membered monocyclic or bicyclic or 7, 8, 9, 10, 11, 12, 13, or 14-membered bicyclic heterocyclic ring which is saturated, partially unsaturated or fully unsaturated, and which consists of carbon atoms and 1, 2, 3 or 4 heteroatoms independently selected from N, O and S; and including any bicyclic group in which any of the above-defined heterocyclic rings is fused to a benzene ring. The nitrogen and sulfur heteroatoms may optionally be oxidized (i.e., N→O and $S(O)_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azocinyl, benzimidazolyl, benzofuranyl, benzothiofuranyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Preferred 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5 to 6 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

In another embodiment, heterocycles include, but are not limited to, pyridyl, pyridinyl, isoxazyl, isoquinolinyl, thienyl, pyrazolyl, furanyl, pyrrolyl, thiazolyl, imidazolyl, pyrazinyl, thiadiazolyl, pyrimidinyl, pyridazinyl, oxazolyl, isothiazolyl, oxadiazolyl, indanonyl, piperazinyl, pyranyl, or pyrrolyl Also included are smaller heterocyclyls, such as, epoxides and aziridines.

As used herein, the term "aromatic heterocyclic group" or "heteroaryl" is intended to mean a stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, benzodioxane, and the like. Heteroaryl groups can be substituted or unsubstituted. The nitrogen atom may be substituted or unsubstituted (i.e., N or NR wherein R is H or another substituent, if defined). The nitrogen and sulfur heteroatoms may optionally be oxidized (i.e., N→O and $S(O)_p$). It is to be noted that total number of S and O atoms in the aromatic heterocycle is not more than 1. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "carbocyclic ring" or "carbocyclyl" refers to stable, saturated, partially saturated or unsaturated, mono or bicyclic hydrocarbon rings that contain 3-12 atoms. Particularly, this includes a monocyclic ring containing 5 or 6 atoms or a bicyclic ring containing 9 or 10 atoms. Suitable values include cyclopropyl, cyclobutyl, cyclopentyl, cyclohexyl, cycloheptyl, dihydroindenyl and tetrahydronaphthyl. The term "optionally substituted" as it refers to "carbocyclic ring" or "carbocyclyl" herein indicates that the carbocyclic ring may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "heteroatoms" shall include oxygen, sulfur and nitrogen.

The compounds of formula I may exist as a free form (with no ionization) or may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for formula I may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Compounds of the formula I may also have prodrug forms. Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

Various forms of prodrugs are well known in the art. For examples of such prodrug derivatives, see:
a) *Design of Prodrugs*, edited by H. Bundgaard, (Elsevier, 1985) and *Methods in Enzymology*, Vol. 112, pp. 309-396, edited by K. Widder, et al. (*Academic Press, 1985*);
b) *A Textbook of Drug Design and Development*, edited by Krosgaard-Larsen and H. Bundgaard, Chapter 5, "Design and Application of Prodrugs," by H. Bundgaard, pp. 113-191 (1991); and
c) H. Bundgaard, *Advanced Drug Delivery Reviews*, 8, 1-38 (1992).

It should further be understood that solvates (e.g., hydrates) of the compounds of formula I are also with the scope of the present invention. Methods of solvation are generally known in the art.

"Stable compound" and "stable structure" are meant to indicate a compound that is sufficiently robust to survive isolation to a useful degree of purity from a reaction mixture, and formulation into an efficacious therapeutic agent. It is preferred that there presently recited compounds do not contain a N-halo, $S(O)_2H$, or $S(O)H$ group. The present invention is directed to stable compounds. Compounds of the invention are intended to cover compounds which are stable compounds.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination. "Therapeutically effective amount" is also intended to include an amount of the combination of compounds which is effective for the treatment of disease.

The present invention further includes compositions comprising one or more compounds of the present invention and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th ed., Mack Publishing Company, Easton, Pa., 1985, which is incorporated herein by reference in its entirety.

UTILITY

The compounds of the invention modulate kinase activity, including the modulation of JAK3. Other types of kinase activity that may be modulated by the compounds of the instant invention include, but are not limited to, other members of the JAK family of enzymes, such as JAK1.

Accordingly, compounds of formula (I) have utility in treating conditions associated with the modulation of kinase activity, and particularly the selective inhibition of JAK3 activity or the inhibition of other JAK family kinases such as JAK1. Such conditions include T-cell mediated diseases in which cytokine levels are modulated as a consequence of intracellular signaling. In another embodiment, compounds of formula (I) have advantageous functional selectivity for JAK3 activity versus other JAK family kinases such as JAK2, preferably from at least 10 fold to over 100 fold more selective.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as selective inhibitors of JAK3 and other JAK family kinases such as JAK1, compounds of Formula (I) are useful in treating cytokine-associated conditions including, but not limited to, autoimmune diseases such as Crohn's and ulcerative colitis, asthma, autoimmune diseases such as Graves' disease, rheumatoid arthritis, systemic lupus erythematosis, psoriasis, dry eye, multiple sclerosis, psoriatic arthritis and ankylosing spondylitis, plus conditions such as solid organ transplant rejection, islet cell transplant rejection and graft vs. host disease.

In view of their activity as inhibitors of JAK3, compounds of Formula (I) are useful in treating malignancies where JAK3 has undergone mutation or overexpression, or where JAK3 plays an important role in growth or survival of the malignant cells. Such malignancies include acute megakaryoblastic leukemia (AMKL), cutaneous T cell lymphoma (CTCL), anaplastic lymphoma kinase (ALK)-expressing anaplastic large cell lymphoma (ALK(+)ALCL), acute lymphoblastic leukemia (ALL) with JAK3 mutations, and cutaneous T-cell lymphoma (CTCL).

More particularly, the specific conditions or diseases that may be treated with the inventive compounds include, without limitation, asthma, allergies, glomerulonephritis, rheumatoid arthritis, systemic lupus erythematosis, scleroderma, chronic thyroiditis, Graves' disease, autoimmune gastritis, diabetes, autoimmune hemolytic anemia, autoimmune neutropenia, thrombocytopenia, atopic dermatitis, myasthenia gravis, multiple sclerosis, inflammatory bowel disease, ulcerative colitis, Crohn's disease, psoriasis, graft vs. host disease, pancreatic β-cell disease; rheumatoid spondylitis, allograft rejections, ulcerative colitis, dry eye and pemphigus vulgaris. Preferred methods of treatment are those wherein the condition is selected from allograft rejection, rheumatoid arthritis, psoriasis, ankylosing spondylitis, psoriatic arthritis, multiple sclerosis, lupus and dry eye.

When the terms "JAK3-associated condition" or "JAK3-associated disease or disorder" are used herein, each is intended to encompass all of the conditions identified above as if repeated at length, as well as any other condition that is affected by JAK3 kinase activity.

The present invention thus provides methods for treating such conditions, comprising administering to a subject in need thereof a therapeutically-effective amount of at least one compound of Formula (I) or a salt thereof "Therapeutically effective amount" is intended to include an amount of a compound of the present invention that is effective when administered alone or in combination to inhibit JAK3 and other JAK family kinases and/or treat diseases.

The methods of treating JAK3 kinase-associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to inhibit JAK3 and/or treat diseases associated with JAK3.

Exemplary of such other therapeutic agents include abatacept, belatacept, corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; p38 inhibitors such as BMS-582949, steroids such as prednisone or dexamethasone; antiviral agents such as abacavir; antiproliferative agents such as methotrexate, leflunomide, FK506 (tacrolimus, Prograf); cytotoxic drugs such as azathiprine and cyclophosphamide; TNF-$\alpha$ inhibitors such as tenidap, anti-TNF antibodies or soluble TNF receptor, and rapamycin (sirolimus or Rapamune) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating JAK3 kinase-associated conditions, including IL-2, IL-4, IL-6, IL-7, IL-9, IL-15, IL-21, and IFN$\gamma$ mediated conditions, as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th ed., 1985, which is incorporated herein by reference in its entirety.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of JAK3 enzyme levels.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to treat the cancer.

By way of general guidance, the daily oral dosage of each active ingredient, when used for the indicated effects, will range between about 0.001 to 1000 mg/kg of body weight, preferably between about 0.001 to 100 mg/kg of body weight per day, and most preferably between about 0.001 to 20 mg/kg/day. Intravenously, the most preferred doses will range from about 0.1 to about 10 mg/kg. Compounds of this invention may be administered in a single daily dose, or the total daily dosage may be administered in divided doses of two, three, or four times daily. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of JAK3 enzyme levels.

BIOLOGICAL ASSAYS

JAK3 Kinase Assay Protocol (Caliper)

The assay reactions were performed in U-bottom 384-well plates. The final assay volume was 30 µl prepared from 15 µl additions of enzyme and substrates (fluoresceinated peptide and ATP) and test compounds in assay buffer (100 mM HEPES pH 7.4, 10 mM $MgCl_2$, 25 mM beta-glycerol phosphate 0.015% Brij35 and 4 mM DTT). The reaction was initiated by the combination of GST-JAK3 enzyme with substrates and test compounds. The reactions were incubated at room temperature for 3 hours and terminated by adding 60 µl of 35 mM EDTA to each sample. Each reaction mixture was analyzed on the Caliper LabChip 3000 (Caliper, Hopkinton, Mass.) by electrophoretic separation of the fluorescent substrate and phosphorylated product. Inhibition data were calculated by comparison with no enzyme control reactions for 100% inhibition, and vehicle-only treated reactions for 0% inhibition. The final concentration of reagents in the assay was: ATP, 8 µM; fluoresceinated peptide, 1.5 µM; GST-JAK3, 4.5 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations. $IC_{50}$ values were derived by non-linear regression analysis.

JAK3 Kinase Assay Protocol (Filter)

Kinase reactions consisted of 5 ng of JAK3 enzyme, 30 uM CSKtide substrate, 0.2 µCi $^{33}P$ γ-ATP, 8 µM ATP in 30 µl kinase buffer (50 mM Hepes, pH 8.0, 10 mM $MgCl_2$, 1 mM EGTA, 2 mM DTT). Reactions were incubated for 30 minutes at room temperature and stopped by the addition of cold trichloroacetic acid (TCA) to a final concentration of 15%. TCA precipitates were collected onto 384 well phosphocellulose filters (Millipore) using a Platemate to transfer the reaction mixture, washed on an EMBLA plate washer and the filters were quantitated using a TopCount 384-well liquid scintillation counter. Dose response curves were generated to determine the concentration required inhibiting 50% of kinase activity ($IC_{50}$). Compounds were dissolved at 10 mM in dimethylsulfoxide (DMSO) and evaluated at six concentrations, each in triplicate. The final concentration of DMSO in the assay equaled 2%. $IC_{50}$ values were derived by non-linear regression analysis.

JAK2 Kinase Assay Protocol

The assay reactions were performed in U-bottom 384-well plates. The final assay volume was 30 µl prepared from 15 µl additions of enzyme and substrates (fluoresceinated peptide and ATP) and test compounds in assay buffer (100 mM HEPES pH 7.4, 10 mM $MgCl_2$, 25 mM beta-glycerol phosphate, 0.015% Brij35 and 4 mM DTT). The reaction was initiated by the combination of GST-JAK2 enzyme with substrates and test compounds. The reactions were incubated at room temperature for 3 hours and terminated by adding 60 µl of 35 mM EDTA to each sample. Each reaction mixture was analyzed on the Caliper LabChip 3000 (Caliper, Hopkinton, Mass.) by electrophoretic separation of the fluorescent substrate and phosphorylated product. Inhibition data were calculated by comparison with no enzyme control reactions for 100% inhibition, and vehicle-only treated reactions for 0% inhibition. The final concentration of reagents in the assay was: ATP, 30 µM; fluoresceinated peptide, 1.5 µM; GST-JAK2, 1.5 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations. $IC_{50}$ values were derived by non-linear regression analysis.

JAK1 Kinase Assay Protocol

The assay reactions were performed in U-bottom 384-well plates. The final assay volume was 30 µl prepared from 15 µl additions of enzyme and substrates (fluoresceinated peptide and ATP) and test compounds in assay buffer (20 mM HEPES pH 7.4, 10 mM $MgCl_2$, 25 mM beta-glycerol phosphate, 0.015% Brij35 and 4 mM DTT). The reaction was initiated by the combination of GST-JAK1 enzyme with substrates and test compounds. The reactions were incubated at room temperature for 3 hours and terminated by adding 60 µl of 35 mM EDTA to each sample. Each reaction mixture was analyzed on the Caliper LabChip 3000 (Caliper, Hopkinton, Mass.) by electrophoretic separation of the fluorescent substrate and phosphorylated product. Inhibition data were calculated by comparison with no enzyme control reactions for 100% inhibition, and vehicle-only treated reactions for 0% inhibition. The final concentration of reagents in the assays was: ATP, 100 µM; fluoresceinated peptide, 1.5 µM; GST-JAK1, 12.5 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations. $IC_{50}$ values were derived by non-linear regression analysis.

TYK2 Kinase Assay Protocol

The assay reactions were performed in U-bottom 384-well plates. The final assay volume was 30 µl prepared from 15 µl additions of enzyme and substrates (fluoresceinated peptide and ATP) and test compounds in assay buffer (20 mM HEPES pH 7.4, 10 mM $MgCl_2$, 25 mM beta-glycerol phosphate, 0.015% Brij35 and 4 mM DTT). The reaction was initiated by the combination of HIS-TYK2 enzyme with substrates and test compounds. The reactions were incubated at room temperature for 3 hours and terminated by adding 60 µl of 35 mM EDTA to each sample. Each reaction mixture was analyzed on the Caliper LabChip 3000 (Caliper, Hopkinton, Mass.) by electrophoretic separation of the fluorescent substrate and phosphorylated product. Inhibition data were calculated by comparison with no enzyme control reactions for 100% inhibition, and vehicle-only treated reactions for 0% inhibition. The final concentration of reagents in the assay was: ATP, 70 µM; fluoresceinated peptide, 1.5 µM; HIS-TYK2, 2.25 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations. $IC_{50}$ values were derived by non-linear regression analysis.

IL-2 Dependent T Cell Proliferation Assay Protocol

IL-2 Expanded PHA Blasts (Activated T cells) were prepared from peripheral blood mononuclear cells (PBMC). PBMCs were prepared from human whole blood. 15 ml blood was mixed with 15 ml RPMI (Gibco#61870) in a 50 ml centrifuge tube and under laid with 12 ml lymphocyte separation media (LSM) (MC Biomedicals #1492254). Tubes were centrifuged at 1800 rpm for 25 minutes and allowed to stop without braking. Red blood cells pelleted under the separation media and the PBMCs were trapped at the interface between the LSM and the serum/RPMI layers. The serum/RPMI mix was pipetted from above the PBMC layer and discarded. The PBMCs from 2 tubes were collected in a pipette along with some of the LSM layer and combined into a single tube. Each tube was brought to 50 ml and centrifuged at 1400 rpm for 10 minutes. Cell pellets were resuspended in RPMI, combined into 1 tube and centrifuged for 5 minutes at 1200 rpm. Cells were resuspended in cell culture media (RPMI w/10% fetal bovine serum (Summit Biotechnology # RS-50-05), 100 U/ml penicillin and 100 µg/ml streptomycin (Gibco #14140-122)) with 5 µg/ml PHA (Sigma #L1668) at $2\times10^6$ cells/ml and incubated for 3 days at 37° C. in 5% $CO_2$. Cells were washed 3x and resuspended at $5\times10^5$ cells/ml and 25 units/ml IL-2 (BD Bioscience #356043) was added. After 4 days incubation at 37° C. in 5% $CO_2$ the cells were washed 3x and resuspended at $2\times10^6$ cells/ml and rested 2 hours at 37° C. in 5% $CO_2$ before use.

Compounds were diluted in DMSO (in triplicate) to 800x final high concentration in the assay and 3-fold serial dilutions were performed to give six concentrations. Each concentration was diluted 1:20 in media to give the intermediate concentration. DMSO was diluted 1:20 in media for use in wells without compound.

45 µl media plus 5 µl of the intermediate dilution of compound or DMSO was added to each test well in the assay plate. 100 µl of cells at $3\times10^5$ cells/ml were added to each well. Plates were incubated 60 minutes at 37° C. in 5% $CO_2$ and 50 µl of IL-2 at 200 units/ml to each well. Negative control wells received 100 µl media. The plates were incubated 3 days at 37° C. in 5% $CO_2$. 0.5 µ$C^3$H-Thymidine in 20 µl media was added to each well and the plates incubated 6 hours at 37° C. in 5% $CO_2$. The plates were harvested onto a Unifilter-96 GF/C Filter Plate (Perkin Elmer 6005174) using a Packard Filtermate Harvester. The bottom of each dried filter plate was sealed, 50 µl Microscint 20 (Perkin Elmer #6013621) added to each well and the top of the plate sealed. Proliferation as measured by $^3$H-Thymidine incorporation was determined by counting on a Packard TopCount-NXT.

IL-2 Induced STAT3 Phosphorylation in PHA Blasts Assay

IL-2 Expanded PHA Blasts were prepared (see IL-2 Dependent T Cell Proliferation Assay Protocol for preparation of IL-2 expanded PHA blasts). Compounds were diluted in DMSO (in duplicate) to 333.3x final high concentration in the assay and 3-fold serial dilutions were performed to give six concentrations. Each concentration was diluted 1:20 in media to give the intermediate concentration. DMSO was diluted 1:20 in RPMI media (Gibco#61870) for use in wells without compound.

173 µl/well of a PHA blast cell suspension at $5.78\times10^6$ cells/ml was added to a round bottom tissue culture plate (Falcon #353077) followed by 12 µl of the Intermediate compound dilution or DMSO for wells without compound. The plate was incubated at 37° C. in 5% $CO_2$ for 30 minutes. 15 µl of 266.7 ng/ml IL-2 (R&D #202-IL-050) in media was added to each well or media only to negative control wells. The plates were mixed on an orbital shaker for 1 minute and incubated at 37° C. in 5% $CO_2$ for a total 10 minutes. Plates were centrifuged 4 minutes at 1500 rpm and 150 µl of culture supernatant was removed from each well leaving the pellet intact. Plates were mixed on an orbital shaker for 1 minute and 50 µl of 2x lysis buffer was added (20 mM Tris, pH7.5, 0.2 M NaCl, 2 mM EDTA, 2 mM EGTA, 2 mM NaF, 2 mM 13-Glycerophosphate, 40 mM Sodium Pyrophosphate, 4 mM $Na_3VO_4$ (add at time of use), 2% Triton X-100 (Sigma T9284), 20% Glycerol (EM Science GX0185-6), 0.2% SDS (Bio-Rad #161-0416), 1.0% Deoxycholate (Sigma D5670), 2x Protease Inhibitor Cocktail (Sigma P2714, dissolved in 10 ml PBS to give 10x concentration, add at time of use)). The plates were incubated on ice for 1 hour and the lysate in each well was mixed by pipetting up and down 5-6 times. STAT3 phosphorylation levels were determined by ELISA (PathScan Phospho-STAT3 ELISA Antibody Pair, Cell Signaling #7146).

ELISA plates were coated with 100 µl/well of a 1:100 dilution of Capture antibody in PBS and incubated at least overnight at 4° C. On day of use plates were washed 3x with wash buffer (PBS (Gibco #14190)+0.05% Tween 20). Plates were blocked with 200 µl/well of Assay Buffer 1 (AB1) (PBS+1% BSA+0.1% Tween 20(Bio-Rad #161-0416)) for 2 hours at room temperature. Plates were washed 3x and 90 µl/well AB1 buffer added. 10 µl/well of assay sample or standards were added followed by 100 µl/well of a 1:100 dilution of Detection Antibody in AB1 Buffer. Plates were incubated overnight at 4° C. and then washed 6x. 100 µl/well of a 1:1000 dilution of anti-mouse IgG HRP-Linked Antibody in AB1 Buffer was added to each well and plates were incubated 1 hour at room temperature. Plates were washed 6×. 100 µl of a 1:1 mix of TMB Peroxidase Substrate (KPL #50-76-01) and Peroxidase Substrate Solution (KPL #50-65-00) was added and the plates were incubated in the dark at room temperature for 10-30 min. The reaction was stopped with 100 µl/well of 1N $H_2SO_4$ and the plates were read at 450 nm with correction at 650 nm within 30 min.

pSTAT3 Standards were prepared from IL-6 stimulated TF-1 cells. TF-1 cells were washed 3× and resuspended at $1\times10^6$ cells/ml and rested overnight without GM-CSF at 37° C. in 5% $CO_2$. The cells were washed 1× and resuspended at $5\times10^6$ cells/ml. IL-6 was added to 20 ng/ml and cells incubated at 37° C. in 5% $CO_2$ for 15 minutes, spun 4 minutes at 1500 rpm and the supernatant removed. 150 µl lysis buffer was added for every $5\times10^6$ cells and incubated on ice for 60 minutes. Using a syringe fitted with a 21 gauge needle, lysates were passed 6 times through the needle. The lysates were transferred to microfuge tubes and centrifuged at 14K rpm for 10 minutes and the supernatants were combined and aliquots frozen on dry ice and stored at −80° C. The lysate was assigned a value of 100 units/ml of pSTAT3 and used as a standard in the pSTAT3 ELISA assay. Standards were diluted in a 1:2 dilution series using a 1:1 mix of 2× lysis buffer and Media.

EPO Induced STAT5A Phosphorylation in TF-1 Cells

TF-1 Cells were carried in cell culture media (RPMI w/10% fetal bovine serum (Summit Biotechnology # RS-50-05), 100 U/ml penicillin and 100 µg/ml streptomycin (Gibco #14140-122))+2 ng/ml GM-CSF (R&D #215GM). On the day before use the cells were washed 3×, resuspended at $1\times10^6$ cells/ml in media without GM-CSF and rested overnight at 37° C. in 5% $CO_2$. The cells were washed 1× and resuspended in media at $2.78\times10^6$ cells/ml. Compounds were prepared as in the IL-2 Induced STAT3 phosphorylation in PHA blasts assay.

173 µl/well of a TF-1 cell suspension at $2.78\times10^6$ cells/ml was added to each well of a round bottom tissue culture plate (Falcon #353077) followed by 12 µl of the intermediate compound dilution or DMSO for wells without compound. The plate was incubated at 37° C. in 5% $CO_2$ for 30 minutes. 15 µl of 13.33 units/ml recombinant human EPO(R&D #287-TC) in media was added to each well or media only to negative control wells. The plates were mixed on an orbital shaker for 1 minute and incubated at 37° C. in 5% $CO_2$ for a total 10 minutes. Plates were centrifuged 4 minutes at 1500 rpm and 150 µl of culture supernatant was removed from each well leaving the pellet intact. Plates were mixed on an orbital shaker for 1 minute and 50 µl of 2× lysis buffer was added (20 mM Tris, pH7.5, 0.2 M NaCl, 2 mM EDTA, 2 mM EGTA, 2 mM NaF, 2 mM β-Glycerophosphate, 40 mM Sodium Pyrophosphate, 4 mM $Na_3VO_4$ (add at time of use), 2% Triton X-100 (Sigma T9284), 20% Glycerol (EM Science GX0185-6), 0.2% SDS (Bio-Rad #161-0416), 1.0% Deoxycholate (Sigma D5670), 2× Protease Inhibitor Cocktail (Sigma P2714, dissolved in 10 ml PBS to give 10× concentration, add at time of use)). The plates were incubated on ice for 1 hour and the lysate in each well was mixed by pipetting up and down 5-6 times. STAT5A phosphorylation levels were determined by ELISA.

ELISA plates (NUNC #439454) were coated with 100 µl/well of a 1:500 dilution of Capture antibody (Invitrogen #13-3600) in carbonate/bicarbonate buffer (Sigma # C3041) and incubated at least overnight at 4° C. On day of use plates were washed 3× with wash buffer (PBS (Gibco #14190)+0.05% Tween 20 (Bio-Rad #170-6531)). Plates were blocked with 200 µl/well of Assay Buffer 2 (AB2) (PBS+2% BSA (Sigma # A-9576)+0.1% Tween 20 (Bio-Rad #161-0416)) for 2 hours at room temperature. Plates were washed 3× and 90 µl/well AB2 buffer added. 10 µl/well of assay sample or standards were added followed by 100 µl/well of a 1:4000 dilution of Detection Antibody (Genway #18-785-210434) in AB2 Buffer. Plates were incubated overnight at 4° C. and then washed 6×. 100 µl/well of a 1:3000 dilution of HRP-Goat anti-rabbit IgG (Invitrogen #65-6120 in AB2 Buffer was added to each well and plates were incubated 1 hour at room temperature. Plates were washed 6×. 100 µl of a 1:1 mix of TMB Peroxidase Substrate (KPL #50-76-01) and Peroxidase Substrate Solution (KPL #50-65-00) was added and the plates were incubated in the dark at room temperature for 10-30 minutes. The reaction was stopped with 100 µl/well of 1N $H_2SO_4$ and the plates were read at 450 nm with correction at 650 nm within 30 min.

pSTAT5A Standards were prepared from GM-CSF stimulated TF-1 cells. TF-1 cells were washed 3× and resuspended at $1\times10^6$ cells/ml and rested overnight without GM-CSF at 37° C. in 5% $CO_2$. The cells were washed 1× and resuspended at $5\times10^6$ cells/ml. GM-CSF was added to 50 ng/ml and cells incubated at 37° C. in 5% $CO_2$ for 15 minutes, spun 4 minutes at 1500 rpm and the supernatant removed. 150 µl lysis buffer was added for every $5\times10^6$ cells and incubated on ice for 60 minutes. Using a syringe fitted with a 21 gauge needle, lysates were passed 6 times through the needle. The lysates were transferred to microfuge tubes and centrifuged at 14K rpm for 10 minutes and the supernatants were combined and aliquots frozen on dry ice and stored at −80° C. The lysate was assigned a value of 100 units/ml of pSTAT5A and used as a standard in the pSTAT5A ELISA assay. Standards were diluted in a 1:2 dilution series using a 1:1 mix of 2× lysis buffer and Media.

IFNα Induced STAT3 Phosphorylation in PHA Blasts

IFNα induced STAT3 phosphorylation in PHA blasts was performed exactly as the IL-2 Induced STAT3 phosphorylation in PHA blasts assay except the cells were stimulated with 15 µl/well of 13,333 units/ml IFNα2a (R&D #11105-1) in media.

Myosin Light Chain Phosphorylation (pMLC) Assay

Mouse aortic smooth muscle A7r5 cells are cultured in complete DMEM Media (Gibco Cat. #11995) substituted with 10% FBS (Gibco Cat. # SH30071) and 1% Penicillin/Streptomycin (Gibco Cat. #15140). $1.5\times10^3$ cells are plated in 384-well tissue culture plates (Becton Dickinson Cat. #3962) and incubated overnight at 37° C. and 5% $CO_2$. Cells are then incubated with test compounds (serially diluted 3-fold with final concentrations ranging from 20 mM to 340 µM) for 60 minutes at 37° C. and 5% $CO_2$. Cell culture media is removed and cells are fixed with 4% paraformaldehyde (JT Baker Cat. #2106) for 60 min at room temperature. After removal of the fixing reagent, 1× permeabilization buffer (Thermo Cat. #1860291) is added for 10 min incubation at room temperature. Permeabilization buffer is removed and 1× blocking solution (Thermo Cat. #1860291) is added for 60 min incubation at room temperature. Blocking solution is removed and cells are incubated overnight at 4° C. with primary anti-pMLC antibody (Cell Signaling Cat. #3674) diluted in 1× blocking buffer for a final concentration of 70 ng/ml. Primary antibody is removed followed by 3 washes with 1×PBS (Gibco Cat. #14190). Cells are incubated for 60 min at room temperature with secondary AlexaFluor 488 Goat-anti rabbit IgG (H+L) antibody (Invitrogen Molecular Probes Cat. # A11008) at a final concentration of 5 ug/ml in 1× blocking buffer mixed with Hoechst nuclear stain (Invitrogen Molecular Probes Cat. # H3570) at 5 ug/ml final concentration. Cells are then washed 3 times with 1×PBS to remove reagents. The plates containing 30 ul 1×PBS per well are then scanned on the Cellomics ArrayScan imager using the Cell Health Profiling BioApplication. The Mean Ring Spot Average Intensity of the FITC channel is used as the final readout to calculate $IC_{50}$ values. 0% inhibition is determined with 0.2% DMSO and 100% inhibition is determined with 1 mM of the Rho Kinase inhibitor H-1152P (Calbiochem Cat. #555550).

Examples herein been tested and found to have activity of less than or equal to 1 uM in at least one of the JAK3 assays described above. The compounds listed in Table 1 have been tested in the above assays with the results indicated.

TABLE 1

| Example # | LLE_JAK3_FB (IC50, uM) | LLE_JAK3_CAL (IC50, uM) | LLE_JAK1 (IC50, uM) |
|---|---|---|---|
| 2 | 0.0009 | 0.0037 | 0.0430 |
| 5 | 0.0484 | 0.024 | 0.1935 |
| 9 | 0.0002 | 0.0007 | 0.0070 |
| 17 | 0.0216 | 0.0224 | 0.1410 |
| 18 | 0.1093 | 0.1055 | 0.5695 |
| 22 | 0.0007 | 0.0028 | 0.0340 |
| 25 | 0.0059 | 0.0047 | 0.0860 |
| 29 | 0.0012 | 0.0053 | 0.0461 |
| 37 | 0.0188 | 0.0006 | 0.0038 |
| 43 | 0.0012 | 0.0025 | 0.0088 |
| 53 | 0.0009 | 0.0014 | 0.0052 |
| 62 | 0.0007 | 0.0018 | 0.0040 |
| 68 | 0.0007 | 0.0010 | — |
| 125 | 0.0186 | 0.0667 | 0.2596 |
| 127 | 0.0260 | 0.0234 | 0.1602 |
| 129 | 0.0110 | 0.0084 | 0.0611 |
| 131 | 0.0113 | 0.0048 | 0.0831 |
| 134 | 0.0087 | 0.0080 | 0.0401 |
| 142 | 0.0286 | 0.0054 | 0.0334 |
| 144 | 0.0012 | 0.0011 | 0.0007 |
| 146 | 0.0151 | 0.0111 | 0.0265 |
| 149 | — | 0.0238 | — |
| 153 | 0.1785 | 0.2228 | 0.4017 |
| 154 | 0.0351 | 0.0563 | 0.1495 |
| 180 | 0.0135 | 0.0609 | 1.1970 |
| 181 | 0.0492 | 0.0964 | 0.1063 |
| 183 | 0.0110 | 0.0273 | 0.0373 |
| 187 | 0.0010 | 0.0013 | 0.0030 |
| 189 | 0.0191 | 0.0085 | 0.0215 |
| 191 | 0.0880 | 0.0406 | 0.0723 |
| 192 | 0.0017 | 0.0021 | 0.0130 |
| 193 | 0.0018 | — | 0.0027 |
| 194 | 0.0013 | 0.0010 | 0.0028 |
| 195 | 0.0053 | 0.0084 | 0.0737 |
| 196 | 0.0013 | 0.0030 | 0.0058 |
| 200 | 0.0011 | 0.0022 | 0.0048 |
| 202 | 0.0018 | 0.0012 | 0.0038 |
| 205 | 0.0079 | 0.0054 | 0.11 |
| 210 | 0.0005 | 0.0008 | 0.0036 |
| 219 | — | 0.0012 | 0.0006 |
| 222 | — | 0.0009 | 0.0004 |
| 224 | — | 0.0003 | 0.0005 |
| 240 | — | 0.88 | 2.2 |
| 241 | 0.0023 | 0.0018 | 0.10 |

GENERAL PROCEDURES

Analytical HPLC Conditions:

Method A: Column. Sunfire C18, (150×4.6 mm), 3.5 µm, SC/862; Linear gradient of 0 to 100% solvent B over 12 min, then 3 min hold at 100% B; Flow rate: 1 mL/min; Buffer: 0.5% TFA, in water with pH adjusted to 2.5 using dilute ammonia; Solvent A: Buffer:acetonitrile (95:5); Solvent B: acetonitrile; Products detected at 220 nm.

Method B: Column: YMC S5 ODS-A S5 4.6×50 mm; Linear gradient of 0 to 100% solvent B over 4 min, with 1 min hold at 100% B; Flow rate: 4 mL/min; Solvent A: 0.2% $H_3PO_4$, 90% water, 10% MeOH; Solvent B: 0.2% $H_3PO_4$, 90% MeOH, 10% water; Products detected at 220 nm.

Method C: Column: X bridge phenyl (4.6×150 mm); Linear gradient of 0 to 100% solvent B over 12 min, then 3 min hold at 100% B; Flow rate: 1 mL/min; Solvent A: 5% MeCN-95% $H_2O$-0.05% TFA; Solvent B: 95% MeOH-5% $H_2O$-0.05% TFA; Products detected at 220 nm.

Method D: Column: Eclipse XDB c18 (150×4 6 mm) 5 micron; Linear gradient of 10 to 100% solvent B over 12 min, then 3 min hold at 100% B; Flow rate: 1 mL/min; Solvent A: 20 mM $NH_4OAc$ in water; Solvent B: Acetonitrile; Products detected at 220 nm.

Method E: Column: XBridge (150×4.6 mm), 3.5 µm SC/840; Flow rate: 1 mL/min; Solvent A: 10 mM $NH_4HCO_3$ in water pH=9.5 adjusted using dil. ammonia; Solvent B: MeOH; Products detected at 220 nm.

Method F: Column: YMC S5 ODS-A S5 4.6×50 mm; Linear gradient of 0 to 100% solvent B over 4 min, with 1 min hold at 100% B; Flow rate: 4 mL/min; Solvent A: 0.2% $H_3PO_4$, 90% water, 10% MeOH; Solvent B: 0.2% $H_3PO_4$, 90% MeOH, 10% water; Products detected at 220 nm.

Method G: Column: YMC S5 ODS-A S5 4.6×50 mm; Linear gradient of 10 to 100% solvent B over 4 min, with 1 min hold at 100% B; Flow rate: 4 mL/min; Solvent A: 0.2% $H_3PO_4$, 90% water, 10% MeOH; Solvent B: 0.2% $H_3PO_4$, 90% MeOH, 10% water; Products detected at 220 nm.

Method H: Column: Waters Acquity UPLC BEH C18, 2.1×50 mm, 1.7-µm particles; Linear gradient of 0 to 100% solvent B over 3 min, with 0.75 min hold at 100% B; Flow rate: 1.1 mL/min; Solvent A: 5:95 acetonitrile:water with 0.05% TFA; Solvent B: 95:5 acetonitrile:water with 0.05% TFA; Temperature: 50° C.; Products detected at 220 nm.

Method I: Column: Supelco Ascentis C18, 4.6×50 mm, 2.7 um; Linear gradient of 0 to 100% solvent B over 4 min, with 1 min hold at 100% B; Flow rate: 4 mL/min; Solvent A: 5:95 acetonitrile:water with 0.05% TFA; Solvent B: 95:5 acetonitrile:water with 0.05% TFA; Products detected at 220 nm.

Method J: Column: Supelco Ascentis C18, 4.6×50 mm, 2.7 um; Linear gradient of 0 to 100% solvent B over 4 min, with 1 min hold at 100% B; Flow rate: 4 mL/min; Solvent A: 5:95 acetonitrile:water with 10 mM $NH_4OAc$; Solvent B: 95:5 acetonitrile:water with 10 mM $NH_4OAc$; Products detected at 220 nm.

Method K: Column: Chromalith Speedrod C18, (50×4 6 mm); Linear gradient of 0 to 100% solvent B over 4 min; Flow rate: 4 mL/min; Solvent A: 10% MeOH-90% $H_2O$-0.2% $H_3PO_4$; Solvent B: 90% MeOH-10% $H_2O$-0.2% $H_3PO_4$; Products detected at 220 nm.

Method L: Column: Sunfire C18, (150×4.6 mm), 3.5 µm, SC/862; Linear gradient of 0 to 100% solvent B over 12 min, then 3 min hold at 100% B; Flow rate: 1 mL/min; Buffer: 0.5% TFA, in water with pH adjusted to 2.5 using dilute ammonia; Solvent A: Buffer:acetonitrile (95:5); Solvent B: acetonitrile; Products detected at 220 nm.

Method M: Column: YMC S5 ODS-A S5 4.6×50 mm; Linear gradient of 0 to 100% solvent B over 4 min, with 1 min hold at 100% B; Flow rate: 4 mL/min; Solvent A: 0.2% TFA, 90% water, 10% MeOH; Solvent B: 0.2% TFA, 90% MeOH, 10% water; Products detected at 220 nm.

Method N: Column: Ascentis Express C18 (5×2.1 mm-2.7 µm); Mobile Phase: A: 2% ACN-98% $H_2O$-10 mM $NH_4COOH$; B: 98% ACN-2% $H_2O$-10 mM $NH_4COOH$; Flow: 1 mL/min. product detected at 220 nm or 254 nm detection wavelength.

Method P: Column–Purospher @ star RP-18 (4×55) mm, 3 uM; Buffer: 20 mM NH₄OAc in water; Mobile Phase:—A: Buffer+ACN (90+10); B: Buffer+ACN (10+90); Flow: 2.5 ml/min, product detected at 220 nm or 254 nm detection wavelength.

Method Q: Column. YMC Combiscreen ODS-A, (4.6×50 mm); Mobile phase: 10-90% aq CH₃OH/0.2% H₃PO₄; Gradient=4.0 min. linear with 1.0 min. hold; Flow rate: 4 ml/min; product detected at 220 nm or 254 nm detection wavelength.

Preparative HPLC Conditions:

Method A: Column: Luna 5u C18 30×100 mm; Flow rate=40 mL/min; Solvent A=10% MeOH-90% H₂O-0.1% TFA; Solvent B=90% MeOH-10% H₂O-0.1% TFA, Start % B=30, Final % B=100, linear gradient time=10 min; Products detected at 220 nm.

Method B: Column: YMC ProC18 S5 ODS 50×4.6 mm; Flow rate=4 mL/min; Solvent A=10% MeOH-90% H₂O-0.2% H₃PO₄; Solvent B=90% MeOH-10% H₂O-0.2% H₃PO₄; Gradient time=4 min; products at 220 nm.

Method C: Column: YMC 20×100; Flow rate=40 mL/min; Solvent A=10% MeOH-90% H₂O-0.1% TFA; Solvent B=90% MeOH-10% H₂O-0.1% TFA; Start % B=30, Final % B=100, linear gradient time=12 min; products detected at 220 nm.

Method D: Column: LUNA 5u C18 21×100; Flow rate=40 mL/min; Solvent A: 10% MeOH/H₂O with 0.1% TFA; Solvent B: 90% MeOH/H₂O with 0.1% TFA; Start 35% Solvent B to 85% Solvent B over 12 min gradient.

Method E: Column: Phenominex Synergy, 4.6×50 mm; Solvent A: 90:10 water/MeOH with 0.2% H₃PO₄; Solvent B: 90:10 MeOH/water with 0.2% H₃PO₄; Gradient: 0-100% B over 4 minutes, then a 1-minute hold at 100% B; Flow: 4 mL/min; products detected at 220 nm or 254 nm wavelength.

Method F: Column: Phenomenex Luna 5u C18 21.2×100 mm; Flow rate=20 mL/min; Solvent A=10% MeOH-90% H₂O-0.1% TFA; Solvent B=90% MeOH-10% H₂O-0.1% TFA; Start % B=10, Final % B=100, linear gradient time=10 min; products detected at 220 nm.

Method G: Column: XBridge phenyl (4.6×150 mm), 3.5 micron SC/749; Buffer: 0.5% TFA, in water pH adjusted to 2.5 using dilute ammonia; Solvent A:Buffer:acetonitrile (95:5); Solvent B: acetonitrile:Buffer (95:5); Flow rate: 1 mL/min; products detected at 220 nm.

Analytical LCMS Conditions:

Method A: Column: Zorbox SB C18 (4.6×50 mm), 5 µm; Linear gradient of 0-100% solvent B over 4 min, then 1 min hold at 100% B; Flow rate: 5 mL/min; Solvent A: 10% MeOH –90% H₂O-0.1% TFA; Solvent B: 90% MeOH-10% water-0.1% TFA; Products detected at 220 nm wavelength w/positive ionization mode.

Method B: Column: Phenomenex Luna 5u C18 30×4.6 mm; Linear gradient of 0-100% solvent B over 2 min, then 0.5 min hold at 100% B; Flow rate: 4 mL/min;
Solvent A: 10% MeOH-90% H₂O-0.1% TFA; Solvent B: 90% MeOH-10% H₂O-0.1% TFA; Products detected at 220 nm wavelength w/positive or negative ionization mode.

Method C: Column: Purosphoer@ star rp-18 (4.6×30) mm, 3 µm; Linear gradient of 0-100% solvent B over 2 min, then 0.5 min hold at 100% B; Flow rate: 2.5 mL/min; Solvent A: 20 mM of NH₄OAc in 90% water-10% acetonitrile; Solvent B: 20 mM of NH₄OAc in 10% H₂O-90% acetonitrile; Products detected at 220 nm wavelength w/positive or negative ionization mode.

Method D: Column: ZORBAX_AQ_FA-P.M; Linear gradient of 0-100% solvent B over 2 min, w/0.5 min hold at 100% B; Flow rate: 1 mL/min; Solvent A: 0.1% HCOOH in water; Solvent B: acetonitrile; Products detected at 220 nm wavelength w/positive ionization mode.

Method E: Column: BEH C18 2.1×50 mm 17u; Linear gradient of 0-100% solvent B over 2 min, then 0.5 min hold at 100% B; Flow rate: 1 mL/min; Solvent A: 100% water w/0.05% TFA; Solvent B: 100% acetonitrile w/0.05% TFA; Products detected at 220 nm wavelength w/positive ionization mode.

Method F: Column: Supelco Ascentis Express C18, 4.6×50 mm, 2.7-µm particles; Linear gradient of 0-100% solvent B over 4 min, then 1 min hold at 100% B; Flow rate: 4 mL/min; Temperature=35° C.; Solvent A: 5:95 acetonitrile:water with 10 mM; NH₄OAc; Solvent B: 90:10 acetonitrile:water with 10 mM NH₄OAc; Products detected at 220 nm wavelength w/positive ionization mode.

Method G: Column: Supelco Ascentis Express C18, 4.6×50 mm, 2.7-µm particles; Mobile Phase A: 5:95 acetonitrile:water with 0.05% TFA; Mobile Phase B: 95:5 acetonitrile:water with 0.05% TFA; Temperature: 35° C.; Gradient: 0-100% B over 4 minutes, then a 1-minute hold at 100% B; Flow: 4 mL/min; Products detected at 220 nm wavelength w/positive ionization mode.

Method H: Column-Ascentis Express C18 (50×2.1 mm 2.7 µm); Mobile Phase A: 2% acetonitrile –98% Water-10 mM Ammonium formate; Mobile Phase B –98% acetonitrile –2% water-10 mM Ammonium formate; Flow: 1 mL/min; Products detected at 220 nm wavelength w/positive ionization mode.

Method I: Column: Purosphoer@ star rp-18 (4.6×30) mm, 3 µm; Linear gradient of 0-100% solvent B over 2 min, then 0.5 min hold at 100% B; Flow rate: 2.5 mL/min; Solvent A: 20 mM of NH₄OAc in 90% water-10% acetonitrile; Solvent B: 20 mM of NH₄OAc in 10% water-90% acetonitrile; Products detected at 220 nm wavelength w/positive or negative ionization mode.

Method J: Column: Chromolith SpeedROD C18 (4.6×30 mm), 5 µm; Mobile phase A: 10 mM NH₄OAc in 90% H₂O, 10% MeOH; Mobile phase B: 10 mM NH₄OAc in 10% H₂O, 90% MeOH; Flow: 5 mL/min; Products detected at 220 nm wavelength w/positive or negative ionization mode.

Method K: Column: Chromolith SpeedROD C18 (4.6×30 mm), 5 µm (positive mode); Mobile phase A: 10% MeOH; 90% H₂O; 0.1% TFA; Mobile phase B: 90% MeOH; 10% H₂O; 0.1% TFA; Flow: 5 mL/min; Products detected at 220 nm wavelength w/positive or negative ionization mode.

PREPARATIONS

Preparations 1 and 2

4-Chloropyrrolo [1,2-b]pyridazine-3-carboxylic acid and 4-Ethyl chloropyrrolo [1,2-b]pyridazine-3-carboxylate

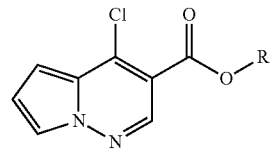

1 (R = H) 2 (R = Ethyl)

Step 1: 2-(1H-pyrrol-1-yl)isoindoline-1,3-dione

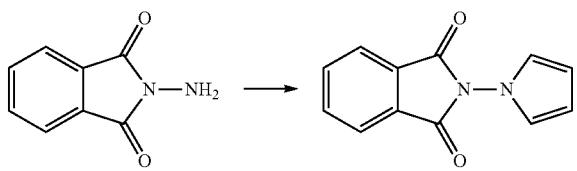 [SMILES: NN1C(=O)c2ccccc2C1=O ; O=C1c2ccccc2C(=O)N1n1cccc1]

To a stirred solution of 1,4-dioxane (50 mL) and N-aminophthalimide (5.0 g, 0.031 mmol) at rt was slowly added 2,5-dimethoxy tetrahydrofuran (15 g, 0.061 mmol). The resulting light yellow solution was heated to 100° C. for ~16 h whereupon 5N HCl was carefully added at 100° C. giving a brown mixture. The mixture was allowed to cool room temperature, the solid thus separated was filtered and was rinsed with 1:3 of 1,4-dioxane in water. Drying afforded 3.5 g (54%) of the title compound as a white solid. LCMS (Condition D) m/z: 213 +ve.

Step 2: 1H-pyrrol-1-amine

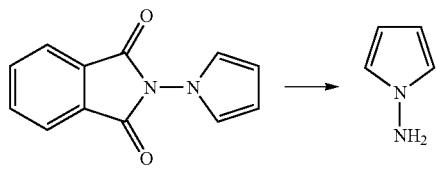 [SMILES: O=C1c2ccccc2C(=O)N1n1cccc1 ; Nn1cccc1]

To a solution of 2-(1H-pyrrol-1-yl)isoindoline-1,3-dione (3.5 g, 0.016 mmol) in MeOH (35 mL) was added hydrazine monohydrate (1 mL, 0.021 mmol). The reaction mixture was heated to 65° C. for 1 h then was cooled and filtered. The resulting solid was rinsed with MeOH and the resulting filtrate was concentrated to give a light yellow solid which was triturated with diethyl ether. The organic solution was then concentrated to give 1 g (74%) of a brown oil as the title compound. $^1$H NMR (400 MHz, DMSO-$d_6$) δ ppm: 5.84 (t, J=2.0 Hz, 2.4 Hz, 2H), 5.86 (d, exchangeable with $D_2O$, 2H), 6.62 (t, J=2.0, 2.4 Hz, 2H).

Step 3: Diethyl 2-((1H-pyrrol-1-ylamino)methylene)malonate

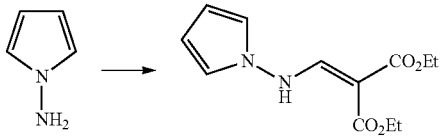 [SMILES: Nn1cccc1 ; CCOC(=O)C(=CNn1cccc1)C(=O)OCC]

A round bottom flask was charged with 1H-pyrrole-1-amine (1 g, 0.012 mmol) and diethyl-2-(ethoxymethylene) malonate (3.16 g, 0.014 mmol) and the flask was equipped with a short path distillation condenser. The mixture was heated to 125° C. for 4 hr while collecting the ethanol distillate. After the reaction was complete as determined by TLC, the mixture was cooled to rt and hexanes was added to give a slurry. The mixture was filtered and the resulting solid was rinsed with additional hexanes and was dried to afford 2.6 g (85%) of a solid as the title compound. $^1$H NMR (400 MHz, DMSO-$d_6$) δ ppm: 1.18-1.22 (m, 6H), 4.06-4.17 (m, 4H), 6.06 (t, J=2.4 Hz, 2H), 6.98 (t, J=1.6, 2.4 Hz, 2H), 7.84 (d, J=11.2 Hz, 1H), 11.24 (d, J=10.8 Hz, 1H). LCMS (Condition D): m/z 253 +ve.

Step 4: Ethyl 4-hydroxypyrrolo[1,2-b]pyridazine-3-carboxylate

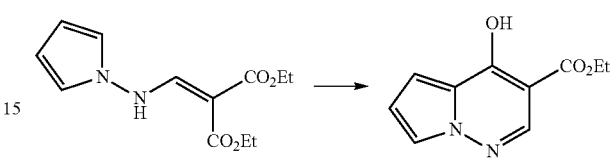

A solution of diethyl-1-(1H pyrrole-1-yl-aminomethylene malonate (2 g, 0.11 mmol) in 135 mL of Dowtherm A was slowly heated to 220° C. using a sand bath and allowed to stir for ~16 h. The reaction mixture was cooled and loaded onto a flash silica gel column and eluted with petroleum ether to remove the Dowtherm followed by a linear gradient of increasing concentration of ethyl acetate in petroleum ether to elute the product. Fractions containing the product were concentrated in vacuo to afford 15 g (68%) of a yellow solid as the title compound. $^1$H NMR (400 MHz, DMSO-$d_6$) δ ppm: 1.36 (t, J=7.2, 7.2 Hz, 3H), 4.38 (q, J=7.2, 6.8 Hz, 2H), 6.86 (q, J=2.8, 6.4 Hz, 1H), 6.99 (q, J=7.2, 6.8 Hz, 1H), 7.96 (q, J=1.6, 3.2 Hz, 1H), 8.32 (s, 1H), 12.1 (s, 1H). LCMS (Condition D): m/z 207 +ve.

Step 5A: 4-Chloropyrrolo[1,2-b]pyridazine-3-carboxylic acid (Preparation 1) and 4-Ethyl chloropyrrolo[1,2-b]pyridazine-3-carboxylate (Preparation 2)

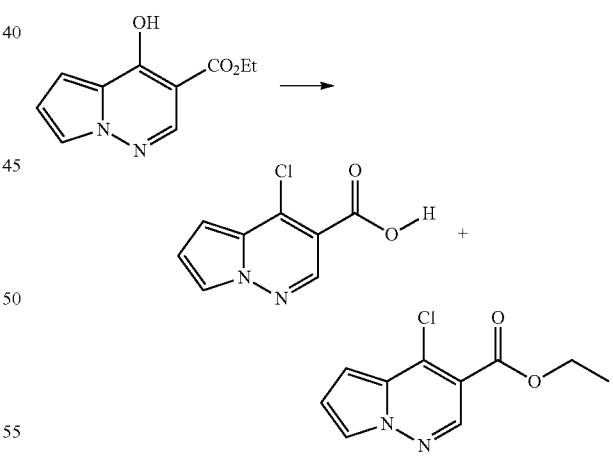

Slurried ethyl 4-hydroxypyrrolo[1,2-b]pyridazine-3-carboxylate (0.296 g, 1.44 mmol) in $POCl_3$ (2.68 mL, 28.7 mmol) and added triethylamine (0.40 mL, 2.87 mmol) dropwise at rt giving a cloudy yellow mixture. This mixture was heated to 110° C. for 10 h, followed by cooling to rt and slowly adding dropwise to crushed ice (~60 mL volume). The resulting mixture was allowed to stir at rt for ~6 h and the resulting solids were collected by vacuum filtration, rinsed with water (5 mL) and air dried in the funnel for ~3 h affording 246 mg (87%) of a brown solid as an ~4:1 mixture of the title compounds, Preparation 1 and Preparation 2, respectively. Material was used as a mixture without any further purification. HPLC (Conditions B): Retention times=2.59 min (Preparation 1) and 3.47 min (Preparation 2). LCMS (Conditions B): Preparation 1 (m/z=197.1, 199.0), Preparation 2 (m/z=225.1, 227.0).

Step 5B: Alternative preparation of Ethyl 4-chloropyrrolo [1,2-b]pyridazine-3-carboxylate (Preparation 2)

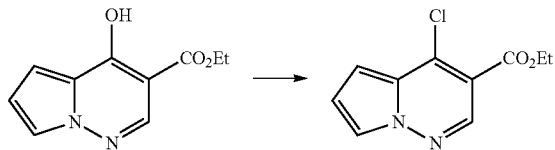 [SMILES: CCOC(=O)c1cnn2cccc2c1O ; CCOC(=O)c1cnn2cccc2c1Cl]

To POCl$_3$ (225 mL, 2.42 mmol) at 0° C. was added ethyl 4-hydroxypyrrolo[1,2-b]pyridazine-3-carboxylate (50 g, 0.242 mmol) and the mixture was stirred until complete dissolution. At this time, triethylamine (36.8 mL, 0.266 mmol) was added dropwise and the resulting mixture was heated to 110° C. and allowed to stir for ~16 h. The resulting mixture was allowed to cool and the POCl$_3$ was removed in vacuo to afford a dark brown residue. This material was dissolved in dichloromethane and was cooled to 0° C. and diluted with 375 mL of ethanol. The resulting mixture was stirred at 0° C. for 30 min and then at rt for 1 h. The ethanol was removed under vacuum and the resulting semi-solid was dissolved in dichloromethane and stirred with 10% aqueous NaHCO$_3$ for 1 h. The mixture was filtered through celite and the phases were separated. The aqueous portion was extracted with additional dichloromethane and the combined organic layers were washed with brine, dried over Na$_2$SO$_4$, decanted and the solvent was removed under vacuum to give the crude product. The crude material was purified by flash silica gel column chromatography to yield 47 g (86%) of a solid as the title compound. $^1$H NMR (400 MHz, CDCl$_3$) δ ppm: 1.43 (t, J=7.2, 6.8 Hz, 3 H), 4.43 (q, J=7.2, 6.8 Hz, 2 H), 6.940-6.99 (m, 2H), 7.84 (q, J=0.8, 1.6 Hz, 1 H), 8.51 (s, 1H)). $^{13}$C-NMR (400 MHz, DMS-d$_6$) ppm: 163.30, 141.89, 138.16, 124.86, 120.69, 114.99, 109.90, 105.22, 61.55, 14.21. LCMS (conditions A): m/z 225. HPLC (condition B): Retention time=3.47 min.

Step 6: Alternative preparation of 4-chloropyrrolo [1,2-b]pyridazine-3-carboxylic acid (Preparation 1)

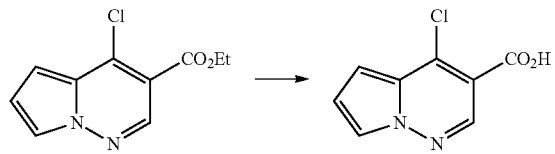 [SMILES: CCOC(=O)c1cnn2cccc2c1Cl ; O=C(O)c1cnn2cccc2c1Cl]

Dissolved ethyl 4-chloropyrrolo[1,2-b]pyridazine-3-carboxylate (Preparation 2 from Step 5B, 2 g, 8.90 mmol) in THF (12 mL) and added water (2 mL) followed by monohydrated lithium hydroxide (0.747 g, 17.81 mmol) and the resulting yellow mixture was sonicated to give a fine dispersion followed by heating to 55° C. and stirring vigorously for one hour. After removing the organics under vacuum, the resulting residue was dissolved in ~50 mL of water and 6 N aqueous HCl added until acidic giving a yellow slurry of the product. The product was extracted with ethyl acetate, washed with brine, dried over Na$_2$SO$_4$, decanted and conc. in vacuo to afford 1.8 g (~quant.) of a yellow solid as the title compound.

LCMS (condition B): m/z=197.1, 199.0. HPLC (condition B): Retention time=2.59 min.

Preparation 3

4-chloropyrrolo [1,2-b]pyridazine-3-carboxamide

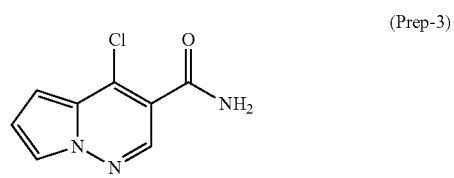 [SMILES: NC(=O)c1cnn2cccc2c1Cl]

(Prep-3)

To POCl$_3$ (450 mL, 4.85 mmol) at 0° C. was slowly added ethyl 4-hydroxypyrrolo[1,2-b]pyridazine-3-carboxylate (from step 4 of Preparations 1 and 2, 100 g, 0.484 mmol) and the resulting mixture was stirred until complete dissolution. At this time, triethylamine (73.7 mL, 0.532 mmol) was added dropwise and the resulting mixture was heated at 110° C. for ~16 h. After cooling to rt, the mixture was carefully concentrated in vacuo and the resulting dark brown residue was dissolved in dichloromethane and cooled to 0° C. This solution was carefully purged with ammonia gas for ~45 min. And then it was allowed to stir at rt for 1 h. The solvent was removed under vacuum and the residue was diluted with ethyl acetate and water and the mixture was filtered through Celite. The organic portion was separated, and aqueous was extracted with ethyl acetate. The combined organic portions were dried over anhyd. sodium sulfate and concentrated under vacuum to afford a semi-solid which was dissolved in ethyl acetate and diluted with petroleum ether to precipitate a solid which was collected by filtration and dried to afford 30 g (69%) of a solid as the title compound. $^1$H NMR (400 MHz, DMSO-d$_6$) δ ppm: 6.86 (q, J=1.6, 5.2 Hz, 1 H), 7.03 (q, J=2.4, 2.0 Hz, 1 H), 7.83 (s, 1H), 7.99 (s, 1H), 8.06 (q, J=2.4, 1.2 Hz, 1H), 8.27 (s, 1H). $^{13}$C-NMR (400 MHz, DMS-d$_6$) ppm: 165.25, 141.39, 132.01, 123.84, 120.09, 117.68, 115.11, 102.47. LCMS (condition H): m/z 195.

Alternative preparation of 4-chloropyrrolo[1,2-b]pyridazine-3-carboxamide (Preparation 3)

Slurried 4-chloropyrrolo[1,2-b]pyridazine-3-carboxylic acid (Preparation 1 from Step 6, 0.4 g, 2.04 mmol) in dichloromethane (6 mL) and cooled in ice bath and successively added oxalyl chloride (0.534 mL, 6.10 mmol) and DMF (0.01 mL, 0.129 mmol). Allowed slurry to warm to rt and stir for 1.5 h giving a clear, yellow-green solution. The reaction was concentrated under vacuum to yield a yellow solid which was redissolved in dichloromethane (10 mL) and reconcentrated to remove all residual oxalyl chloride. This solid was dissolved in dichloromethane (6 mL) and the solution was added dropwise via pipette into a well-stirred ammonia in dichloromethane solution (prepared by extracting 15 mL of conc aq ammonium hydroxide with 3×10 mL portions of dichloromethane) at 0° C. After stirring for 1.5 h at 0° C., water was added to dissolve most solids (~15 mL) and the layers were separated and the aqueous portion was extracted with additional dichloromethane. The combined extracts were washed with brine, dried over anhyd. $Na_2SO_4$, decanted and concentrated on rotovap to yield 370 mg (93%) of a yellow solid as the title compound. Material was used as is without any further purification. LCMS (condition B): m/z 195, 197. HPLC (condition B): retention time=1.75 min.

Preparation 4

Ethyl 3-carbamoyl-4-chloropyrrolo[1,2-b]pyridazine-6-carboxylate

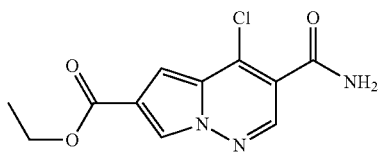

(Prep-4)

Step 1: Ethyl 2-formamidoacetate

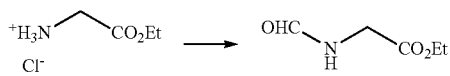

To a 5 L three neck round bottom flask equipped with a mechanic stirrer, a pressure-equalizing funnel and a condenser bearing a calcium chloride drying tube was added glycine ethyl ester hydrochloride (500 g, 3.583 mol) and methyl formate (1.8 L). The suspension was brought to reflux and triethylamine (556 mL) was added to the reaction. The reaction was stirred and refluxed overnight. The reaction was cooled to room temperature and filtered through a Buchner funnel to remove triethylamine hydrochloride salt. The filtrate was concentrated and dried over high vacuum to yield 320 g (93%) of the title compound.

Step 2: Ethyl 2-isocyanoacetate

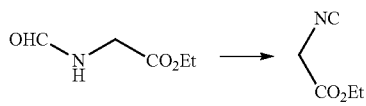

To a round bottom flask was added ethyl 2-formamidoacetate (600 g, 4.5 mol), dry $CH_2Cl_2$ (6 L) and triethylamine (1.512 kg). The reaction mixture was cooled to −10° C. and then $POCl_3$ (700 g) was added dropwise at −10° C. After the addition, the reaction was stirred at 0° C. for additional 1 hour. The reaction was cooled to −20° C. and slowly was saturated sodium carbonate solution (3.6 L) added to the reaction. After the addition, the reaction was brought to room temperature and was stirred at room temperature for 0.5 hr. Then the organic layer was separated and the aqueous layer was extracted with $CH_2Cl_2$ (2×3 L). The combined organic layer was washed with brine and dried over anhydrous $K_2CO_3$ solid. The solution was filtered and concentrated at 45° C. to yield 560 g (96%) title compound. $^1$H NMR (400 MHz, $CDCl_3$) δ ppm: 8.2 (1H, s), 6.9 (1H, br s), 4.14 (2H, q, J=4 Hz), 3.91 (2H, d, J=6.4 Hz), 1.19 (3H, t, J=4 Hz).

Step 3: Diethyl 1H-pyrrole-2,4-dicarboxylate

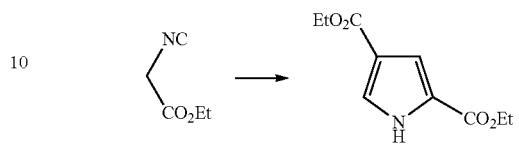

To a round bottom flask under argon was added ethyl 2-isocyanoacetate (100 g, 0.884 mol), dry THF (1.0 L) followed by DBU (132 g, 0.867 mol). The reaction was cooled to 0° C. and formaldehyde (16 g) was added portionwise into the reaction mixture. The reaction was then stirred at room temperature overnight. Then THF was removed under high vacuum and the residue as dissolved with water and extracted with EtOAc (2×1 L). The combined organic layer was washed with water and brine and concentrated. The residue was purified by flash silica gel column chromatography to yield 40 g (26%) of a white solid as the title compound. $^1$H NMR (400 MHz, $CDCl_3$) δ ppm: 9.85 (1H, br s), 7.54 (1H, m), 7.30 (1H, m), 4.36-4.6 (4H, merging quartets), 1.37-1.26 (6H, merging triplets). LCMS (condition A): m/z=210.2 −ve.

Step 4: Diethyl 1-amino-1H-pyrrole-2,4-dicarboxylate

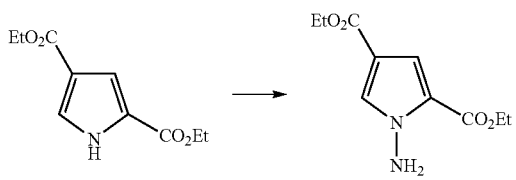 [SMILES: CCOC(=O)c1c[nH]c(C(=O)OCC)c1 ; CCOC(=O)c1cc(C(=O)OCC)n(N)c1]

To a flask was added MTBE (2 L) and ammonium chloride (60 g, 1.13 mol). The reaction was cooled to −20° C. Then concentrated aq ammonium hydroxide (160 mL) was added to the reaction followed by slow addition of commercial-grade sodium hypochlorite solution (149 g, 1.5 L). After addition, the reaction was stirred at −20° C. for additional 30 minutes. The MTBE layer was separated and washed with brine and dried over $Na_2SO_4$. In a separate flask under nitrogen was added diethyl 1H-pyrrole-2,4-dicarboxylate (40 g, 190 mmol) and dry DMF (400 mL). The reaction was cooled to 0° C. whereupon sodium hydroxide (190 mmol) was added portionwise to the reaction. The reaction was stirred at 0° C. for additional 1 hour before it was cooled to −20° C. At this time, the previously prepared MTBE solution of chloramine was added slowly to the reaction and the reaction was stirred at −20° C. for 1 hour. The reaction was quenched with saturated sodium thiosulfate solution. The organic layer of the reaction was separated and washed with water and brine, dried over sodium sulfate, filtered and concentrated to yield 40 g (95%) of the title compound. $^1$H NMR (400 MHz, $CDCl_3$) δ ppm: 7.48 (1H, d, J=1.6 Hz), 7.24 (1H, d, J=1.6 Hz), 5.65 (2H, s), 4.32-4.23 (4H, merging quartets), 1.367-1.32 (6H, merging triplets). LCMS (condition A) m/z=227.2 +ve.

Step 5: Ethyl 3-cyano-4-hydroxypyrrolo[1,2-b]pyridazine-6-carboxylate

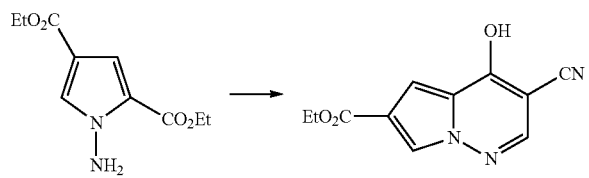 [SMILES: CCOC(=O)c1cc(C(=O)OCC)n(N)c1 ; CCOC(=O)c1cc2c(O)c(C#N)cnn2c1]

To a round bottom flask was added diethyl 1-amino-1H-pyrrole-2,4-dicarboxylate (40 g, 177 mmol), diethoxypropionitrile (53 mL) and p-TSA (10 g, 0.052 mmol). The reaction was heated at 125° C. for 3 hours and the EtOH was removed. The reaction was cooled to room temperature before DBU (30 g, 340 mmol) was added. The reaction was then heated at 80° C. for 2 hours. The reaction was cooled to room temperature and diluted with $CH_2Cl_2$. The mixture was washed with 5% citric acid solution (2×), water and brine solution. The organic layer was concentrated and the residue was purified by flash silica gel column chromatography (10% MeOH in $CHCl_3$) to yield 20 g (50%) of the title compound as a brown oil. LCMS (condition A): m/z=230.2 −ve. $^1$H NMR (400 MHz, $CDCl_3$) δ ppm: 9.53 (1H, br s), 8.32 (1H, s), 7.75 (1H, s), 6.75 (1H, s), 4.25 (2H, q), 1.28 (3H, t).

Step 6: Ethyl 4-chloro-3-cyanopyrrolo[1,2-b]pyridazine-6-carboxylate

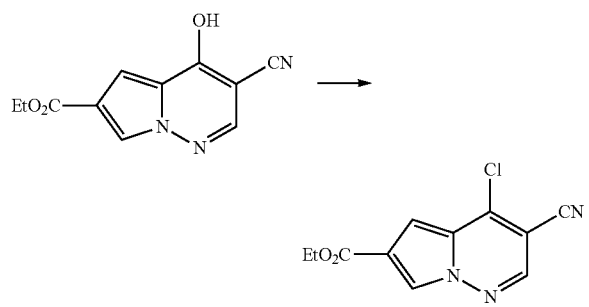

To a round bottom flask was added $POCl_3$ (200 mL) and ethyl 3-cyano-4-hydroxypyrrolo[1,2-b]pyridazine-6-carboxylate (20 g, 80 mmol). The reaction was heated under nitrogen at 75° C. for 2 hours. The reaction was cooled to room temperature and $POCl_3$ was removed under vacuum. The residue was poured onto ice-water. The aqueous solution was extracted with $CH_2Cl_2$. The organic layer was washed with saturated sodium carbonate solution, dried and concentrated. The resulting residue was purified by flash silica gel column chromatography to yield 10 g (48%) of the title compound as a yellow solid. $^1$H NMR (400 MHz, $CDCl_3$) δ ppm: 8.33 (1H, d, J=1.3 Hz), 8.11 (1H, s), 7.41 (1H, d, J=1.6 Hz), 4.41 (2H, q, J=6.8 Hz), 1.41 (3H, t, J=6.8 Hz).

Step 7: Ethyl 3-carbamoyl-4-chloropyrrolo[1,2-b]pyridazine-6-carboxylate

To a round bottom flask was added concentrated $H_2SO_4$ (100 mL) followed by ethyl 4-chloro-3-cyanopyrrolo[1,2-b]pyridazine-6-carboxylate (10 g, 40 mmol). The reaction was stirred at room temperature under nitrogen overnight. The reaction mixture was poured onto ice cold saturated sodium carbonate solution. The aqueous solution was extracted with EtOAc (4×) and the combined organic layer was concentrated to yield 7 g (70%) of the title compound as a yellow solid. HPLC (condition S): retention time=8.04 min. LCMS (condition A): m/z=268.0 +ve. $^1$H NMR (400 MHz, $CDCl_3$) δ ppm: 8.49 (1H, d, J=1.6 Hz), 8.40 (1H, s), 8.08 & 7.98 (1H, two br s), 7.12 (1H, d, J=1.6 Hz), 4.34 (2H, q, J=7.2 Hz), 1.34 (3H, t, J=7.2 Hz).

Preparation 5

6-bromo-4-chloropyrrolo[1,2-b]pyridazine-3-carboxamide

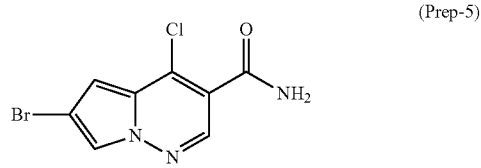

(Prep-5)

Step 1: 1-(4-Bromo-1H-pyrrol-2-yl)-2,2,2-trichloroethanone

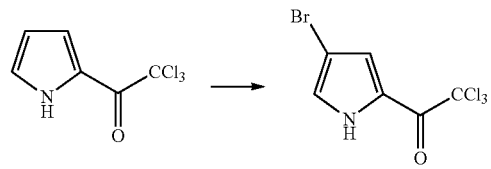

To a 100 mL 3-neck round bottom equipped with a dropping funnel was added trichloroacetyl pyrrole (50 g, 236.4 mmol) and $CCl_4$(1.0 L). After trichloroacetyl pyrrole was dissolved, the reaction was cooled to 0° C. and iodine (0.176 g) was added to the reaction. At this time, a solution of bromine (12 mL) in $CCl_4$ (100 mL) was added dropwise very slowly to the reaction through a dropping funnel over 20 minutes and the resulting mixture was stirred at 0° C. for additional 20 minutes. The resulting mixture was transferred into a separatory funnel and washed with 10% $Na_2S_2O_3$ solution, saturated $NaHCO_3$ solution and brine (2×). The organic layer was dried and concentrated to give 50 g (60%) of the title compound as a white solid. LCMS (condition A): m/z=287.8, 289.8, 290.8 −ve. $^1$H NMR (400 MHz, $CDCl_3$) δ ppm: 12.8 (1H, br.s), 7.56 (1H, m), 7.33 (1H, m).

Step 2: Methyl 4-bromo-1H-pyrrole-2-carboxylate

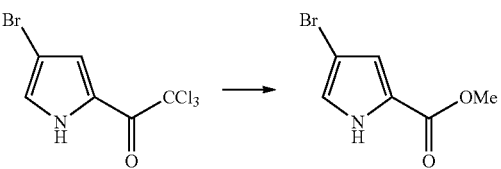

To a dry round bottom flask containing dry MeOH (60 mL) was added sodium (5 g, 257.7 mmol) portionwise. After all the sodium was dissolved, the solution was slowly added to a flask which contained 1-(4-bromo-1H-pyrrol-2-yl)-2,2,2-trichloroethanone (50.0 g, 171.8 mmol) in MeOH (860 mL) through a dropping funnel giving a yellow reaction mixture. After the addition was complete, the reaction was stirred for an additional 10 minutes, then concentrated and cooled in an ice bath. The resulting solid that precipitated was collected by vacuum filtration and washed with water until neutral pH. The solid was dried to yield 25 g (71%) of the title compound as a white solid. LCMS (condition A): m/z=204.0 −ve. $^1$H NMR (400 MHz, DMSO-$d_6$) δ ppm: 7.16 (1H, d, 1.2H), 6.89 (1H, d, 1.2H).

Step 3: Methyl 1-amino-4-bromo-1H-pyrrole-2-carboxylate

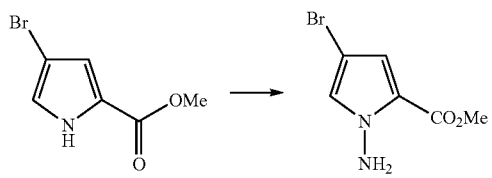 [SMILES: COC(=O)c1cc(Br)c[nH]1 ; COC(=O)c1cc(Br)cn1N]

To a 5 L 3-neck round bottom flask was added conc. NH$_4$OH (2.0 L) and the solution was cooled to −20° C. Ammonia gas was purged into the solution until the volume doubled. In a separate 10 L 3-neck round bottom flask was added solid NH$_4$Cl (87 g) and MTBE (5.0 L) and the mixture was cooled to −5° C. At this time, 555 mL of the previously prepared concentrated NH$_4$OH solution was added to this mixture followed by a slow addition of commercial grade sodium hypochlorite solution (2.0 L) over 60 minutes. After the addition was complete, the reaction was stirred at −5° C. for additional 30 minutes. The MTBE layer was separated and washed with brine (720 mL) and was dried over Na$_2$SO$_4$ and decanted. To a separate 20 L round bottom flask was added methyl 4-bromo-1H-pyrrole-2-carboxylate (100 g, 0.49 mol) and DMF (2.0 L) under nitrogen. Then sodium hydride (60% dispersion in mineral oil, 24 g, 0.58 mol) was added to the reaction portionwise at room temperature. After the addition was complete, the reaction mixture was stirred at room temperature for 45 minutes, cooled to −20° C., and then the previously prepared chloramine solution was added in one portion to the reaction mixture. The resulting mixture was allowed to warm to ambient temperature and stirred for 30 minutes. The reaction mixture was washed with 10% aq. Na$_2$S$_2$O$_3$ solution (720 mL) and the organic layer was separated and washed again with water (720 mL) and brine (720 mL) before drying over Na$_2$SO$_4$, filtering and concentrating under vacuum to afford ~52 g of a semi-solid as the crude product. To this material was added toluene (1.2 L) to give a homogeneous mixture. Methane sulfonic acid (60 g, 0.62 mol) was added dropwise and stirred for 30 minutes. The resulting precipitated solid was collected by vacuum filtration and was rinsed with additional toluene and dried to yield 139 g (90%) of the methane sulfonic acid salt of the title compound. HPLC (condition S): retention time=8.922 min.

LCMS (condition A): m/z 218.0 −ve. $^1$H NMR (400 MHz, DMSO-$d_6$) δ ppm: 7.21 (1H, d, 2.0 Hz), 6.77 (1H, d, 2.0 Hz), 3.75 (3H, s), 2.50 (3H, s).

Step 4: 6-Bromo-4-hydroxypyrrolo[1,2-b]pyridazine-3-carbonitrile

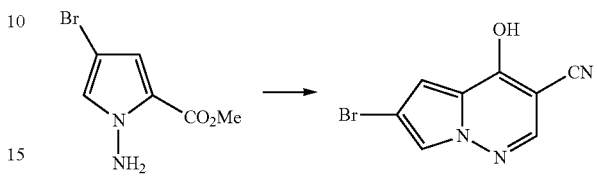

To a round bottom flask was added the methane sulfonic acid salt of methyl 1-amino-4-bromo-1H-pyrrole-2-carboxylate (140 g, 0.444 mol), isopropanol (700 mL) and 3,3-diethoxypropionitrile (128 g, 0.888 mol). The reaction mixture was slowly brought to 85° C. over 1 hour and then stirred at 85° C. for 2 hours. At this time, the ethanol that was generated and the isopropanol was removed under vacuum. The resulting residue was dissolved in CH$_2$Cl$_2$ and washed with water and brine solution. The organic layer was separated, dried over Na$_2$SO$_4$, filtered and concentrated. The resulting residue was transferred into a 2 L round bottom flask and dichloroethane (900 mL) and DBU (210 gm, 1.36 mol) were successively added to the reaction mixture. The resulting mixture was then stirred at 85° C. for 5 hours then cooled to rt and diluted with CH$_2$Cl$_2$ followed by washing with water then brine solution. The organic layer was separated, dried over Na$_2$SO$_4$, filtered and concentrated. The resulting residue was purified by flash silica gel column chromatography to yield 58 g of title compound as the crude product containing residual DBU. This material was used as is in the next transformation. LCMS (condition A) m/z=236.0 −ve. $^1$H NMR (400 MHz, DMSO-$d_6$) δ ppm: 9.76 (1H, br.s), 7.62 (1H, s), 7.39 (1H, d, 2.0Hz), 6.43 (1H, d, 2.0 Hz). The product is contaminated with DBU and was used directly as such without further purification in the next step.

Step 5: 6-Bromo-4-chloropyrrolo[1,2-b]pyridazine-3-carbonitrile

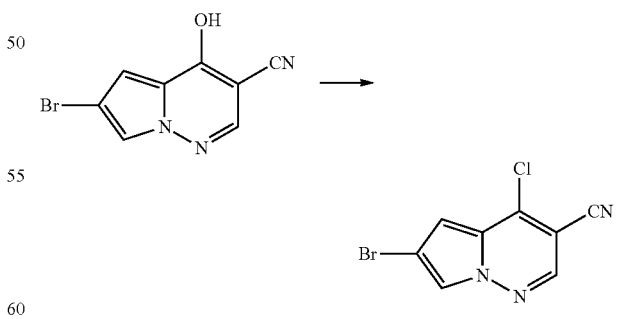

To a 25 mL round bottom flask was added 6-bromo-4-hydroxypyrrolo [1,2-b]pyridazine-3-carbonitrile (16.5 g, 69.47 mmol) and POCl$_3$ (85 mL, 0.88 mol) and the reaction mixture was stirred and heated at 75° C. for 3 hours. The POCl$_3$ was removed under vacuum and the resulting residue was dissolved in CH$_2$Cl$_2$. The solution was cooled to 0° C.

and saturated aq. NaHCO₃ solution was added and the biphasic mixture was stirred vigorously while allowing to warm to rt. The organic layer was separated and concentrated and the obtained residue was purified by flash silica gel column chromatography to yield 8.5 g (29%) of the title compound as a yellow solid. HPLC (condition P): retention time=16.74 min. ¹H NMR (400 MHz, CDCl₃) δ ppm: 8.09 (1H, s), 7.94 (1H, d, 2.0 Hz), 7.06 (1H, d, 2.0 Hz).

Step 6: 6-Bromo-4-chloropyrrolo[1,2-b]pyridazine-3-carboxamide (Preparation 5)

To a 50 mL round bottom flask was added 6-bromo-4-chloropyrrolo[1,2-b]pyridazine-3-carbonitrile (12 g, 0.046 mol) and concentrated H₂SO₄ (60 mL). The reaction mixture was heated at 55° C. for 2 hours then cooled to room temperature and slowly diluted with ice water to precipitate the product which was collected by vacuum filtration, rinsed with water and dried to yield 11.2 g (89%) of the title compound as a yellow solid. HPLC (condition P): retention time=7.780 min.

LCMS (condition C): m/z 274.0, 276.0 –ve. ¹H NMR (400 MHz, DMSO-d₆) δ ppm: 8.32 (2H, s), 8.05 (1H, s), 7.90 (1H, s), 7.01 (1H, s).

Preparation 6

4-chloro-6-fluoropyrrolo[1,2-b]pyridazine-3-carboxamide

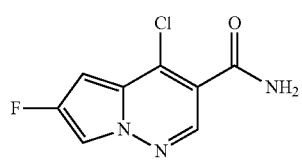

(Prep-6)

Step 1: (R)-1-tert-butyl 2-methyl 4-oxopyrrolidine-1,2-dicarboxylate

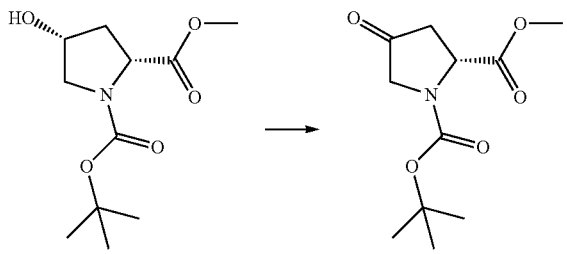 [SMILES: COC(=O)[C@H]1C[C@@H](O)CN1C(=O)OC(C)(C)C ; COC(=O)[C@H]1CC(=O)CN1C(=O)OC(C)(C)C]

To slurry of pyridinium dichromate (9.97 g, 26.5 mmol) in dichloromethane (60 mL) at rt was added (2R,4R)-1-tert-butyl 2-methyl 4-hydroxypyrrolidine-1,2-dicarboxylate (5.00 g, 20.39 mmol) in several portions. The resulting mixture was stirred overnight at rt. Celite (5 g) was added and the mixture stirred for 40 min, filtered and the filter cake was rinsed with additional dichloromethane (50 mL×3). The resulting filtrate was concentrated and toluene (40 mL) was added followed by concentration again under vacuum to give ~6.5 g of a brown syrup as the crude product. Purification by flash silica gel chromatography (120 g column, EtOAc in hexane, 0 to 100% gradiant, 85 mL/min) afforded 4.18 g (84%) of the title compound as a white solid. LCMS (condition A): m/z 144 (M-Boc) –ve. ¹H NMR (400 MHz, CDCl₃) δ ppm 4.64-4.89 (1 H, m), 3.84-3.96 (2 H, m), 3.77 (3 H, s), 2.81-3.10 (1 H, m), 2.59 (1 H, dd, J=18.93, 1.76 Hz), 1.52 (9 H, s).

Step 2: (R)-1-tert-butyl 2-methyl 4,4-difluoropyrrolidine-1,2-dicarboxylate

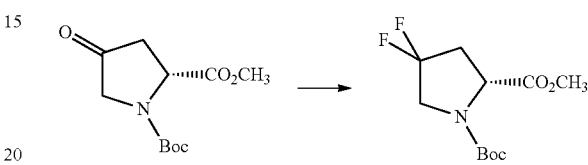

DAST (2.74 mL, 20.72 mmol) was added dropwise to a stirred solution of (R)-1-tert-butyl 2-methyl 4-oxopyrrolidine-1,2-dicarboxylate (1.68 g, 6.91 mmol) in dichloroethane (20 mL) at rt and the resulting mixture was heated at 60° C. for 3 h. After cooling to rt, the mixture was slowly quenched with sat. aq. sodium bicarbonate (60 mL) and extracted with ethyl acetate (300 mL). The extracts were washed with brine and dried over magnesium sulfate, filtered, and concentrated to give 6.90 g of the crude product as a brown oil. This material was purified by flash silica gel chromatography (120 g column, EtOAc in Hexane 0 to 100%, 85 mL/min) to afford 4.80 g (76%) of the title compound as a tan oil. LCMS (condition A): m/z 288.0 (M+Na) –ve. ¹H NMR (400 MHz, MeOD) δ ppm 4.50-4.68 (1 H, m), 3.74-3.96 (5 H, m), 2.88 (1 H, d, J=9.79 Hz), 2.46-2.62 (1 H, m), 1.40-1.60 (9 H, m).

Step 3: (R)-methyl 4,4-difluoropyrrolidine-2-carboxylate

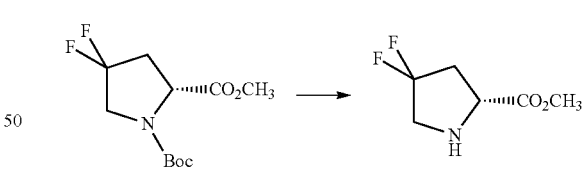

To solution of (R)-1-tert-butyl 2-methyl 4,4-difluoropyrrolidine-1,2-dicarboxylate (4.33 g, 16.32 mmol) in dichloromethane (30 mL) was added trifluoroacetic acid (12.58 mL, 163 mmol) and the resulting mixture was stirred at rt for 5 h, then concentrated and sat. aqueous sodium bicarbonate (50 mL) was added followed by stirring for 20 min before extracting with diethyl ether (40 mL×3). The combined extracts were washed with brine and dried over sodium sulfate, filtered, and concentrated at rt (note: product is volatile) to afford 2.0 g (74%) of the title compound as a light tan oil that was used directly in the next transformation without any further purification. ¹H NMR (400 MHz, MeOD) δ ppm 4.03

(1 H, dd, J=8.80, 6.82 Hz), 3.77 (3 H, s), 3.22-3.32 (1 H, m), 3.07-3.23 (1 H, m), 2.51-2.69 (1 H, m), 2.30-2.50 (1 H, m).

Step 4: methyl 4-fluoro-1H-pyrrole-2-carboxylate

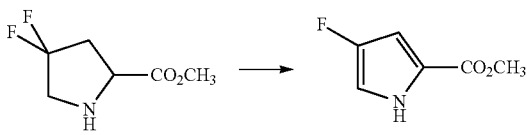 [SMILES: COC(=O)C1CC(F)(F)CN1 ; COC(=O)c1cc(F)c[nH]1]

To solution of (R)-methyl 4,4-difluoropyrrolidine-2-carboxylate (2.00 g, 12.11 mmol) in THF (40 mL) was added manganese dioxide (8.42 g, 97 mmol) and the resulting mixture was heated at reflux (oil bath temp ~70° C.) for 3 h. After cooling to rt, the reaction mixture was filtered through a pad of Celite, rinsed with additional THF (20 mL×4), and DCM (40 mL×4) and the resulting filtrate was concentrated under vacuum to afford a dark brown oil as the crude product which was purified via flash silica gel chromatography (eluent: $CH_2Cl_2$/MeOH, 0-10%) to afford 0.98 g (56%) of the title compound as a white solid. HPLC (condition B): retention time=1.71 min. LCMS (condition B): m/z 144 +ve. $^1$H NMR (400 MHz, MeOD) δ ppm 6.81 (1 H, dd, J=3.63, 1.87 Hz), 6.59 (1 H, d, J=1.32 Hz), 3.86 (3 H, s).

Step 5: methyl 1-amino-4-fluoro-1H-pyrrole-2-carboxylate

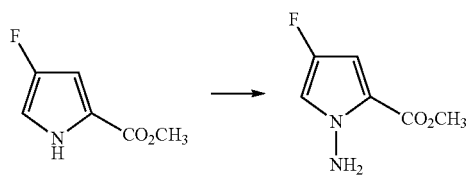 [SMILES: COC(=O)c1cc(F)c[nH]1 ; COC(=O)c1cc(F)cn1N]

A mixture of ammonium chloride (6.0 g, 112 mmol) in diethyl ether (220 mL) was cooled to −5° C., and concentrated aq. ammonium hydroxide (9.4 mL) was added dropwise with vigorous stirring. After the addition was complete, commercial grade aq. sodium hypochlorite solution (145 mL) was added via addition funnel at a rate such that the internal temperature was maintained below 0° C. The mixture was then stirred for 15 min, then the layers were separated, and the organic layer was washed with brine and dried over anhyd. calcium chloride. The resulting solution of chloramine was used directly as follows: In a separate flask, containing a solution of methyl 4-fluoro-1H-pyrrole-2-carboxylate (0.98 g, 6.85 mmol) in DMF (15 mL) at 0° C. was added 60% sodium hydride dispersion (0.329 g, 8.22 mmol) and the resulting mixture was allowed to warm to rt and stir for 45 minutes. At this time, a portion of the previously prepared chloramine solution (55 mL) was added via syringe over ~1 minute. After stirring for an additional 1.5 h at rt, the reaction mixture was quenched by adding sat. aq. $Na_2S_2O_3$ followed by diluting with water and extracting with diethyl ether (100 mL×2). The combined extracts were dried over anhyd. sodium sulfate, filtered and concentrated under vacuum to afford 0.98 g (91%) of the title compound as a light tan oil. HPLC (condition B): retention time=1.57 min. LCMS (condition B): m/z 159 +ve. $^1$H NMR (400 MHz, MeOD) δ ppm 6.86 (1 H, d), 6.51 (1 H, d, J=2.42 Hz), 3.85 (3 H, s).

Step 6: Ethyl 6-fluoro-4-hydroxypyrrolo[1,2-b]pyridazine-3-carboxylate

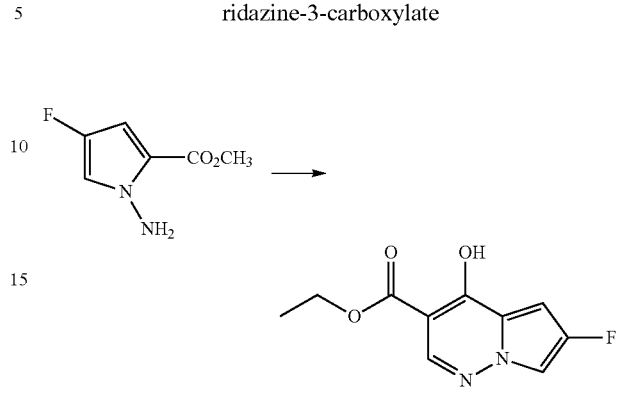

A mixture of methyl 1-amino-4-fluoro-1H-pyrrole-2-carboxylate (0.980 g, 6.20 mmol), (E)-ethyl 3-ethoxyacrylate (1.25 g, 8.68 mmol) and toluenesulfonic acid (0.059 g, 0.310 mmol) in ethanol (15 mL) was heated at 85° C. for 2 h then at reflux (100° C. bath) for an additional 2 h. The mixture was cooled and concentrated to remove the ethanol/water and additional ethanol was added and reconcentrated. The process was repeated until all of the water had been removed then residue was dissolved in ethanol (15 mL) and sodium tert-butoxide (1.190 g, 12.39 mmol) was added to make orange clear solution. This mixture was heated at 85° C. for 1 h, then cooled and concentrated to remove the ethanol and the reaction mixture was neutralized with HCl in dioxane (0.5 mL of 4N solution) then concentrated to afford a tan semi solid. This material was slurried in water and stirred for 1 h and the resulting solid was collected and rinsed with water and filtered and dried to afford the title compound (740 mg, 3.30 mmol, 53.3% yield) as a light yellow solid. HPLC (condition B): retention time=3.57 min. LCMS (condition B): m/z 224.9 +ve.

Step 7: 6-fluoro-4-hydroxypyrrolo[1,2-b]pyridazine-3-carboxylic acid

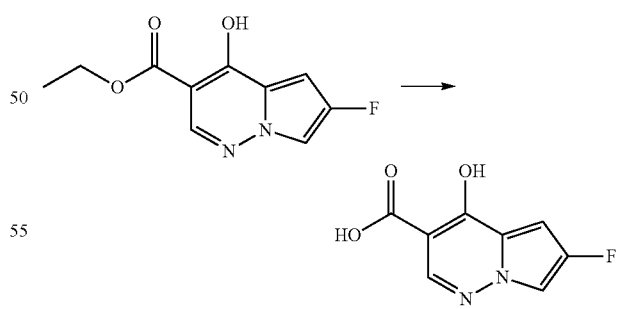

To a solution of ethyl 6-fluoro-4-hydroxypyrrolo[1,2-b]pyridazine-3-carboxylate (700 mg, 3.12 mmol) in MeOH (3 mL) and THF (3 mL) was added 3 N aq. sodium hydroxide (5.20 mL, 15.61 mmol) and the resulting mixture was stirred at 65° C. for 3 h. The mixture was cooled and concentrated to remove the MeOH and THF and the obtained residue was cooled in an ice bath and 3N aq. HCl was added dropwise with stirring until pH of the mixture was ~2. The resulting slurry was stirred for 30 min, and filtered to collect the solid. The solid was rinsed with water and dried to afford 550 mg (90%) of the title compound as a white solid. HPLC (condition B): retention time=2.37 min. LCMS (condition B): m/z 197 +ve.

Step 8: 4-chloro-6-fluoropyrrolo[1,2-b]pyridazine-3-carboxamide

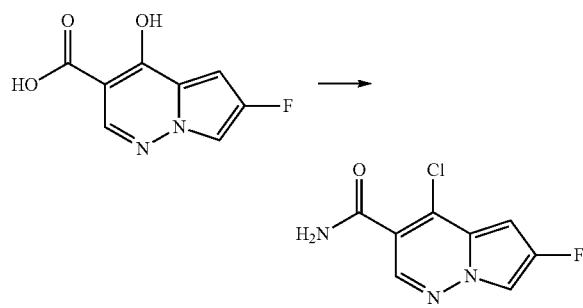

To a slurry of 6-fluoro-4-hydroxypyrrolo[1,2-b]pyridazine-3-carboxylic acid (0.400 g, 2.039 mmol) in POCl₃ (15.64 g, 102 mmol) was added diisopropylethylamine (0.39 mL, 2.24 mmol) and the resulting mixture was heated at 120° C. for 3 h with stirring. The reaction was cooled to rt and concentrated to remove the excess POCl₃ and the resulting residue was dissolved in dichloromethane (15 mL) and reconcentrated and the process was repeated 2 more times to afford a brown oil. This material was dissolved in dichloromethane (10 mL) and the solution was added dropwise via pipette into a 0° C. well stirred solution of ammonia in dichloromethane (~100 mL, prepared by extracting 100 mL of conc. Aq ammonium hydroxide with 3×30 mL portions of dichloromethane). After the addition was complete, the mixture was concentrated under vacuum and water was added to give a slurry which was filtered to collect the precipitated solid. The solid was rinsed with additional water and dried to afford 355 mg (81%) of the title compound as a yellow solid. HPLC (condition B): retention time=2.05 min. LCMS (condition B): m/z 197 +ve.

Preparation 7

4,6-dichloropyrrolo[1,2-b]pyridazine-3-carboxamide

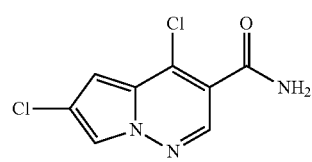
(Prep-7)

Step 1: Ethyl 4-chloro-1H-pyrrole-2-carboxylate

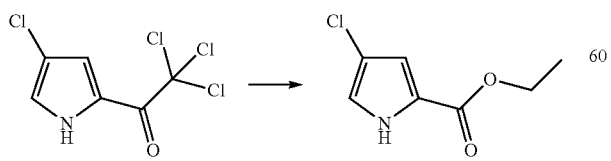

Sodium (0.168 g, 7.29 mmol) was dissolved in anhydrous ethanol (10 mL) then 2,2,2-trichloro-1-(4-chloro-1H-pyrrol-2-yl)ethanone (1.50 g, 6.08 mmol) was added in small portions and the resulting dark brown solution was stirred at room temperature for 30 minutes. The reaction mixture was concentrated under vacuum to dryness and the obtained residue was cooled in an ice bath and 3 N aq. HCl (~2 mL) was added slowly and the mixture was extracted with diethyl ether (100 mL×2). The combined extracts were successively washed with water, sat. aqueous sodium bicarbonate and brine, then dried over magnesium sulfate, filtered and concentrated to afford 1.0 g (95%) of the title compound as a tan oil which solidified upon standing. HPLC (condition B): retention time=2.71 min. LCMS (condition B): m/z 174 +ve. ¹H NMR (400 MHz, MeOD) δ ppm 6.97 (1 H, d, J=1.54 Hz), 6.78 (1 H, d, J=1.54 Hz), 4.34 (2 H, q, J=7.19 Hz), 1.39 (3 H, t, J=7.15 Hz).

Step 2: Ethyl 1-amino-4-chloro-1H-pyrrole-2-carboxylate

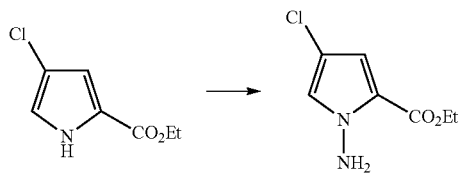 [SMILES: CCOC(=O)c1cc(Cl)c[nH]1 ; CCOC(=O)c1cc(Cl)cn1N]

Prepared using the procedure described in Step 5 of Preparation 5 to afford the title compound as a yellow solid (86% yield). HPLC (condition B): retention time=2.66 min. LCMS (condition B): m/z 189 +ve. ¹H NMR (400 MHz, MeOD) δ ppm 6.99 (1 H, d, J=2.20 Hz), 6.72 (1 H, d, J=2.20 Hz), 4.34 (2 H, q, J=7.04 Hz), 1.38 (3 H, t, J=7.15 Hz).

Step 3: Ethyl 6-chloro-4-hydroxypyrrolo[1,2-b]pyridazine-3-carboxylate

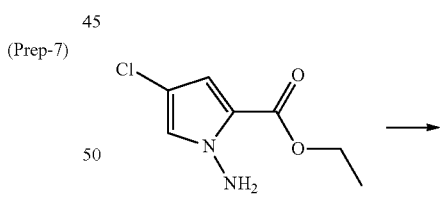

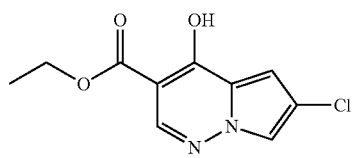

Prepared using the procedure described in Step 6 of Preparation 6 to afford the title compound as a yellow solid (20% yield). HPLC (condition B): retention time=3.88 min. LCMS (condition B): m/z 241 +ve.

Step 4: 6-Chloro-4-hydroxypyrrolo[1,2-b]pyridazine-3-carboxylic acid

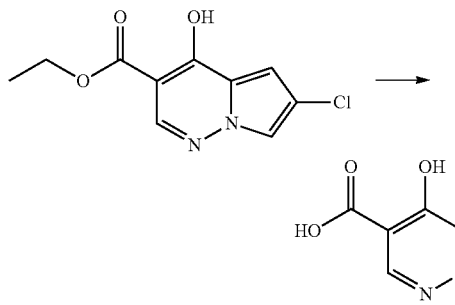

Prepared using the procedure described in Step 7 of Preparation 6 to afford the title compound as a yellow solid (91% yield). HPLC (condition B): retention time=2.25 min. LCMS (condition B): m/z 197 +ve.

Step 5: 4,6-Dichloropyrrolo[1,2-b]pyridazine-3-carboxamide

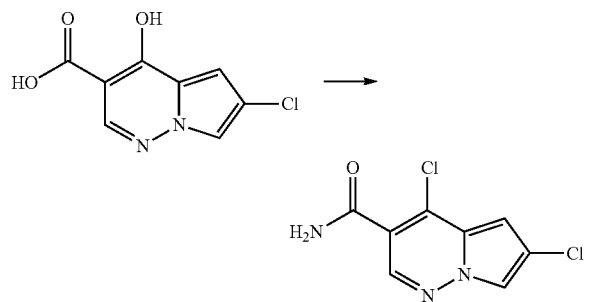

Prepared using the procedure described in Step 8 of Preparation 6 to afford the title compound as a yellow solid (58% yield). HPLC (condition B): retention time=2.61 min. LCMS (condition B): m/z 230.9, 232.9 +ve.

EXAMPLES AND INTERMEDIATES

Intermediate 1

(6-bromo-4-(((1R)-1,2,2-trimethylpropyl)amino)pyrrolo[1,2-b]pyridazine-3-carboxamide (Int-1)

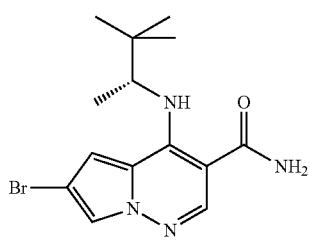

To an NMP (3643 µL) solution of 6-bromo-4-chloropyrrolo[1,2-b]pyridazine-3-carboxamide (Preparation 5, 100 mg, 0.364 mmol), (R)-3,3-dimethylbutan-2-amine (73.7 mg, 0.729 mmol), and Hunig's Base (318 µl, 1.821 mmol) were added. The reaction was heated to 80° C. for 3 hours. The reaction was cooled to room temperature and diluted with ethyl acetate. The ethyl acetate solution was washed with water and brine, dried over sodium sulfate, and concentrated in vacuo, yielding a light yellow solid. The product was chromatographed using reverse-phase preparative HPLC (condition C) yielding the trifluoroacetic acid salt of (R)-6-bromo-4-(3,3-dimethylbutan-2-ylamino)pyrrolo-[1,2-b]pyridazine-3-carboxamide (137 mg, 0.302 mmol, 83% yield) as a white solid. $^1$H NMR (400 MHz, MeOD) δ ppm 8.12 (1 H, s), 7.57-7.64 (1 H, m), 6.95-7.01 (1 H, m), 3.99-4.07 (1 H, m), 1.32 (3 H, d, J=6.6 Hz), 1.04 (9 H, s). HPLC (Method E): ret. time=3.473 min; LCMS [m/z, [M+H]$^+$] 339.2, 441.1.

Example 1

6-(3-oxo-4-morpholinyl)-4-(((1R)-1,2,2-trimethylpropyl)amino)pyrrolo[1,2-b]pyridazine-3-carboxamide (1)

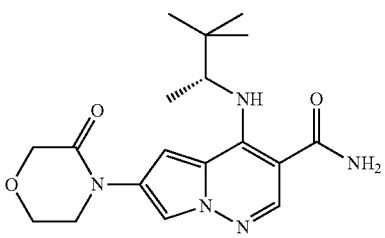

A vial charged with (R)-6-bromo-4-(3,3-dimethylbutan-2-ylamino)pyrrolo[1,2-b]pyridazine-3-carboxamide (Intermediate 1, 20 mg, 0.059 mmol), morpholin-3-one (5.96 mg, 0.059 mmol), copper(I) iodide (2.246 mg, 0.012 mmol), and potassium carbonate (16.30 mg, 0.118 mmol) was flushed with a gentle stream of nitrogen. Dioxane (118 µl) and N1,N2-dimethylethane-1,2-diamine (2.51 µl, 0.024 mmol) were added. The suspension was purged with nitrogen, and the reaction was heated to 105° C. for 16 hours. The reaction was cooled to room temperature, diluted with warm MeOH, and filtered. The collected solid was washed with MeOH, and the filtrate was concentrated in vacuo, yielding a brown oil. The product was chromatographed using reverse-phase HPLC (condition D), yielding the trifluoroacetic acid salt of (R)-4-(3,3-dimethylbutan-2-ylamino)-6-(3-oxomorpholino)pyrrolo[1,2-b]pyridazine-3-carboxamide (6.2 mg, 0.012 mmol, 21.10% yield) as a white powder. $^1$H NMR (400 MHz, MeOD) δ ppm 8.11-8.17 (1 H, m), 7.96-8.02 (1 H, m), 7.14-7.20 (1 H, m), 4.27-4.34 (2 H, m), 4.09-4.14 (1 H, m), 4.05-4.09 (2 H, m), 3.85-3.94 (2 H, m), 1.32-1.38 (3 H, m), 1.05 (9 H, s). HPLC (Method E): ret. time=2.841 min; LCMS [m/z, [M+H]$^+$] 360.2.

Examples 2 to 31

Examples in the table below were prepared from (R)-6-bromo-4-(3,3-dimethylbutan-2-ylamino)pyrrolo[1,2-b]pyridazine-3-carboxamide (Intermediate 1) using commercially available reagents according to the procedure described for Example 1. All examples are homochiral.

| Ex. # | Structure | HPLC Rt, min (conditions) | LCMS [m/z (M + H)] |
|---|---|---|---|
| 2 | 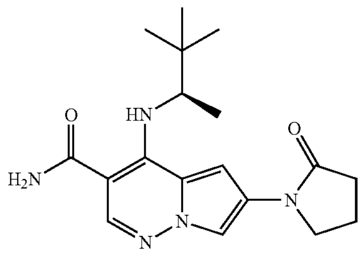 [SMILES: C[C@@H](Nc1c(C(N)=O)cnn2cc(N3CCCC3=O)cc12)C(C)(C)C] | 1.860 (E) | 344.11 |
| 3 | 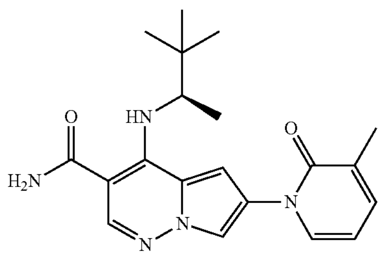 [SMILES: Cc1cccn(-c2cc3c(N[C@H](C)C(C)(C)C)c(C(N)=O)cnn3c2)c1=O] | 2.028 (H) | 368.07 |
| 4 | 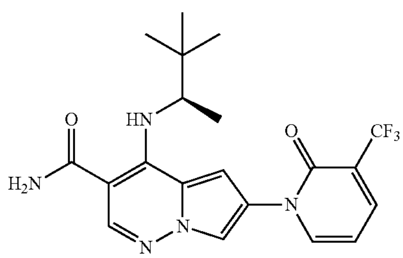 [SMILES: C[C@@H](Nc1c(C(N)=O)cnn2cc(-n3cccc(C(F)(F)F)c3=O)cc12)C(C)(C)C] | 2.418 (H) | 422.0 |
| 5 | 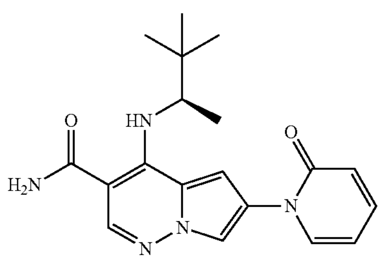 [SMILES: C[C@@H](Nc1c(C(N)=O)cnn2cc(-n3ccccc3=O)cc12)C(C)(C)C] | 1.762 (H) | 354.09 |
| 6 | 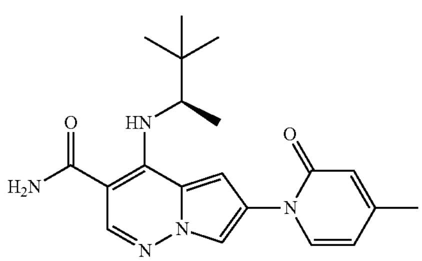 [SMILES: Cc1ccn(-c2cc3c(N[C@H](C)C(C)(C)C)c(C(N)=O)cnn3c2)c(=O)c1] | 1.912 (H) | 368.11 |
| 7 | 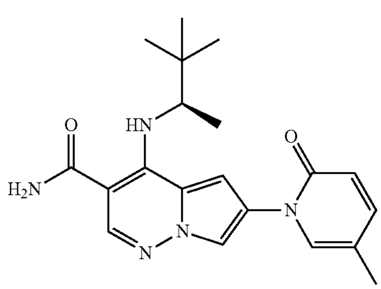 [SMILES: Cc1ccc(=O)n(-c2cc3c(N[C@H](C)C(C)(C)C)c(C(N)=O)cnn3c2)c1] | 1.930 (H) | 368.09 |

-continued

| Ex. # | Structure | HPLC Rt, min (conditions) | LCMS [m/z (M + H)] |
|---|---|---|---|
| 8 | Diastereomeric mixture | 2.951 (E) | 374.3 |
| 9 | 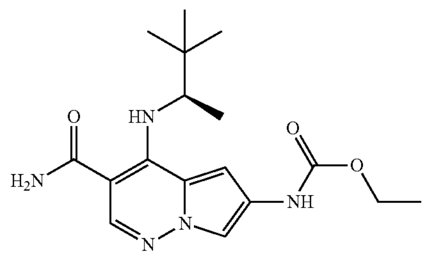 [SMILES: CCOC(=O)Nc1cc2c(N[C@H](C)C(C)(C)C)c(C(N)=O)cnn2c1] | 3.120 (E) | 348.3 |
| 10 | 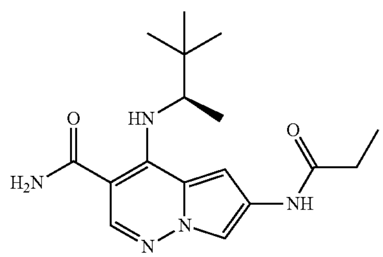 [SMILES: CCC(=O)Nc1cc2c(N[C@H](C)C(C)(C)C)c(C(N)=O)cnn2c1] | 2.928 (E) | 332.3 |
| 11 | 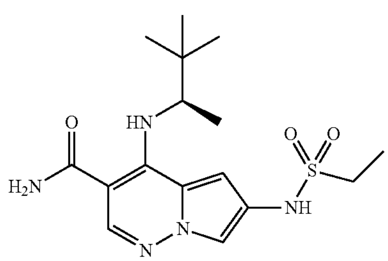 [SMILES: CCS(=O)(=O)Nc1cc2c(N[C@H](C)C(C)(C)C)c(C(N)=O)cnn2c1] | 2.70 (E) | 368.2 |
| 12 | 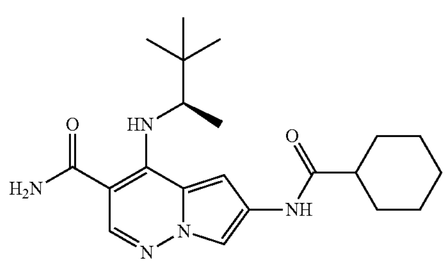 [SMILES: C[C@@H](Nc1c(C(N)=O)cnn2cc(NC(=O)C3CCCCC3)cc12)C(C)(C)C] | 2.137 (H) | 386.13 |

-continued

| Ex. # | Structure | HPLC Rt, min (conditions) | LCMS [m/z (M + H)] |
|---|---|---|---|
| 13 | 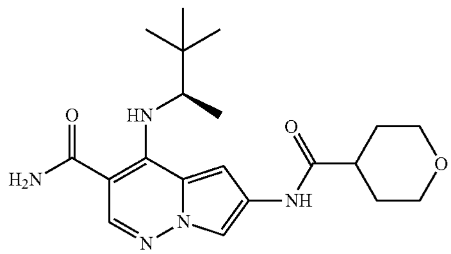 [SMILES: C[C@@H](Nc1c(C(N)=O)cnn2cc(NC(=O)C3CCOCC3)cc12)C(C)(C)C] | 1.675 (H) | 388.13 |
| 14 | 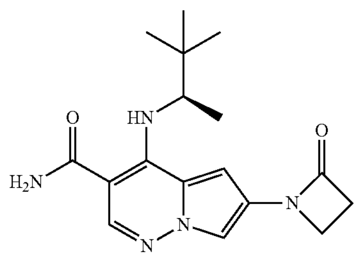 [SMILES: C[C@@H](Nc1c(C(N)=O)cnn2cc(N3CCC3=O)cc12)C(C)(C)C] | 1.787 (H) | 330.19 |
| 15 | Diastereomeric mixture | 2.058 (H) | 358.13 |
| 16 | Diastereomeric mixture | 1.943 (H) | 358.19 |
| 17 | 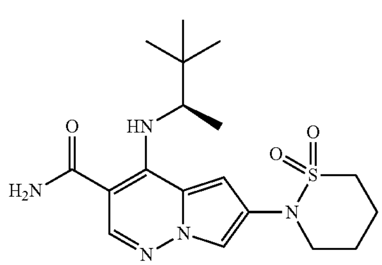 [SMILES: C[C@@H](Nc1c(C(N)=O)cnn2cc(N3CCCCS3(=O)=O)cc12)C(C)(C)C] | 3.398 (H) | 394.2 |

-continued

| Ex. # | Structure | HPLC Rt, min (conditions) | LCMS [m/z (M + H)] |
|---|---|---|---|
| 18 | 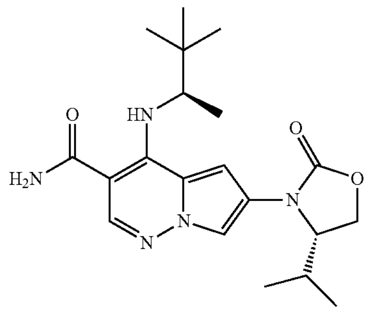 [SMILES: CC(C)[C@H]1COC(=O)N1c1cc2c(N[C@H](C)C(C)(C)C)c(C(N)=O)cnn2c1] | 3.238 (E) | 388.1 |
| 19 | 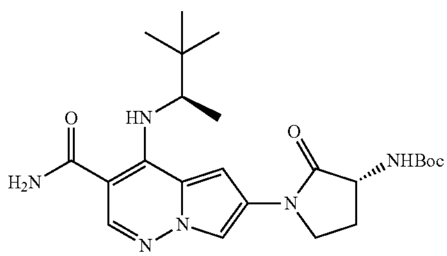 [SMILES: C[C@@H](Nc1c(C(N)=O)cnn2cc(N3CC[C@@H](NC(=O)OC(C)(C)C)C3=O)cc12)C(C)(C)C] | 3.235 (E) | 459.1 |
| 20 | 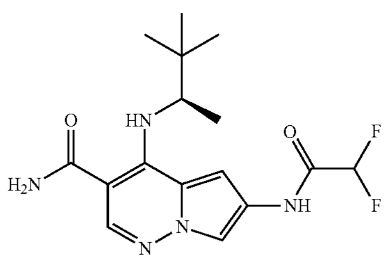 [SMILES: C[C@@H](Nc1c(C(N)=O)cnn2cc(NC(=O)C(F)F)cc12)C(C)(C)C] | 2.966 (E) | 354.0 |
| 21 | 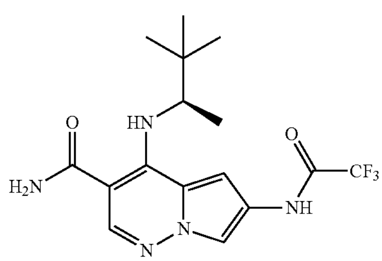 [SMILES: C[C@@H](Nc1c(C(N)=O)cnn2cc(NC(=O)C(F)(F)F)cc12)C(C)(C)C] | 3.246 (E) | 372.0 |
| 22 | 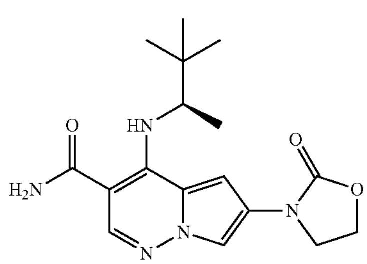 [SMILES: C[C@@H](Nc1c(C(N)=O)cnn2cc(N3CCOC3=O)cc12)C(C)(C)C] | 3.291 (G) | 346.3 |

-continued

| Ex. # | Structure | HPLC Rt, min (conditions) | LCMS [m/z (M + H)] |
|---|---|---|---|
| 23 | 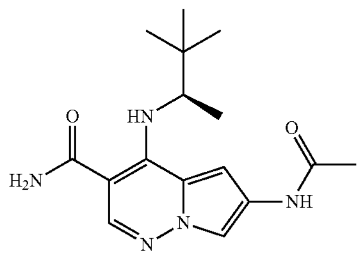 [SMILES: CC(=O)Nc1cc2c(N[C@H](C)C(C)(C)C)c(C(N)=O)cnn2c1] | 3.253 (G) | 318.2 |
| 24 | 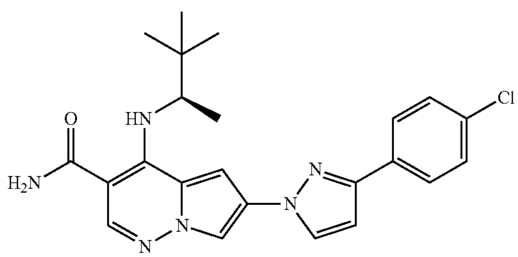 [SMILES: C[C@@H](Nc1c(C(N)=O)cnn2cc(-n3ccc(-c4ccc(Cl)cc4)n3)cc12)C(C)(C)C] | 4.471 (G) | 437.2 |
| 25 | 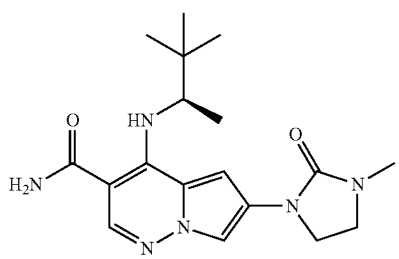 [SMILES: C[C@@H](Nc1c(C(N)=O)cnn2cc(N3CCN(C)C3=O)cc12)C(C)(C)C] | 2.122 (H) | 359.2 |
| 26 | 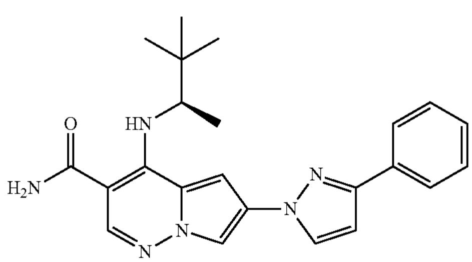 [SMILES: C[C@@H](Nc1c(C(N)=O)cnn2cc(-n3ccc(-c4ccccc4)n3)cc12)C(C)(C)C] | 2.130 (H) | 403.3 |
| 27 | 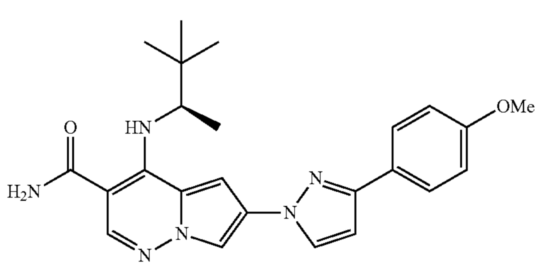 [SMILES: COc1ccc(-c2ccn(-c3cc4c(N[C@H](C)C(C)(C)C)c(C(N)=O)cnn4c3)n2)cc1] | 2.070 (H) | 433.3 |

-continued
| Ex. # | Structure | HPLC Rt, min (conditions) | LCMS [m/z (M + H)] |
|---|---|---|---|
| 28 | 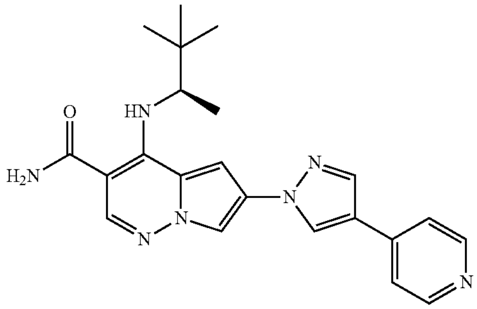 [SMILES: C[C@@H](Nc1c(C(N)=O)cnn2cc(-n3cc(-c4ccncc4)cn3)cc12)C(C)(C)C] | 3.195 (E) | 404.1 |
| 29 | 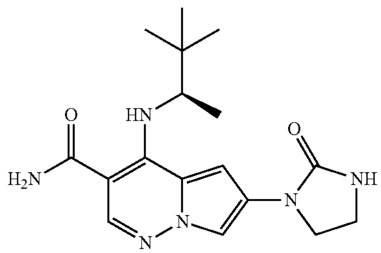 [SMILES: C[C@@H](Nc1c(C(N)=O)cnn2cc(N3CCNC3=O)cc12)C(C)(C)C] | 1.210 (E) | 345.3 |
| 30 | 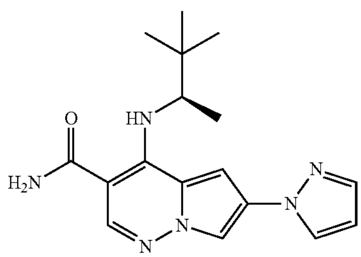 [SMILES: C[C@@H](Nc1c(C(N)=O)cnn2cc(-n3cccn3)cc12)C(C)(C)C] | 1.600 (E) | 327.3 |
| 31 | Diastereomeric mixture | 3.366 (E) | 420.0 |
Intermediate 2
4-(((1R)-2-fluoro-1,2-dimethylpropyl)amino)pyrrolo[1,2-b]pyridazine-3-carboxamide
(Int-2)
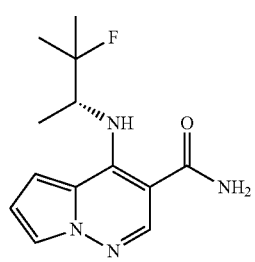
Step 1: ((R)-2-Hydroxy-1,2-dimethyl-propyl)-carbamic acid tert-butyl ester
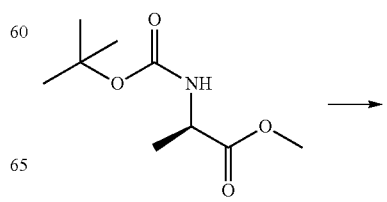

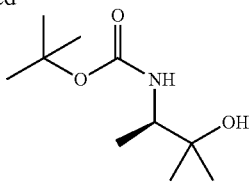

To a solution of (R)-methyl 2-(tert-butoxycarbonylamino) propanoate (10 g, 49.2 mmol) in THF (80 mL) at 0° C. was added methyl magnesium bromide (65.6 mL, 197 mmol) dropwise. The reaction mixture was warmed up to RT and stirred for 16 hrs. The reaction mixture was poured into 200 mL of ice water. The mixture was extracted with ethyl acetate (100 mL×3). The combined organic phases were concentrated to yield a crude product to which was added 100 mL of diethyl ether. Filtration and concentration yielded the title compound (10 g, 100%). $^1$H-NMR (400 MHz, CDCl$_3$) δ ppm 3.60 (1H, ddd, J=14.5, 7.1, 6.8 Hz), 1.46 (9 H, s), 1.24 (3 H, s), 1.18 (3 H, s), 1.14 (3 H, d, J=7.0 Hz).

Step 2: ((R)-2-Fluoro-1,2-dimethyl-propyl)-carbamic acid tert-butyl ester

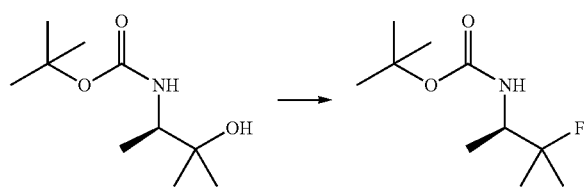

A solution of ((R)-2-Hydroxy-1,2-dimethyl-propyl)-carbamic acid tert-butyl ester (4 g, 19.68 mmol) in CH$_2$Cl$_2$ (100 mL) at −78° C. was added DAST (2.86 mL, 21.65 mmol) dropwise and the resulting mixture was warmed to rt and stirred for 16 hrs. The reaction mixture was quenched with sat. NaHCO$_3$ (100 mL). The organic phase was saved. The water layer was extracted with CH$_2$Cl$_2$ (100 mL×2). The combined organic phases were washed with 50 mL of water and 50 mL of brine and dried over Na$_2$SO$_4$. Filtration and concentration yielded a crude product which was purified on silica gel column with hexanes/EtOAc (10/1) to yield the title compound (2.65 g, 66%). $^1$H-NMR (400 MHz, CDCl$_3$) δ ppm 3.65-3.80 (1 H, m), 1.46 (9 H, s), 1.39 (3 H, d, J=2.6 Hz), 1.34 (3 H, d, J=2.2 Hz), 1.19 (3 H, d, J=6.8 Hz). $^{19}$F NMR (376 MHz, with $^1$H coupling, CDCl$_3$) δ ppm −155.78, −155.39 (1 F, m).

Step 3: (R)-2-Fluoro-1,2-dimethyl-propylamine

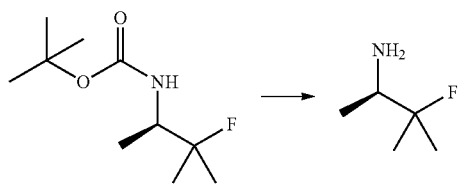

To a solution of ((R)-2-fluoro-1,2-dimethyl-propyl)-carbamic acid tert-butyl ester (2.65 g, 12.91 mmol) in dichloromethane (25 mL) was added 4N HCl in dioxane (22.59 mL, 90 mmol) and the resulting mixture was stirred at rt for 2 hrs. The reaction mixture was concentrated to yield the HCl salt of the title compound (1.95 g, ~100%). $^1$H NMR (400 MHz, CDCl$_3$) δ ppm 8.67 (2 H, br. s.), 3.41-3.52 (1 H, m), 1.53 (2 H, d, J=4.6 Hz), 1.48 (2 H, d, J=4.8 Hz), 1.45 (2 H, d, J=6.8 Hz). $^{19}$F NMR (376 MHz, with $^1$H decoupling, CDCl$_3$) δ ppm −143.96 (1 F, s).

Step 4: 4-(((1R)-2-fluoro-1,2-dimethylpropyl)amino) pyrrolo[1,2-b]pyridazine-3-carboxamide (Intermediate 2)

A solution of 4-chloropyrrolo[1,2-b]pyridazine-3-carboxamide (Preparation 3, 50 mg, 0.26 mmol), (R)-2-Fluoro-1,2-dimethyl-propylamine hydrochloride salt (47 mg, 0.33 mmol, from step 3), and diisopropylethylamine (0.089 mL, 0.51 mmol) in NMP (0.5 mL) was heated to 100° C. for 1 hour in the CEM microwave. The mixture was cooled to rt, diluted with MeOH and purified by reverse-phase Prep HPLC (condition A). The fraction containing the major product was concentrated on the rotovap to remove the MeOH and the aqueous slurry of the product was neutralized by addition of ~1 mL of saturated aq sodium bicarbonate. Sonication of the slurry followed by vacuum filtration and air drying in the funnel afforded 22 mg (33%) of a pale yellow solid as the title compound. HPLC (condition A): retention time=7.70 min. LCMS (condition B): m/z 265.2. $^1$H NMR (500 MHz, CD$_3$OD) δ ppm 10.74 (1 H, br. s.), 8.16 (1 H, s), 7.41-7.80 (1 H, m), 7.01 (1 H, dd, J=4.72, 1.39 Hz), 6.72 (1 H, dd, J=4.58, 2.64 Hz), 4.28-4.64 (1 H, m), 1.46-1.55 (6 H, m), 1.44 (3 H, d).

Intermediate 3

6-bromo-4-(((1R)-2-fluoro-1,2-dimethylpropyl) amino)pyrrolo[1,2-b]pyridazine-3-carboxamide

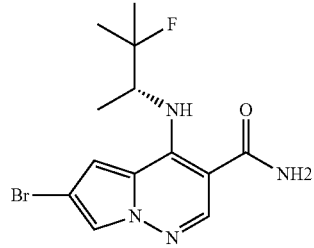

(Int-3)

A solution of 6-bromo-4-chloropyrrolo[1,2-b]pyridazine-3-carboxamide (Preparation 5, 519 mg, 1.89 mmol), (R)-2-fluoro-1,2-dimethyl-propylamine hydrochloride salt (402 mg, 2.84 mmol, from Intermediate 2, step 3), and diisopropylethylamine (0.99 mL, 5.68 mmol) in NMP (2.0 mL) was heated to 100° C. for 1 hour in the CEM microwave. The mixture was cooled to rt, diluted with water and the resulting precipitate then filtered and allowed to air dry. This afforded 595 mg (92%) of a pale white solid as the title compound. HPLC (condition B): retention time=3.67 min. LCMS (condition B): m/z 343.1, 345.1. $^1$H NMR (500 MHz, CD$_3$OD) δ ppm 8.16 (1 H, s), 7.67 (1 H, d, J=1.66 Hz), 7.04 (1 H, d, J=1.39 Hz), 4.11-4.60 (1 H, m), 1.45-1.54 (6 H, m), 1.43 (3 H, d, J=6.66 Hz).

Example 32

4-(((1R)-2-fluoro-1,2-dimethylpropyl)amino)-6-phenylpyrrolo[1,2-b]pyridazine-3-carboxamide

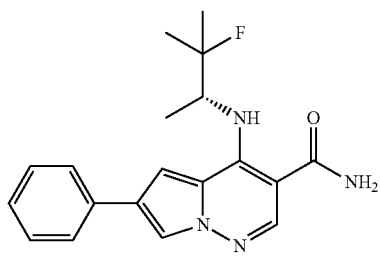

(32)

Potassium phosphate (2M aqueous solution, 0.22 mL, 0.44 mmol) was added in one portion to a stirred solution of 6-bromo-4-(((1R)-2-fluoro-1,2- dimethylpropyl)amino)pyrrolo[1,2-b]pyridazine-3-carboxamide (Intermediate 3, 20 mg, 0.058 mmol), phenyl boronic acid (11 mg, 0.087 mmol), X-Phos ligand (2.8 mg, 0.0058 mmol) and palladium acetate (0.7 mg, 0.0029 mmol) in anhydrous 1,4-dioxane (0.25 mL). The resulting biphasic mixture was then heated in the CEM microwave at 120° C. for 10 min. The reaction was allowed to cool to rt and the phases separated. The aqueous phase was extracted with ethyl acetate (2×5 mL). The combined organics were then dried (MgSO$_4$) and evaporated in vacuo before purifying by reverse-phase Prep HPLC (condition A). The fraction containing the major product was concentrated on the rotovap to afford 10.1 mg (45%) of the title compound as a white solid. HPLC (condition B): retention time=3.84 min. LCMS (condition B): MH+m/z 341.2. $^1$H NMR (400 MHz, MeOD) δ ppm 8.38 (1 H, d, J=3.52 Hz), 8.15 (1 H, d, J=1.76 Hz), 7.76-8.03 (3 H, m), 7.61-7.76 (1 H, m), 7.53 (1 H, br. s.), 7.38 (1 H, br. s.), 4.87 (1 H, buried s.), 1.60-2.06 (9 H, m).

Examples 33 to 67

Examples 35 to 67 in the table below were prepared from 6-bromo-4-(((1R)-2-fluoro-1,2-dimethylpropyl)amino)pyrrolo[1,2-b]pyridazine-3-carboxamide (Intermediate 3) and commercially available boronic acids or esters using the procedure described in Example 32.

| Ex # | Structure | HPLC Rt, min. (conditions) | LCMS [m/z (M + H)] |
|---|---|---|---|
| 33 | 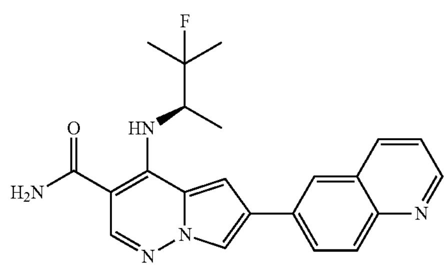 [SMILES: C[C@@H](Nc1c(C(N)=O)cnn2cc(-c3ccc4ncccc4c3)cc12)C(C)(C)F] | 2.50 (G) | 392.3 |
| 34 | 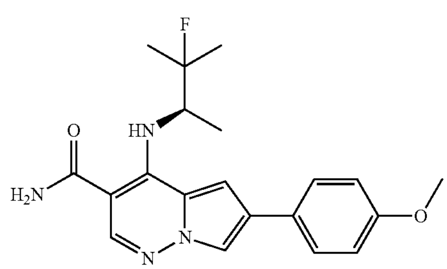 [SMILES: COc1ccc(-c2cc3c(N[C@H](C)C(C)(C)F)c(C(N)=O)cnn3c2)cc1] | 1.89 (H) | 371.2 |
| 35 | 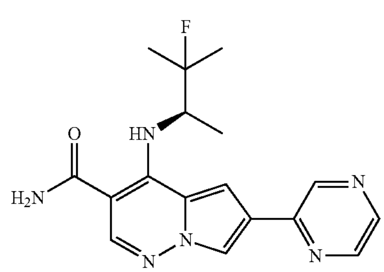 | 1.35 (H) | 343.2 |

-continued

| Ex # | Structure | HPLC Rt, min. (conditions) | LCMS [m/z (M + H)] |
|---|---|---|---|
| 36 | 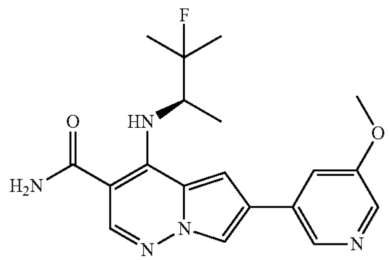 | 1.14 (H) | 372.2 |
| 37 | 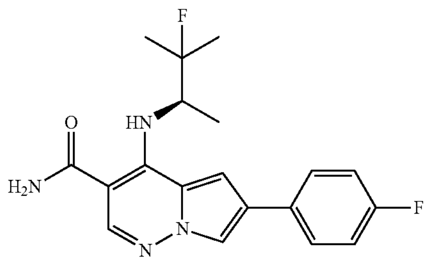 [SMILES: C[C@@H](Nc1c(C(N)=O)cnn2cc(-c3ccc(F)cc3)cc12)C(C)(C)F] | 1.99 (H) | 359.2 |
| 38 | 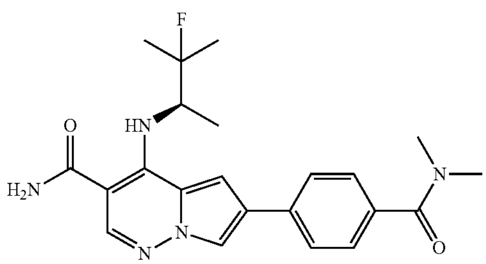 [SMILES: C[C@@H](Nc1c(C(N)=O)cnn2cc(-c3ccc(C(=O)N(C)C)cc3)cc12)C(C)(C)F] | 1.50 (H) | 412.3 |
| 39 | 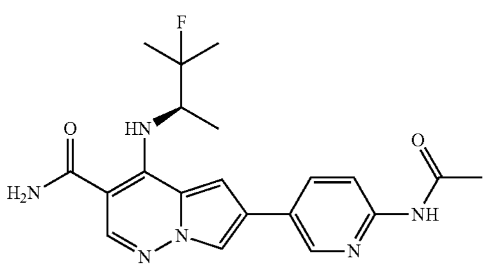 [SMILES: CC(=O)Nc1ccc(-c2cc3c(N[C@H](C)C(C)(C)F)c(C(N)=O)cnn3c2)cn1] | 1.15 (H) | 399.2 |
| 40 | 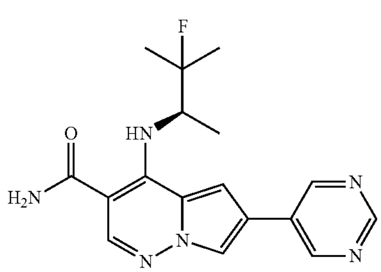 [SMILES: C[C@@H](Nc1c(C(N)=O)cnn2cc(-c3cncnc3)cc12)C(C)(C)F] | 1.63 (I) | 343.1 |

-continued

| Ex # | Structure | HPLC Rt, min. (conditions) | LCMS [m/z (M + H)] |
|---|---|---|---|
| 41 | 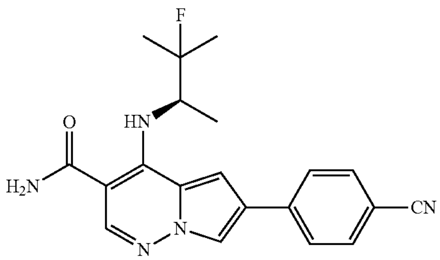 | 2.31 (I) | 366.1 |
| 42 | 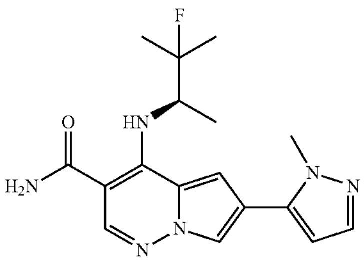 [SMILES: C[C@@H](Nc1c(C(N)=O)cnn2cc(-c3ccnn3C)cc12)C(C)(C)F] | 1.73 (I) | 345.1 |
| 43 | 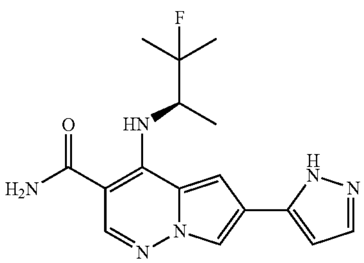 [SMILES: C[C@@H](Nc1c(C(N)=O)cnn2cc(-c3ccn[nH]3)cc12)C(C)(C)F] | 1.55 (I) | 331.1 |
| 44 | 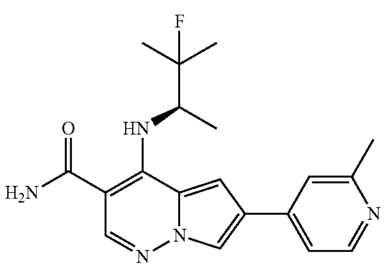 [SMILES: Cc1cc(-c2cc3c(N[C@H](C)C(C)(C)F)c(C(N)=O)cnn3c2)ccn1] | 1.92 (J) | 356.1 |
| 45 | 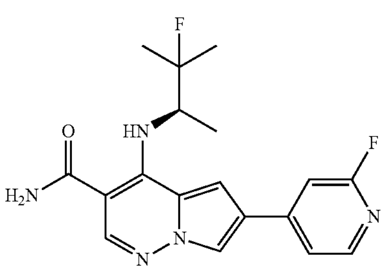 [SMILES: C[C@@H](Nc1c(C(N)=O)cnn2cc(-c3ccnc(F)c3)cc12)C(C)(C)F] | 2.20 (J) | 360.1 |

-continued

| Ex # | Structure | HPLC Rt, min. (conditions) | LCMS [m/z (M + H)] |
|---|---|---|---|
| 46 | 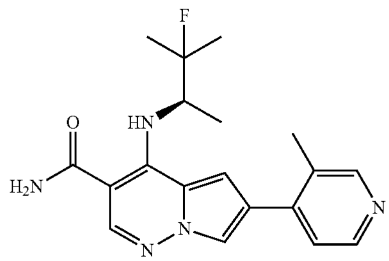 [SMILES: Cc1cnccc1-c1cc2c(N[C@H](C)C(C)(C)F)c(C(N)=O)cnn2c1] | 1.93 (J) | 356.1 |
| 47 | 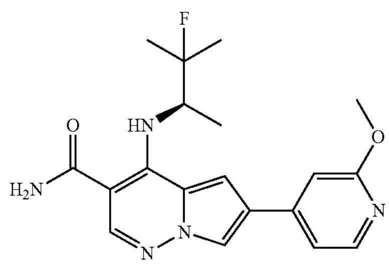 [SMILES: COc1cc(-c2cc3c(N[C@H](C)C(C)(C)F)c(C(N)=O)cnn3c2)ccn1] | 2.13 (J) | 372.3 |
| 48 | 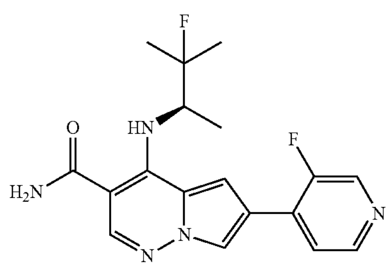 [SMILES: C[C@@H](Nc1c(C(N)=O)cnn2cc(-c3ccncc3F)cc12)C(C)(C)F] | 1.91 (J) | 360.2 |
| 49 | 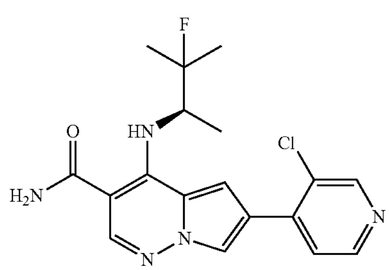 [SMILES: C[C@@H](Nc1c(C(N)=O)cnn2cc(-c3ccncc3Cl)cc12)C(C)(C)F] | 2.05 (J) | 376.2 |
| 50 | 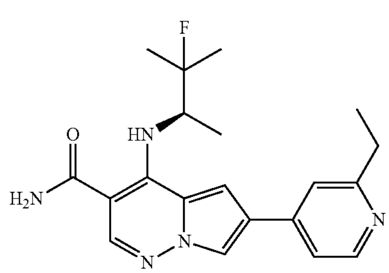 [SMILES: CCc1cc(-c2cc3c(N[C@H](C)C(C)(C)F)c(C(N)=O)cnn3c2)ccn1] | 1.44 (I) | 370.1 |

-continued
| Ex # | Structure | HPLC Rt, min. (conditions) | LCMS [m/z (M + H)] |
|---|---|---|---|
| 51 | 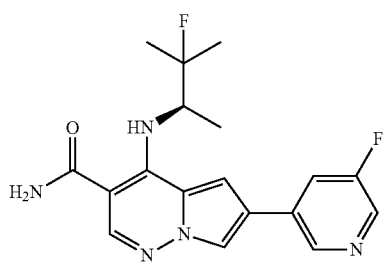 [SMILES: C[C@@H](Nc1c(C(N)=O)cnn2cc(-c3cncc(F)c3)cc12)C(C)(C)F] | 1.92 (I) | 360.1 |
| 52 | 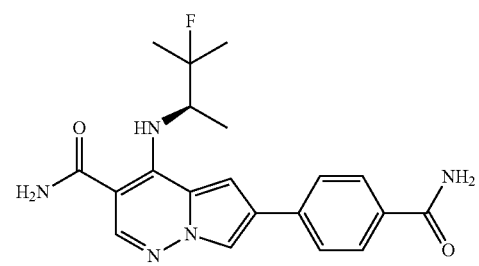 [SMILES: C[C@@H](Nc1c(C(N)=O)cnn2cc(-c3ccc(C(N)=O)cc3)cc12)C(C)(C)F] | 1.69 (I) | 384.1 |
| 53 | 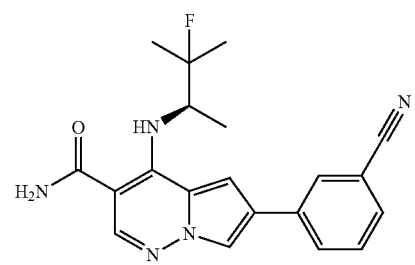 [SMILES: C[C@@H](Nc1c(C(N)=O)cnn2cc(-c3cccc(C#N)c3)cc12)C(C)(C)F] | 3.24 (G) | 366.0 |
| 54 | 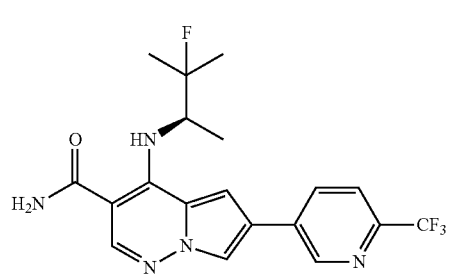 [SMILES: C[C@@H](Nc1c(C(N)=O)cnn2cc(-c3ccc(C(F)(F)F)nc3)cc12)C(C)(C)F] | 2.46 (I) | 410.0 |
| 55 | 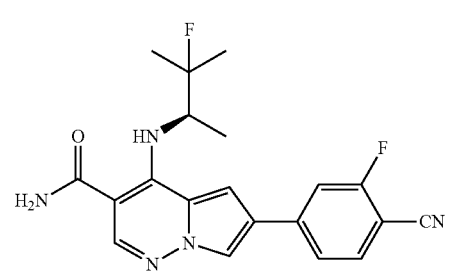 [SMILES: C[C@@H](Nc1c(C(N)=O)cnn2cc(-c3ccc(C#N)c(F)c3)cc12)C(C)(C)F] | 2.43 (I) | 384.0 |

-continued
| Ex # | Structure | HPLC Rt, min. (conditions) | LCMS [m/z (M + H)] |
|---|---|---|---|
| 56 | 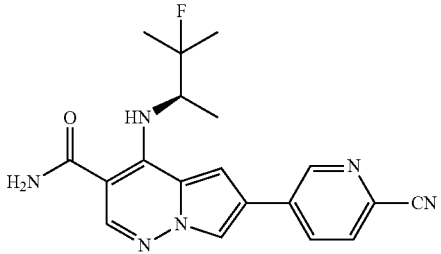 [SMILES: C[C@@H](Nc1c(C(N)=O)cnn2cc(-c3ccc(C#N)nc3)cc12)C(C)(C)F] | 2.10 (I) | 367.1 |
| 57 | 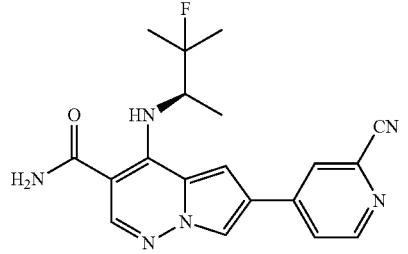 [SMILES: C[C@@H](Nc1c(C(N)=O)cnn2cc(-c3ccnc(C#N)c3)cc12)C(C)(C)F] | 2.04 (J) | 367.3 |
| 58 | 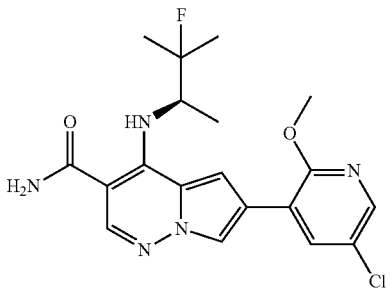 [SMILES: COc1ncc(Cl)cc1-c1cc2c(N[C@H](C)C(C)(C)F)c(C(N)=O)cnn2c1] | 2.87 (I) | 406.9 |
| 59 | 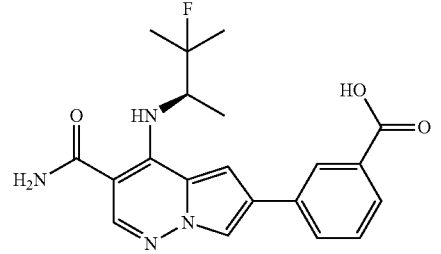 [SMILES: C[C@@H](Nc1c(C(N)=O)cnn2cc(-c3cccc(C(=O)O)c3)cc12)C(C)(C)F] | 1.42 (H) | 385.3 |

-continued

| Ex # | Structure | HPLC Rt, min. (conditions) | LCMS [m/z (M + H)] |
|---|---|---|---|
| 60 | 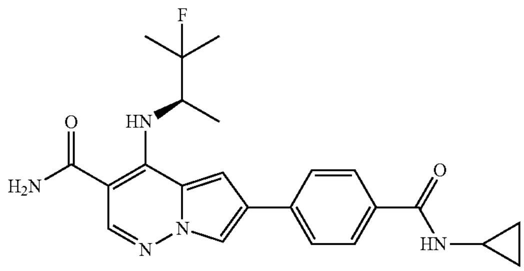 [SMILES: C[C@@H](Nc1c(C(N)=O)cnn2cc(-c3ccc(C(=O)NC4CC4)cc3)cc12)C(C)(C)F] | 2.03 (I) | 424.1 |
| 61 | 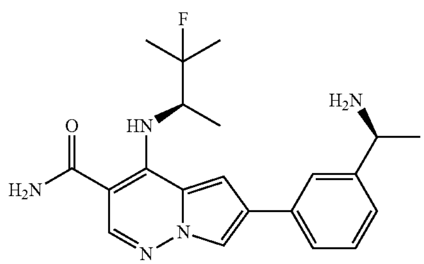 [SMILES: C[C@H](N)c1cccc(-c2cc3c(N[C@H](C)C(C)(C)F)c(C(N)=O)cnn3c2)c1] | 2.47 (G) | 384.2 |
| 62 | 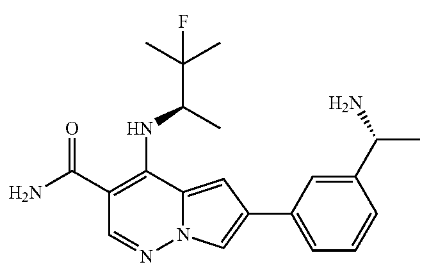 [SMILES: C[C@@H](N)c1cccc(-c2cc3c(N[C@H](C)C(C)(C)F)c(C(N)=O)cnn3c2)c1] | 2.48 (G) | 384.0 |
| 63 | 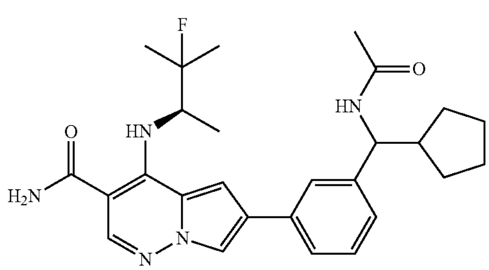 [SMILES: CC(=O)NC(c1cccc(-c2cc3c(N[C@H](C)C(C)(C)F)c(C(N)=O)cnn3c2)c1)C1CCCC1] | 1.79 (H) | 480.4 |

-continued
| Ex # | Structure | HPLC Rt, min. (conditions) | LCMS [m/z (M + H)] |
|---|---|---|---|
| 64 | 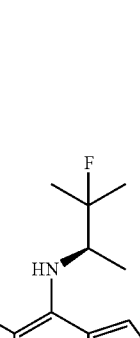 | 4.92 (A) | 342.2 |
| 65 | 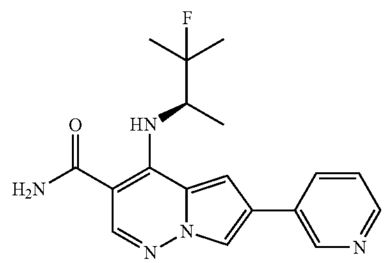 [SMILES: C[C@@H](Nc1c(C(N)=O)cnn2cc(-c3cccnc3)cc12)C(C)(C)F] | 4.86 (A) | 342.2 |
| 66 | 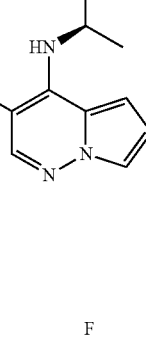 | 4.79 (A) | 342.2 |
| 67 | 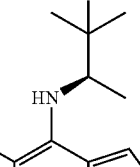 | 1.64 (H) | 380.2 |

Example 68

6-(3-(aminomethyl)phenyl)-4-(((1R)-2-fluoro-1,2-dimethylpropyl)amino) pyrrolo[1,2-b]pyridazine-3-carboxamide (68)

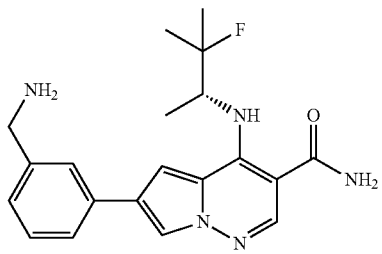

A suspension of (R)-6-(3-cyanophenyl)-4-(3-fluoro-3-methylbutan-2-ylamino)pyrrolo[1,2-b]pyridazine-3-carboxamide (Example 53, 110 mg, 0.301 mmol) and Raney 3201 Nickel (17.67 mg, 0.301 mmol) in ethanol (5 mL) was bubbled with ammonia gas for 3 minutes then stirred under a balloon of hydrogen for 6 hrs. The reaction mixture was filtered and concentrated to yield the title compound (108 mg, 97%). HPLC (condition G): retention time=2.330 minute. LC/MS (M+H)$^+$=370.3. $^1$H NMR (400 MHz, MeOD) δ ppm 8.18 (1 H, s), 8.01 (1 H, d, J=1.8 Hz), 7.78-7.84 (2 H, m), 7.50 (1 H, t, J=8.0 Hz), 7.35 (1 H, d, J=7.7 Hz), 7.28 (1 H, d, J=1.8 Hz), 4.45-4.61 (1 H, m), 4.18 (2 H, s), 1.52 (3 H, d, J=2.4 Hz), 1.45-1.49 (6 H, m).

Example 69

6-(3-(((cyclopropylcarbonyl)amino)methyl)phenyl)-4-(((1R)-2-fluoro-1,2-dimethylpropyl)amino)pyrrolo[1,2-b]pyridazine-3-carboxamide (69)

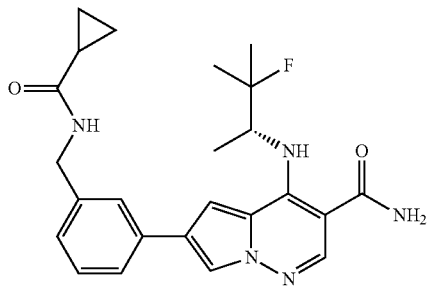

To a solution of 6-(3-(aminomethyl)phenyl)-4-(((1R)-2-fluoro-1,2-dimethylpropyl)amino)pyrrolo[1,2-b]pyridazine-3-carboxamide (Example 68, 15 mg, 0.041 mmol), cyclopropanecarboxylic acid (3.40 µl, 0.041 mmol) and triethylamine (8.49 µl, 0.061 mmol) in DMF (0.5 mL) was added BOP (17.96 mg, 0.041 mmol) and the resulting mixture was stirred at rt for 30 minutes. The reaction mixture was purified by reverse-phase preparative HPLC (condition C) to yield the title compound (9.6 mg, 53%). HPLC (condition J): retention time=2.140 minute. LC/MS (M+H)$^+$=438.2. $^1$H NMR (500 MHz, MeOD) δ ppm 8.08 (1 H, s), 7.86 (1 H, d, J=1.7 Hz), 7.50-7.57 (2 H, m), 7.35 (1 H, t, J=7.6 Hz), 7.19 (1 H, d, J=7.5 Hz), 7.09 (1 H, d, J=1.7 Hz), 4.39-4.49 (3 H, m), 1.54-1.61 (1 H, m), 1.51 (3 H, d, J=3.6 Hz), 1.44-1.48 (6 H, m), 0.89-0.95 (2 H, m), 0.72-0.78 (2 H, m).

Example 70

6-(3-(((cyclopropylcarbamoyl)amino)methyl)phenyl)-4-(((1R)-2-fluoro-1,2-dimethylpropyl)amino) pyrrolo[1,2-b]pyridazine-3-carboxamide (70)

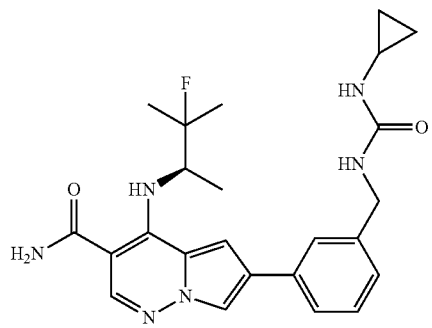

A solution of (R)-6-(3-(aminomethyl)phenyl)-4-(3-fluoro-3-methylbutan-2-ylamino)pyrrolo[1,2-b]pyridazine-3-carboxamide (Example 68, 18.5 mg, 0.050 mmol), 1,1'-carbonyldiimidazole (16.24 mg, 0.100 mmol), and Et$_3$N (0.017 mL, 0.125 mmol) in ClCH$_2$CH$_2$Cl (1 mL) was stirred at 23° C. for 1 hr then cyclopropanamine (8.67 µl, 0.125 mmol) was added and the resulting mixture was heated to 80° C. for 30 minutes. The reaction was cooled, concentrated and redissolved in 1 mL of MeOH with a few drops of DMF. The reaction mixture was purified by reverse-phase preparative HPLC (condition C) to yield the title compound (14.2 mg, 61%). HPLC (condition H): retention time=1.42 minute. LC/MS (M+H)$^+$=453.4.

Examples 71 to 72

Examples 71 and 72 in the table below were prepared from 6-(3-(aminomethyl)-phenyl)-4-(((1R)-2-fluoro-1,2-dimethylpropyl)amino)pyrrolo[1,2-b]pyridazine-3-carboxamide (Example 68) using commercially available reagents according to the procedure described in Example 69.

| Ex # | Structure | HPLC Rt, min. (conditions) | LCMS [m/z (M + H)] |
|---|---|---|---|
| 71 | (structure) | 1.67 (H) | 454.4 |

| Ex # | Structure | HPLC Rt, min. (conditions) | LCMS [m/z (M + H)] |
|---|---|---|---|
| 72 | (structure shown) | 1.68 (H) | 474.3 |

Intermediate 4

6-bromo-4-(((1R)-1-cyclopropylethyl)amino)pyrrolo[1,2-b]pyridazine-3-carboxamide

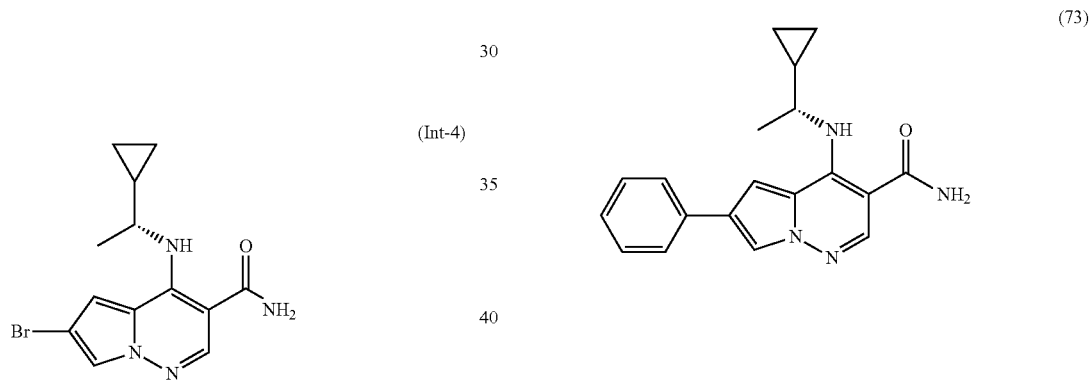

(Int-4)

A solution of 6-bromo-4-chloropyrrolo[1,2-b]pyridazine-3-carboxamide (Preparation 5, 500 mg, 1.821 mmol), (R)-1-cyclopropylethanamine HCl salt (277 mg, 2.277 mmol) and DIPEA (0.795 mL, 4.55 mmol) in NMP (5 mL) was heated to 100° C. for 4 hr. The reaction mixture was added 10 mL of water and stirred for 10 minutes. The solid was collected by vacuum filtration and dried to afford the title compound (485.4 mg, 79%). HPLC (condition G): retention time=2.29 min. LCMS (condition B): m/z 324.1. $^1$H NMR (400 MHz, DMSO-$d_6$) δ ppm 10.70 (1 H, d, J=8.1 Hz), 8.22 (1 H, s), 7.84 (1 H, d, J=1.8 Hz), 6.99 (1 H, d, J=1.8 Hz), 3.78-3.91 (1H, m), 1.29 (3 H, d, J=6.2 Hz), 0.99-1.11 (1 H, m), 0.42-0.53 (2 H, m), 0.33-0.40 (1H, m), 0.22-0.29 (1 H, m).

Example 73

4-(((1R)-1-cyclopropylethyl)amino)-6-phenylpyrrolo[1,2-b]pyridazine-3-carboxamide (73)

A degassed solution of (R)-6-bromo-4-(1-cyclopropylethylamino) pyrrolo[1,2-b]pyridazine-3-carboxamide (Intermediate 4, 20 mg, 0.062 mmol), phenylboronic acid (22.64 mg, 0.186 mmol), potassium carbonate (0.077 mL, 0.155 mmol, 2M) and palladium tetrakis(triphenylphosphine) (4.29 mg, 3.71 μmol) in DME (1 mL) was heated to 90° C. for 1 hr. The reaction mixture was concentrated and redissolved in 1 mL of MeOH, and purified by reverse-phase preparative HPLC (condition C) to yield the title compound (9.8 mg, 48%). HPLC (condition I): retention time=2.49 min. LC/MS (M+H)$^+$=321.1. $^1$H NMR (500 MHz, MeOD) δ ppm 8.04 (1 H, s), 7.82 (1 H, d, J=1.7 Hz), 7.61 (1 H, d, J=1.1 Hz), 7.59 (1 H, d, J=0.8 Hz), 7.56 (1 H, s), 7.37 (2 H, t, J=7.8 Hz), 7.21-7.26 (1 H, m), 4.05 (1 H, quin, J=6.4 Hz), 1.44 (3 H, d, J=6.4 Hz), 1.08-1.17 (1 H, m), 0.52-0.62 (2 H, m), 0.35-0.41 (2 H, m).

Examples 74-86

Examples 74-86 in the table below were prepared from 6-bromo-4-(((1R)-1-cyclopropylethyl)amino)pyrrolo[1,2-b]pyridazine-3-carboxamide (Intermediate 4) using commercially available boronic esters or acids according to the procedure described in Example 73.

| Ex # | Structure | HPLC Rt, min. (conditions) | LCMS [m/z (M + H)] |
|---|---|---|---|
| 74 | 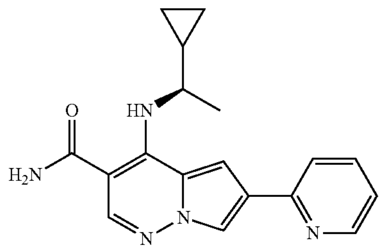 [SMILES: C[C@@H](Nc1c(C(N)=O)cnn2cc(-c3ccccn3)cc12)C1CC1] | 2.09 (G) | 322.2 |
| 75 | 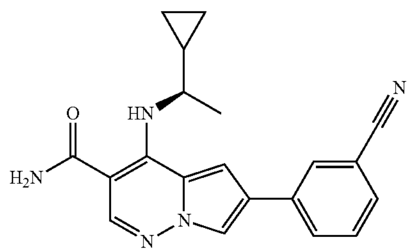 [SMILES: C[C@@H](Nc1c(C(N)=O)cnn2cc(-c3cccc(C#N)c3)cc12)C1CC1] | 2.50 (J) | 346.1 |
| 76 | 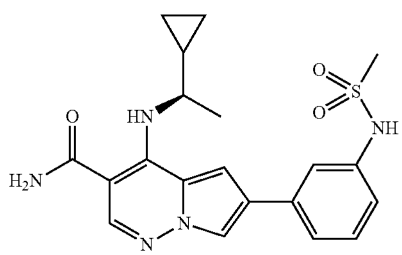 [SMILES: C[C@@H](Nc1c(C(N)=O)cnn2cc(-c3cccc(NS(C)(=O)=O)c3)cc12)C1CC1] | 2.09 (J) | 414.1 |
| 77 | 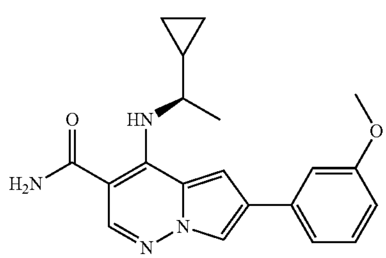 [SMILES: COc1cccc(-c2cc3c(N[C@H](C)C4CC4)c(C(N)=O)cnn3c2)c1] | 2.45 (I) | 351.1 |
| 78 | 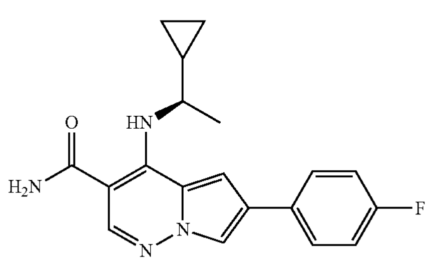 [SMILES: C[C@@H](Nc1c(C(N)=O)cnn2cc(-c3ccc(F)cc3)cc12)C1CC1] | 2.52 (I) | 339.1 |
| 79 | 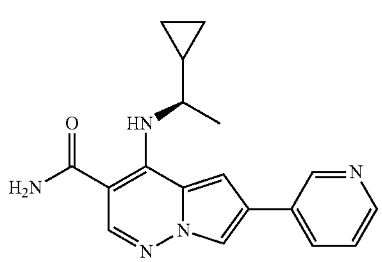 [SMILES: C[C@@H](Nc1c(C(N)=O)cnn2cc(-c3cccnc3)cc12)C1CC1] | 1.21 (I) | 322.1 |

-continued
| Ex # | Structure | HPLC Rt, min. (conditions) | LCMS [m/z (M + H)] |
|---|---|---|---|
| 80 | 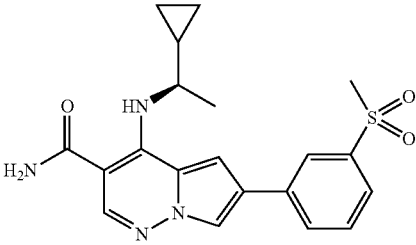 [SMILES: C[C@@H](Nc1c(C(N)=O)cnn2cc(-c3cccc(S(C)(=O)=O)c3)cc12)C1CC1] | 1.97 (I) | 399.4 |
| 81 | 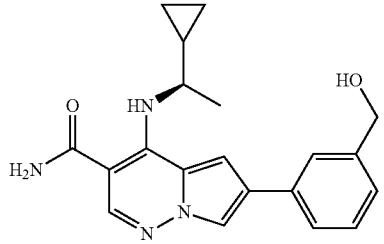 [SMILES: C[C@@H](Nc1c(C(N)=O)cnn2cc(-c3cccc(CO)c3)cc12)C1CC1] | 1.88 (I) | 351.1 |
| 82 | 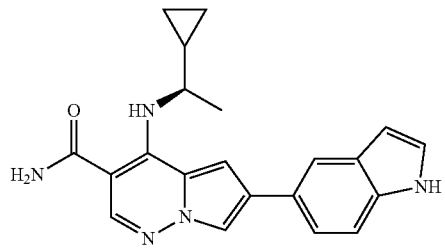 [SMILES: C[C@@H](Nc1c(C(N)=O)cnn2cc(-c3ccc4[nH]ccc4c3)cc12)C1CC1] | 1.64 (H) | 360.3 |
| 83 | 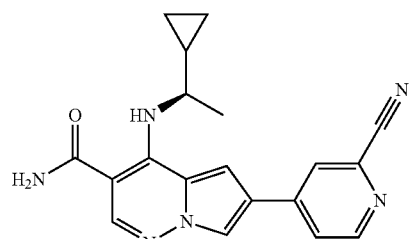 | 1.54 (H) | 347.3 |
| 84 | 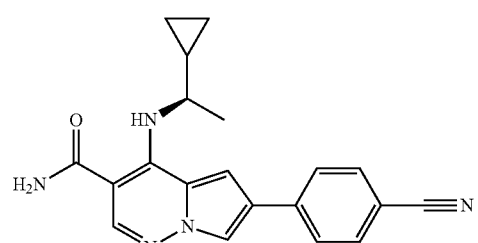 | 3.35 (G) | 346.1 |
| 85 | 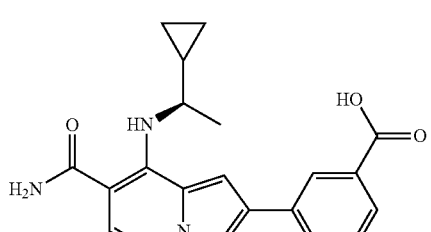 | 2.13 (I) | 365.1 |

| Ex # | Structure | HPLC Rt, min. (conditions) | LCMS [m/z (M + H)] |
|---|---|---|---|
| 86 | 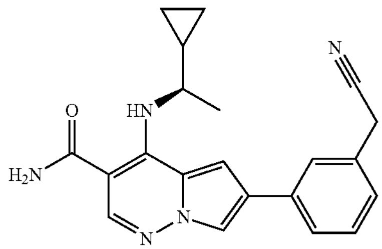 [SMILES: C[C@@H](Nc1c(C(N)=O)cnn2cc(-c3cccc(CC#N)c3)cc12)C1CC1] | 2.41 (I) | 360.0 |

Example 87

(R)-6-(3-(aminomethyl)phenyl)-4-(((1R)-1-cyclopropylethyl)amino)pyrrolo[1,2-b]pyridazine-3-carboxamide

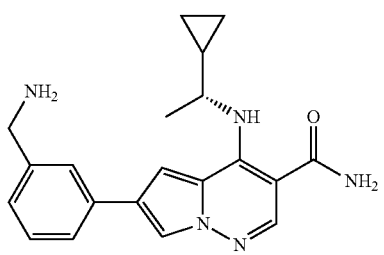

(87)

A suspension solution of (R)-6-(3-cyanophenyl)-4-(1-cyclopropylethylamino)pyrrolo[1,2-b]pyridazine-3-carboxamide (Example 75, 157 mg, 0.455 mmol) and Raney 3201 Nickel (26.7 mg, 0.455 mmol) in ethanol (5 mL) was bubbled with ammonia gas for 3 minutes and then stirred under a balloon of hydrogen for 16 hrs. The reaction mixture was filtered and concentrated to yield the title compound (125 mg, 79%). HPLC (condition G): retention time=2.47 minute. LC/MS (M+H)$^+$=350.4. $^1$H NMR (400 MHz, MeOD) δ ppm 8.15 (1 H, s), 7.97 (1 H, d, J=1.8 Hz), 7.76-7.82 (2 H, m), 7.49 (1 H, t, J=7.7 Hz), 7.34 (1 H, d, J=7.5 Hz), 7.24 (1 H, d, J=1.8 Hz), 4.18 (2 H, s), 4.11 (1 H, quin, J=6.4 Hz), 1.46 (3 H, d, J=6.4 Hz), 1.11-1.22 (1 H, m), 0.54-0.65 (2 H, m), 0.35-0.44 (2 H, m).

Example 88

(R)-4-(1-cyclopropylethylamino)-6-(3-(isobutyramidomethyl)phenyl)pyrrolo[1,2-b]pyridazine-3-carboxamide

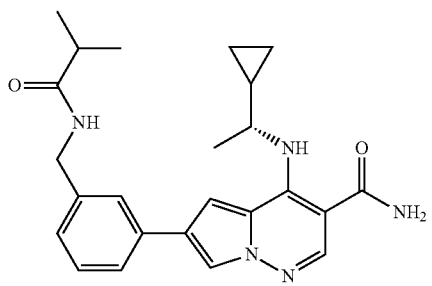

(88)

To a solution of 6-(3-(aminomethyl)phenyl)-4-(((1R)-1-cyclopropylethyl)amino)pyrrolo[1,2-b]pyridazine-3-carboxamide (Example 87, 15 mg, 0.043 mmol), isobutyric acid (3.99 µl, 0.043 mmol) and triethylamine (8.97 µl, 0.064 mmol) in DMF (0.5 mL) was added BOP (18.99 mg, 0.043 mmol) followed by stirring at rt for 30 minutes. The reaction mixture was purified by reverse-phase preparative HPLC (condition C) to yield the title compound (8.7 mg, 48%). HPLC (condition H): retention time=1.69 minute. LC/MS (M+H)$^+$=420.3. $^1$H NMR (500 MHz, MeOD) δ ppm 8.04 (1 H, s), 7.82 (1 H, d, J=1.9 Hz), 7.48-7.52 (2 H, m), 7.33 (1 H, t, J=7.9 Hz), 7.15 (1 H, d, J=7.5 Hz), 7.06 (1 H, d, J=1.7 Hz), 4.41 (2 H, s), 4.04 (1 H, qd, J=6.4, 6.2 Hz), 2.48 (1 H, spt, J=6.9 Hz), 1.44 (3 H, d, J=6.4 Hz), 1.16 (6 H, d, J=6.9 Hz), 1.09-1.15 (1 H, m), 0.50-0.63 (2 H, m), 0.32-0.40 (2 H, m).

Examples 89-110

Examples 89-110 in the table below were prepared from 6-(3-(aminomethyl)phenyl)-4-(((1R)-1-cyclopropylethyl)amino)pyrrolo[1,2-b]pyridazine-3-carboxamide (Example 87) and commercially available reagents using methods readily known to those skilled in the art. Examples 89, 90, 94, 96-100, and 102-110 were prepared using appropriate acid chlorides under standard acylation conditions or the appropriate carboxylic acid under standard amide coupling conditions using BOP and triethylamine in DMF. Example 91 was prepared by sulfonylation under standard conditions using methanesulfonyl chloride in the presence of triethylamine in DMF. Examples 92 and 95 were prepared using 1,1-carbonyldiimidazole and the appropriate amine using the method described for the preparation of Example 70. Example 93 was prepared using diphenyl cyanocarbonimidate and the appropriate amine Example 101 was prepared using trimethylsilylisocyanate under standard conditions.

| Ex # | Structure | HPLC Rt (minutes) | LCMS [m/z (M + H)] |
|---|---|---|---|
| 89 | 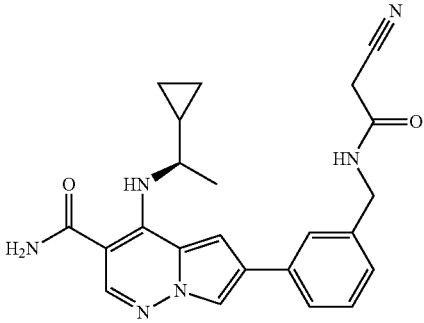 [SMILES: C[C@@H](Nc1c(C(N)=O)cnn2cc(-c3cccc(CNC(=O)CC#N)c3)cc12)C1CC1] | 1.51 (H) | 417.2 |
| 90 | 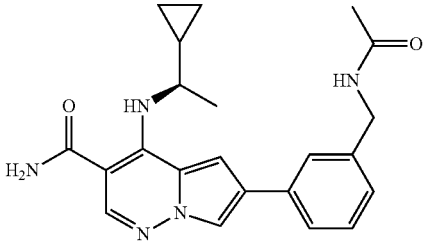 [SMILES: CC(=O)NCc1cccc(-c2cc3c(N[C@H](C)C4CC4)c(C(N)=O)cnn3c2)c1] | 1.44 (H) | 392.2 |
| 91 | 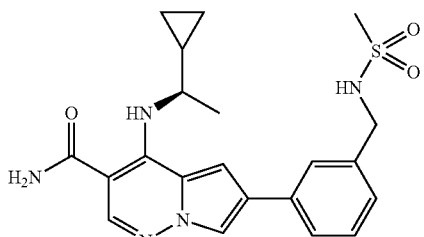 | 1.57 (H) | 428.2 |
| 92 | 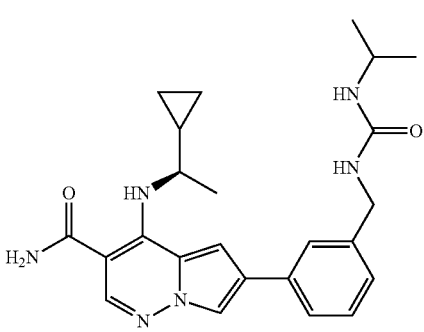 [SMILES: CC(C)NC(=O)NCc1cccc(-c2cc3c(N[C@H](C)C4CC4)c(C(N)=O)cnn3c2)c1] | 1.63 (H) | 435.3 |
| 93 | 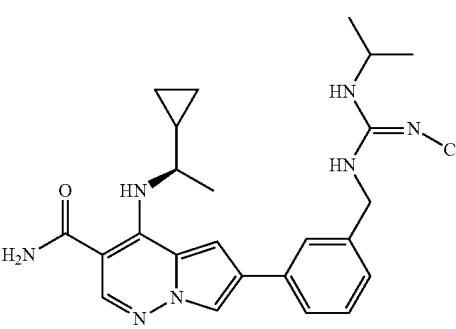 | 1.70 (H) | 459.3 |

-continued

| Ex # | Structure | HPLC Rt (minutes) | LCMS [m/z (M + H)] |
|---|---|---|---|
| 94 | 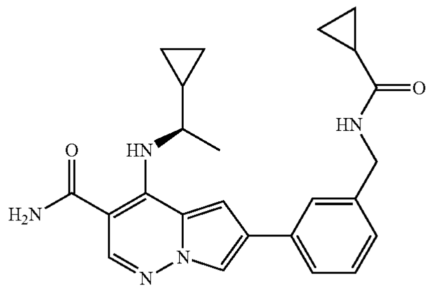 [SMILES: C[C@@H](Nc1c(C(N)=O)cnn2cc(-c3cccc(CNC(=O)C4CC4)c3)cc12)C1CC1] | 1.53 (H) | 418.3 |
| 95 | 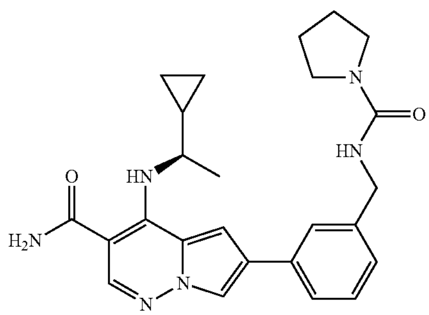 [SMILES: C[C@@H](Nc1c(C(N)=O)cnn2cc(-c3cccc(CNC(=O)N4CCCC4)c3)cc12)C1CC1] | 1.54 (H) | 447.3 |
| 96 | 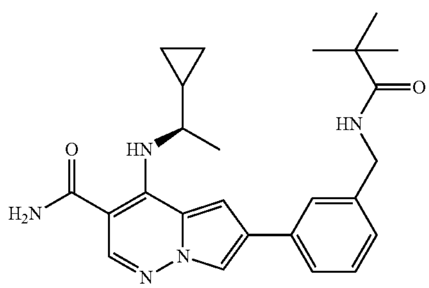 [SMILES: C[C@@H](Nc1c(C(N)=O)cnn2cc(-c3cccc(CNC(=O)C(C)(C)C)c3)cc12)C1CC1] | 1.71 (H) | 434.4 |
| 97 | 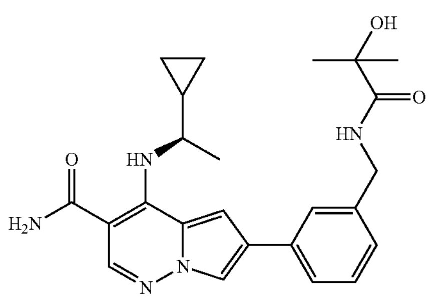 [SMILES: C[C@@H](Nc1c(C(N)=O)cnn2cc(-c3cccc(CNC(=O)C(C)(C)O)c3)cc12)C1CC1] | 1.41 (H) | 436.4 |
| 98 | 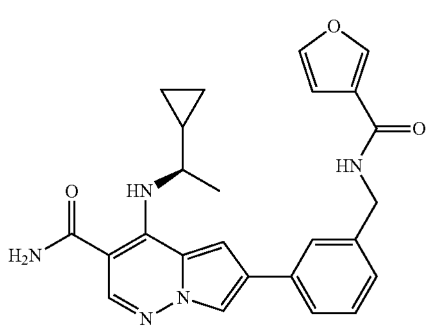 [SMILES: C[C@@H](Nc1c(C(N)=O)cnn2cc(-c3cccc(CNC(=O)c4ccoc4)c3)cc12)C1CC1] | 1.58 (H) | 444.4 |

-continued

| Ex # | Structure | HPLC Rt (minutes) | LCMS [m/z (M + H)] |
|---|---|---|---|
| 99 | 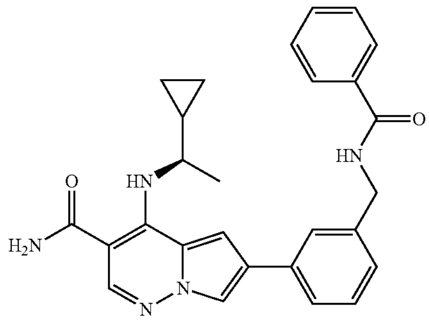 [SMILES: C[C@@H](Nc1c(C(N)=O)cnn2cc(-c3cccc(CNC(=O)c4ccccc4)c3)cc12)C1CC1] | 1.73 (H) | 454.4 |
| 100 | 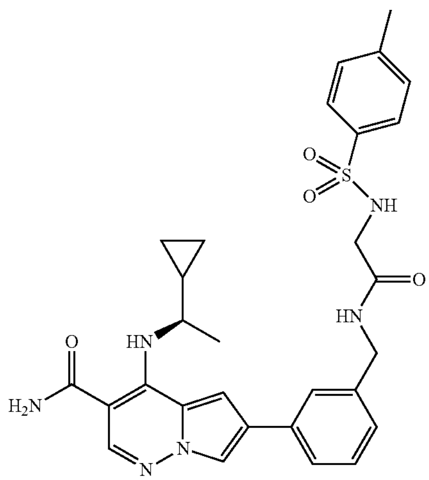 [SMILES: Cc1ccc(S(=O)(=O)NCC(=O)NCc2cccc(-c3cc4c(N[C@H](C)C5CC5)c(C(N)=O)cnn4c3)c2)cc1] | 1.68 (H) | 561.4 |
| 101 | 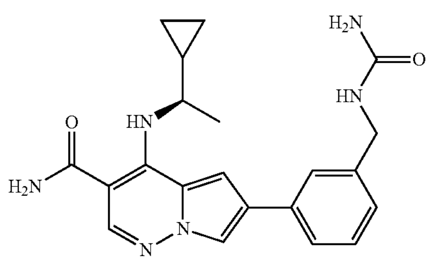 [SMILES: C[C@@H](Nc1c(C(N)=O)cnn2cc(-c3cccc(CNC(N)=O)c3)cc12)C1CC1] | 1.26 (H) | 393.3 |
| 102 | 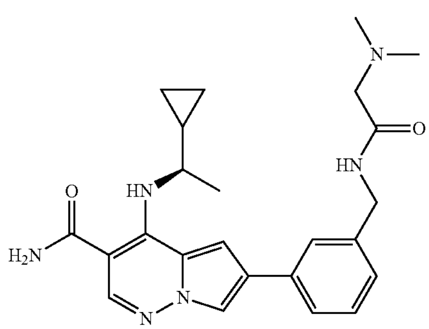 [SMILES: C[C@@H](Nc1c(C(N)=O)cnn2cc(-c3cccc(CNC(=O)CN(C)C)c3)cc12)C1CC1] | 1.18 (H) | 435.4 |

-continued
| Ex # | Structure | HPLC Rt (minutes) | LCMS [m/z (M + H)] |
|---|---|---|---|
| 103 | 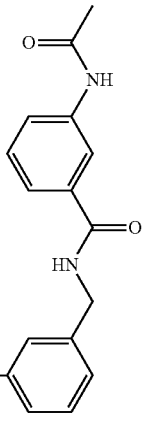 | 1.49 (H) | 511.4 |
| 104 | 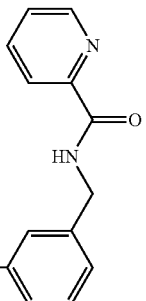 | 1.71 (H) | 455.4 |
| 105 | 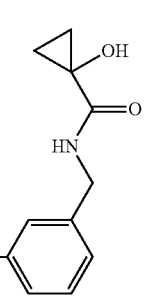 | 1.40 (H) | 434.4 |
| 106 | 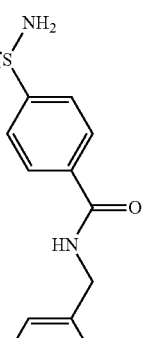 | 3.06 (G) | 533.3 |

-continued

| Ex # | Structure | HPLC Rt (minutes) | LCMS [m/z (M + H)] |
|---|---|---|---|
| 107 | 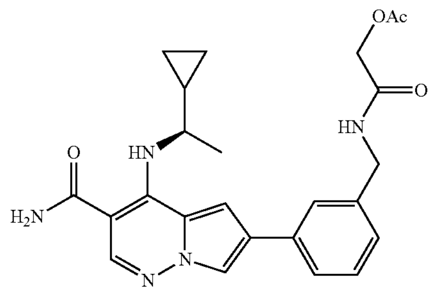 [SMILES: CC(=O)OCC(=O)NCc1cccc(-c2cc3c(N[C@H](C)C4CC4)c(C(N)=O)cnn3c2)c1] | 3.06 (G) | 450.4 |
| 108 | 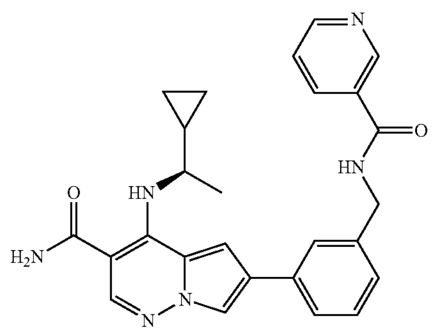 [SMILES: C[C@@H](Nc1c(C(N)=O)cnn2cc(-c3cccc(CNC(=O)c4cccnc4)c3)cc12)C1CC1] | 3.07 (G) | 455.1 |
| 109 | 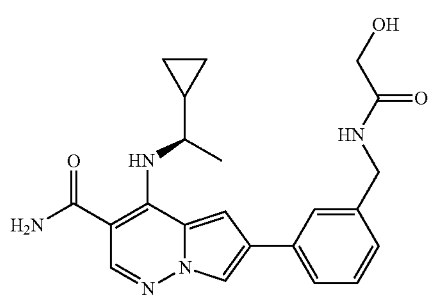 [SMILES: C[C@@H](Nc1c(C(N)=O)cnn2cc(-c3cccc(CNC(=O)CO)c3)cc12)C1CC1] | 2.96 (G) | 408.1 |
| 110 | 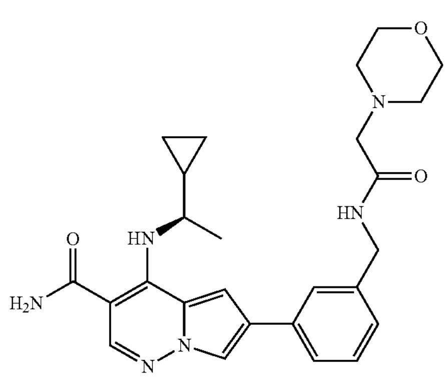 [SMILES: C[C@@H](Nc1c(C(N)=O)cnn2cc(-c3cccc(CNC(=O)CN4CCOCC4)c3)cc12)C1CC1] | 2.70 (G) | 477.2 |

Example 111 to 115

Example 111 in the table below was prepared from Example 84 using the procedure described for Example 87. Examples 112 and 113 were prepared from Example 84 and the appropriate acid chlorides using standard acylation methods. Examples 114 and 115 were prepared from Example 84 using diphenyl cyanocarbonimidate and the appropriate amine under standard conditions.

| Ex # | Structure | HPLC Rt, min. (conditions) | LCMS [m/z (M + H)] |
|---|---|---|---|
| 111 | 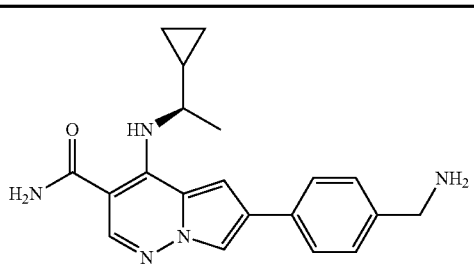 | 2.34 (G) | 350.1 |
| 112 | 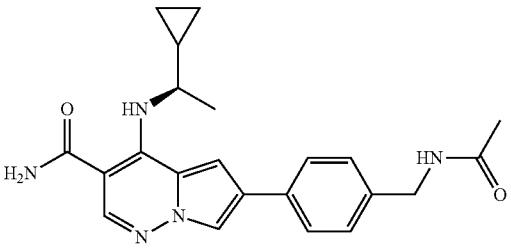 [SMILES: CC(=O)NCc1ccc(-c2cc3c(N[C@H](C)C4CC4)c(C(N)=O)cnn3c2)cc1] | 1.31 (H) | 392.4 |
| 113 | 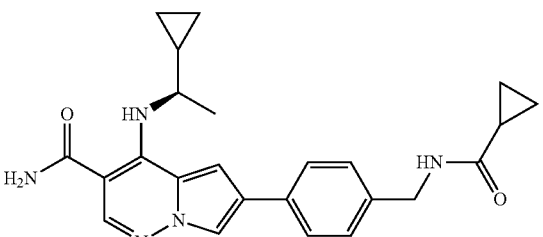 | 1.50 (H) | 418.4 |
| 114 | 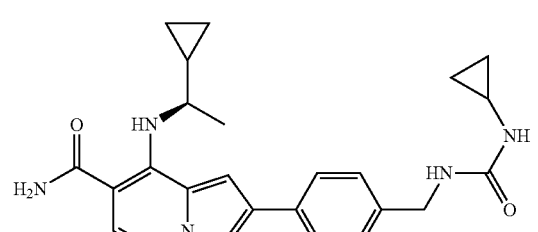 | 1.41 (H) | 433.4 |
| 115 | 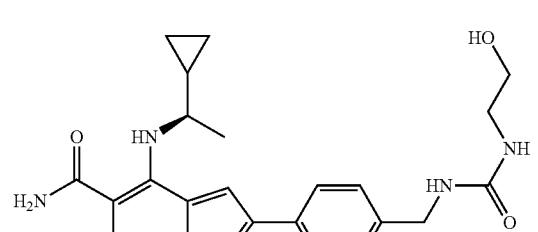 | 1.19 (H) | 437.4 |

Example 116

4-(((1R)-1-cyclopropylethyl)amino)-6-(3-(dimethylcarbamoyl)phenyl)pyrrolo[1,2-b]pyridazine-3-carboxamide

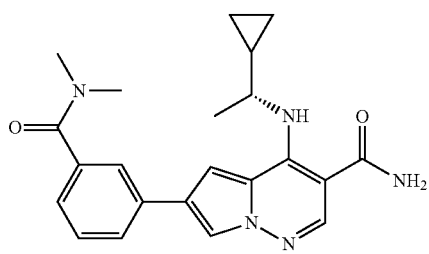

(116)

To a solution of (R)-3-(3-carbamoyl-4-(1-cyclopropylethylamino) pyrrolo[1,2-b]pyridazin-6-yl)benzoic acid (Example 85, 15 mg, 0.041 mmol), dimethylamine (0.021 mL, 0.041 mmol) and triethylamine (8.61 µl, 0.062 mmol) in DMF (0.5 mL) was added BOP (18.21 mg, 0.041 mmol) which was stirred at 23° C. for 30 minutes. The reaction mixture was purified by reverse-phase preparative HPLC (condition C) to yield the title compound (5.7 mg, 35%). HPLC (condition H): retention time=1.47 minutes. LC/MS (M+H)$^+$=392.3. $^1$H NMR (500 MHz, MeOD) δ ppm 8.06 (1 H, s), 7.86 (1 H, d, J=1.9 Hz), 7.67-7.71 (1 H, m), 7.64 (1 H, t, J=1.4 Hz), 7.45 (1 H, t, J=7.6 Hz), 7.24-7.27 (1 H, m), 7.09 (1 H, d, J=1.7 Hz), 4.01-4.09 (1H, m), 3.13 (3 H, s), 3.04 (3 H, s), 1.44 (3 H, d, J=6.4 Hz), 1.09-1.18 (1 H, m), 0.57 (2H, dd, J=13.5, 8.7 Hz), 0.34-0.41 (2 H, m).

Examples 117 to 119

Examples 117 to 119 in the table below were prepared from (R)-3-(3-carbamoyl-4-(1-cyclopropylethylamino)pyrrolo[1,2-b]pyridazin-6-yl)benzoic acid (Example 85) and the appropriate commercially available amine using the general procedure described for Example 116.

| Ex # | Structure | HPLC Rt, min. (conditions) | LCMS [m/z (M + H)] |
|---|---|---|---|
| 117 | 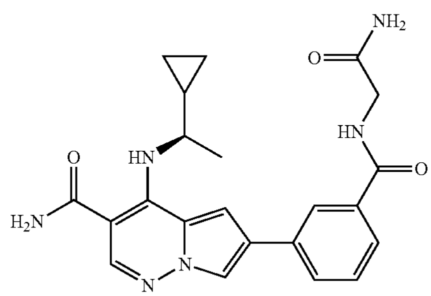 [SMILES: C[C@@H](Nc1c(C(N)=O)cnn2cc(-c3cccc(C(=O)NCC(N)=O)c3)cc12)C1CC1] | 1.18 (H) | 421.3 |
| 118 | 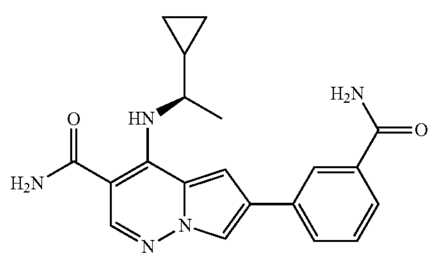 [SMILES: C[C@@H](Nc1c(C(N)=O)cnn2cc(-c3cccc(C(N)=O)c3)cc12)C1CC1] | 1.27 (H) | 364.3 |
| 119 | 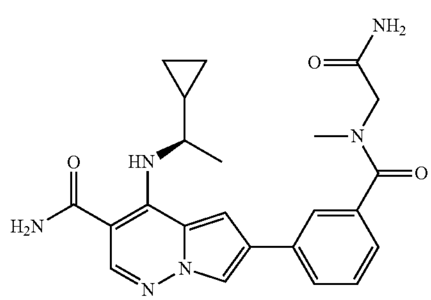 [SMILES: C[C@@H](Nc1c(C(N)=O)cnn2cc(-c3cccc(C(=O)N(C)CC(N)=O)c3)cc12)C1CC1] | 1.18 (H) | 435.4 |

Intermediate 5

4-(((1R)-1-(1-fluorocyclopropyl)ethyl)amino)pyrrolo[1,2-b]pyridazine-3-carboxamide

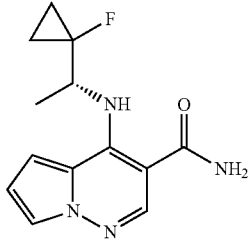
(Int-5)

Step 1: (R)-2-Dibenzylamino-propionic acid methyl ester.

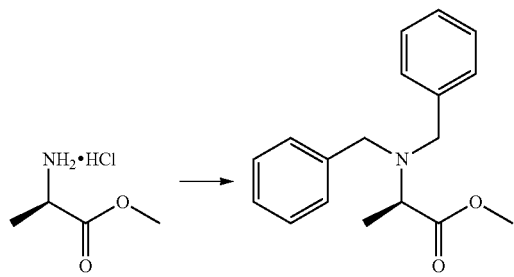

Potassium carbonate (49.5 g, 358 mmol) and benzyl bromide (42.5 mL, 358 mmol) were each added to a partial solution of (R)-methyl 2-aminopropanoate hydrochloride (10 g, 71.6 mmol) in acetonitrile (200 mL) and the reaction was allowed to stir at 60° C. overnight. The reaction was filtered and the filtrate evaporated in vacuo. The residue was purified by column chromatography using hexane (to elute the excess benzyl bromide) followed by 5:1 hexane:ethyl acetate to elute the product. After concentration and drying of the fractions containing the major product, the title compound (20.13 g, 71.0 mmol, 99% yield) was obtained as a colorless oil. HPLC (condition B): retention time=2.80 min. LCMS (condition B): m/z 284.2. $^1$H NMR (500 MHz, MeOD) δ ppm 7.38-7.44 (4 H, m), 7.34 (4 H, t, J=7.63 Hz), 7.22-7.30 (2 H, m), 3.84 (2 H, d, J=13.87 Hz), 3.77 (3 H, s), 3.65 (2 H, d, J=13.87 Hz), 3.52 (1 H, q, J=7.12 Hz), 1.35 (3 H, d, J=7.21 Hz).

Step 2: 1-((R)-1-Dibenzylamino-ethyl)-cyclopropanol.

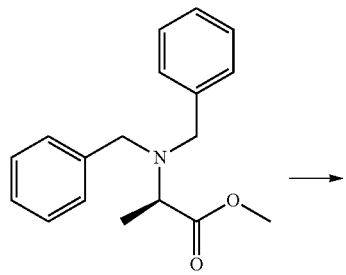

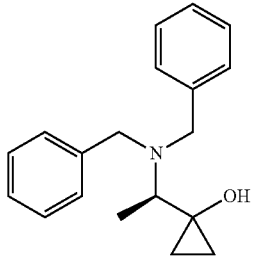

Ethylmagnesium bromide (52.9 mL, 52.9 mmol) was added dropwise via a pressure equalizing dropping funnel to a solution of (R)-methyl 2-(dibenzylamino) propanoate (5.0 g, 17.65 mmol) and titanium (IV) isopropoxide (1.034 mL, 3.53 mmol) in THF (50 mL) at rt. The mixture was stirred at rt overnight before quenching with sat. ammonium chloride solution. The separated organic layer was then evaporated in vacuo to give the crude title compound (5.3 g, 18.83 mmol, 107% yield) which was used immediately in the next step without further purification. HPLC (condition B): retention time=2.06 min. LCMS (condition B): m/z 282.2. $^1$H NMR (500 MHz, MeOD) δ ppm 7.38-7.43 (3 H, m), 7.30-7.35 (3 H, m), 7.21-7.28 (2 H, m), 4.15 (1 H, q, J=7.21 Hz), 4.03 (2 H, d, J=13.87 Hz), 3.60 (2 H, d, J=13.59 Hz), 2.66 (1 H, q, J=6.94 Hz), 2.06 (1 H, s), 1.29 (1 H, t, J=7.07 Hz), 1.17 (2 H, d, J=6.66 Hz), 0.78 (1 H, ddd, J=10.61, 6.17, 4.86 Hz), 0.57-0.64 (1 H, m), 0.50-0.57 (1 H, m), 0.44-0.50 (1 H, m).

Step 3: Dibenzyl-[(R)-1-(1-fluoro-cyclopropyl)-ethyl]-amine.

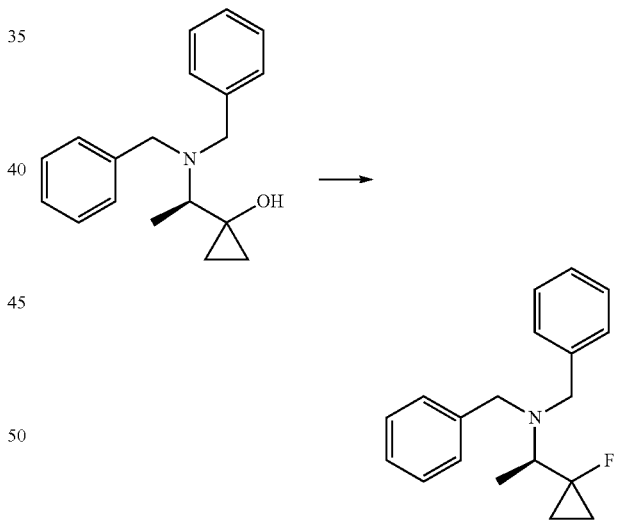

DAST (2.99 ml, 22.60 mmol) was added dropwise to a stirred solution of (R)-1-(1-(dibenzylamino)ethyl)cyclopropanol (5.3 g, 18.83 mmol) in dichloromethane (94 ml) at −78° C. under a nitrogen atmosphere. The reaction was allowed to stir for about 2 hrs before quenching with sat. sodium bicarbonate solution (100 mL) via dropwise addition. The quenched reaction was allowed to warm slowly to rt overnight. The organic layer was separated, dried (MgSO$_4$) and evaporated in vacuo before purifying by column chromatography using hexane to 2% ethyl acetate in hexane as eluent to give the title compound (1.16 g, 4.09 mmol, 21.73% yield). HPLC (condition B): retention time=3.69 min. LCMS (condition B): m/z 284.2. $^1$H NMR (400 MHz, MeOD) δ ppm 7.11-7.52 (10 H, m), 4.98-5.32 (1 H, m), 3.76-4.08 (4 H, m), 1.08-1.42 (3 H, m), 0.47-0.82 (4 H, m).

Step 4: (R)-1-(1-fluorocyclopropyl)ethanamine hydrochloride

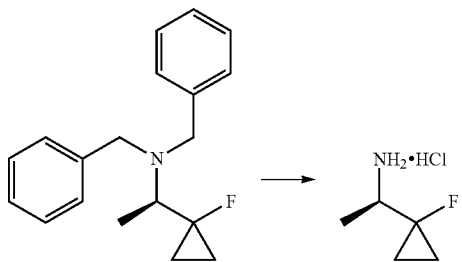

Pearlman's catalyst (0.575 g, 4.09 mmol) was added to a solution of dibenzyl-[(R)-1-(1-fluoro-cyclopropyl)-ethyl]-amine (1.16 g, 4.09 mmol) in anhydrous MeOH (16 mL) and the mixture hydrogenated under a balloon of hydrogen overnight. The mixture was then filtered and hydrochloric acid (1.25M in MeOH) (4.09 ml, 5.12 mmol) added. The mixture was then evaporated in vacuo to give the title compound (243 mg, 1.741 mmol, 42.5% yield). $^1$H NMR (400 MHz, MeOD) δ ppm 4.50-4.79 (1 H, m), 1.38-1.53 (3 H, m), 0.94-1.22 (4 H, m).

Step 5: (R)-4-(1-(1-fluorocyclopropyl)ethylamino) pyrrolo[1,2-b]pyridazine-3-carboxamide (Intermediate 5)

A solution of 4-chloropyrrolo[1,2-b]pyridazine-3-carboxamide (Preparation 3, 20 mg, 0.102 mmol), (R)-1-(1-fluorocyclopropyl)ethanamine hydrochloride (22 mg, 0.153 mmol), and diisopropylethylamine (0.054 mL, 0.31 mmol) in NMP (0.5 mL) was heated to 120° C. for 10 min in the CEM microwave. The mixture was cooled to rt, diluted with MeOH and purified by reverse-phase Prep HPLC (condition A). The fraction containing the major product was concentrated on the rotovap to remove the MeOH and the aqueous slurry of the product was neutralized by addition of ~1 mL of saturated aqueous sodium bicarbonate. Sonication of the slurry followed by vacuum filtration and air drying in the funnel afforded 4 mg (14%) of a pale yellow solid as the title compound. HPLC (condition B): retention time=3.26 min. LCMS (condition B): MH$^+$ m/z 263.2. $^1$H NMR (500 MHz, MeOD) δ ppm 8.17 (1 H, s), 7.64 (1 H, dd, J=2.64, 1.53 Hz), 7.27 (1 H, dd, J=4.44, 1.39 Hz), 6.74 (1 H, dd, J=4.44, 2.77 Hz), 5.07 (1 H, br. s.), 1.37-1.56 (3 H, m), 1.01-1.37 (4 H, m).

Intermediate 6

(R)-6-bromo-4-(1-(1-fluorocyclopropyl)ethylamino) pyrrolo[1,2-b]pyridazine-3-carboxamide (Int-6)

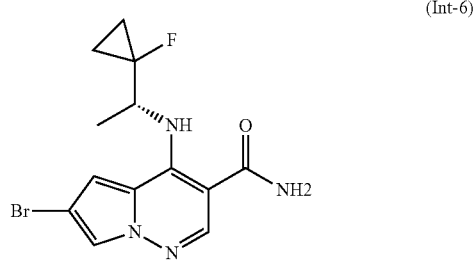 [SMILES: C[C@@H](Nc1c(C(N)=O)cnn2cc(Br)cc12)C1(F)CC1]

A solution of 6-bromo-4-chloropyrrolo[1,2-b]pyridazine-3-carboxamide (Preparation 5, 200 mg, 0.73 mmol), (R)-1-(1-fluorocyclopropyl)ethanamine hydrochloride (153 mg, 1.1 mmol, from step 4 of Intermediate 5), and diisopropyl-ethylamine (0.38 mL, 2.2 mmol) in NMP (0.7 mL) was heated to 150° C. for 1 hour in the CEM microwave. The mixture was cooled to rt, diluted with MeOH and purified by reverse-phase Prep HPLC (condition A). The fraction containing the major product was concentrated on the rotovap to remove the MeOH and the aqueous slurry of the product was neutralized by addition of ~1 mL of saturated aqueous sodium bicarbonate. Sonication of the slurry followed by vacuum filtration and air drying in the funnel afforded 40 mg (16%) of a pale yellow solid as the title compound. HPLC (condition B): retention time=3.75 min. LCMS (condition B): MH$^+$ m/z 342.7.

Example 120

4-(((1R)-1-(1-fluorocyclopropyl)ethyl)amino)-6-phenylpyrrolo[1,2-b]pyridazine-3-carboxamide (120)

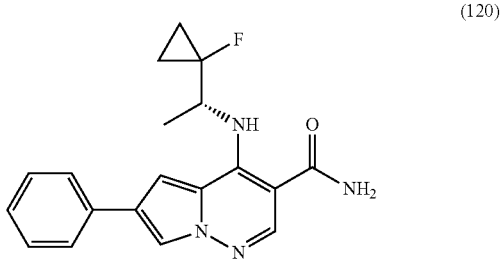 [SMILES: C[C@@H](Nc1c(C(N)=O)cnn2cc(-c3ccccc3)cc12)C1(F)CC1]

Potassium phosphate (2M aqueous solution, 0.11 mL, 0.22 mmol) was added in one portion to a stirred solution of (R)-6-bromo-4-(1-(1-fluorocyclopropyl)ethylamino)-pyrrolo[1,2-b]pyridazine-3-carboxamide (Intermediate 6, 10 mg, 0.029 mmol), phenyl boronic acid (5.4 mg, 0.044 mmol), X-Phos ligand (1.4 mg, 0.0029 mmol) and palladium acetate (0.3 mg, 0.0015 mmol) in anhydrous 1,4-dioxane (0.12 mL). The resulting biphasic mixture was then heated in the CEM microwave at 140° C. for 30 min. The reaction was allowed to cool to rt and the phases separated. The aqueous phase was extracted with ethyl acetate (2×5 mL). The combined organics were then dried (MgSO$_4$) and evaporated in vacuo before purifying by reverse-phase Prep HPLC (condition A). The fraction containing the major product was concentrated on the rotovap to afford 2 mg (20%) of the title compound as a white solid. HPLC (condition B): retention time=4.00 min. LCMS (condition B): MH$^+$ m/z 339.2. $^1$H NMR (400 MHz, MeOD) δ ppm 8.20 (1 H, s), 8.02 (1 H, d, J=1.76 Hz), 7.71 (1 H, dd, J=8.36, 1.10 Hz), 7.57 (1 H, d, J=1.98 Hz), 7.45 (2 H, t, J=7.70 Hz), 7.31 (2 H, t, J=7.37 Hz), 5.07 (1 H, br. s.), 1.40-1.64 (4 H, m), 1.35 (3 H, br. s.).

Example 121

(S)-methyl 2-(3-carbamoyl-6-phenylpyrrolo[1,2-b]pyridazin-4-ylamino)-2-phenylacetate

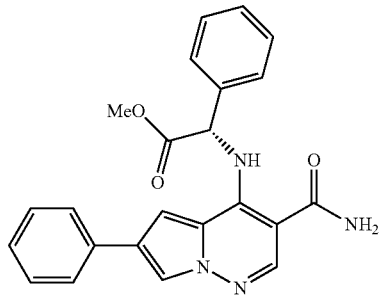

(121)

Step 1: (S)-methyl 2-(6-bromo-3-carbamoylpyrrolo[1,2-b]pyridazin-4-ylamino)-2-phenylacetate

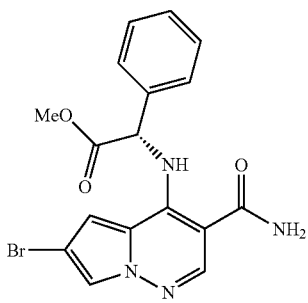 [SMILES: COC(=O)[C@@H](Nc1c(C(N)=O)cnn2cc(Br)cc12)c1ccccc1]

6-Bromo-4-chloropyrrolo[1,2-b]pyridazine-3-carboxamide (Preparation 5, 2.0 g, 7.29 mmol), (S)-methyl 2-amino-2-phenylacetate hydrochloride (2.20 g, 10.93 mmol) and DIPEA (3.82 mL, 21.86 mmol) in NMP (10 mL) were heated in the CEM microwave at 80° C. for 1 hr. The reaction was then quenched with ice-water and the resulting precipitate filtered. The crude solid was purified by column chromatography using hexane:ethyl acetate as eluent to give the title compound (1.32 g, 3.27 mmol, 44.9% yield) as a white solid. HPLC (condition B): retention time=0.93 min. LCMS (condition B): m/z 403.2, 405.2. $^1$H NMR (400 MHz, DMSO-$d_6$) δ ppm 11.52 (1 H, d, J=7.48 Hz), 8.31 (1 H, s), 7.88 (1 H, d, J=1.54 Hz), 7.11-7.72 (3H, m), 6.93 (2 H, d, J=1.76 Hz), 6.12 (1 H, d, J=7.70 Hz), 3.31 (3 H, s).

Step 2

Example 121

Potassium phosphate (2M aqueous solution, 2.89 mL, 5.75 mmol) was added in one portion to a stirred solution of (S)-methyl 2-(6-bromo-3-carbamoylpyrrolo[1,2-b]pyridazin-4-ylamino)-2-phenylacetate (773 mg, 1.92 mmol, from step 1), phenyl boronic acid (351 mg, 2.88 mmol), X-Phos ligand (91 mg, 0.192 mmol) and palladium acetate (21.52 mg, 0.096 mmol) in anhydrous 1,4-dioxane (7.6 mL). The resulting biphasic mixture was then heated in the CEM microwave at 120° C. for 30 min. The reaction was allowed to cool to rt and the phases separated. The aqueous phase was extracted with ethyl acetate (2×10 mL). The combined organics were then dried (MgSO$_4$) and evaporated in vacuo before purifying by column chromatography using hexane:ethyl acetate as eluent to give the title compound (880 mg, 2.253 mmol, 100% yield) as a yellow solid. HPLC (condition B): retention time=0.97 min. LCMS (condition B): MH$^+$ m/z 401.3. $^1$H NMR (400 MHz, DMSO-$d_6$) δ ppm 11.54 (1 H, d, J=7.70 Hz), 8.29 (2 H, s), 8.18 (2 H, d, J=1.32 Hz), 7.72 (2 H, d, J=7.48 Hz), 7.59 (1 H, d, J=7.48 Hz), 7.30-7.50 (4 H, m), 7.18-7.30 (1 H, m), 6.31 (1 H, d, J=7.48 Hz), 3.31 (3 H, s).

Example 122

(S)-2-(3-carbamoyl-6-phenylpyrrolo[1,2-b]pyridazin-4-ylamino)-2-phenylacetic acid

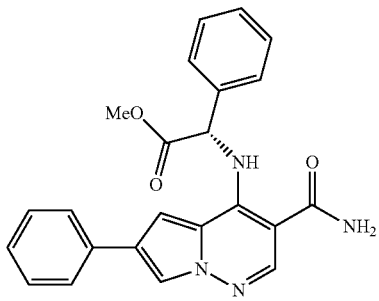

(122)

Sodium hydroxide (11.200 ml, 11.20 mmol) added in one portion to a heterogeneous mixture of (S)-methyl 2-(3-carbamoyl-6-phenylpyrrolo[1,2-b]pyridazin-4-ylamino)-2-phenylacetate (Example 121, 900 mg, 2.248 mmol) in MeOH (30 ml) and THF (15 ml). The reaction was allowed to stir at rt for ca. 2.5 hrs before removing the solvent in vacuo and cooling the flask in an ice bath. 1N aq. HCl was added and the yellow precipitate was then filtered and allowed to dry overnight. This afforded the title compound (915 mg, 100%) as a pale yellow solid. HPLC (condition B): retention time=0.87 min. LCMS (condition B): MH$^+$ m/z 387.2. $^1$H NMR (400 MHz, DMSO-$d_6$) δ ppm 11.38 (1 H, d, J=7.04 Hz), 8.23 (1 H, s), 8.10 (1 H, d, J=1.54 Hz), 7.66 (2 H, d, J=7.26 Hz), 7.55 (2 H, d, J=7.48 Hz), 7.36 (5 H, q, J=7.92 Hz), 7.12-7.29 (4 H, m), 5.93 (1 H, br. s.).

Example 123

4-(((1S)-2-((cyanomethyl)amino)-2-oxo-1-phenylethyl)amino)-6-phenylpyrrolo[1,2-b]pyridazine-3-carboxamide

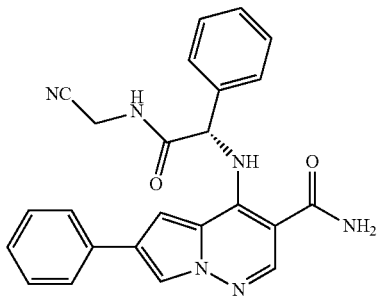

(123)

BOP reagent (17.2 mg, 0.039 mmol) was added in one portion to a solution of (S)-2-(3-carbamoyl-6-phenylpyrrolo[1,2-b]pyridazin-4-ylamino)-2-phenylacetic acid (Example 122, 10 mg, 0.026 mmol), 2-aminoacetonitrile (1.82 mg, 0.032 mmol) and triethylamine (0.011 ml, 0.078 mmol) in DMF (0.01 ml). The reaction was allowed to stir at rt for 1 hour before being purified by reverse-phase Prep HPLC (condition A). The fraction containing the major product was concentrated on the rotovap to remove the MeOH and the aqueous slurry of the product was neutralized by addition of ~1 mL of saturated aq sodium bicarbonate. Sonication of the slurry followed by vacuum filtration and air drying in the funnel afforded the title compound (7 mg, 60% yield). HPLC (condition B): retention time=1.57 min. LCMS (condition B): MH+ m/z 425.2. $^1$H NMR (500 MHz, MeOD) δ ppm 8.33 (1H, s), 8.07 (1 H, d, J=1.66 Hz), 7.86 (1 H, s), 7.75 (4 H, dd, J=7.63, 2.08 Hz), 7.60 (2H, t, J=7.49 Hz), 7.49-7.57 (3 H, m), 7.41 (1 H, t, J=7.35 Hz), 7.31 (1 H, d, J=1.66 Hz), 6.11 (1 H, s), 4.22-4.44 (1 H, m), 3.17 (2 H, s).

Examples 124 to 125

Examples 124 to 125 in the table below were prepared from Example 122 and the appropriate commercially available amines using the procedure described for Example 123.

| Ex # | Structure | HPLC Rt, min. (conditions) | LCMS [m/z (M + H)] |
|---|---|---|---|
| 124 | 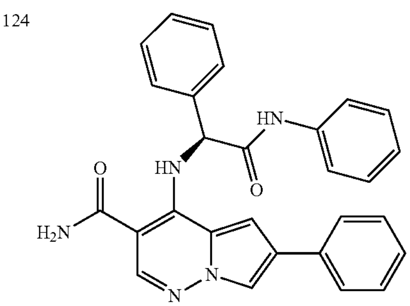 | 1.92 (H) | 462.2 |
| 125 | 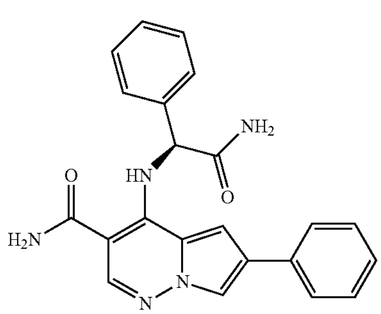 [SMILES: NC(=O)c1cnn2cc(-c3ccccc3)cc2c1N[C@H](C(N)=O)c1ccccc1] | 1.98 (H) | 386.0 |

Example 126

(R)-4-(1-cyclopropylethylamino)-6-(5-thioxo-4,5-dihydro-1,3,4-oxadiazol-2-yl) pyrrolo[1,2-b]pyridazine-3-carboxamide

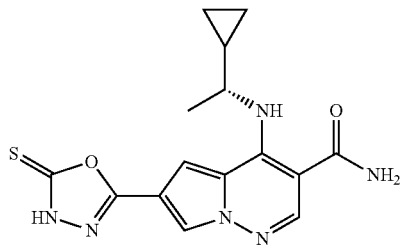

(126)

Step 1: (R)-ethyl 3-carbamoyl-4-((1-cyclopropylethyl)amino)pyrrolo[1,2-b]pyridazine-6-carboxylate A solution of ethyl 3-carbamoyl-4-chloropyrrolo[1,2-b]pyridazine-6-carboxylate (1.0 g, 3.74 mmol), (R)-1-cyclopropylethanamine, HCl (0.500 g, 4.11 mmol) and DIPEA (1.468 mL, 8.41 mmol) in NMP (Volume: 5 mL) was heated to 100° C. for 4 hr. The reaction mixture was added 30 mL of water and stirred for 10 minutes. The solid was collected as the desired product (1.1 g, 86% yield). $^1$H NMR (400 MHz, CD$_3$OD) δ 8.22 (s, 1H), 8.03 (d, J=1.8 Hz, 1H), 7.34 (d, J=1.8 Hz, 1H), 4.38 (q, J=7.2 Hz, 2H), 4.08-3.96 (m, 1H), 1.46 (d, J=6.4 Hz, 3H), 1.41 (t, J=7.2 Hz, 3H), 1.22-1.12 (m, 1H), 0.62 (dd, J=10.9, 8.3 Hz, 2H), 0.43-0.36 (m, 2H). MS (ES+) m/z: 317.1 (M+H); HPLC: 92.6%, retention time: 3.080 min (analytical HPLC Method Q).

Step 2: (R)-3-carbamoyl-4-((1-cyclopropylethyl)amino)pyrrolo[1,2-b]pyridazine-6-carboxylic acid

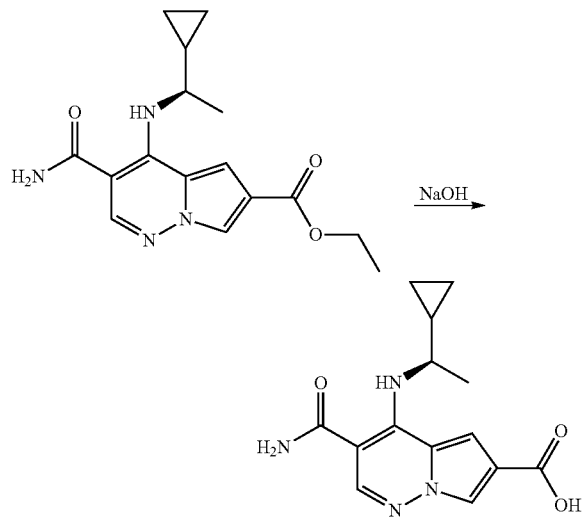

A solution of (R)-ethyl 3-carbamoyl-4((1-cyclopropylethyl)amino) pyrrolo[1,2-b]pyridazine-6-carboxylate (1.1 g, 3.48 mmol) and NaOH 1N solution (5.22 mL, 5.22 mmol) in EtOH (Volume: 20 mL) was heated to 100° C. for 15 minutes. The reaction mixture was concentrated to yield a crude product. The crude product was added to 30 mL of water and acidified with 1 N HCl solution until a pH of about 4. The solid was collected as the desired product (0.972 g, 91% yield). MS (ES+) m/z: 289.1 (M+H); HPLC: 94.3%, retention time: 2.467 min (analytical HPLC Method Q).

Step 3: (R)-4-(1-cyclopropylethylamino)-6-(hydrazinecarbonyl)pyrrolo[1,2-b]-yridazine-3-carboxamide

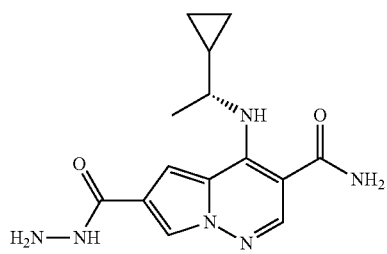 [SMILES: C[C@@H](Nc1c(C(N)=O)cnn2cc(C(=O)NN)cc12)C1CC1]

HOBT (0.319 g, 2.081 mmol) was added followed by EDC (0.432 g, 2.255 mmol) to a stirred solution of (R)-3-carbamoyl-4-(1-cyclopropylethylamino) pyrrolo[1,2-b]pyridazine-6-carboxylic acid (0.5 g, 1.734 mmol) in anhydrous DMF (5.78 ml). The reaction mixture was allowed to stir at room temperature for about 1 hr before the dropwise addition of hydrazine (1.089 ml, 34.7 mmol). The resulting mixture was allowed to stir at rt for 30 min. before quenching with water. The mixture was stirred at rt overnight. The resulting precipitate was filtered with suction and dried to give the title compound (400 mg, 1.323 mmol, 76% yield). HPLC (condition B): retention time=3.00 min. LCMS (condition B): m/z 303.0. $^1$H NMR (500 MHz, DMSO-d$_6$) δ ppm 10.81 (1 H, d, J=8.32 Hz), 9.52 (1 H, br. s.), 8.24 (1 H, s), 8.01 (1 H, d, J=1.39 Hz), 7.30 (1 H, s), 3.75-4.13 (1 H, m), 1.18-1.52 (3 H, m), 0.93-1.18 (1 H, m), 0.40-0.68 (2 H, m), 0.14-0.40 (2 H, m).

Step 3

Example 126

Di(1H-imidazol-1-yl)methanethione (295 mg, 1.654 mmol) was added in one portion to a solution of (R)-4-(1-cyclopropylethylamino)-6-(hydrazinecarbonyl)pyrrolo[1,2-b]pyridazine-3-carboxamide (400 mg, 1.323 mmol) in anhydrous THF (10 ml). The reaction mixture was allowed to reflux for 8 hrs, then cooled to rt and evaporated in vacuo. MeOH was added and the resulting precipitate was then filtered to give 150 mg (33%) of the title compound. The filtrate was evaporated in vacuo and taken on directly into the next reaction. HPLC (condition B): retention time=3.97 min. LCMS (condition B): MH$^+$ m/z 345.0. $^1$H NMR (400 MHz, DMSO-d$_6$) δ ppm 10.92 (1 H, br. s.), 8.16-8.39 (2 H, m), 7.25 (1 H, s), 3.95 (1 H, br. s.), 1.34 (3 H, d, J=6.16 Hz), 1.11 (1 H, br. s.), 0.19-0.59 (4 H, m).

Example 127

(R)-4-(1-cyclopropylethylamino)-6-(5-(methylthio)-1,3,4-oxadiazol-2-yl)pyrrolo[1,2-b]pyridazine-3-carboxamide

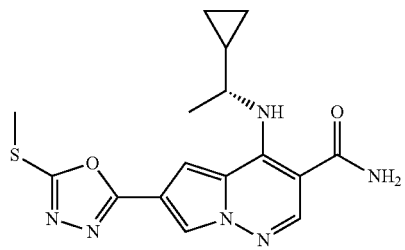

(127)

Iodomethane (0.069 ml, 1.111 mmol) was added in one portion to a stirred solution of (R)-4-(1-cyclopropylethylamino)-6-(5-thioxo-4,5-dihydro-1,3,4-oxadiazol-2-yl)pyrrolo[1,2-b]pyridazine-3-carboxamide (Example 126, 306 mg, 0.889 mmol) and triethylamine (0.310 ml, 2.221 mmol) in absolute EtOH (3.55 ml). The reaction mixture was allowed to stir at rt for 2 hrs before evaporating in vacuo. The residue was then partitioned between 1N HCl and ethyl acetate. The organic layer was dried (MgSO$_4$) and evaporated in vacuo. The residue was treated with MeOH and the solid filtered to give the title compound (135 mg, 0.377 mmol, 42.4% yield) as a white solid. The filtrate (which contained the remainder of the product) was evaporated and retained. HPLC (condition B): retention time=3.98 min. LCMS (condition B): MH$^+$ m/z 358.9. $^1$H NMR (500 MHz, DMSO-d$_6$) δ ppm 10.88 (1 H, d, J=8.32 Hz), 8.31 (1 H, s), 8.27 (1 H, d, J=1.66 Hz), 7.32 (1 H, d, J=1.94 Hz), 3.89-4.04 (1 H, m), 3.30 (3 H, s), 1.34 (3 H, d, J=6.38 Hz), 1.01-1.20 (1 H, m), 0.44-0.58 (2 H, m), 0.35-0.44 (1 H, m), 0.20-0.35 (1 H, m).

Example 128

4-(((1R)-1-cyclopropylethyl)amino)-6-(5-(4-morpholinyl)-1,3,4-oxadiazol-2-yl)pyrrolo[1,2-b]pyridazine-3-carboxamide (128)

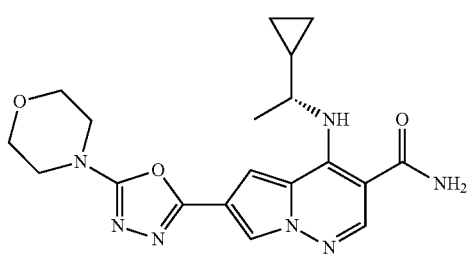

Morpholine (13 mg, 0.14 mmol) was added in one portion to a solution of (R)-4-(1-cyclopropylethylamino)-6-(5-(methylthio)-1,3,4-oxadiazol-2-yl)pyrrolo[1,2-b]pyridazine-3-carboxamide (Example 127, 10 mg, 0.028 mmol) in NMP (0.1 mL). The resulting mixture was heated in the CEM microwave at 200° C. for 1 hour before purifying by reverse-phase Prep HPLC (condition A). The fraction containing the major product was concentrated on the rotovap to remove the MeOH and the aqueous slurry of the product was neutralized by addition of ~1 mL of saturated aqueous sodium bicarbonate. Sonication of the slurry followed by vacuum filtration and air drying in the funnel afforded the title compound (5 mg, 45% yield). HPLC (condition B): retention time=0.73 min. LCMS (condition B): MH+ m/z 398.3. $^1$H NMR (500 MHz, DMSO-$d_6$) δ ppm 10.84 (1 H, br. s.), 8.28 (1 H, s), 8.15 (1 H, d, J=1.39 Hz), 7.22 (1 H, d, J=1.39 Hz), 3.99 (1 H, d, J=1.39 Hz), 3.68-3.82 (4 H, m), 3.44-3.53 (4 H, m), 1.34 (3 H, d, J=6.38 Hz), 1.11 (1 H, d, J=6.94 Hz), 0.44-0.56 (1H, m), 0.39 (1 H, br. s.), 0.31 (2 H, br. s.).

Examples 129 to 143

Examples in the table below were prepared from 6-bromo-4-(((1R)-2-fluoro-1,2-dimethylpropyl)amino)pyrrolo[1,2-b]pyridazine-3-carboxamide (Intermediate 3) and the appropriate commercially available amide, lactam or sultam using the procedure described for Example 37. All examples were analyzed by HPLC (condition H).

| Ex. # | Structure | HPLC Rt, min. (conditions) | LCMS [m/z (M + H)] |
|---|---|---|---|
| 129 | 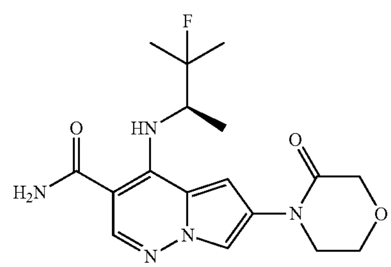 [SMILES: C[C@@H](Nc1c(C(N)=O)cnn2cc(N3CCOCC3=O)cc12)C(C)(C)F] | 1.51 | 364.05 |
| 130 | 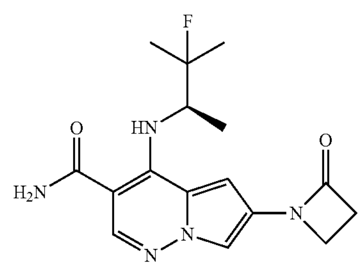 [SMILES: C[C@@H](Nc1c(C(N)=O)cnn2cc(N3CCC3=O)cc12)C(C)(C)F] | 1.53 | 334.03 |
| 131 | 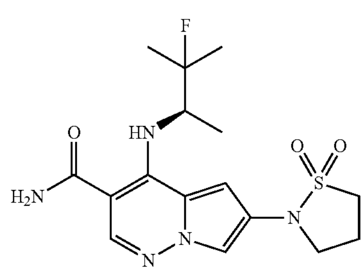 [SMILES: C[C@@H](Nc1c(C(N)=O)cnn2cc(N3CCCS3(=O)=O)cc12)C(C)(C)F] | 1.55 | 384.02 |

-continued

| Ex. # | Structure | HPLC Rt, min. (conditions) | LCMS [m/z (M + H)] |
|---|---|---|---|
| 132 | 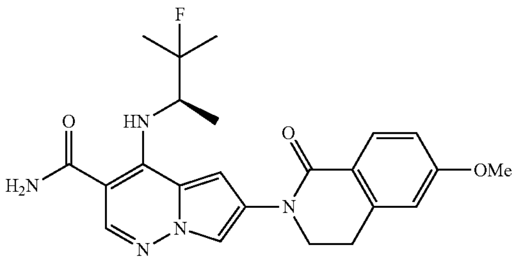 [SMILES: COc1ccc2c(c1)CCN(c1cc3c(N[C@H](C)C(C)(C)F)c(C(N)=O)cnn3c1)C2=O] | 2.15 | 440.05 |
| 133 | Mixture of diastereomers | 2.23 | 424.10 |
| 134 | Mixture of diastereomers | 1.78 | 362.06 |
| 135 | 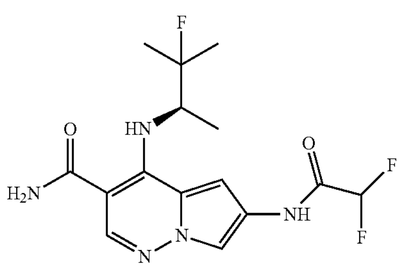 [SMILES: C[C@@H](Nc1c(C(N)=O)cnn2cc(NC(=O)C(F)F)cc12)C(C)(C)F] | 1.62 | 358.03 |
| 136 | 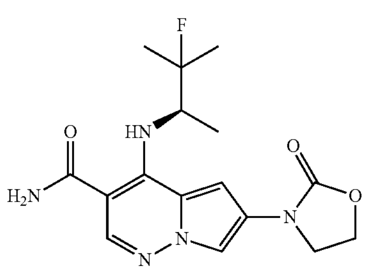 [SMILES: C[C@@H](Nc1c(C(N)=O)cnn2cc(N3CCOC3=O)cc12)C(C)(C)F] | 1.51 | 350.03 |

-continued
| Ex. # | Structure | HPLC Rt, min. (conditions) | LCMS [m/z (M + H)] |
|---|---|---|---|
| 137 | 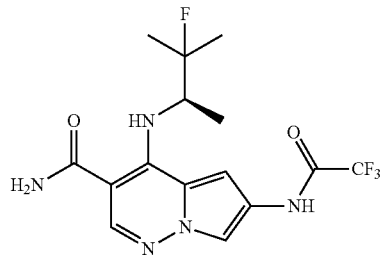 [SMILES: C[C@@H](Nc1c(C(N)=O)cnn2cc(NC(=O)C(F)(F)F)cc12)C(C)(C)F] | 1.91 | 376.02 |
| 138 | 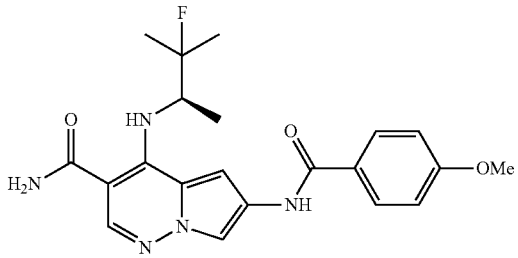 [SMILES: COc1ccc(C(=O)Nc2cc3c(N[C@H](C)C(C)(C)F)c(C(N)=O)cnn3c2)cc1] | 1.97 | 414.05 |
| 139 | 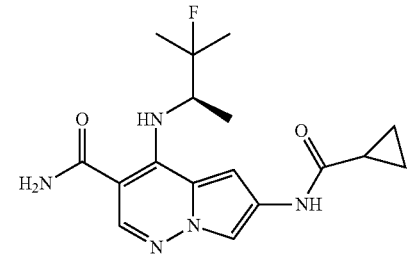 [SMILES: C[C@@H](Nc1c(C(N)=O)cnn2cc(NC(=O)C3CC3)cc12)C(C)(C)F] | 1.58 | 348.11 |
| 140 | 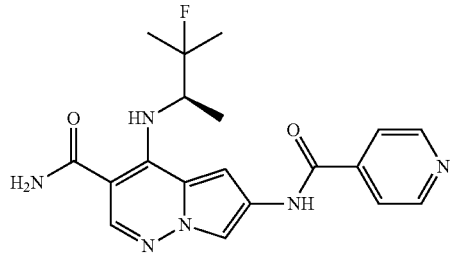 [SMILES: C[C@@H](Nc1c(C(N)=O)cnn2cc(NC(=O)c3ccncc3)cc12)C(C)(C)F] | 1.50 | 385.11 |
| 141 | 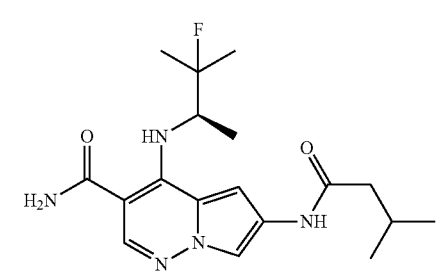 [SMILES: CC(C)CC(=O)Nc1cc2c(N[C@H](C)C(C)(C)F)c(C(N)=O)cnn2c1] | 1.85 | 364.11 |

| Ex. # | Structure | HPLC Rt, min. (conditions) | LCMS [m/z (M + H)] |
|---|---|---|---|
| 142 | 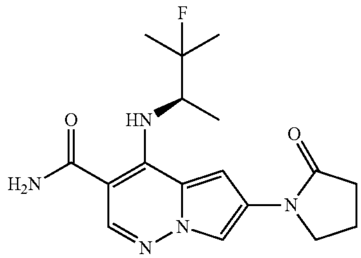 [SMILES: C[C@@H](Nc1c(C(N)=O)cnn2cc(N3CCCC3=O)cc12)C(C)(C)F] | 1.663 | 347.2 |
| 143 | 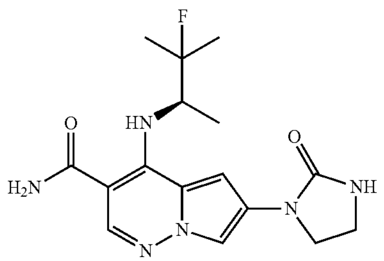 [SMILES: C[C@@H](Nc1c(C(N)=O)cnn2cc(N3CCNC3=O)cc12)C(C)(C)F] | 2.33 (E) | 349.0 |

Example 144

4-(((1R,3 S)-3-amino-2,2,3-trimethylcyclopentyl)amino)-6-(4-(3-oxo-4-morpholinyl)phenyl)pyrrolo[1,2-b]pyridazine-3-carboxamide (144)

Step 1: 4-(4-bromophenyl)morpholin-3-one

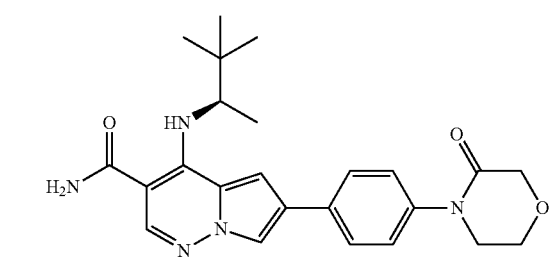

A solution of 1,4-dibromobenzene (283 mg, 1.200 mmol), morpholin-3-one (101 mg, 1 mmol), dibasic potassium phosphate (348 mg, 2 mmol), copper (I) iodide (38.1 mg, 0.20 mmol) and N,N'-dimethylethylenediamine (0.043 ml, 0.40 mmol) in dioxane (3 ml) was purged with nitrogen for 2 min, sealed in a reaction vial and heated in a heating block at 105° C. for 15 h. The crude product mixture was filtered, and charged to a 12 g silica gel cartridge which was eluted with 0-50% EtOAc in hexanes to give the title compound (173 mg, 0.676 mmol, 67.6% yield) as a white solid. $^1$H NMR (400 MHz, CDCl$_3$) δ ppm 10.56 (1 H, none), 7.55 (2 H, d, J=8.80 Hz), 7.24 (2 H, d, J=8.58 Hz), 4.04 (2 H, dd, J=5.83, 4.29 Hz), 3.73-3.79 (2 H, m). HPLC (condition G): ret. time 2.213 min. LC/MS [m/z, (M+H)] 258.0.

Step 2: 4-(4-(4,4,5,5-tetramethyl-1,3,2-dioxaborolan-2-yl)phenyl)morpholin-3-one

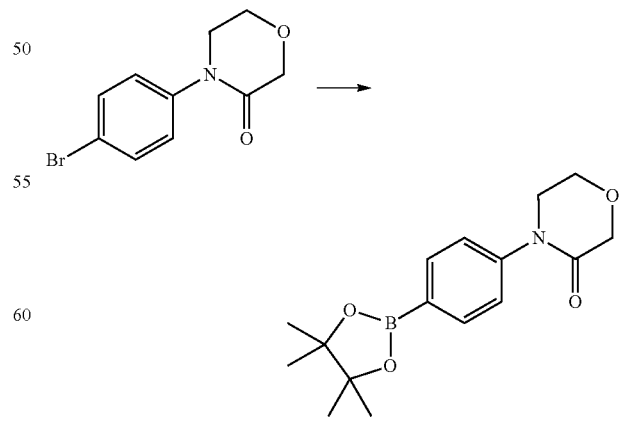

A solution of 4-(4-bromophenyl)morpholin-3-one (150 mg, 0.586 mmol), 4,4,4',4',5,5,5',5'-octamethyl-2,2'-bi(1,3,2- dioxaborolane) (297 mg, 1.171 mmol) and potassium acetate (172 mg, 1.757 mmol) in dioxane (2.0 ml) was purged with nitrogen for 5 min, followed by addition of PdCl$_2$(dppf)-dichloromethane adduct (1:1) (47.8 mg, 0.059 mmol). After purging with nitrogen for additional 2 min, the reaction mixture was sealed in a small vial and heated in a heating block at 100° C. for 12 hrs. The reaction mixture was diluted with ethyl acetate, washed with water and concentrated to give a brown residue. The crude product was charged to a 12 g silica gel cartridge which was eluted with 10-50% EtOAc in hexane to afford after concentration under vacuum the title compound (113 mg, 0.373 mmol, 63.6% yield) as a white solid. $^1$H NMR (400 MHz, MeOD) δ ppm 7.81 (2 H, d, J=8.36 Hz), 7.36-7.42 (2 H, m), 4.29 (2 H, s), 4.04 (2 H, dd, J=5.83, 4.29 Hz), 3.80 (2 H, dd, J=5.83, 4.29 Hz), 1.35 (12 H, s). HPLC (conditions G): ret. time 3.886 min. LC/MS [m/z, (M+H)] 304.0.

Step 3

Example 144

A solution of 4-(3-(4,4,5,5-tetramethyl-1,3,2-dioxaborolan-2-yl)phenyl)morpholin-3-one (47.8 mg, 0.158 mmol), 4-((1R,3S)-3-amino-2,2,3-trimethylcyclopentylamino)-6-bromopyrrolo[1,2-b]pyridazine-3-carboxamide (20 mg, 0.053 mmol), 1,1'-bis(di-t-butyl/diphenylphosphino)ferrocene (2.495 mg, 5.26 μmol), palladium (II) acetate (1.181 mg, 5.26 μmol) and dibasic potassium phosphate (0.079 mL, 0.158 mmol) in DMF (0.4 mL) was purged with nitrogen for 5 min. The reaction mixture was sealed and heated at 93° C. for 120 min. The reaction mixture was diluted with MeOH and filtered. The filtrate was purified by reverse-phase preparative HPLC [Column: YMC 20×100; Mobil phase: B in A: 20%-100% (A: 10% MeOH in H$_2$O with 0.1% TFA, B: 90% MeOH in H$_2$O with 0.1% TFA; gradient time: 15 min., hold time: 5 min] to afford the title compound (7.2 mg, 0.012 mmol, 23.18% yield) as a white solid. $^1$H NMR (400 MHz, MeOD) δ ppm 8.19 (1 H, s), 8.02 (2 H, d, J=1.76 Hz), 7.73 (1 H, t, J=1.76 Hz), 7.66-7.70 (1 H, m), 7.49 (2 H, t, J=7.81 Hz), 7.22-7.29 (2 H, m), 4.71 (1 H, t, J=9.02 Hz), 4.32 (2 H, s), 4.08 (2 H, dd, J=5.83, 4.29 Hz), 3.82-3.87 (2 H, m), 2.45-2.56 (1 H, m), 2.10-2.21 (1 H, m), 2.00-2.09 (1 H, m), 1.77-1.90 (1 H, m), 1.50 (3 H, s), 1.18 (3 H, s), 1.07 (3 H, s). HPLC (conditions G): ret. time 2.478 min.

Examples 145 to 177

Step 1: 6-bromo-4-(isopropylamino)pyrrolo[1,2-b]pyridazine-3-carboxamide

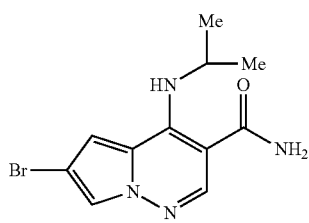 [SMILES: CC(C)Nc1c(C(N)=O)cnn2cc(Br)cc12]

A solution of 6-bromo-4-chloropyrrolo[1,2-b]pyridazine-3-carboxamide (Preparation 5, 865 mg, 3.15 mmol) and propan-2-amine (3.725 g, 63.0 mmol) in DMF (3 mL) was heated at 120° C. for 1 h. The reaction mixture was cooled to room temperature and diluted with water. The precipitated product was filtered, washed with water and dried in vacuo to obtain the title compound as a white solid (893 mg, 95% yield). HPLC (condition B): retention time=3.28 min. LCMS MH$^+$ m/z 297.00. $^1$H NMR (400 MHz, DMSO-d$_6$) δ ppm 8.22 (1 H, s), 7.86 (1 H, d, J=1.76 Hz), 7.02 (1 H, d, J=1.76 Hz), 4.24-4.53 (1 H, m), 1.29 (6 H, d, J=6.16 Hz).

Step 2:

Examples 145 to 177 in table below were prepared following one of the general methods described below using the appropriate commercially available boronic acid or (4,4,5,5-tetramethyl-1,3,2-dioxaborolan-2-yl)ester:

Method A: A mixture of 6-bromo-4-(isopropylamino)pyrrolo[1,2-b]pyridazine-3-carboxamide (20 mg, 67 μmol), tetrakis(triphenylphosphine)palladium (15.6 mg, 13 μmol) or PdCl$_2$(dppf)-CH$_2$Cl$_2$ adduct (5.50 mg, 6.73 μmol), the appropriate boronic acid or (4,4,5,5-tetramethyl-1,3,2-dioxaborolan-2-yl)ester (135 μmol) and potassium triphosphate (67 μL, 135 μmol) in DMF (500 μL-2 mL) was purged with nitrogen and then heated to 80-90° C. for 3 h. The mixture was cooled to room temperature, filtered, and then purified to obtain the final compound via preparative LC/MS using the following conditions: Waters XBridge C18, 19×250 mm, 5 μm particles; Guard Column: Waters XBridge C18, 19×10 mm, 5 μm particles; Mobile Phase A: 5:95 acetonitrile:water with 0.05% TFA; Mobile Phase B: 95:5 acetonitrile:water with 0.05% TFA; Gradient: 0-100% B over 25 min with 5 min hold; Flow rate: 20 mL/min.

Method B: A mixture of 6-bromo-4-(isopropylamino)pyrrolo[1,2-b]pyridazine-3-carboxamide (20 mg, 67 μmol), PdCl$_2$(dppf)-CH$_2$Cl$_2$ adduct (5.50 mg, 6.73 μmol), appropriate boronic acid or (4,4,5,5-tetramethyl-1,3,2-dioxaborolan-2-yl)ester (135 μmol) and potassium triphosphate (67 μL, 135 μmol) in DMF (2 mL) was purged with nitrogen and then heated to 140° C. under microwave conditions for 25 min. The mixture was cooled to room temperature, filtered, and then purified to obtain the final compound via preparative LC/MS using the following conditions: Waters XBridge C18, 19×250 mm, 5 μm particles; Guard Column: Waters XBridge C18, 19×10 mm, 5 μm particles; Mobile Phase A: 5:95 acetonitrile:water with 0.05% TFA; Mobile Phase B: 95:5 acetonitrile:water with 0.05% TFA; Gradient: 0-100% B over 25 min with 5 min hold; Flow rate: 20 mL/min.

| Ex# | Structure | HPLC Rt, min. (condition I) | LCMS [m/z (M + H)] (condition F) |
|---|---|---|---|
| 145 | 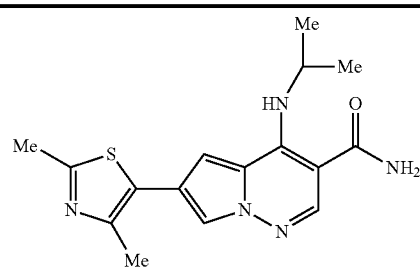 | 1.92 | 330.03 |
| 146 | 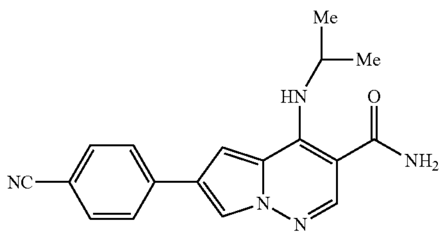 [SMILES: CC(C)Nc1c(C(N)=O)cnn2cc(-c3ccc(C#N)cc3)cc12] | 2.21 | 320.05 |
| 147 | 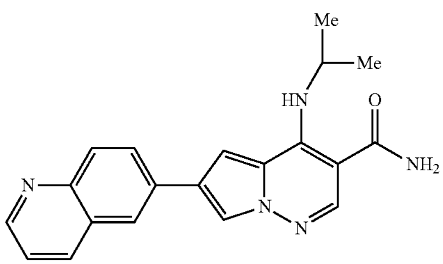 [SMILES: CC(C)Nc1c(C(N)=O)cnn2cc(-c3ccc4ncccc4c3)cc12] | 1.99 | 346.01 |
| 148 | 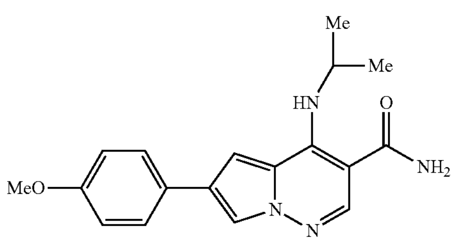 [SMILES: COc1ccc(-c2cc3c(NC(C)C)c(C(N)=O)cnn3c2)cc1] | 2.35 | 325.05 |
| 149 | 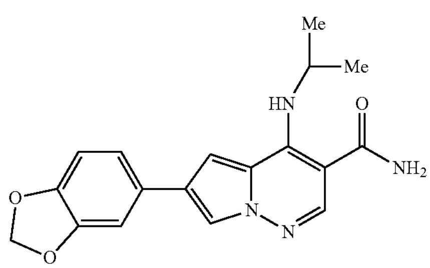 [SMILES: CC(C)Nc1c(C(N)=O)cnn2cc(-c3ccc4c(c3)OCO4)cc12] | 2.31 | 339.01 |
| 150 | 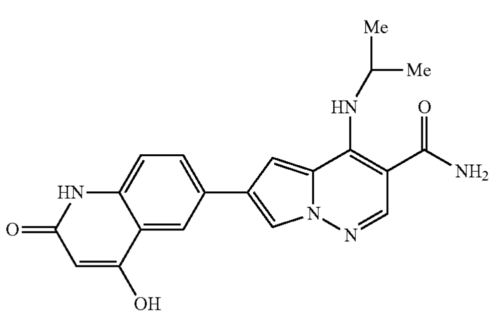 [SMILES: CC(C)Nc1c(C(N)=O)cnn2cc(-c3ccc4[nH]c(=O)cc(O)c4c3)cc12] | 1.32 | 378.01 |

-continued
| Ex# | Structure | HPLC Rt, min. (condition I) | LCMS [m/z (M + H)] (condition F) |
|---|---|---|---|
| 151 | 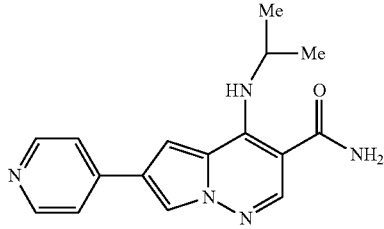 [SMILES: CC(C)Nc1c(C(N)=O)cnn2cc(-c3ccncc3)cc12] | 1.63 | 296.08 |
| 152 | 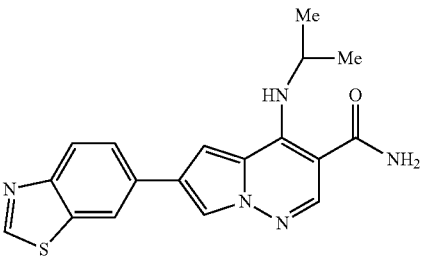 [SMILES: CC(C)Nc1c(C(N)=O)cnn2cc(-c3ccc4ncsc4c3)cc12] | 2.09 | 351.99 |
| 153 | 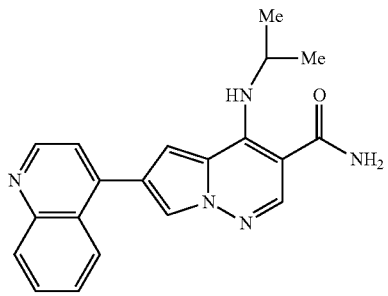 [SMILES: CC(C)Nc1c(C(N)=O)cnn2cc(-c3ccnc4ccccc34)cc12] | 2.12 | 346.1 |
| 154 | 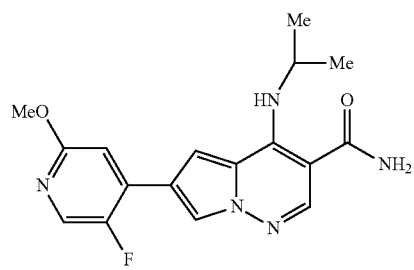 [SMILES: COc1cc(-c2cc3c(NC(C)C)c(C(N)=O)cnn3c2)c(F)cn1] | 2.4 | 344.1 |
| 155 | 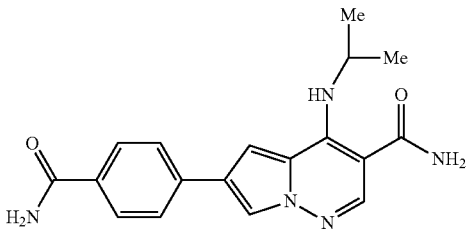 [SMILES: CC(C)Nc1c(C(N)=O)cnn2cc(-c3ccc(C(N)=O)cc3)cc12] | 1.54 | 338.1 |

-continued

| Ex# | Structure | HPLC Rt, min. (condition I) | LCMS [m/z (M + H)] (condition F) |
|---|---|---|---|
| 156 | 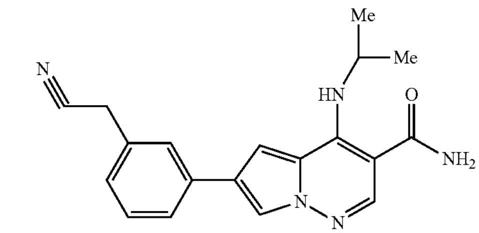 [SMILES: CC(C)Nc1c(C(N)=O)cnn2cc(-c3cccc(CC#N)c3)cc12] | 2.12 | 334.07 |
| 157 | 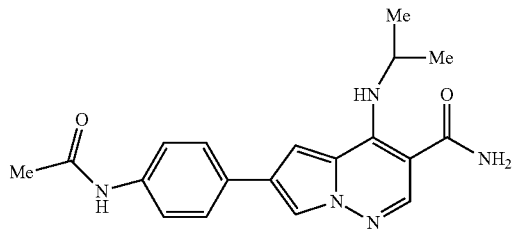 [SMILES: CC(=O)Nc1ccc(-c2cc3c(NC(C)C)c(C(N)=O)cnn3c2)cc1] | 1.73 | 352.1 |
| 158 | 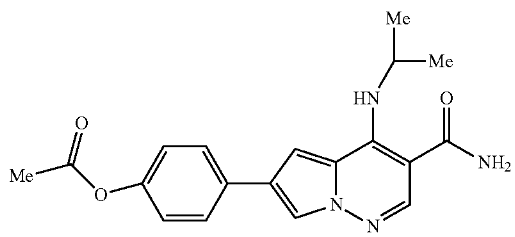 [SMILES: CC(=O)Oc1ccc(-c2cc3c(NC(C)C)c(C(N)=O)cnn3c2)cc1] | 2.26 | 353.1 |
| 159 | 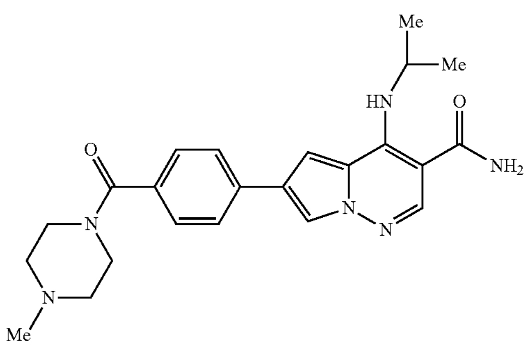 [SMILES: CC(C)Nc1c(C(N)=O)cnn2cc(-c3ccc(C(=O)N4CCN(C)CC4)cc3)cc12] | 1.49 | 421.2 |
| 160 | 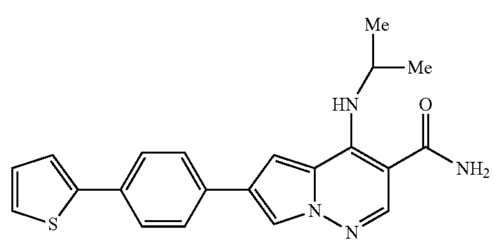 [SMILES: CC(C)Nc1c(C(N)=O)cnn2cc(-c3ccc(-c4cccs4)cc3)cc12] | 3.02 | 377.0 |

| Ex# | Structure | HPLC Rt, min. (condition I) | LCMS [m/z (M + H)] (condition F) |
|---|---|---|---|
| 161 | 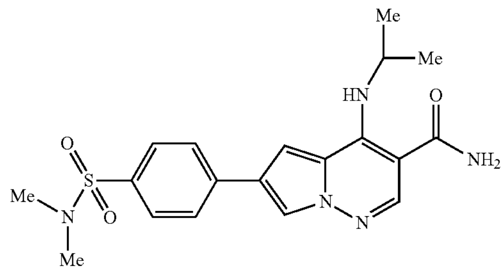 [SMILES: CC(C)Nc1c(C(N)=O)cnn2cc(-c3ccc(S(=O)(=O)N(C)C)cc3)cc12] | 2.08 | 402.2 |
| 162 | 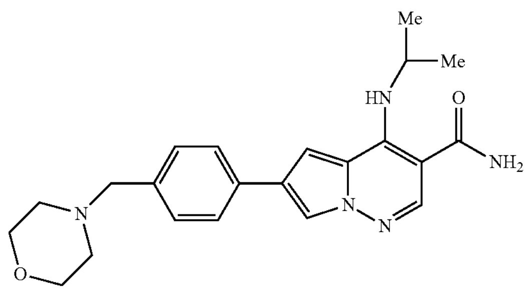 [SMILES: CC(C)Nc1c(C(N)=O)cnn2cc(-c3ccc(CN4CCOCC4)cc3)cc12] | 2.03 | 394.0 |
| 163 | 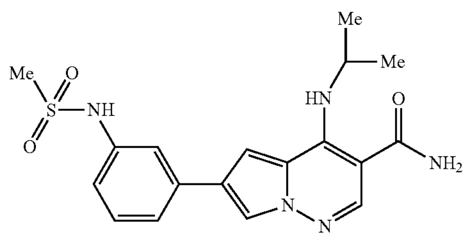 [SMILES: CC(C)Nc1c(C(N)=O)cnn2cc(-c3cccc(NS(C)(=O)=O)c3)cc12] | 1.91 | 388.0 |
| 164 | 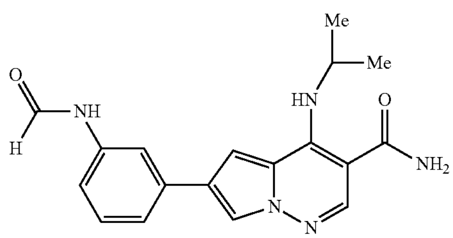 [SMILES: CC(C)Nc1c(C(N)=O)cnn2cc(-c3cccc(NC=O)c3)cc12] | 1.78 | 338.1 |
| 165 | 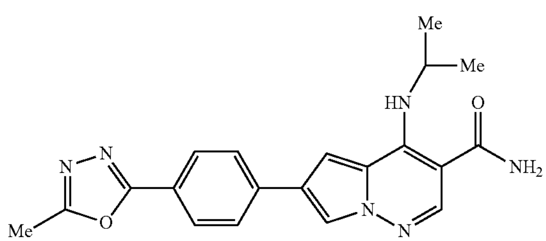 [SMILES: Cc1nnc(-c2ccc(-c3cc4c(NC(C)C)c(C(N)=O)cnn4c3)cc2)o1] | 1.94 | 377.0 |
| 166 | 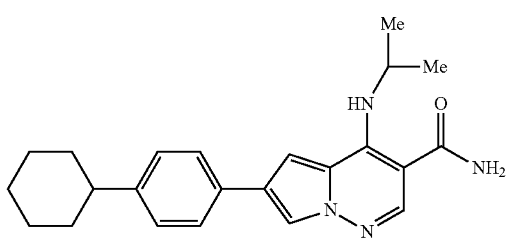 [SMILES: CC(C)Nc1c(C(N)=O)cnn2cc(-c3ccc(C4CCCCC4)cc3)cc12] | 3.62 | 377.2 |

| Ex# | Structure | HPLC Rt, min. (condition I) | LCMS [m/z (M + H)] (condition F) |
|---|---|---|---|
| 167 | 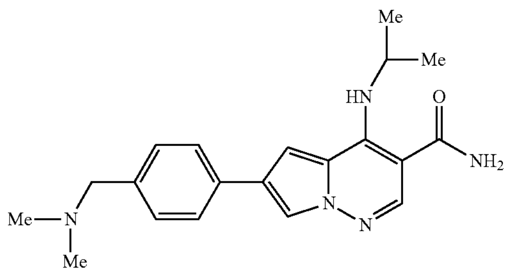 [SMILES: CC(C)Nc1c(C(N)=O)cnn2cc(-c3ccc(CN(C)C)cc3)cc12] | 1.43 | 352.1 |
| 168 | 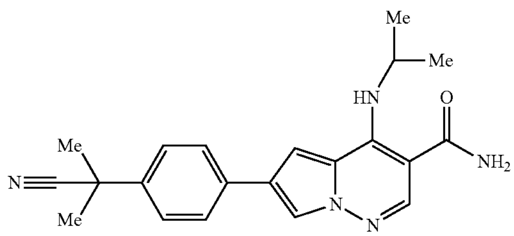 [SMILES: CC(C)Nc1c(C(N)=O)cnn2cc(-c3ccc(C(C)(C)C#N)cc3)cc12] | 2.5 | 362.1 |
| 169 | 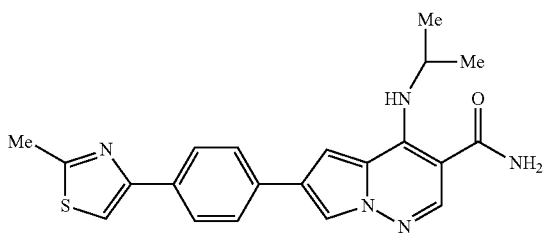 [SMILES: Cc1nc(-c2ccc(-c3cc4c(NC(C)C)c(C(N)=O)cnn4c3)cc2)cs1] | 2.54 | 392.05 |
| 170 | 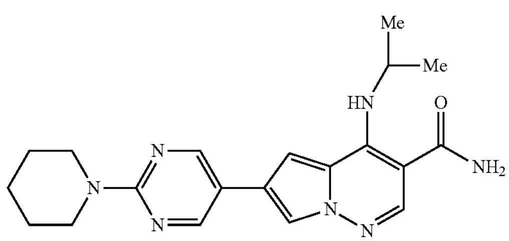 [SMILES: CC(C)Nc1c(C(N)=O)cnn2cc(-c3cnc(N4CCCCC4)nc3)cc12] | 2.59 | 380.1 |
| 171 | 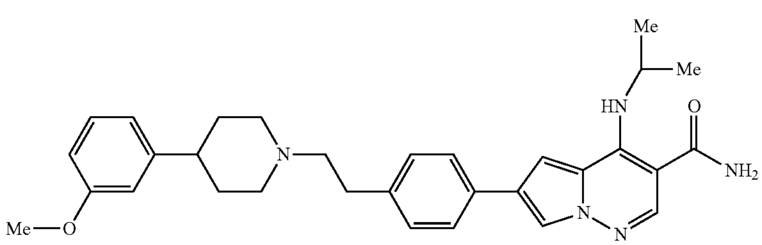 [SMILES: COc1cccc(C2CCN(CCc3ccc(-c4cc5c(NC(C)C)c(C(N)=O)cnn5c4)cc3)CC2)c1] | 2.4 | 512.15 |

| Ex# | Structure | HPLC Rt, min. (condition I) | LCMS [m/z (M + H)] (condition F) |
|---|---|---|---|
| 172 | 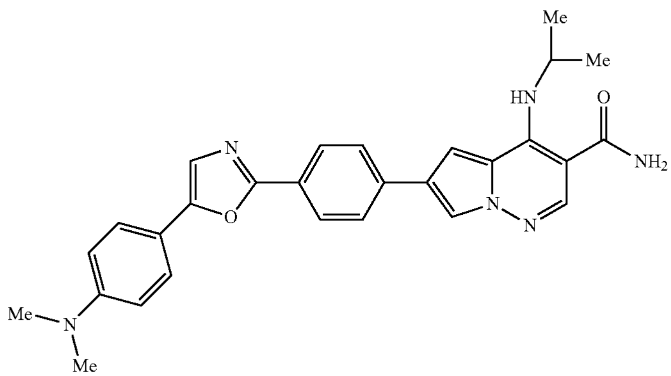 [SMILES: CC(C)Nc1c(C(N)=O)cnn2cc(-c3ccc(-c4ncc(-c5ccc(N(C)C)cc5)o4)cc3)cc12] | 3.1 | 481.01 |
| 173 | 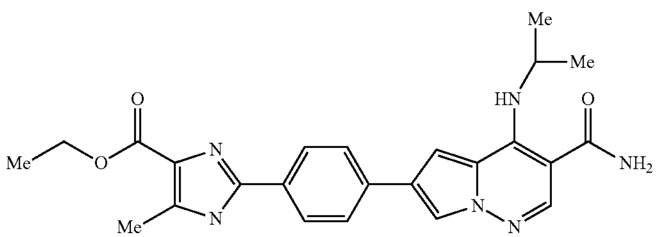 [SMILES: CCOC(=O)c1nc(-c2ccc(-c3cc4c(NC(C)C)c(C(N)=O)cnn4c3)cc2)[nH]c1C] | 1.6 | 447.08 |
| 174 | 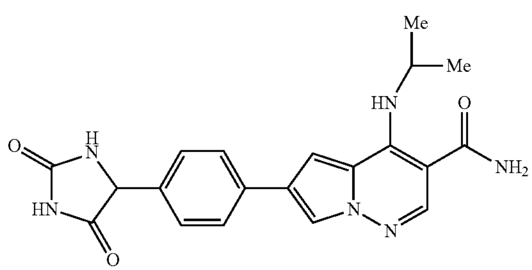 [SMILES: CC(C)Nc1c(C(N)=O)cnn2cc(-c3ccc(C4NC(=O)NC4=O)cc3)cc12] | 1.5 | 393.05 |
| 175 | 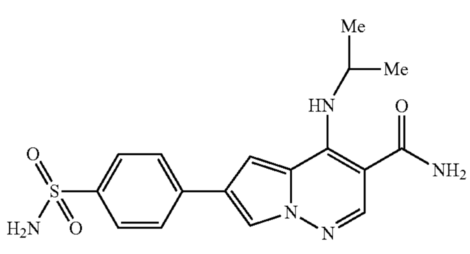 [SMILES: CC(C)Nc1c(C(N)=O)cnn2cc(-c3ccc(S(N)(=O)=O)cc3)cc12] | 1.6 | 374.06 |

| Ex# | Structure | HPLC Rt, min. (condition I) | LCMS [m/z (M + H)] (condition F) |
|---|---|---|---|
| 176 | ![structure] | 1.4 | 351.05 |
| 177 | ![structure] | 2.69 | 480.3 |

Intermediate 7

6-bromo-4-(((1R)-1-(2-fluorophenyl)ethyl)amino)pyrrolo[1,2-b]pyridazine-3-carboxamide

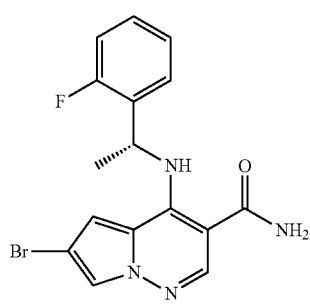

(Int-7)

A mixture of Preparation 5 (50 mg, 0.182 mmol) and (R)-1-(2-fluorophenyl)-ethanamine (30 mg, 0.22 mmol) in DMF (0.5 mL) was added DIPEA (0.07 mL, 0.4 mmol) and the mixture was heated at 100° C. for 2 h. The reaction was cooled to rt and added water (3 mL) then stirred rapidly for several hours and filtered to afford the title compound (28 mg, 39% yield). LCMS 378.99 (M+2)$^+$; $^1$H NMR (CD$_3$OD, 400 MHz) δ 8.11 (s, 1H), 7.51 (d, J=1.8 Hz, 1H), 7.36 (ddd, J=9.2, 7.5, 1.5 Hz, 1H), 7.27 (m, 1H), 7.14 (m, 2H), 6.69 (d, J=1.7 Hz, 1H), 5.80 (q, J=6.6 Hz, 1H), 1.67 (d, J=6.6 Hz, 3H).

Example 178

4-(((1R)-1-(2-fluorophenyl)ethyl)amino)-6-phenylpyrrolo[1,2-b]pyridazine-3-carboxamide

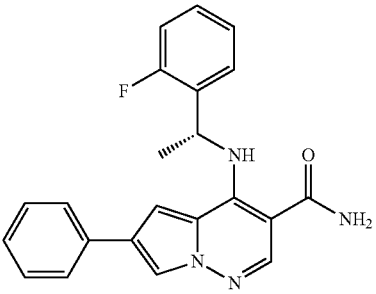

(178)

(R)-6-bromo-4-(1-(2-fluorophenyl)ethylamino)pyrrolo[1,2-b]pyridazine-3-carboxamide (Intermediate 7, 1 equiv), phenylboronic acid (1 equiv), PdCl$_2$(dppf)-CH$_2$Cl$_2$ complex (0.05 equiv) and 2M K$_3$PO$_4$ (3.4 equiv) in dioxane (0.5 mL) was purged with N$_2$ then at 140° C. for 0.5 h. Following cooling to rt, the product was isolated via reverse-phase preparative HPLC (condition F) of the crude reaction mixture to afford the title compound (3.8 mg) as a brown solid. HPLC (conditions B): retention time=4.28 min; LCMS: 375.14 (M+H)$^+$; $^1$H NMR (CD$_3$OD, 400 MHz) δ 8.17 (s, 1H), 7.88 (d, J=1.7 Hz, 1H), 7.52 (d, J=7.0 Hz, 2H), 7.14-7.44 (m, 7H), 7.03 (d, J=1.8 Hz, 1H), 5.80 (q, J=6.6 Hz, 1H), 1.70 (d, J=6.6 Hz, 3H).

Examples 179-182

Examples 179-182 in the table below were prepared from Preparation 5 and commercially available amines, boronic acids or boronic esters where applicable using the general methods described for the preparation of Intermediate 7 and Example 178.

| Ex# | Name | Structure | HPLC Rt, min (Condition) | LCMS m/z (M + H)+ |
|---|---|---|---|---|
| 179 | 4-(((1R)-1-(2-fluorophenyl)ethyl)amino)-6-(4-pyridinyl)pyrrolo[1,2-b]pyridazine-3-carboxamide | 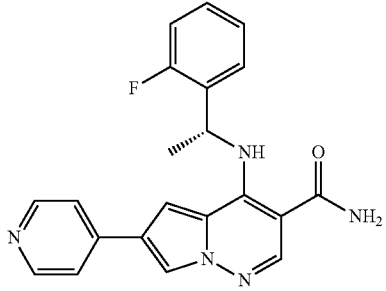 [SMILES: C[C@@H](Nc1c(C(N)=O)cnn2cc(-c3ccncc3)cc12)c1ccccc1F] homochiral | 1.77 (I) | 376.03 |
| 180 | 4-(((1R)-1-(2-fluorophenyl)ethyl)amino)-6-(6-methoxy-3-pyridinyl)pyrrolo[1,2-b]pyridazine-3-carboxamide | 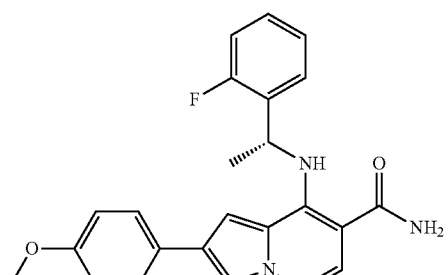 homochiral | 3.13 (J) | 406.07 |
| 181 | (+/−)-4-((1-(2,5-difluorophenyl)ethyl)amino)-6-(4-pyridinyl)pyrrolo[1,2-b]pyridazine-3-carboxamide | 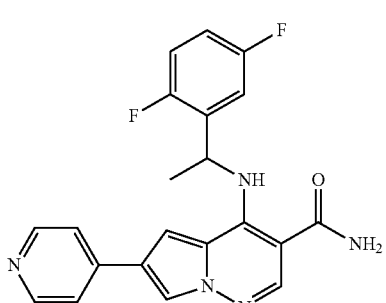 | 1.73 (I) | 394.05 |
| 182 | 4-(((1R)-1-(2-fluorophenyl)ethyl)amino)-6-(4-(isopropylcarbamoyl)phenyl)pyrrolo[1,2-b]pyridazine-3-carboxamide | 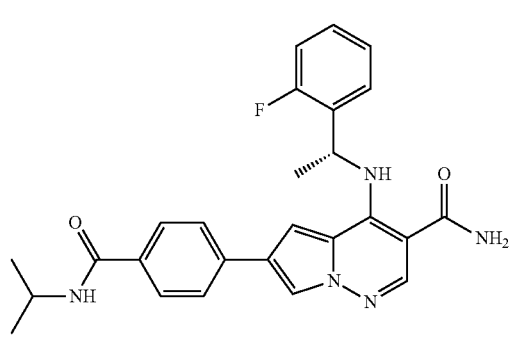 [SMILES: CC(C)NC(=O)c1ccc(-c2cc3c(N[C@H](C)c4ccccc4F)c(C(N)=O)cnn3c2)cc1] homochiral | 2.27 (I) | 460.4 |

Intermediate 8

6-bromo-4-(propylamino)pyrrolo[1,2-b]pyridazine-3-carboxamide

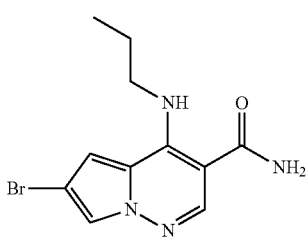
(Int-8)

A mixture of 6-bromo-4-chloropyrrolo[1,2-b]pyridazine-3-carboxamide (Preparation 5, 137 mg, 0.5 mmol), n-propylamine (123 mL, 1.500 mmol) and diisopropylethylamine (0.349 mL, 2.000 mmol) in N-methylpyrrolidinone (1.5 mL) was heated to 105° C. for 0.75 hr. After cooling to rt, water (15 ml) was added and the resulting suspension was stirred at rt for 1 hr. The suspension was filtered and the filter cake was dried. The filter cake was rinsed with hexane and dried to afford the title compound (120 mg, 0.382 mmol, 76% yield) as a tan solid. HPLC (condition M): retention time=2.56 min.; LCMS (ES+) m/z: 297.00/299.00; $^1$H NMR (400 MHz, MeOD) δ ppm 1.09 (t, J=7.4 Hz, 3 H), 1.72-1.83 (m, 2 H), 3.70 (t, J=6.9 Hz, 2 H), 7.01 (d, J=1.8 Hz, 1 H), 7.60 (d, J=1.8 Hz, 1 H), 8.09 (s, 1 H).

Example 183

6-phenyl-4-(propylamino)pyrrolo[1,2-b]pyridazine-3-carboxamide

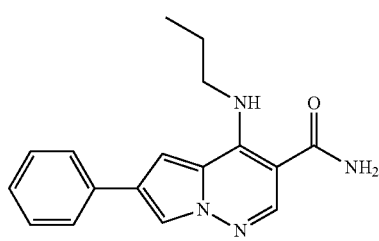
(183)

Nitrogen was bubbled through a mixture of 6-bromo-4-(propylamino) pyrrolo[1,2-b]pyridazine-3-carboxamide (Intermediate 8, 20 mg, 0.067 mmol), phenylboronic acid (24.62 mg, 0.202 mmol), tetrakis(triphenylphosphine) palladium(0) (7.78 mg, 6.73 µmol) and potassium carbonate, 2M (0.135 mL, 0.269 mmol) in dimethoxyethane (0.6 mL) for ~1 minute. The reaction mixture was then heated to 90-95° C. for 2 hr. The reaction mixture was partitioned between EtOAc (20 ml) and water (20 ml). The organic layer was washed with brine (20 ml), dried (MgSO$_4$) and concentrated to a brown residue that was dissolved in MeOH and was subjected to preparative HPLC (Phenomenex 30×100 mm S-5 column; eluting with 45-90% aqueous MeOH+0.1% TFA over an 12 minute gradient, flow rate=1 mL/min, 220 wavelength detection). The product containing fraction was concentrated to afford the title compound (16 mg, 0.054 mmol, 80% yield) as a tan solid. HPLC (condition M): retention time=2.93 min.; LCMS (ES+) m/z: 295.14 (M+H); $^1$H NMR (400 MHz, MeOD) δ ppm 1.12 (t, J=7.3 Hz, 3 H), 1.77-1.87 (m, 2 H), 3.83 (t, J=6.5 Hz, 2 H), 7.20-7.31 (m, 2 H), 7.32-7.44 (m, 2 H), 7.66 (d, J=7.5 Hz, 2 H), 7.91 (s, 1 H), 8.09 (s, 1 H).

Example 184

4-(benzylamino)-6-phenylpyrrolo[1,2-b]pyridazine-3-carboxamide

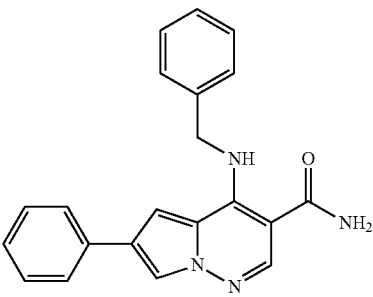
(184)

Step 1: 6-bromo-4-methoxypyrrolo[1,2-b]pyridazine-3-carboxamide

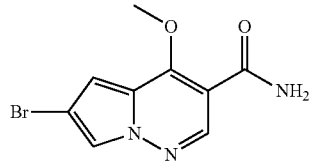

A mixture of 6-bromo-4-chloropyrrolo[1,2-b]pyridazine-3-carboxamide (Preparation 5, 285 mg, 1.038 mmol), sodium methoxide (1.402 mL, 5.19 mmol) in MeOH (5 mL) was stirred at rt for 3 days. The volatiles were removed in vacuo and the residue was partitioned between EtOAc (50 ml) and water (50 ml). The organic layer was washed with brine (50 ml), dried (MgSO$_4$) and concentrated to afford a yellow solid that was chromatographed on a 24 gm silica gel cartridge, eluting with a 0-100% EtOAc/hexanes gradient. Fractions containing the product were concentrated to afford the title compound (112 mg, 0.405 mmol, 39.0% yield) as a yellow solid. HPLC (condition M): retention time=1.70 min.; LCMS (ES+) m/z: 271.9 (bromine pattern); H $^1$NMR (400 MHz, CDCl$_3$) δ ppm 4.44 (s, 3 H), 5.71 (brs, 1 H), 6.99 (d, J=1.8 Hz, 1 H), 7.22 (brs, 1 H), 7.81 (d, J=1.8 Hz, 1 H), 8.69 (s, 1 H).

Step 2: 4-methoxy-6-phenylpyrrolo[1,2-b]pyridazine-3-carboxamide

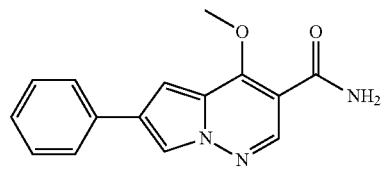 [SMILES: COc1c(C(N)=O)cnn2cc(-c3ccccc3)cc12]

Nitrogen was bubbled through a mixture of 6-bromo-4-methoxypyrrolo[1,2-b]pyridazine-3-carboxamide (77 mg, 0.285 mmol), phenyl boronic acid (104 mg, 0.855 mmol), tetrakis(triphenylphosphine)palladium (32.9 mg, 0.029 mmol) and 2M aq. potassium carbonate, (0.570 mL, 1.140 mmol) in DME (0.75 mL) for ~1 minute. The reaction mixture was then heated to 90-95° C. for 1 hr. The reaction mixture was partitioned between EtOAc (30 ml) and water (30 ml). The organic layer was washed with brine (30 ml), dried (MgSO$_4$) and concentrated to afford a yellow solid that was chromatographed on a 12 g silica gel cartridge, eluting with a 0-100% EtOAc/hexanes gradient. The pure fractions were concentrated to a tan solid that was contaminated with a small amount of triphenylphosphine oxide. The material was triturated with ethyl ether to afford the title compound (62 mg, 0.229 mmol, 80% yield) as a tan solid. HPLC (condition M): retention time=2.36 min.; LCMS (ES+) m/z: 268.11 (M+H); $^1$H NMR (400 MHz, CDCl$_3$) δ ppm 4.52 (s, 3 H), 5.73 (s, 1 H), 7.20 (d, J=1.8 Hz, 1 H), 7.27-7.35 (m, 2 H), 7.41-7.47 (m, 2 H), 7.63-7.68 (m, 2 H), 8.10 (d, J=1.8 Hz, 1 H), 8.69 (s, 1 H).

Step 3

Example 184

A mixture of 4-methoxy-6-phenylpyrrolo[1,2-b]pyridazine-3-carboxamide (10 mg, 0.037 mmol) and benzylamine (0.041 mL, 0.374 mmol) in NMP (0.2 mL) was heated to 80° C. for 45 minutes. The reaction mixture was diluted with MeOH and was subjected to preparative HPLC (Phenominex 30×100 mm S-5 column; eluting with 45-90% aqueous MeOH+0.1% TFA over an 10 minute gradient, flow rate=1 mL/min, 220 nm wavelength detection). The pure fraction was concentrated to afford the title compound (5 mg, 0.014 mmol, 37.0% yield) as a light tan solid. HPLC (condition M): retention time=3.07 min. LCMS (ES+) m/z: 343.08 (M+H); $^1$H NMR (400 MHz, DMSO-d$_6$) δ ppm 5.07 (d, J=5.5 Hz, 2 H), 7.22 (t, J=7.3 Hz, 1 H), 7.31 (d, J=7.3 Hz, 1 H), 7.34-7.42 (m, 5 H), 7.43-7.49 (m, 2 H), 7.73 (d, J=7.3 Hz, 2 H), 8.18 (d, J=1.8 Hz, 1 H), 8.23 (s, 1 H), 10.87 (s, 1 H).

Example 185

(R)-4-(1-cyclopropylethylamino)-6-(2-oxopyrrolidin-1-yl)pyrrolo[1,2-b]pyridazine-3-carboxamide

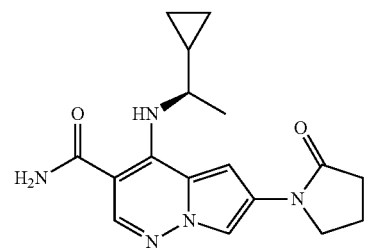

(185)

Example 185 was prepared from 6-bromo-4-(((1R)-1-cyclopropylethyl)amino)-pyrrolo[1,2-b]pyridazine-3-carboxamide (Intermediate 4) and 2-pyrrolidinone according to the procedure described for Example 37. HPLC (condition G): retention time=7.10 min. LCMS (ES+) m/z: 328.1.

Example 186

(R)-4-(1-cyclopropylethylamino)-6-(3-vinylphenyl)pyrrolo[1,2-b]pyridazine-3-carboxamide

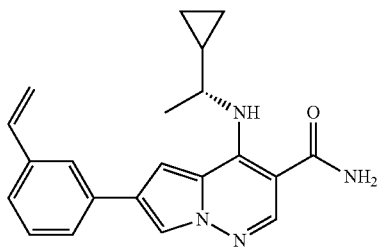

(186)

A degassed solution of (R)-6-bromo-4-(1-cyclopropylethylamino) pyrrolo[1,2-b]pyridazine-3-carboxamide (Intermediate 4, 25 mg, 0.077 mmol), 3-vinylphenyl boronic acid (34.3 mg, 0.232 mmol) and 2M aq. potassium carbonate (0.116 mL, 0.232 mmol) in DME (1 mL) was added Pd(Ph$_3$P)$_4$ (5.36 mg, 4.64 mmol) and the resulting reaction mixture was heated to 90° C. for 2 hrs. The reaction mixture was diluted with 10 mL of EtOAc which was washed with 5 mL of water and 5 mL of brine. The organic phase was concentrated to yield a crude product which was purified on a preparative silica gel TLC plate with hexanes/EtOAc (2/1) as the eluent to yield a product. After trituration in MeOH, the resulting solid obtained was dried to afford the title compound (7.25 mg, 26%). HPLC (condition G): retention time=3.833 min. LC/MS (M+H)$^+$=m/z 347.2. $^1$H NMR (400 MHz, MeOD) δ ppm 8.12 (1 H, s), 7.93-7.95 (1 H, m), 7.72 (1 H, s), 7.55-7.60 (1 H, m), 7.34-7.37 (2 H, m), 7.22 (1 H, d, J=1.8 Hz), 6.81 (1 H, dd, J=17.8, 11.0 Hz), 5.86 (1 H, dd, J=17.7, 1.0 Hz), 5.27 (1 H, dd, J=11.0, 0.9 Hz), 4.09-4.17 (1 H, m), 1.46 (3 H, d, J=6.4 Hz), 1.11-1.21 (1 H, m), 0.53-0.64 (2 H, m), 0.37-0.47 (2 H, m).

Example 187

(R)-4-(1-cyclopropylethylamino)-6-(3-(1,2-dihydroxyethyl)phenyl)pyrrolo[1,2-b]-pyridazine-3-carboxamide (Diastereomeric Mixture)

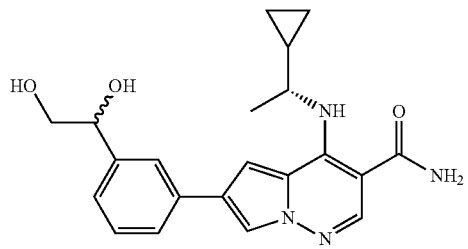

(187)

A solution of (R)-4-(1-cyclopropylethylamino)-6-(3-vinylphenyl)pyrrolo[1,2-b]pyridazine-3-carboxamide (Example 186, 25 mg, 0.072 mmol) in THF/water (4/1 (1 mL) at 0° C. was added 4-methylmorpholine N-oxide (0.037 mL, 0.180 mmol) and osmium tetroxide (4% in water, 0.018 mL, 2.89 µmol). The reaction mixture was warmed up to rt and stirred for 16 hrs. The reaction mixture was purified on prep HPLC (condition A) to yield the title compound as a diastereomeric mixture (14 mg, 39%). HPLC (condition G): retention time=2.843 minute. LC/MS (M+H)⁺=m/z 381.1. ¹H NMR (400 MHz, MeOD) δ ppm 8.12 (1 H, s), 7.93 (1 H, d, J=2.0 Hz), 7.71 (1 H, t, J=1.7 Hz), 7.59 (1 H, ddd, J=7.8, 1.4, 1.3 Hz), 7.37 (1 H, t, J=7.7 Hz), 7.25-7.29 (1 H, m), 7.21 (1 H, d, J=1.8 Hz), 4.75 (1 H, dd, J=7.0, 4.8 Hz), 4.12 (1 H, quin, J=6.4 Hz), 3.63-3.73 (2 H, m), 1.46 (3 H, dd, J=6.4, 0.9 Hz), 1.13-1.19 (1 H, m), 0.53-0.62 (2 H, m), 0.38-0.44 (2 H, m).

Intermediate 9

(+/−)-6-bromo-4-(1-cyclopropylethylamino)pyrrolo[1,2-b]pyridazine-3-carboxamide

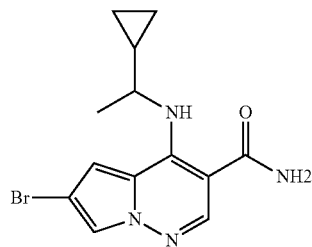

(Int-9)

1-Cyclopropylethanamine (93 mg, 1.09 mmol) and 6-bromo-4-chloropyrrolo[1,2-b]pyridazine-3-carboxamide (Preparation 5, 100 mg, 0.36 mmol) in NMP (0.5 mL) were heated in the CEM microwave at 120° C. for 10 min. The reaction was allowed to cool to room temperature before the addition of MeOH. The resulting precipitate was then filtered and air dried to afford the title compound (72 mg, 61%). HPLC (condition G): retention time=3.87 min. LCMS (condition B): m/z 323.0, 325.0. ¹H NMR (500 MHz, MeOD) δ ppm 8.69 (1 H, d, J=4.99 Hz), 8.40-8.49 (2 H, m), 8.32-8.40 (1 H, m), 8.28 (1 H, s), 7.76 (1 H, td, J=6.59, 1.25 Hz), 7.68 (1 H, d, J=1.94 Hz), 4.12 (1 H, quin, J=6.45 Hz), 1.52 (3 H, d, J=6.38 Hz), 1.14-1.29 (1 H, m), 0.58-0.75 (2 H, m), 0.35-0.51 (2 H, m).

Example 188

(+/−)-4-(1-cyclopropylethylamino)-6-(pyridin-2-yl)pyrrolo[1,2-b]pyridazine-3-carboxamide

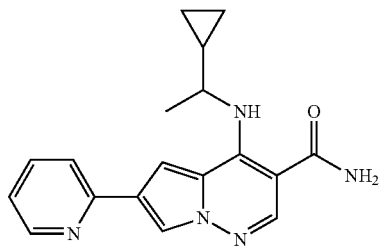

(188)

Pd₂dba₃ (0.850 mg, 0.928 mmol) and dicyclohexyl(2',4',6'-triisopropylbiphenyl-2-yl)phosphine (1.770 mg, 3.71 mmol) were added to a degassed (nitrogen bubbled through for ca. 10 min) solution of (+/−)-6-bromo-4-(1-cyclopropylethylamino)pyrrolo[1,2-b]pyridazine-3-carboxamide (Intermediate 9, 20 mg, 0.062 mmol), 6-methyl-2-(pyridin-2-yl)-1,3,6,2-dioxazaborocane-4,8-dione (21.72 mg, 0.093 mmol), potassium carbonate (42.8 mg, 0.309 mmol) and copper (II) acetate (5.62 mg, 0.031 mmol). The vial was sealed (screw-cap) and immersed in an oil bath pre-heated to 100° C. The reaction was allowed to stir at this temperature for 2 hrs. After cooling to rt, the mixture was filtered and purified by direct injection onto a preparative HPLC (condition A) to give the title compound (7.63 mg, 0.023 mmol, 36.4% yield). HPLC (condition I): retention time=5.08 minutes. LC/MS (M+H)⁺=m/z 322.2. ¹H NMR (500 MHz, MeOD) δ ppm 8.69 (1 H, d, J=4.99 Hz), 8.40-8.49 (1 H, m), 8.32-8.40 (1 H, m), 8.28 (1 H, s), 7.76 (1 H, td, J=6.59, 1.25 Hz), 7.68 (1 H, d, J=1.94 Hz), 7.52 (1 H, d, J=1.94 Hz), 4.12 (1 H, quin, J=6.45 Hz), 1.52 (2 H, d, J=6.38 Hz), 1.14-1.29 (1 H, m), 0.58-0.75 (1 H, m), 0.35-0.51 (1 H, m).

Example 189

4-((1-(hydroxymethyl)cyclopropyl)methylamino)-6-phenylpyrrolo[1,2-b]pyridazine-3-carboxamide

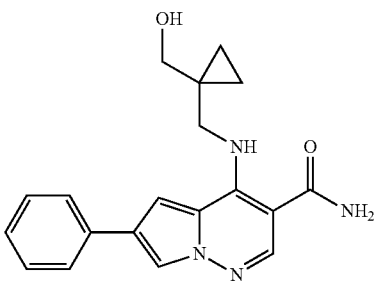

(189)

Step 1: 6-bromo-4-((1-(hydroxymethyl)cyclopropyl)methylamino)pyrrolo[1,2-b]-pyridazine-3-carboxamide

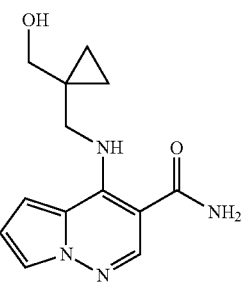

A solution of 6-bromo-4-chloropyrrolo[1,2-b]pyridazine-3-carboxamide (Preparation 5, 45 mg, 0.164 mmol), (1-(aminomethyl)cyclopropyl)methanol HCl salt (25.9 mg, 0.189 mmol) and DIPEA (0.072 mL, 0.410 mmol) in NMP (0.5 mL) was heated to 110° C. for 1 hr. The reaction mixture was purified on preparative HPLC to afford the title compound (41 mg, 74%). HPLC (condition G): retention time=2.73 min. LCMS (condition B): m/z 339.1, 341.1.

Step 2

Example 189

To a degassed solution of 6-bromo-4-((1-(hydroxymethyl)cyclopropyl)-methylamino)pyrrolo[1,2-b]pyridazine-3-carboxamide (20 mg, 0.059 mmol), phenylboronic acid (22.70 mg, 0.177 mmol) and aq. potassium carbonate (0.074 mL, 0.147 mmol) in DME (1 mL) was added palladium tetrakis (4.09 mg, 3.54 μmol) and the solution heated to 90° C. for 16 hrs. Purification by preparative HPLC afforded the title compound (5.3 mg, 27% yield). HPLC (condition G): retention time=1.52 minutes. LC/MS (M+H)$^+$=m/z 336.2. $^1$H NMR (400 MHz, MeOD) δ ppm 8.34 (1 H, s), 8.14 (1 H, d, J=1.76 Hz), 7.89-8.01 (2 H, m), 7.86 (2 H, s), 7.59-7.78 (2 H, m), 7.43-7.59 (2 H, m), 4.22 (2 H, s), 3.86 (2 H, s), 0.79-1.07 (4 H, m).

Example 190

6-(3-(acetamidomethyl)phenyl)-4-((1-hydroxymethyl)cyclopropyl)methylamino) pyrrolo[1,2-b]pyridazine-3-carboxamide

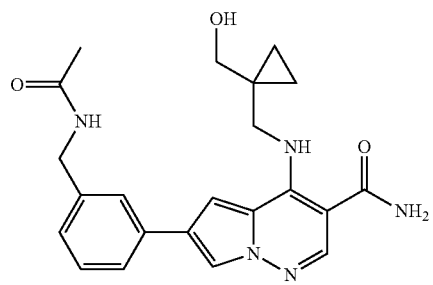

(190)

Prepared from 6-bromo-4-((1-(hydroxymethyl)cyclopropyl)methylamino)pyrrolo[1,2-b]-pyridazine-3-carboxamide (from step 1 of Example 189) using the procedure described in step 2 of Example 189. HPLC (condition G): retention time=1.13 minutes. LC/MS (M+H)$^+$=m/z 407.2. $^1$H NMR (500 MHz, MeOD) δ ppm 7.82 (1 H, s), 7.65 (1 H, d, J=1.66 Hz), 7.30-7.44 (2 H, m), 7.16 (1 H, t, J=7.77 Hz), 7.08 (1 H, d, J=1.66 Hz), 6.99 (1 H, d, J=7.77 Hz), 4.22 (2 H, s), 4.16 (2 H, br. s.), 3.74 (2 H, s), 3.15 (3 H, s), 0.47 (4 H, d, J=12.48 Hz).

Example 191

6-(3-(cyanomethyl)phenyl)-4-(methylamino)pyrrolo[1,2-b]pyridazine-3-carboxamide

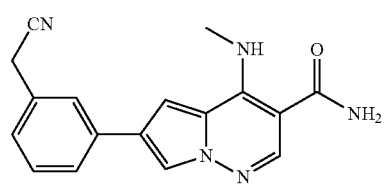

(191)

Step 1: 6-bromo-4-(methylamino)pyrrolo[1,2-b]pyridazine-3-carboxamide

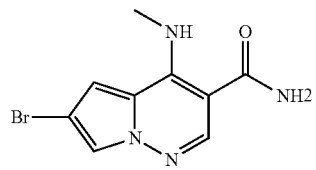

A solution of 6-bromo-4-chloropyrrolo[1,2-b]pyridazine-3-carboxamide (Preparation 5, 200 mg, 0.733 mmol), and methylamine (0.5 mL, 8M solution in EtOH) was heated to 80° C. for 1 hr in the CEM microwave. The reaction mixture was evaporated in vacuo to give the title compound (192 mg, 98%). HPLC (condition G): retention time=0.77 min. LCMS (condition B): m/z 269.0, 271.0.

Step 2

Example 191

Potassium phosphate (2M aqueous solution, 0.11 mL, 0.22 mmol) was added in one portion to a stirred solution of 6-bromo-4-(methylamino)pyrrolo[1,2-b]pyridazine-3-carboxamide (20 mg, 0.074 mmol, from step 1), 3-(cyanomethyl)phenyl boronic acid (18 mg, 0.12 mmol), X-Phos ligand (3.5 mg, 0.0075 mmol) and palladium acetate (0.8 mg, 0.0037 mmol) in anhydrous 1,4-dioxane (0.25 mL). The resulting biphasic mixture was then heated in the CEM microwave at 120° C. for 10 min. The reaction was allowed to cool to rt and the phases separated. The aqueous phase was extracted with ethyl acetate (2×5 mL). The combined organics were then dried (MgSO$_4$) and evaporated in vacuo before purifying by reverse-phase Prep HPLC (condition A). The fraction containing the major product was concentrated on the rotovap to afford 7.5 mg (33.4%) of the title compound as a white solid. HPLC (condition B): retention time=0.78 min. LCMS (condition B): m/z 306.2. $^1$H NMR (400 MHz, DMSO-d$_6$) δ ppm 10.44 (1 H, d, J=5.50 Hz), 8.07-8.34 (2 H, m), 7.70-7.90 (2 H, m), 7.32-7.49 (2 H, m), 7.24 (1 H, d, J=7.92 Hz), 4.04 (2 H, s), 3.42 (3 H, d).

Example 192

(R)-6-(2-aminopyrimidin-5-yl)-4-(1-cyclopropylethylamino)pyrrolo[1,2-b]pyridazine-3-carboxamide

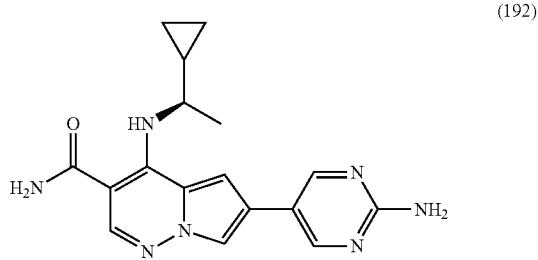 [SMILES: C[C@@H](Nc1c(C(N)=O)cnn2cc(-c3cnc(N)nc3)cc12)C1CC1]

(192)

161

Step 1: (R)-6-bromo-4-(1-cyclopropylethylamino)
pyrrolo[1,2-b]pyridazine-3-carboxamide

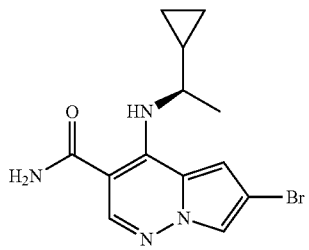 [SMILES: C[C@@H](Nc1c(C(N)=O)cnn2cc(Br)cc12)C1CC1]

A solution of 6-bromo-4-chloropyrrolo[1,2-b]pyridazine-3-carboxamide (Preparation 5, 474.3 mg, 1.728 mmol), (R)-1-cyclopropylethylamine (162 mg, 1.901 mmol) and DIPEA (0.453 mL, 2.59 mmol) in NMP (Volume: 5 mL) was heated to 100° C. for 4 hr. The reaction was cooled and 10 mL of water was added and the resulting mixture was stirred for 10 minutes. The solid was collected by vacuum filtration and dried to afford the title compound (470 mg, 80%). HPLC (Method N): retention time=3.258 min. LC/MS (M+H)$^+$ =325.1. $^1$H NMR (400 MHz, CD$_3$OD) δ 8.11 (s, 1H), 7.60 (dd, J=1.8, 0.7 Hz, 1H), 6.94 (d, J=1.8 Hz, 1H), 4.12-3.73 (m, 1H), 1.39 (d, J=6.4 Hz, 3H), 1.18-1.04 (m, 1H), 0.64-0.49 (m, 2H), 0.41-0.27 (m, 2H).

Step 2

Example 192

To a degassed solution of (R)-6-bromo-4-(1-cyclopropylethylamino) pyrrolo[1,2-b]pyridazine-3-carboxamide (20 mg, 0.062 mmol), 5-(4,4,5,5-tetramethyl-1,3,2-dioxaborolan-2-yl)pyrimidin-2-amine (41.0 mg, 0.186 mmol) and aqueous potassium carbonate (0.093 mL, 0.186 mmol) in DME (Volume: 1 mL) was added palladium tetrakis (4.29 mg, 3.71 mmol) and the resulting mixture was heated to 90° C. for 2 hrs. The reaction mixture was cooled and diluted with 10 mL of EtOAc and was washed with 5 mL of water, 5 mL of brine and dried over sodium sulfate. Filtration and concentration yielded the crude product which was triturated in MeOH (2 mL) to afford the title compound as a solid (13.8 mg, 66%). HPLC (Method N) retention time=2.312 minute. LC/MS (M+H)$^+$=338.1. $^1$H NMR (400 MHz, DMSO-d$_6$) δ 10.68 (d, J=8.4 Hz, 1H), 8.68 (s, 2H), 8.18 (s, 1H), 8.10 (d, J=1.8 Hz, 1H), 7.21 (d, J=1.8 Hz, 1H), 6.64 (s, 2H), 4.10-3.97 (m, 1H), 1.33 (d, J=6.4 Hz, 3H), 1.13-1.02 (m, 1H), 0.54-0.46 (m, 2H), 0.44-0.37 (m, 1H), 0.32-0.25 (m, 1H).

Example 193

(+/−)-4-(4-amino-3,3-dimethyl-4-oxobutan-2-ylamino)-6-phenylpyrrolo[1,2-b]-pyridazine-3-carboxamide (193)

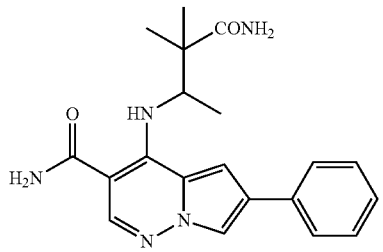

162

Step 1: Methyl 2,2-dimethyl-3-oxobutanoate

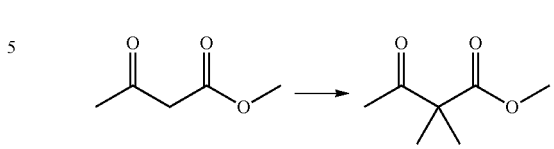

In a 1 L 3-necked round bottomed flask, sodium hydride (60% suspension in mineral oil) (34.4 g, 0.861 mol) was taken in dry THF (800 ml) and stirred at −20° C. under nitrogen atmosphere. To this suspension was added methyl acetoacetate (50 g, 0.431 mol) drop-wise over 20 minutes and reaction mixture was stirred at −20° C. for 30 minutes. Methyl iodide (122 g, 0.861 mol) was added drop-wise over 30 minutes. After the completion of addition, the reaction mixture was allowed to attain rt and was stirred overnight. GCMS analysis (Column: DB1, J & W 30 μm×0.25 μm; Mobile Phase: Helium; Flow rate: 1.2 ml/min; Run time: 16 min; Inj. Vol.: 1 μl; Split ratio: 1:20; Inlet temp.: 250° C.; Method: In. Temp. 50° C. hold for 1 min., Ramp rate: 25° C./min up to 300° C. hold for 5 min; retention time=3.963 min, (M+1)=145) indicated completion of the reaction. It was then diluted with water (500 ml) and extracted with ethyl acetate (3×250 ml). The combined organic layers were dried over anhydrous sodium sulfate, filtered and concentrated under vacuum to afford the title compound (50 g) which was used as obtained for the next step.

Step 2: Methyl
3-(benzylamino)-2,2-dimethylbutanoate

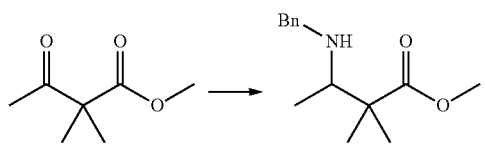

To a solution of methyl 2,2-dimethyl-3-oxobutanoate (50 g, 0.347 mol) in dichloromethane (500 ml) was added triethylamine (290 ml, 2.081 mol) and benzylamine (44.6 g, 0.416 mol) at 0° C. To this reaction mixture, a 1.0 M solution of TiCl$_4$ in dichloromethane (173 ml, 0.173 mol) was added drop-wise and reaction mixture was allowed to attain rt and stirred overnight. After completion of the reaction, the reaction mixture was diluted with diethyl ether (300 ml) and filtered over a celite pad. The filtrate was concentrated under vacuum to give a brown colored oily residue (85 g) that was dissolved in MeOH (600 ml) and stirred at 0° C. Sodium cyanoborohydride (34.3 g, 0.546 mol) was added portion wise at 0° C. and reaction mixture was allowed to attain rt and stir for 4 h. After completion of the reaction, the reaction mixture was concentrated under vacuum and the crude mass was dissolved in ethyl acetate (100 ml) and washed with water (100 ml). The aqueous layer was extracted with ethyl acetate (2×100 ml). The combined organic layers were dried over anhyd. sodium sulfate, filtered and concentrated under vacuum. The crude product obtained was purified by column chromatography using 5% ethyl acetate in hexanes as the eluent to give the title compound (28 g). $^1$H NMR (400 MHz, CDCl$_3$): δ 1.03-1.05 (d, J=6.4 Hz, 3H), 1.09-1.14 (dd, J=8.4

Hz, 6.8 Hz, 6H), 2.16-2.17 (s, 2H), 2.85-2.90 (m, 1H), 3.63 (s, 3H), 3.88-3.92 (d, J=13.2 Hz, 1H), 7.21-7.32 (m, 5H).

Step 3: Methyl 3-amino-2,2-dimethylbutanoate

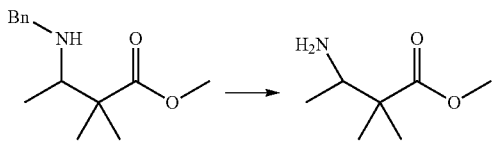

To a solution of methyl 3-(benzylamino)-2,2-dimethylbutanoate (5 g) in MeOH (150 ml) was added 10% palladium on carbon (1.5 g) at rt and the reaction mixture was stirred under hydrogen (balloon pressure) overnight at rt. After completion, the reaction mixture was filtered over a celite pad and the residue was washed with MeOH (25 ml). A saturated solution of hydrogen chloride in MeOH (50 ml) was added to the reaction mixture and allowed to stir overnight at rt. Methanol was removed under reduced pressure and the crude mass was triturated with diethyl ether (50 ml) to give the hydrochloride salt of the title compound (2.6 g). $^1$H NMR (400 MHz, DMSO-$d_6$): δ 1.11-1.15 (m, 9H), 3.41-3.43 (m, 1H), 3.64 (s, 3H), 8.148 (bs, 3H).

Step 4: methyl 3-(6-bromo-3-carbamoylpyrrolo[1,2-b]pyridazin-4-ylamino)-2,2-dimethylbutanoate

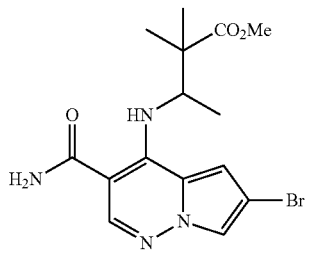 [SMILES: COC(=O)C(C)(C)C(C)Nc1c(C(N)=O)cnn2cc(Br)cc12]

To a solution of 6-bromo-4-chloropyrrolo[1,2-b]pyridazine-3-carboxamide (Preparation 5, 1.0 gm, 3.64 mmol) and methyl 3-amino-2,2-dimethylbutanoate hydrochloride (1.0 g, 5.50 mmol) in DMA (10 ml) was added DIPEA (3.14 ml, 18.2 mmol) at rt. The reaction mixture was stirred at 110° C. overnight. Upon completion, the reaction mixture was cooled to rt and DMA was removed under reduced pressure to give a dark oily compound. It was dissolved in ethyl acetate (50 ml) and washed with water (20 ml). The aqueous layer was extracted with ethyl acetate (3×50 ml). The combined organic layers were washed with brine (50 ml), dried over anhyd. sodium sulfate, filtered and concentrated under vacuum. The crude compound was purified by column chromatography using 40% ethyl acetate in hexanes as the eluting solvent to give the title compound (700 mg, 50%). $^1$NMR (400 MHz, DMSO-$d_6$): δ 1.22-1.24 (m, 9H), 3.57-3.574 (s,3H), 4.47-4.51 (m, 1H), 7.046 (s, 1H), 7.89 (s, 1H), 8.24 (s, 1H), 10.92-10.94 (d, J=9.2 Hz).

Step 5: Methyl 3-(3-carbamoyl-6-phenylpyrrolo[1,2-b]pyridazin-4-ylamino)-2,2-dimethylbutanoate

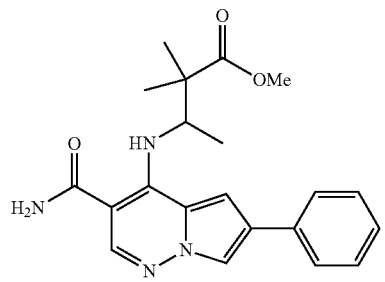 [SMILES: COC(=O)C(C)(C)C(C)Nc1c(C(N)=O)cnn2cc(-c3ccccc3)cc12]

To a solution of methyl 3-(6-bromo-3-carbamoylpyrrolo [1,2-b]pyridazin-4-ylamino)-2,2-dimethylbutanoate (1.0 g, 2.61 mmol) in toluene (10 ml) was added phenyl boronic acid (0.44 g, 3.91 mmol) and stirred for 10 minutes at RT. Sodium carbonate (0.553 gm, 5.22 mmol), Pd(dppf)$_2$ (0.10 gm, 3.91 mmol), water (2.0 ml) and tetrabutyl ammonium hydroxide (1 drop) was added at room temperature under nitrogen atmosphere and the reaction mixture was degassed with nitrogen for 15 minutes. The reaction mixture was stirred at 110° C. in a CEM microwave synthesizer for 8 hours. Upon completion, the reaction mixture was cooled to room temperature and the layers were separated. The aqueous layer was washed with ethyl acetate (3×50 ml). The combined organic layers were washed with brine (25 ml), dried over anhyd. sodium sulfate, filtered and concentrated under vacuum. The crude compound was purified by column chromatography using 30% ethyl acetate in hexanes as the eluting solvent to give the title compound (600 mg, 60%). $^1$H NMR (400 MHz, DMSO-$d_6$): δ 1.32-1.34 (m, 6H), 1.37-1.39 (m, 3H), 3.73 (s, 3H), 4.68-4.70 (m, 1H), 7.157-7.161 (d, J=1.6 Hz, 1H), 7.27-7.31 (m, 1H), 7.41-7.44 (m, 2H), 7.62-7.65 (m, 2H), 7.87-7.88 (m, 2H). 10.60-10.63 (d, J=10 Hz, 1H).

Step 6: 3-(3-carbamoyl-6-phenylpyrrolo[1,2-b]pyridazin-4-ylamino)-2,2-dimethylbutanoic acid

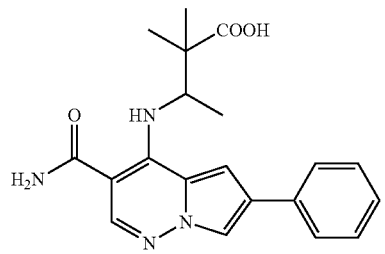 [SMILES: CC(Nc1c(C(N)=O)cnn2cc(-c3ccccc3)cc12)C(C)(C)C(=O)O]

Methyl 3-(3-carbamoyl-6-phenylpyrrolo[1,2-b]pyridazin-4-ylamino)-2,2-dimethylbutanoate (0.2 g, 0.526 mmol) was taken in a mixture of MeOH (30 mL) and water (3 mL). Potassium hydroxide (0.442 g, 7.89 mmol) was added and the reaction mixture was heated at reflux overnight. After completion of the reaction, MeOH was concentrated under reduced pressure and the crude mass was cooled to 0° C. and acidified to pH 5 by stirring in 1.5N HCl solution for 15 min.

An off white colored solid separated out which was filtered and dried under vacuum to give the title compound (0.16 g, 83.3% yield). $^1$H NMR (400 MHz, DMSO-d$_6$): δ 1.22-1.23 (d, J=7.2 Hz, 6H), 1.31-1.32 (d, J=6.4 Hz, 3H), 4.70-4.75 (m, 1H), 7.26-7.29 (t, J=6.8 Hz, J=7.2 Hz, 2H), 7.40-7.44 (t, J=7.6, J=7.6 Hz, 2H), 7.78-7.80 (d, J=7.6 Hz, 2H), 8.20-8.23 (d, J=13.2 Hz, 2H), 10.95-10.98 (d, J=9.6 Hz, 1H), 12.45 (s, 1H).

Step 7

Example 193

3-(3-Carbamoyl-6-phenylpyrrolo[1,2-b]pyridazin-4-ylamino)-2,2-dimethylbutanoic acid (160 mg, 0.43 mmol) was dissolved in THF (15 mL) under nitrogen atmosphere. HOBT (88.6 mg, 0.65 mmol), EDC (125.7 mg, 0.65 mmol), DIPEA (0.19 ml, 1.09 mmol) were added and the reaction mixture was stirred for 1 h at room temperature. A freshly prepared saturated solution of ammonia in THF (20 mL) was added to reaction mixture at 0° C. and the reaction mixture was stirred at room temperature overnight. The reaction mixture was quenched in water (50 mL) and extracted with ethyl acetate (3×50 ml). The combined organic layer was washed with brine (50 ml), dried over anhyd. sodium sulfate, filtered and concentrated under reduced pressure. The semi-solid obtained was stirred in diethyl ether (10 ml) and filtered to afford the title compound as an off-white solid (90 mg, 56.3%). $^1$H NMR (400 MHz, DMSO-d$_6$): δ 1.14-1.18 (d, J=16.4 Hz, 6H), 1.24-1.26 (d, J=6.8 Hz, 3H), 4.71-4.75 (m, 1H), 6.97 (s, 1H), 7.26-7.31 (m, 3H), 7.41-7.45 (t, J=8 Hz, J=7.6 Hz, 2H), 7.77-7.79 (d, J=7.2 Hz), 8.18-8.19 (d, J=1.6 Hz, 1H), 8.23 (s, 1H), 10.88-10.90 (d, J=9.2 Hz, 1H).

Example 194

(R)-4-(4-amino-3,3-dimethyl-4-oxobutan-2-ylamino)-6-phenylpyrrolo[1,2-b]-pyridazine-3-carboxamide

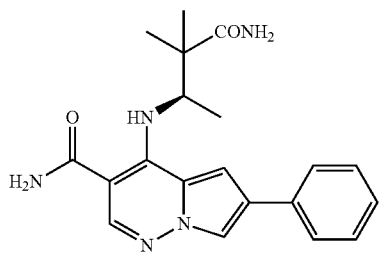

(194)

Step 1: (R)-methyl 3-(6-bromo-3-carbamoylpyrrolo[1,2-b]pyridazin-4-ylamino)-2,2-dimethylbutanoate

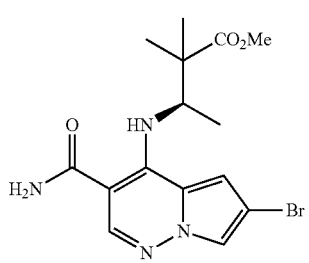 [SMILES: COC(=O)C(C)(C)[C@@H](C)Nc1c(C(N)=O)cnn2cc(Br)cc12]

(+/−)-methyl-3-(6-bromo-3-carbamoylpyrrolo[1,2-b]pyridazin-4-ylamino)-2,2-dimethylbutanoate was resolved by chiral preparative HPLC (column: CHIRALPAK-ADH 205× 4.6 mm, 5 micron; mobile phase: 0.2:% diethylamine in hexanes:ethanol (90:10); flow rate: 1.0 ml/min) to give enantiomer A and enantiomer B.

Enantiomer A: Chiral HPLC retention time=10.58 min. $^1$H NMR (400 MHz, DMSO-d$_6$): δ 1.21-1.24 (m, 9H), 3.57 (s,1H), 4.47-4.51 (m, 1H), 7.04-7.05 (d, J=1.6 Hz, 1H), 7.30-7.72 (bd, 2H), 7.889-7.894 (d, J=2.0 Hz, 1H), 8.24 (s, 1H), 10.92-10.94 (d, J=10 Hz, 1H). $[α]^{24.8}$=−20.436 (c=0.55, MeOH).

Enantiomer B: Chiral HPLC retention time=13.06 min. $^1$H NMR (400 MHz, DMSO d$_6$): δ 1.21-1.24 (m, 9H), 3.57 (s, 1H), 4.47-4.51 (m, 1H), 7.04-7.05 (s, 1H), 7.28-7.67 (bd, 2H), 7.890-7.894 (s, 1H), 8.24 (s, 1H), 10.92-10.94 (d, J=10 Hz, 1H). $[α]^{24.8}$=12.0 (c=0.1, MeOH).

Step 2: (R)-Methyl 3-(3-carbamoyl-6-(6-methoxypyridin-3-yl)pyrrolo[1,2-b]pyridazin-4-ylamino)-2,2-dimethylbutanoate

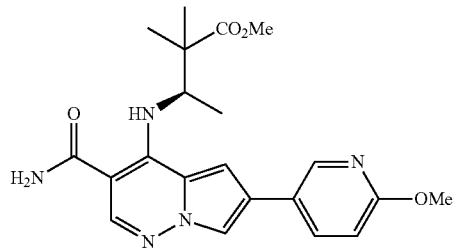 [SMILES: COC(=O)C(C)(C)[C@@H](C)Nc1c(C(N)=O)cnn2cc(-c3ccc(OC)nc3)cc12]

A mixture of (R)-methyl 3-((6-bromo-3-carbamoylpyrrolo[1,2-b]pyridazin-4-yl)amino)-2,2-dimethylbutanoate (170 mg, 0.444 mmol) and (6-methoxypyridin-3-yl) boronic acid (102 mg, 0.665 mmol) were taken in 1,4-dioxane (5 mL) in a sealed tube. To this mixture were added 2-(dicyclohexylphosphino)-2',4',6'-triisopropylbiphenyl (21.15 mg, 0.044 mmol) and palladium (II) acetate (4.98 mg, 0.022 mmol) followed by K$_3$PO$_4$ (2M solution) (0.554 mL, 1.109 mmol). The reaction mixture was degassed and heated to 135° C. for 1 h. After completion of the reaction, the reaction mixture was cooled, quenched with water (50 mL) and extracted with ethyl acetate (3×50 mL). The combined organic layer was washed with brine (60 mL), dried over anhyd. sodium sulfate, filtered and concentrated under reduced pressure to afford the crude product as a brown liquid. The crude product was purified by flash chromatography over silica gel and eluted using 40% ethyl acetate in petroleum ether to give the title compound (125 mg, 0.293 mmol, 66.2% yield) as an off white solid. $^1$H NMR (400 MHz, DMSO-d$_6$): δ 1.24-1.25 (d, J=1.6 Hz, 6H), 1.28-1.3 (d, J=6.8 Hz, 3H), 3.57 (s, 3H), 3.89 (s, 3H), 4.65-4.69 (m, 1H), 6.87-6.89 (d, J=8.4 Hz, 1H), 7.28-7.29 (d, J=1.6 Hz, 1H), 8.12-8.15 (dd, J=2.4 Hz, J=2.8 Hz, 1H), 8.205-8.209 (d, J=1.6

Hz, 2H), 8.65-8.66 (d, J=2.4 Hz, 1H), 10.91-10.94 (d, J=10 Hz, 1H). [α]$^{24.8}$=8.0 (c=0.1, MeOH).

Step 3: (R)-3-((3-carbamoyl-6-(6-methoxypyridin-3-yl)pyrrolo[1,2-b]pyridazin-4-yl)amino)-2,2-dimethylbutanoic acid

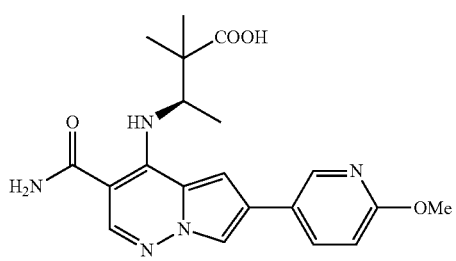

(R)-methyl-3-((3-carbamoyl-6-(6-methoxypyridin-3-yl)pyrrolo[1,2-b]pyridazin-4-yl)amino)-2,2-dimethylbutanoate (125 mg, 0.304 mmol) was dissolved in MeOH (25 mL) and water (1.0 mL). Potassium hydroxide (256 mg, 4.56 mmol) was added and the reaction mixture was heated at reflux overnight. After completion, the reaction mixture was cooled to room temperature and MeOH was removed under reduced pressure. The crude mass obtained was acidified to pH 5 at 0° C. using 1.5N HCl and stirred at room temperature for 15 minutes to give a solid that was collected by vacuum filtration and dried to afford the title compound (100 mg, 0.252 mmol, 83% yield) as an off-white solid. $^1$H NMR (400 MHz, DMSO-d$_6$): δ 1.13-1.15 (d, J=8.4 Hz, 6H), 1.25-1.26 (d, J=6.4 Hz, 3H), 3.86 (s, 3H), 4.68 (m, 1H), 6.84-6.86 (d, J=8.4 Hz, 1H), 7.25 (s, 1H), 8.06-8.064 (d, J=2 Hz, 1H), 8.15-8.18 (d, J=12 Hz, 2H), 8.59 (s, 1H), 10.86-10.89 (d, J=10 Hz, 1H). [α]$^{24.8}$=1.6 (c=0.1, MeOH)

Step 4

Example 194

(R)-3-((3-carbamoyl-6-(4-methoxyphenyl)pyrrolo[1,2-b]pyridazin-4-yl)amino)-2,2-dimethylbutanoic acid (100 mg, 0.252 mmol) was dissolved in THF (25 mL). DIPEA (0.110 mL, 0.631 mmol), HOBT (57.9 mg, 0.378 mmol), and EDC (72.5 mg, 0.378 mmol) were added and the reaction mixture was stirred at room temperature for 1 h. A saturated solution of ammonia in THF (20 mL) was added at −20° C. and the reaction mixture was stirred at room temperature overnight. After completion, the reaction mixture was quenched in water (50 mL) and extracted with ethyl acetate (3×50 mL). The combined organic layer was washed with brine (50 mL), dried over anhyd. sodium sulfate, filtered and concentrated under reduced pressure. The crude compound obtained was purified by preparative HPLC to give the title compound (40 mg, 0.101 mmol, 40.1% yield) as a white solid. $^1$H NMR (400 MHz, DMSO-d$_6$): δ 1.17-1.19 (d, J=6.4 Hz, 6H), 1.23-1.25 (d, J=8 Hz, 3H), 3.89 (s, 3H), 4.68-4.718 (q, 1H), 6.88-6.90 (d, J=8.4 Hz, 1H), 6.95 (s, 1H), 7.24 (s, 1H), 7.29-7.30 (d, J=1.6 Hz, 1H), 8.08-8.10 (dd, J=2.8 Hz, J=2.4 Hz, 1H), 8.18- 8.19 (d, J=1.6 Hz, 1H), 8.22 (s, 1H), 8.62-8.63 (d, J=2 Hz, 1H), 10.85-10.88 (d, J=9.2 Hz, 1H). [α]$^{25}$=12.0 (c=0.1, MeOH)

Example 195

(R)-4-(1-cyclopropylethylamino)-6-(5-(methylamino)-1,3,4-oxadiazol-2-yl)pyrrolo[1,2-b]pyridazine-3-carboxamide

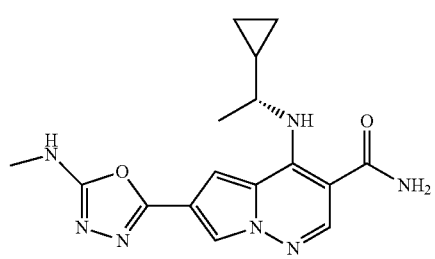

(195)

Methylamine (2 mL, 16 mmol, 8.0M solution in ethanol) was added in one portion to (R)-4-(1-cyclopropylethylamino)-6-(5-(methylthio)-1,3,4-oxadiazol-2-yl)pyrrolo[1,2-b]pyridazine-3-carboxamide (7 mg, 0.018 mmol). The resulting mixture was heated in the CEM microwave at 200° C. for 1 hour. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10 mM NH$_4$OAc; Mobile Phase B: 95:5 acetonitrile:water with 10 mM NH$_4$OAc; Gradient: 0-100% B over 25 minutes, then a 5-minute hold at 100% B; Flow: 20 mL/min. Fractions containing the desired product were combined and dried via centrifugal evaporation to afford the title compound (3.1 mg). $^1$H NMR (500 MHz, MeOD) δ 8.15 (s, 1H), 7.98 (d, J=1.5 Hz, 1H), 7.26 (d, J=2.0 Hz, 1H), 4.07-3.78 (m, 1H), 3.10 (s, 3H), 1.50-1.36 (m, 3H), 1.19-1.04 (m, 1H), 0.70-0.48 (m, 2H), 0.43-0.23 (m, 2H). HPLC (method H) retention time=1.04 min. M+H=341.2.

Example 196

4-((2R,3R)-1,3-dihydroxybutan-2-ylamino)-6-phenylpyrrolo[1,2-b]pyridazine-3-carboxamide

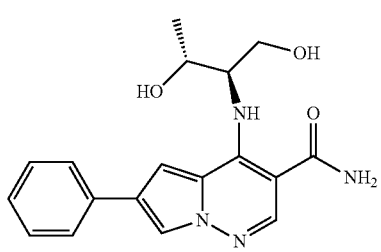

(196)

169

Step 1: 6-bromo-4-(ethylthio)pyrrolo[1,2-b]pyridazine-3-carboxamide

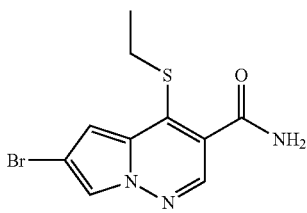 [SMILES: CCSc1c(C(N)=O)cnn2cc(Br)cc12]

A mixture of 6-bromo-4-chloropyrrolo[1,2-b]pyridazine-3-carboxamide (Preparation 5, 5 g, 18.21 mmol), ethanethiol (1.482 mL, 20.04 mmol) and potassium carbonate (5.03 g, 36.4 mmol) in NMP (volume: 60 mL) was stirred at rt for 18 hr. Water (500 ml) was added and the resulting suspension was stirred at rt for 1 hr. The suspension was filtered and the filter cake was air dried. The solid obtained was then washed with hexane and dried to afford a dark yellow solid. This solid was dissolved in warm EtOAc (200 ml) and decolorizing carbon was added. The mixture was allowed to stand for 10 minutes. The mixture was filtered through celite and the filter cake was washed thoroughly with warm EtOAc. The filtrate was concentrated and dried under high vacuum to afford the title compound (3.56 g, 11.86 mmol, 65.1% yield) as a yellow solid. $^1$H NMR (400 MHz, CDCl$_3$) δ ppm 1.29 (t, J=7.5 Hz, 3 H) 3.11 (q, J=7.4 Hz, 2 H) 5.98 (brs, 1 H) 7.03 (d, J=1.8 Hz, 1 H) 7.83 (d, J=1.8 Hz, 1 H) 7.95 (brs, 1 H) 8.66 (s, 1 H). LCMS (M+H)=299.95/301.95.

Step 2: 4-(ethylthio)-6-phenylpyrrolo[1,2-b]pyridazine-3-carboxamide

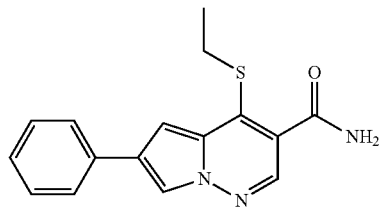 [SMILES: CCSc1c(C(N)=O)cnn2cc(-c3ccccc3)cc12]

A mixture of 6-bromo-4-(ethylthio)pyrrolo[1,2-b]pyridazine-3-carboxamide (1.2 g, 4.00 mmol), phenylboronic acid (0.731 g, 6.00 mmol), palladium (II) acetate (0.090 g, 0.400 mmol), 2M potassium phosphate, tribasic (7.60 mL, 15.19 mmol) and 2-(dicyclohexylphosphino)-2',4',6'-triisopropylbyphenyl (0.381 g, 0.800 mmol) in dioxane (volume: 30 mL) was heated to 125° C. in a pressure vessel, behind a blast shield for 4 hr. Additional phenylboronic acid (0.366 g, 3.00 mmol), palladium (II) acetate (0.045 g, 0.200 mmol), 2-(dicyclohexylphosphino)-2',4',6'-triisopropylbiphenyl (0.191 g, 0.400 mmol) and 2M potassium phosphate, tribasic (7.60 mL, 15.19 mmol) were added and heating was continued for 1 hr. The reaction mixture was partitioned between EtOAc (250 ml) and water (250 ml). The organic layer was washed with brine (100 ml), dried (MgSO$_4$) and concentrated to a yellow solid that was triturated with ethyl ether. Filtration, washing with ethyl ether/hexane, 1:1 and drying afforded the title compound (0.91 g, 3.06 mmol, 77% yield) as a yellow solid that was used in the next step without further purification. $^1$H NMR (400 MHz, MeOD) δ ppm 1.28 (t, J=7.4 Hz, 3 H) 3.19 (q, J=7.5 Hz, 2 H) 7.23 (d, J=1.8 Hz, 1 H) 7.28 (d, J=7.5 Hz, 1 H) 7.40 (t, J=7.7 Hz, 2 H) 7.74 (d, J=7.3 Hz, 2 H) 8.16 (s, 1 H) 8.21 (d, J=1.8 Hz, 1 H). LCMS (M+H)=298.07.

Step 3: 4-(Ethylsulfinyl)-6-phenylpyrrolo[1,2-b]pyridazine-3-carboxamide

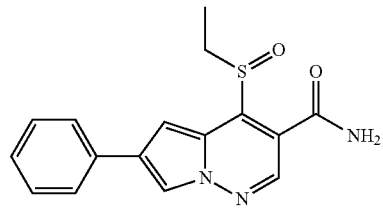 [SMILES: CCS(=O)c1c(C(N)=O)cnn2cc(-c3ccccc3)cc12]

Oxone (4139 mg, 6.73 mmol) as a solution in water (volume: 40.0 mL) was added to a stirred suspension of 4-(ethylthio)-6-phenylpyrrolo[1,2-b]pyridazine-3-carboxamide (910 mg, 3.06 mmol) in acetone (volume: 40 mL) at rt. The reaction mixture was stirred at rt for 3 hr. After the reaction mixture was diluted with water (5 ml), the acetone was removed by rotovap and the resulting suspension was filtered and the filter cake was washed with water. Drying afforded the title compound (890 mg, 2.84 mmol, 93% yield) as a yellow solid. The material was used as is in the next step. $^1$H NMR (400 MHz, DMSO-d$_6$) δ ppm 1.34 (t, J=7.5 Hz, 3 H) 3.31-3.39 (m, 2 H) 7.31 (t, J=7.4 Hz, 1 H) 7.40-7.48 (m, 2 H) 7.74 (s, 1 H) 7.80 (d, J=7.3 Hz, 2 H) 7.98 (d, J=1.7 Hz, 1 H) 8.19-8.30 (m, 1 H) 8.49 (s, 1 H) 8.67 (d, J=1.8 Hz, 1 H). LCMS (M+H)=314.05.

Step 4

Example 196

A mixture of 4-(ethylsulfinyl)-6-phenylpyrrolo[1,2-b]pyridazine-3-carboxamide (50 mg, 0.160 mmol) and (2R,3R)-2-aminobutane-1,3-diol (84 mg, 0.798 mmol) in DMF (0.75 mL) was stirred at 80° C. for 1.5 hr. The DMF was removed under high vacuum on the rotovap to afford a yellow solid residue. This residue was triturated with water and was allowed to stand overnight. The suspension was filtered and the filtercake was dried to afford a yellow solid. Trituration 2 times with ethyl ether and drying afforded 43 mg of a yellow solid. The yellow solid was suspended in ~10 ml of EtOAc: MeOH, 1:1. The suspension was heated to reflux and was subsequently allowed to cool to rt. Filtration and drying afforded the title compound (29 mg, 0.085 mmol, 68.7% yield) as a tan solid. $^1$H NMR (400 MHz, DMSO-d$_6$) δ 10.68 (d, J=8.8 Hz, 1H), 8.19 (s, 1H), 8.15 (d, J=1.5 Hz, 1H), 7.77 (d, J=7.3 Hz, 2H), 7.40 (t, J=7.7 Hz, 2H), 7.31 (d, J=1.3 Hz, 1H), 7.28-7.22 (m, 1H), 5.09-4.85 (m, 2H), 4.25-4.01 (m, 2H), 3.77-3.53 (m, 2H), 1.12 (d, J=6.4 Hz, 3H).

LCMS (M+H)=341.14.

Example 197

4-((R)-1-cyclopropylethylamino)-6-(3-(1,2-dihydroxyethyl)phenyl)pyrrolo[1,2-b]pyridazine-3-carboxamide (Isomers A and B)

(197-Isomers A and B)

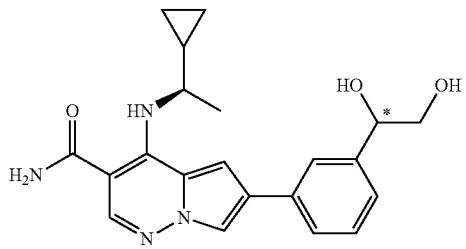

Step 1: (R)-6-bromo-4-(1-cyclopropylethylamino)pyrrolo[1,2-b]pyridazine-3-carboxamide

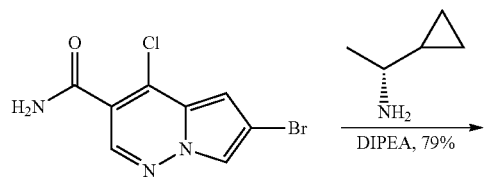

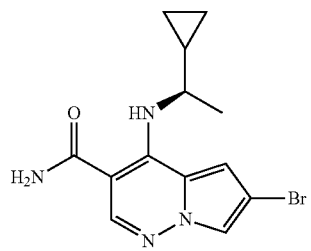

A solution of 6-bromo-4-chloropyrrolo[1,2-b]pyridazine-3-carboxamide (2.0 g, 7.29 mmol), (R)-1-cyclopropylethanamine, HCl (0.975 g, 8.01 mmol) and DIPEA (2.99 mL, 17.12 mmol) in NMP (Volume: 15 mL) was heated to 100° C. for 4 hr. The reaction mixture was added 60 mL of water and stirred for 10 minutes. The solid was collected as the desired product (1.85 g, 79% yield). $^1$H NMR (400 MHz, CD$_3$OD) δ 8.12 (s, 1H), 7.61 (d, J=1.8 Hz, 1H), 6.95 (d, J=1.8 Hz, 1H), 3.92 (quin, J=6.4 Hz, 1H), 1.40 (d, J=6.4 Hz, 3H), 1.18-1.05 (m, 1H), 0.65-0.49 (m, 2H), 0.41-0.30 (m, 2H). MS (ES+) m/z: 323.1, 325.1 (M+H); HPLC: 93%, retention time: 3.318 min (analytical HPLC Method B).

Step 2: (R)-4-(1-cyclopropylethylamino)-6-(3-vinylphenyl)pyrrolo[1,2-b]pyridazine-3-carboxamide

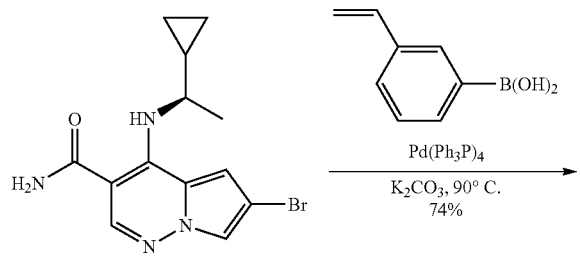

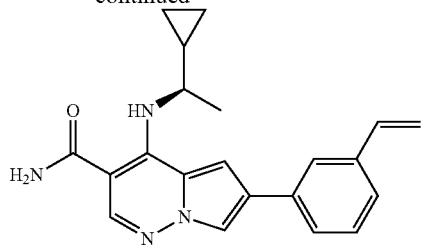

To a degassed solution of (R)-6-bromo-4-(1-cyclopropylethylamino)pyrrolo[1,2-b]pyridazine-3-carboxamide (100 mg, 0.309 mmol), 3-vinylphenylboronic acid (137 mg, 0.928 mmol) and K$_2$CO$_3$ (0.464 mL, 0.928 mmol) in DME (Volume: 2 mL) was added Pd(Ph$_3$P)$_4$ (21.45 mg, 0.019 mmol). The reaction mixture was heated to 90° C. for 2 hrs. The reaction mixture was diluted with 10 mL of EtOAc and then washed with 5 mL of water and 5 mL of brine. The organic phase was concentrated to yield a crude product which was purified on prep silica gel TLC plate with hexanes/EtOAc(2/1) to yield a product. It was triturated in MeOH. The solid was collected as the desired product (79.7 mg, 74% yield). MS (ES+) m/z: 347.3 (M+H); HPLC: 86%, retention time: 3.808 min (analytical HPLC Method B).

Step 3: ((R)-4-(1-cyclopropylethylamino)-6-(3-(1,2-dihydroxyethyl)phenyl)pyrrolo[1,2-b]pyridazine-3-carboxamide

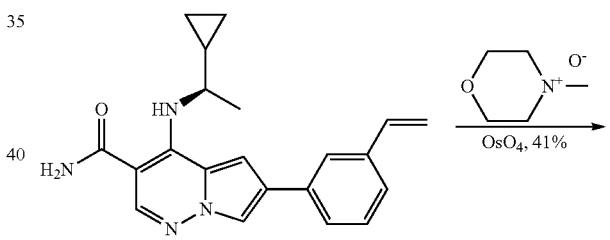

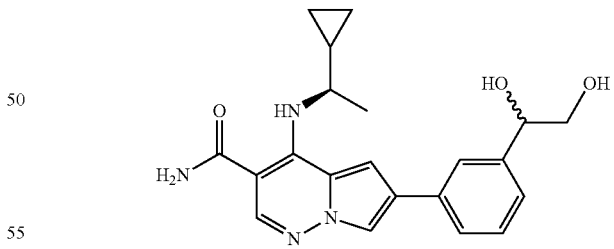

To a solution of (R)-4-(1-cyclopropylethylamino)-6-(3-vinylphenyl)pyrrolo[1,2-b]pyridazine-3-carboxamide (54.7 mg, 0.158 mmol) in THF/water (4/1) (Volume: 2 mL) at 0° C. were added 4-methylmorpholine N-oxide (0.082 mL, 0.395 mmol) and osmium tetroxide 4% in water (0.039 mL, 6.32 μmol). The reaction mixture was warmed up to 23° C. and stirred for 16 hrs. The reaction mixture was purified on Preparative HPLC (Method A) to yield the desired product (32.2 mg, 41% yield). MS (ES+) m/z: 381.2 (M+H); HPLC: 100%, retention time: 2.836 min (analytical HPLC Method B).

Step 4: 4-((R)-1-cyclopropylethylamino)-6-(3-(1,2-dihydroxyethyl)phenyl)pyrrolo[1,2-b]pyridazine-3-carboxamide (PK1) and 4-((R)-1-cyclopropylethylamino)-6-(3-(1,2-dihydroxyethyl)phenyl)pyrrolo[1,2-b]pyridazine-3-carboxamide (PK2)

((R)-4-(1-cyclopropylethylamino)-6-(3-(1,2-dihydroxyethyl)phenyl)pyrrolo[1,2-b]pyridazine-3-carboxamide (32.2 mg, 0.065 mmol) was separated under the Chiral —SFC conditions (Column: ChiralCel OJ-H 25×3 cm, 5 µm; Column Temp. 40° C.; Flow rate: 150 mL/min; Mobile Phase: CO$_2$/MeOH=70/30; Injection Volume: 1.5 mL (total 5.0 mL); Detector Wavelength: 220 nm). The isolated enantiomers were named "Isomer A" and "Isomer B" in the elution order. The enantiomeric purity of both isolated enantiomer was determined to be greater than 99.5% on the SFC/UV/area % at 220 nm. (Column: ChiralCel OJ-H 25×3 cm, 5 µm; Column Temp. 40° C.; Flow rate: 2.0 mL/min; Mobile Phase: CO$_2$/MeOH=70/30; Detector Wavelength: 220 nm).

4-((R)-1-cyclopropylethylamino)-6-(3-(1,2-dihydroxyethyl)phenyl)pyrrolo[1,2-b]pyridazine-3-carboxamide (Isomer A) (8.22 mg, 35% yield). $^1$H NMR (400 MHz, CD$_3$OD) δ 8.12 (s, 1H), 7.93 (d, J=1.8 Hz, 1H), 7.71 (s, 1H), 7.60 (d, J=7.9 Hz, 1H), 7.38 (t, J=7.7 Hz, 1H), 7.27 (d, J=7.7 Hz, 1H), 7.22 (d, J=1.8 Hz, 1H), 4.75 (dd, J=7.0, 4.8 Hz, 1H), 4.18-4.06 (m, 1H), 3.75-3.61 (m, 2H), 1.46 (d, J=6.4 Hz, 3H), 1.22-1.09 (m, 1H), 0.66-0.51 (m, 2H), 0.47-0.35 (m, 2H). MS (ES+) m/z: 381.1 (M+H); HPLC: 97%, retention time: 2.861 min (analytical HPLC Method B).

4-((R)-1-cyclopropylethylamino)-6-(3-(1,2-dihydroxyethyl)phenyl)pyrrolo[1,2-b]pyridazine-3-carboxamide (Isomer B) (8.70 mg, 35% yield). $^1$H NMR (400 MHz, CD$_3$OD) δ 8.15 (s, 1H), 7.95 (d, J=1.8 Hz, 1H), 7.74 (s, 1H), 7.62 (d, J=7.7 Hz, 1H), 7.40 (t, J=7.7 Hz, 1H), 7.30 (d, J=7.7 Hz, 1H), 7.24 (d, J=1.8 Hz, 1H), 4.78 (dd, J=7.0, 4.8 Hz, 1H), 4.21-4.10 (m, 1H), 3.77-3.65 (m, 2H), 1.49 (d, J=6.4 Hz, 3H), 1.25-1.13 (m, 1H), 0.69-0.54 (m, 2H), 0.49-0.37 (m, 2H). MS (ES+) m/z: 381.2 (M+H); HPLC: 100%, retention time: 2.863 min (analytical HPLC Method B).

TABLE 12

| Ex # | Structure | HPLC Rt (minutes) | LCMS [m/z (M + H)] |
|---|---|---|---|
| 198 | 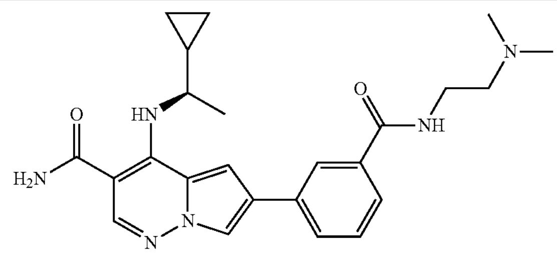 [SMILES: C[C@@H](Nc1c(C(N)=O)cnn2cc(-c3cccc(C(=O)NCCN(C)C)c3)cc12)C1CC1] | 2.668 | 467.10 |
| 199 | 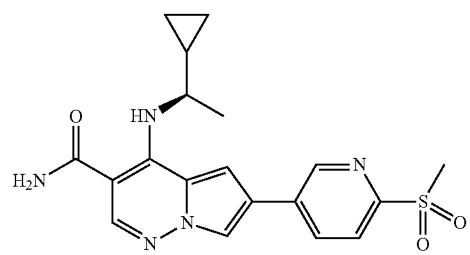 [SMILES: C[C@@H](Nc1c(C(N)=O)cnn2cc(-c3ccc(S(C)(=O)=O)nc3)cc12)C1CC1] | 2.728 | 400.08 |
| 200 | 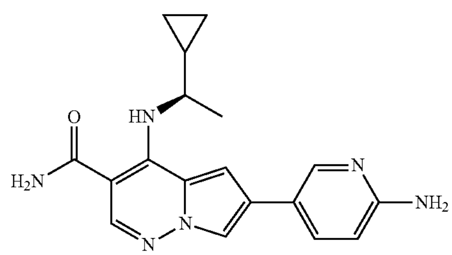 [SMILES: C[C@@H](Nc1c(C(N)=O)cnn2cc(-c3ccc(N)nc3)cc12)C1CC1] | 0.69 | 337.17 |
| 201 | 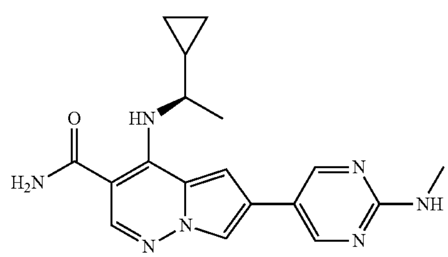 [SMILES: CNc1ncc(-c2cc3c(N[C@H](C)C4CC4)c(C(N)=O)cnn3c2)cn1] | 2.661 | 352.08 |

TABLE 12-continued

| Ex # | Structure | HPLC Rt (minutes) | LCMS [m/z (M + H)] |
|---|---|---|---|
| 202 | 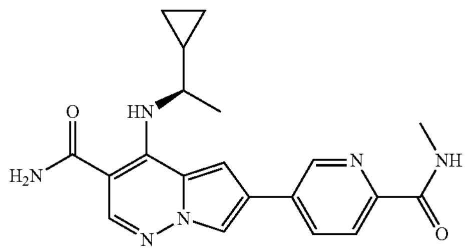 [SMILES: CNC(=O)c1ccc(-c2cc3c(N[C@H](C)C4CC4)c(C(N)=O)cnn3c2)cn1] | 1.36 | 379.18 |
| 203 | 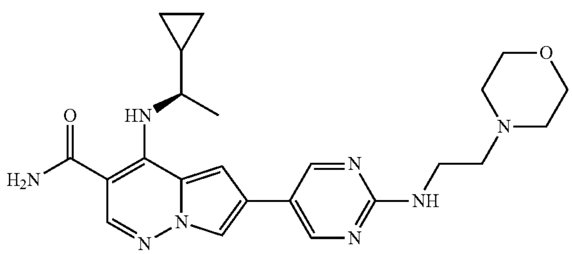 [SMILES: C[C@@H](Nc1c(C(N)=O)cnn2cc(-c3cnc(NCCN4CCOCC4)nc3)cc12)C1CC1] | 1.00 | 451.25 |
| 204 | 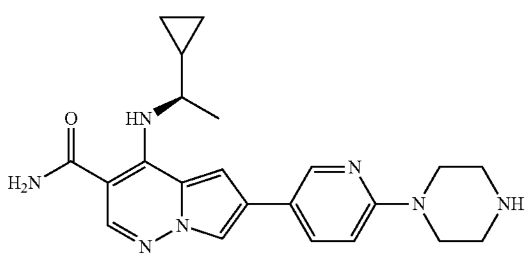 [SMILES: C[C@@H](Nc1c(C(N)=O)cnn2cc(-c3ccc(N4CCNCC4)nc3)cc12)C1CC1] | 0.88 | 406.23 |
| 205 | 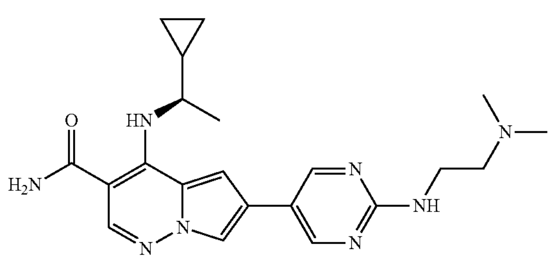 [SMILES: C[C@@H](Nc1c(C(N)=O)cnn2cc(-c3cnc(NCCN(C)C)nc3)cc12)C1CC1] | 1.00 | 409.24 |
| 206 | 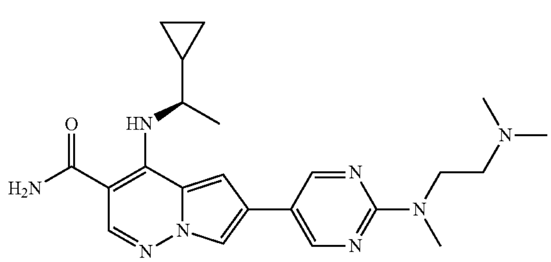 [SMILES: C[C@@H](Nc1c(C(N)=O)cnn2cc(-c3cnc(N(C)CCN(C)C)nc3)cc12)C1CC1] | 1.56 | 423.30 |

Example 207

(S)-6-(3-(dimethylamino)phenyl)-4-(1-hydroxy-4-methylpentan-2-ylamino)pyrrolo[1,2-b]pyridazine-3-carboxamide

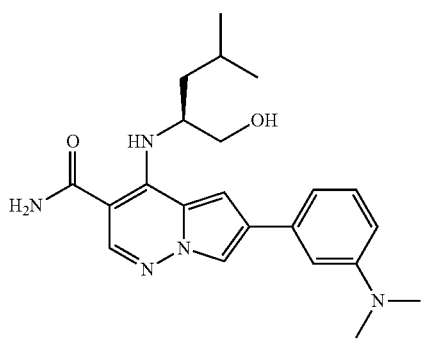

(207)

Step 1: (S)-6-bromo-4-(1-hydroxy-4-methylpentan-2-ylamino)pyrrolo[1,2-b]pyridazine-3-carboxamide

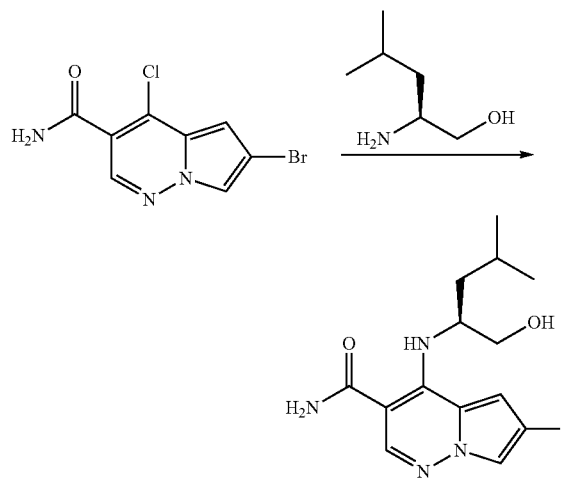

A mixture of 6-bromo-4-chloropyrrolo[1,2-b]pyridazine-3-carboxamide (0.85 g, 3.10 mmol), (S)-2-amino-4-methylpentan-1-ol (0.544 g, 4.64 mmol) and diisopropylethylamine (1.082 mL, 6.19 mmol) in DMA (Volume: 10 mL) was heated to 125° C. for 1.25 hr. After cooling to rt, ice cold water (~60 ml) was added to the rapidly stirring reaction mixture. The reaction mixture was stirred for 15 minutes, was sonicated for 15 minutes and was stirred and additional 15 minutes. The resulting suspension was filtered and the filter cake was washed with water. Drying afforded (S)-6-bromo-4-(1-hydroxy-4-methylpentan-2-ylamino)pyrrolo[1,2-b]pyridazine-3-carboxamide (0.94 g, 2.57 mmol, 83% yield) as a tan solid. $^1$H NMR (400 MHz, DMSO-$d_6$) δ ppm 0.80 (d, J=6.4 Hz, 3H) 0.91 (d, J=6.4 Hz, 3 H) 1.40 (m, 1 H) 1.56-1.60 (m, 1 H) 1.61-1.70 (m, 1 H) 3.39-3.48 (m, 1 H) 3.58 (m, 1 H) 4.08-4.17 (m, 1 H) 4.98 (dd, J=6.2, 4.8 Hz, 1 H) 7.04 (d, J=1.5 Hz, 1 H) 7.84 (d, J=1.8 Hz, 1 H) 8.21 (s, 1 H) 10.59 (d, J=8.6 Hz, 1 H). MS (ES+) m/z: 354.9, 356.9 (M+H); LC retention time: 2.517 min (analytical HPLC Method B).

Step 2: (S)-6-(3-(dimethylamino)phenyl)-4-(1-hydroxy-4-methylpentan-2-ylamino)pyrrolo[1,2-b]pyridazine-3-carboxamide

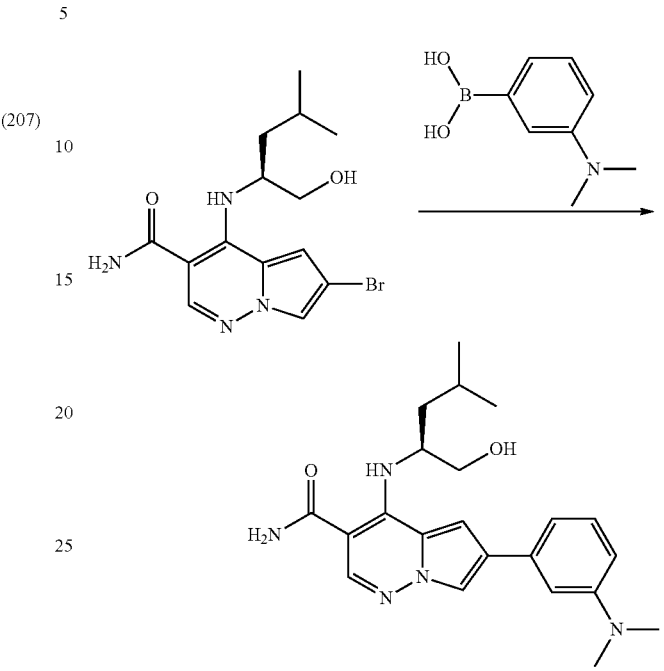

A mixture of (S)-6-bromo-4-(1-hydroxy-4-methylpentan-2-ylamino)pyrrolo[1,2-b]pyridazine-3-carboxamide (23 mg, 0.070 mmol), 3-(N,N-dimethylamino)phenyl boronic acid (16 mg, 0.1 mmol), palladium (II) acetate (1.46 mg, 0.0065 mmol), potassium phosphate, tribasic, 2M (0.1 mL, 0.2 mmol) and 2-(dicyclohexylphosphino)-2',4',6'-triisopropylbyphenyl (6.2 mg, 0.013 mmol) in dioxane (Volume: 0.65 mL) was heated to 90° C. overnight. The reaction mixture was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10 mM ammonium acetate; Mobile Phase B: 95:5 acetonitrile:water with 10 mM ammonium acetate; Gradient: 20-100% B over 25 minutes, then a 5-minute hold at 100% B; Flow: 20 mL/min. Fractions containing the desired product were combined and dried via centrifugal evaporation to afford the title compound (3.8 mg, 15% yield). MS (ES+) m/z: 396.1 (M+H); LC retention time: 1.83 min (analytical HPLC Method B).

Example 208

4-(3-amino-2,2-dimethylpropylamino)-6-(4-cyanophenyl)pyrrolo[1,2-b]pyridazine-3-carboxamide

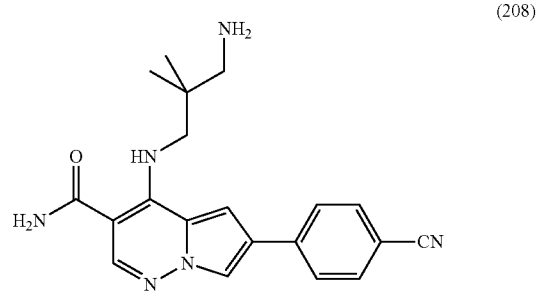 [SMILES: CC(C)(CN)CNc1c(C(N)=O)cnn2cc(-c3ccc(C#N)cc3)cc12]

(208)

Step 1: 6-(4-cyanophenyl)-4-(ethylthio)pyrrolo[1,2-b]pyridazine-3-carboxamide

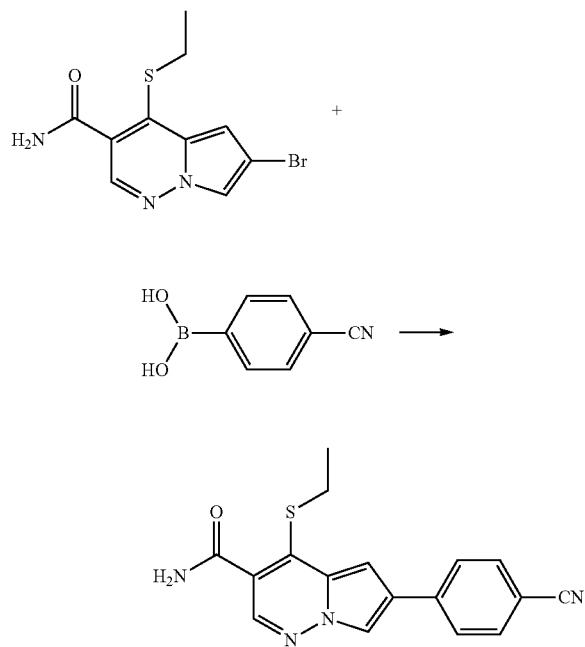

A mixture of 6-bromo-4-(ethylthio)pyrrolo[1,2-b]pyridazine-3-carboxamide (1.2 g, 4.00 mmol), 4-cyanophenylboronic acid (0.881 g, 6.00 mmol), palladium (II) acetate (0.090 g, 0.400 mmol) and 2-(dicyclohexylphosphino)-2',4',6'-triisopropylbyphenyl (XPhos) (0.381 g, 0.800 mmol) was pumped under vacuum and backfilled with nitrogen three times. Next, potassium phosphate, tribasic, 2M (7.60 mL, 15.19 mmol) and dioxane (Volume: 30 mL) were quickly added. The resulting orange suspension was again pumped under vacuum and backfilled with nitrogen three times. The reaction vessel was sealed and heated behind a blast shield in a 125° C. oil bath for 4 h. LCMS and HPLC showed that the desired product was formed, but the reaction was incomplete. The mixture was cooled to room temperature and 4-cyanophenylboronic acid (0.366 g, 3.00 mmol), palladium (II) acetate (0.045 g, 0.200 mmol) and 2-(dicyclohexylphosphino)-2',4',6'-triisopropylbiphenyl (0.191 g, 0.400 mmol) were added. The resulting mixture was again pumped under vacuum and backfilled with nitrogen three times. The reaction vessel was sealed and heated behind a blast shield in a 125° C. oil bath for 1.5 h. The reaction mixture was partitioned between EtOAc (250 ml) and water (250 ml). The two phases were separated. The aqueous phase was extracted with EtOAc (2×50 mL). The combined organic phase was washed with brine (100 mL), dried (MgSO$_4$) and concentrated to give a yellow solid. The solid residue was treated with Et$_2$O (50 mL), stirred for 30 min, filtered, and washed with 1:1 mixture of Et$_2$O-hexanes (2×15 mL) to give a yellow solid (889 mg). $^1$H NMR, HPLC and LCMS showed that the main component was the desired product, but the material was impure. The filtrate was found to contain a minor amount of the desired product. The impure material was treated with Et$_2$O (50 mL), stirred for 30 min, filtered, washed with 1:1 mixture of Et$_2$O-hexanes (2×15 mL) to give the title compound as yellow solid (787 mg). $^1$H NMR showed some improvement, but the material was still impure. The mixture was taken to the next reaction without purification.

Step 2: 6-(4-cyanophenyl)-4-(ethylsulfinyl)pyrrolo[1,2-b]pyridazine-3-carboxamide

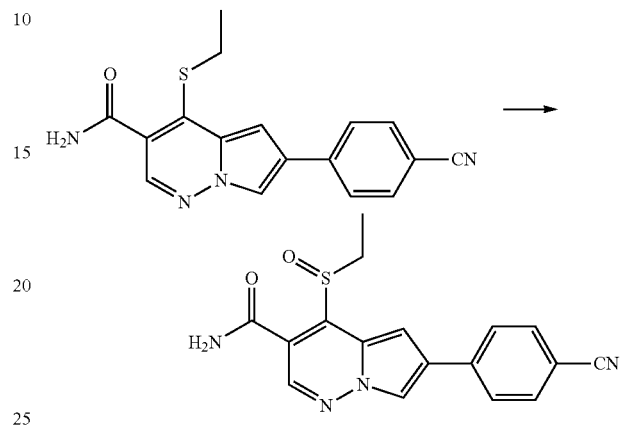

A solution of oxone (3.30 g, 5.37 mmol) in water (Volume: 40 mL) was added dropwise to a yellow suspension of impure 6-(4-cyanophenyl)-4-(ethylthio)pyrrolo[1,2-b]pyridazine-3-carboxamide (0.787 g, 2.441 mmol) in acetone (Ratio: 1.000, Volume: 40 mL) at rt. The resulting suspension was stirred at rt for 3 h. LCMS and HPLC showed that the starting material was consumed and the desired product was formed. The suspension was filtered, washed with water (2×10 mL), and dried under high vacuum to give a green-yellow solid. $^1$H NMR and HPLC indicated that the desired product was the major component, but the material was impure. The amount of the material is more than theoretical weight and the material is not totally soluble when making NMR solution, indicating the possible presence of inorganic salt. The material was treated with water (10 mL), stirred for 15 min, filtered, washed with H$_2$O (2×5 mL), and dried under high vacuum to give a green-yellow solid (591.3 mg; 44% yield over 2 steps). $^1$H NMR, LCMS and HPLC indicated that the material was not pure, but the major component is consistent with the desired product. $^1$H NMR (400 MHz, DMSO-d$_6$) δ ppm 8.83 (1 H, d, J=1.54 Hz), 8.54 (1 H, s), 8.28 (1 H, br. s.), 8.07 (1 H, d, J=1.54 Hz), 8.03 (2 H, d, J=8.36 Hz), 7.89 (2 H, d, J=8.36 Hz), 7.80 (1 H, br. s.), 3.31-3.46 (2 H, m), 1.35 (3 H, t, J=7.48 Hz).

Step 3

Example 208

A mixture of 6-(4-cyanophenyl)-4-(ethylsulfinyl)pyrrolo[1,2-b]pyridazine-3-carboxamide (15 mg, 0.044 mmol), 2,2-dimethylpropane-1,3-diamine (22.65 mg, 0.222 mmol) and in NMP (0.2 mL) was agitated at rt for 2 hr. The crude reaction mixture was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10 mM ammonium acetate; Mobile Phase B: 95:5 methanol:water with 10 mM ammonium acetate; Gradient: 20-100% B over 25 minutes, then a 5-minute hold at 100% B; Flow: 20 mL/min. Fractions containing the desired product were combined and dried via centrifugal evaporation to afford the title compound (8.9 mg, 53% yield). $^1$H NMR (500 MHz, DMSO-$d_6$) δ 11.00 (t, J=4.5 Hz, 1H), 8.52-8.35 (m, 1H), 8.27 (s, 1H), 8.04 (d, J=8.4 Hz, 2H), 7.87 (d, J=8.4 Hz, 5H), 7.54 (d, J=1.5 Hz, 1H), 3.78 (d, J=4.5 Hz, 2H), 2.94-2.82 (m, 2H), 1.19-1.04 (m, 6H). MS (ES+) m/z: 363.2 (M+H); LC retention time: 1.528 min (analytical HPLC Method B).

Example 209

6-(6-methoxypyridin-3-yl)-4-((4,4,4-trifluoro-3-hydroxybutan-2-yl)amino)pyrrolo[1,2-b]pyridazine-3-carboxamide

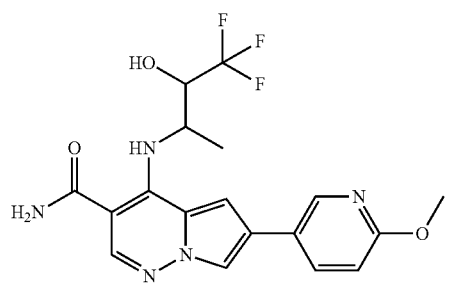
(209)

Step 1: 4-(ethylthio)-6-(6-methoxypyridin-3-yl)pyrrolo[1,2-b]pyridazine-3-carboxamide

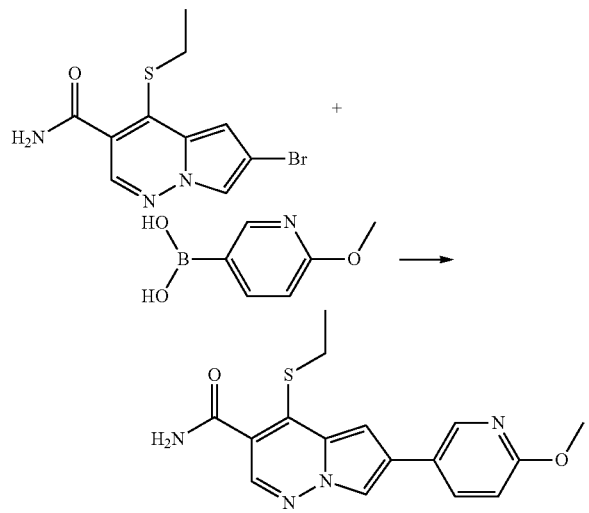

A mixture of 6-bromo-4-(ethylthio)pyrrolo[1,2-b]pyridazine-3-carboxamide (1.2 g, 4.00 mmol), (6-methoxypyridin-3-yl)boronic acid (0.881 g, 6.00 mmol), palladium (II) acetate (0.090 g, 0.400 mmol) and 2-(dicyclohexylphosphino)-2',4',6'-triisopropylbyphenyl (XPhos) (0.381 g, 0.800 mmol) was pumped under vacuum and backfilled with nitrogen three times. Next, potassium phosphate, tribasic, 2M (7.60 mL, 15.19 mmol) and dioxane (Volume: 30 mL) were quickly added. The resulting orange suspension was again pumped under vacuum and backfilled with nitrogen three times. The reaction vessel was sealed and heated behind a blast shield in a 125° C. oil bath for 4 h. LCMS and HPLC showed that the desired product was formed, but the reaction was incomplete. The mixture was cooled to room temperature and 4-cyanophenylboronic acid (0.366 g, 3.00 mmol), palladium (II) acetate (0.045 g, 0.200 mmol) and 2-(dicyclohexylphosphino)-2',4',6'-triisopropylbiphenyl (0.191 g, 0.400 mmol) were added. The resulting mixture was again pumped under vacuum and backfilled with nitrogen three times. The reaction vessel was sealed and heated behind a blast shield in a 125° C. oil bath for 1.5 h. The reaction mixture was partitioned between EtOAc (250 ml) and water (250 ml). The two phases were separated. The aqueous phase was extracted with EtOAc (2×50 mL). The combined organic phase was washed with brine (100 mL), dried (MgSO$_4$) and concentrated to give a yellow solid. The solid residue was treated with Et$_2$O (50 mL), stirred for 30 min, filtered, and washed with 1:1 mixture of Et$_2$O-hexanes (2×15 mL) to give a yellow solid (889 mg). $^1$H NMR, HPLC and LCMS showed that the main component was the desired product, but the material was impure. The filtrate was found to contain a minor amount of the desired product. The impure material was treated with Et$_2$O (50 mL), stirred for 30 min, filtered, washed with 1:1 mixture of Et$_2$O-hexanes (2×15 mL) to give the title compound as yellow solid (787 mg). $^1$H NMR showed some improvement, but the material was still impure. The mixture was taken to the next reaction without purification.

Step 2: 4-(ethylsulfinyl)-6-(6-methoxypyridin-3-yl)pyrrolo[1,2-b]pyridazine-3-carboxamide

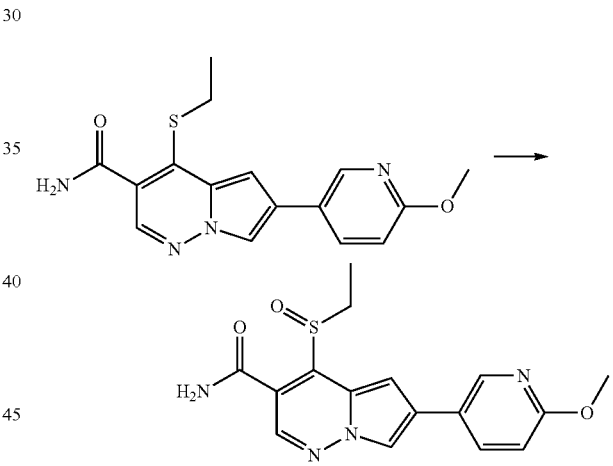

A solution of oxone (3.30 g, 5.37 mmol) in water (Volume: 40 mL) was added dropwise to a yellow suspension of impure 4-(ethylthio)-6-(6-methoxypyridin-3-yl)pyrrolo[1,2-b]pyridazine-3-carboxamide (0.787 g, 2.441 mmol) in acetone (Ratio: 1.000, Volume: 40 mL) at rt. The resulting suspension was stirred at rt for 3 h. LCMS and HPLC showed that the starting material was consumed and the desired product was formed. The suspension was filtered, washed with water (2×10 mL), and dried under high vacuum to give a green-yellow solid. $^1$H NMR and HPLC indicated that the desired product was the major component, but the material was impure. The amount of the material is more than theoretical weight and the material is not totally soluble when making NMR solution, indicating the possible presence of inorganic salt. The material was treated with water (10 mL), stirred for 15 min, filtered, washed with H$_2$O (2×5 mL), and dried under high vacuum to give a green-yellow solid (591.3 mg; 44% yield over 2 steps). $^1$H NMR, LCMS and HPLC indicated that the material was not pure, but the major component is consistent with the desired product. $^1$H NMR (400 MHz, DMSO-d6) δ ppm 8.83 (1 H, d, J=1.54 Hz), 8.54 (1H, s), 8.28 (1 H, br. s.), 8.07 (1 H, d, J=1.54 Hz), 8.03 (2H, d, J=8.36 Hz), 7.89 (2 H, d, J=8.36 Hz), 7.80 (1 H, br. s.), 3.31-3.46 (2 7H, m), 1.35 (3 H, t, J=7.48 Hz).

Step 3

Example 209

A suspension of 4-(ethylsulfinyl)-6-(6-methoxypyridin-3-yl)pyrrolo[1,2-b]pyridazine-3-carboxamide (30.0 mg, 0.087 mmol), 3-amino-1,1,1-trifluorobutan-2-ol (24.93 mg, 0.174 mmol), and Hunig's Base (0.061 mL, 0.348 mmol) in DMA (0.54 mL) was stirred in a $N_2$-flushed sealed vial at 115° C. for 2 hrs and 45 min. Within 1 minute of heating, the substrate dissolved. HPLC and LC/MS after 1.5 hr indicated a nearly complete reaction (2 peaks with m/e 410.11, M+H for desired product, diastereoisomers separated). The crude reaction mixture was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10 mM ammonium acetate; Mobile Phase B: 95:5 methanol:water with 10 mM ammonium acetate; Gradient: 20-100% B over 25 minutes, then a 5-minute hold at 100% B; Flow: 20 mL/min. Fractions containing the desired product were combined and dried via centrifugal evaporation to afford the title compound.

Isomer A: LC/MS: m/e 410.2 (M+H). $^1$H NMR (500 MHz, CD3OD/CDCl3) δ 8.40 (d, J=2.0 Hz, 1H), 8.10 (s, 1H), 7.91 (dd, J=8.9, 2.5 Hz, 1H), 7.84 (d, J=2.0 Hz, 1H), 7.09 (d, J=1.5 Hz, 1H), 6.85 (d, J=8.4 Hz, 1H), 4.81-4.71 (m, 1H), 4.10 (qd, J=7.0, 1.7 Hz, 1H), 3.95 (s, 3H), 1.56 (d, J=6.4 Hz, 3H).

Isomer B: LC/MS: m/e 410.2 (M+H). $^1$H NMR (500 MHz, CD3OD/CDCl3) δ 8.38 (d, J=2.0 Hz, 1H), 8.12 (s, 1H), 7.93-7.80 (m, 2H), 7.05 (d, J=2.0 Hz, 1H), 6.85 (d, J=8.4 Hz, 1H), 4.84-4.71 (m, 1H), 4.36-4.22 (m, 1H), 3.95 (s, 3H), 1.50 (d, J=6.4 Hz, 3H).

Example 210

(R)-4-(1-cyclopropyl-1-hydroxypropan-2-ylamino)-6-(6-methoxypyridin-3-yl)pyrrolo[1,2-b]pyridazine-3-carboxamide, Isomer A

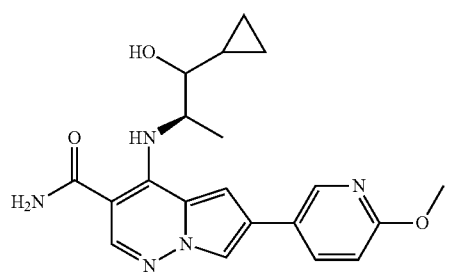

(210)

Step 1: (R)-tert-butyl (1-oxopropan-2-yl)carbamate

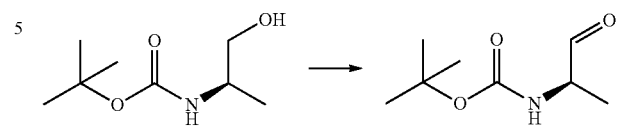

Water (2.57 ml, 143 mmol) was added dropwise to a mixture of (R)-tert-butyl (1-hydroxypropan-2-yl)carbamate (17.85 g, 102 mmol) and Dess-Martin Periodinane (60.5 g, 143 mmol) in anhydrous DCM (500 ml) at rt under a nitrogen atmosphere. The reaction was allowed to stir at rt overnight before diluting with diethyl ether and filtering. The filtrate was evaporated in vacuo and the residue diluted with diethyl ether. The organic was then washed with a 1:1 mixture of 10% aq sodium thiosulfate solution: sat. sodium bicarbonate solution, followed by brine and water. The aqueous phase was then back extracted with one portion of diethyl ether, the combined organics were then dried (MgSO4) and evaporated in vacuo to give (R)-tert-butyl (1-oxopropan-2-yl)carbamate (15 g, 87 mmol, 85% yield) as a white solid.

Step 2: tert-butyl((2R)-1-cyclopropyl-1-hydroxypropan-2-yl)carbamate

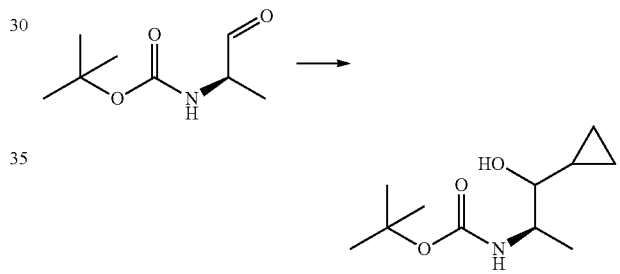

Cyclopropylmagnesium bromide (32 mL, 16.00 mmol) was added dropwise to a solution of (R)-tert-butyl 1-oxopropan-2-ylcarbamate (1.10 g, 6.35 mmol) in anhydrous THF (Volume: 25.4 mL) at −78° C. The reaction mixture was then allowed to warm to 0° C. and stirred at this temp for 4 hrs before quenching with sat. ammonium chloride solution. The evaporated organic was then purified by column chromatography using hexane:ethyl acetate as eluent to give tert-butyl (2R)-1-cyclopropyl-1-hydroxypropan-2-ylcarbamate (745 mg, 3.46 mmol, 54.5% yield). $^1$H NMR (500 MHz, CCl3D) δ 4.80 (br. s., 1H), 3.94-3.66 (m, 1H), 3.07-2.90 (m, 1H), 2.87-2.65 (m, 1H), 2.44-2.13 (m, 1H), 1.48-1.37 (m, 9H), 1.24-1.12 (m, 3H), 1.06-0.91 (m, 1H), 0.91-0.78 (m, 1H), 0.64-0.46 (m, 2H), 0.42-0.15 (m, 2H).

Step 3: (2R)-2-amino-1-cyclopropylpropan-1-ol hydrochloride

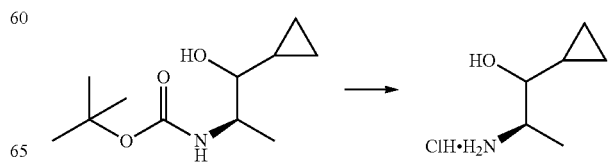

HCl (4M in 1,4-dioxane) (15 mL, 60.0 mmol) was added in one portion to a solution of tert-butyl (2R)-1-cyclopropyl-1-hydroxypropan-2-ylcarbamate (745 mg, 3.46 mmol) in DCM (Volume: 10 mL). The reaction mixture was then allowed to stir at rt for 4 hrs before evaporating in vacuo. to give (2R)-2-amino-1-cyclopropylpropan-1-ol hydrochloride (525 mg, 3.46 mmol, 100% yield). $^1$H NMR (500 MHz, CD$_3$OD) δ 3.78-3.72 (m, 1H), 3.25 (t, J=7.1 Hz, 3H), 3.05 (dd, J=8.3, 3.6 Hz, 1H), 2.87 (t, J=7.8 Hz, 2H), 1.39-1.32 (m, 3H), 0.89 (qt, J=8.1, 5.0 Hz, 1H), 0.67-0.51 (m, 2H), 0.46-0.32 (m, 2H).

Step 4: 6-bromo-4-((1-cyclopropyl-1-hydroxypropan-2-yl)amino)pyrrolo[1,2-b]pyridazine-3-carboxamide

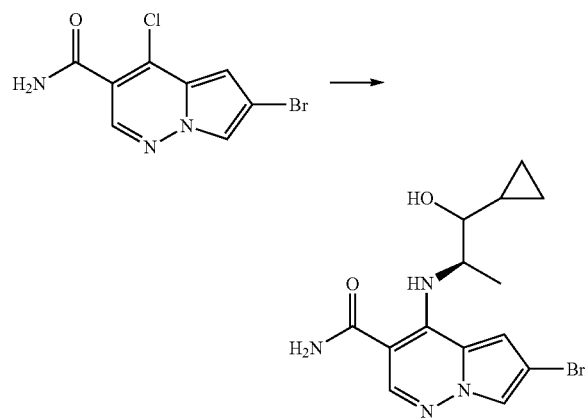

6-bromo-4-chloropyrrolo[1,2-b]pyridazine-3-carboxamide (272 mg, 0.989 mmol), (2R)-2-amino-1-cyclopropylpropan-1-ol hydrochloride (300 mg, 1.978 mmol) and DIPEA (0.691 ml, 3.96 mmol) were heated to 110° C. in NMP (3.297 ml) for 4 hrs. The reaction was then cooled to rt and ice-water added. After the ice had melted, the mixture was extracted with ethyl acetate (3×). The combined organics were then dried (MgSO$_4$) and evaporated in vacuo before purifying by column chromatography using hexane ethyl acetate as eluent to give 6-bromo-4-(((2R)-1-cyclopropyl-1-hydroxypropan-2-yl)amino)pyrrolo[1,2-b]pyridazine-3-carboxamide (111 mg, 0.299 mmol, 30.2% yield) as a mixture of diastereoisomers. $^1$H NMR (500 MHz, CCl$_3$D) δ 7.93-7.78 (m, 1H), 7.68-7.52 (m, 1H), 6.93 (d, J=1.7 Hz, 1H), 5.44 (br. s., 1H), 4.53-4.27 (m, 1H), 4.13 (q, J=7.2 Hz, 1H), 2.99 (dd, J=9.2, 3.1 Hz, 1H), 1.48 (d, J=6.7 Hz, 3H), 1.27 (t, J=7.1 Hz, 2H), 1.14-0.99 (m, 1H), 0.65-0.53 (m, 2H), 0.43-0.27 (m, 2H).

Step 5

Example 210

A mixture of 6-bromo-4-((1-cyclopropyl-1-hydroxypropan-2-yl)amino) pyrrolo[1,2-b]pyridazine-3-carboxamide (15 mg, 0.4 mmol), (6-methoxypyridin-3-yl)boronic acid (25 mg, 6.00 mmol), palladium (II) acetate (0.090 g, 0.400 mmol) and 2-(dicyclohexylphosphino)-2',4',6'-triisopropylbyphenyl (XPhos) (0.381 g, 0.800 mmol) was pumped under vacuum and backfilled with nitrogen three times. Next, potassium phosphate, tribasic, 2M (0.76 mL, 1.19 mmol) and dioxane (Volume: 2 mL) were quickly added. The resulting orange suspension was again pumped under vacuum and backfilled with nitrogen three times. The reaction vessel was sealed and heated behind a blast shield in a 125° C. oil bath for 4 h. The crude reaction mixture was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 methanol:water with 10-mM ammonium acetate; Mobile Phase B: 95:5 methanol:water with 10-mM ammonium acetate; Gradient: 30-100% B over 25 minutes, then a 5-minute hold at 100% B; Flow: 20 mL/min. Fractions containing the desired product were combined and dried via centrifugal evaporation to afford the title compound (11.8 mg, 43% yield). $^1$H NMR (500 MHz, CH$_3$OD) δ 8.42 (d, J=2.5 Hz, 1H), 8.20-8.04 (m, 1H), 7.95 (dd, J=8.9, 2.5 Hz, 1H), 7.84 (d, J=1.5 Hz, 1H), 7.27-7.05 (m, 1H), 6.95-6.72 (m, 1H), 4.54 (qd, J=6.6, 3.0 Hz, 1H), 3.96 (m, 3H), 3.07 (dd, J=8.7, 3.2 Hz, 1H), 1.50 (d, J=6.4 Hz, 3H), 1.13-0.93 (m, 1H), 0.65-0.49 (m, 2H), 0.42-0.35 (m, 1H), 0.34-0.28 (m, 1H); MS (ES+) m/z: 382.1 (M+H); LC retention time: 1.825 min (analytical HPLC Method B).

TABLE 13

| Ex # | Structure | HPLC Rt (minutes) | LCMS [m/z (M + H)] |
|---|---|---|---|
| 211 | 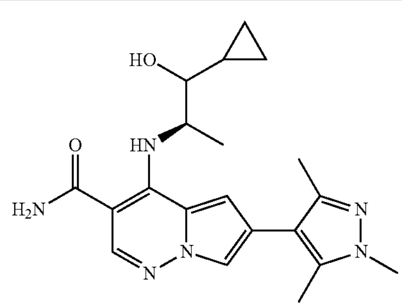 [SMILES: Cc1nn(C)c(C)c1-c1cc2c(N[C@H](C)C(O)C3CC3)c(C(N)=O)cnn2c1] | 0.97 | 382.2 |

TABLE 13-continued

| Ex # | Structure | HPLC Rt (minutes) | LCMS [m/z (M + H)] |
|---|---|---|---|
| 212 | 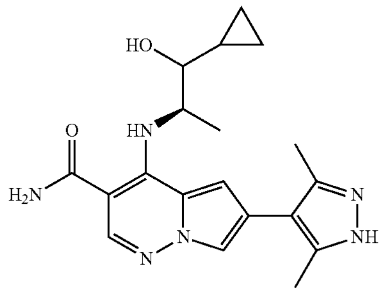 [SMILES: Cc1n[nH]c(C)c1-c1cc2c(N[C@H](C)C(O)C3CC3)c(C(N)=O)cnn2c1] | 0.81 | 368.2 |
| 213 | 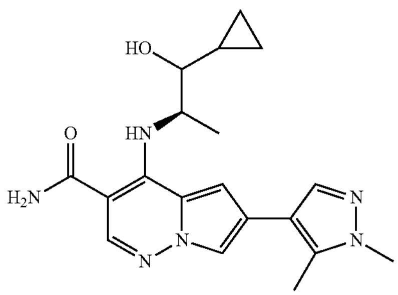 [SMILES: Cc1c(-c2cc3c(N[C@H](C)C(O)C4CC4)c(C(N)=O)cnn3c2)cnn1C] | 1.34 | 368.0 |
| 214 | 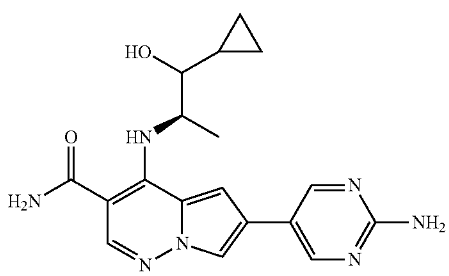 [SMILES: C[C@@H](Nc1c(C(N)=O)cnn2cc(-c3cnc(N)nc3)cc12)C(O)C1CC1] | 0.56 | 368.2 |
| 215 | 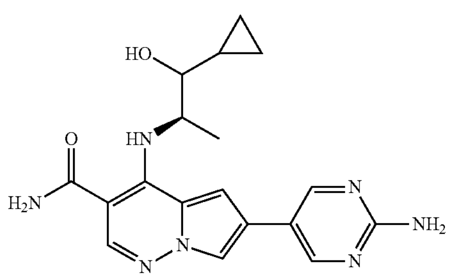 [SMILES: C[C@@H](Nc1c(C(N)=O)cnn2cc(-c3cnc(N)nc3)cc12)C(O)C1CC1] | 0.55 | 368.2 |
| 216 | 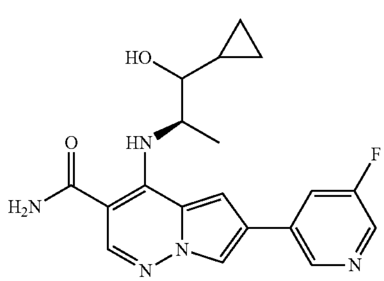 [SMILES: C[C@@H](Nc1c(C(N)=O)cnn2cc(-c3cncc(F)c3)cc12)C(O)C1CC1] | 1.21 | 369.2 |

TABLE 13-continued

| Ex # | Structure | HPLC Rt (minutes) | LCMS [m/z (M + H)] |
|---|---|---|---|
| 217 | 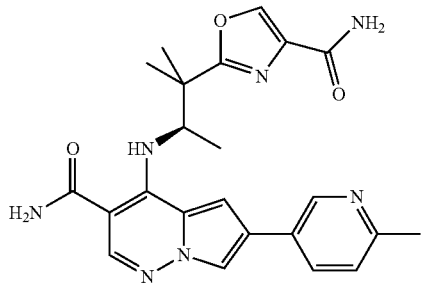 | 1.61 | 419.2 |

Example 218

(R)-2-(3-((3-carbamoyl-6-(6-methylpyridin-3-yl)pyrrolo[1,2-b]pyridazin-4-yl)amino)-2-methylbutan-2-yl)oxazole-4-carboxamide

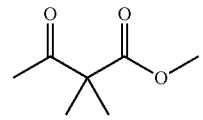

(218)

Step 1: Methyl 2,2dimethyl-3-oxobutanoate

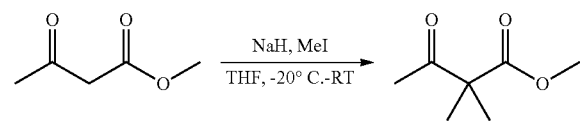

60% sodium hydride (68 g, 1.70 mole) was taken in dry THF (1000 mL) and stirred at −20° C. Methyl 3-oxobutanoate (100 g, 861 mmoles) was added drop-wise over 20 minutes at the same temperature with continuous stirring. Methyl iodide (244 g, 1.72 mole) was added drop-wise over 30 minutes at the same temp and then the reaction mixture was allowed to reach RT and stirred for overnight. It was then diluted with water and extracted with EtOAc (3×100 mL). The combined organic layers were dried over anhydrous $Na_2SO_4$ and concentrated under vacuum. Crude product was purified by distillation (at bath temp. 100° C.) at 77° C. to afford a colorless oil (50 g, 40.3%). $^1$HNMR (400 MHz, DMSO) δ ppm: 1.20 (d, J=7.2 Hz, 1H), 1.29 (s, 6H), 2.13 (s, 3H), 2.19 (s, 1H), 3.66-3.67 (m, 3H).

Step 2: (R)-methyl 2,2-dimethyl-3-((R)-1-phenylethyl)amino)butanoate

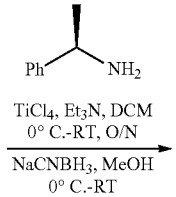

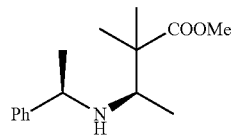

To a solution of methyl 2,2dimethyl-3-oxobutanoate (50 g, 347 mmoles) in DCM (1000 mL) was added $Et_3N$ (288 mL, 2.06 mole) and (R)-1-phenylethanamine (44 mL, 345 mmoles) at 0° C. $TiCl_4$ (19 mL, 172 mmoles) was added drop-wise and reaction mixture was allowed to stir overnight at RT. After reaction was completed, the mixture was diluted with diethyl ether (500 mL) and filtered through celite. Filtrate was concentrated under vacuum. The crude product (85 g, 364 mmoles) was taken in MeOH (100 mL) was treated with $NaHCO_3$ (20.60 g, 517 mmoles) at 0° C. and stirred for 4 h at RT, then filtered. The filtrate was concentrated under vacuum and diluted with ice cold water (200 mL) and extracted with EtOAc (3×150 mL). The combined organic layer was dried over $Na_2SO_4$ and concentrated under vacuum. Crude product obtained was purified by column chromatography (silica 60-120, 5% Ethyl Acetate: Pet-Ether) to give title compound as yellow oil (21 g, 24.44%). $^1$H NMR (400 MHz, DMSO) δ ppm: 0.74 (d, J=6.8 Hz, 3H), 1.02 (s, 3H), 1.07 (s, 3H), 1.17 (d, J=6.4 Hz, 3H), 1.52 (m, 1H), 2.75-2.79 (m, 1H), 3.59 (s, 3H), 3.65-3.69 (m, 1H), 7.19-7.29 (m, 5H).

Step 3: (R)-methyl 3-amino-2,2-dimethylbutanoate hydrochloride

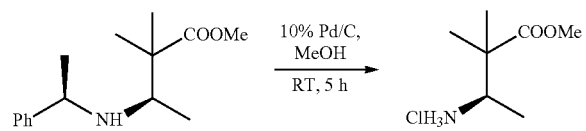

To a solution of (R)-methyl 2,2-dimethyl-3-((R)-1-phenylethyl)amino) butanoate (21.8 g, 87 mmol) in MeOH (150 mL) was added 10% palladium carbon (6 g, 61.2 mmol) at RT. The reaction was performed under hydrogen atmosphere through bladder. Reaction mixture was stirred for 5 h at RT at balloon pressure. After completion of reaction, it was filtered through celite and washed with methanol. The crude reaction mixture was quenched with hydrochloric acid in methanol (40 mL) and stirred for overnight at RT. The solvent was evaporated under recued pressure to get desired product as hydrochloride salt (15 g, 94%). $^1$HNMR (400 MHz, $D_2O$) δ ppm: 1.22-1.24 (m, 9H), 3.54-3.59 (m, 1H), 3.72 (s, 3H).

Step 4: (R)-methyl 3-((tert-butoxycarbonyl)amino)-2,2-dimethylbutanoate

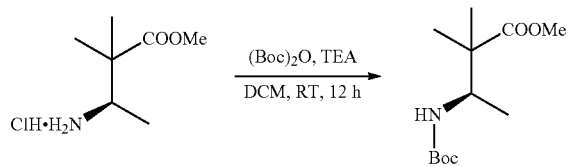

(R)-methyl 3-amino-2,2-dimethylbutanoate hydrochloride (4.0 g, 22.02 mmol) was taken in DCM (240 mL) and $(Boc)_2O$ (14.42 g, 66.10 mmol) and TEA (30.7 mL, 220 mmol) were added at 0° C. The reaction mixture was allowed to stir for 12 h at RT. DCM was removed under vacuum. Crude product thus obtained was dissolved in EtOAc and filtered through celite. Filtrate was concentrated under vacuum to get desired product as white solid (5.2 g, 96%). $^1$H NMR (400 MHz, DMSO) δ ppm: 0.93 (d, J=6.8 Hz, 3H), 1.03 (s, 3H), 1.04 (s, 3H), 1.38 (s, 9H), 3.60 (s, 3H), 3.84-3.90 (m, 1H), 6.65 (d, J=10 Hz, 1H).

Step 5: (R)-3-((tert-butoxycarbonyl)amino)-2,2-dimethylbutanoic acid

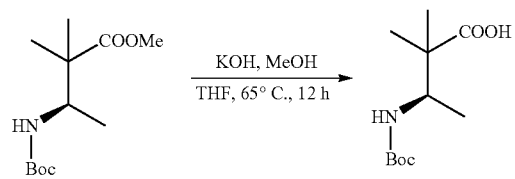 [SMILES: COC(=O)C(C)(C)[C@@H](C)NC(=O)OC(C)(C)C ; C[C@@H](NC(=O)OC(C)(C)C)C(C)(C)C(=O)O]

(R)-3-((tert-butoxycarbonyl)amino)-2,2-dimethylbutanoic acid (5.2 g, 21.20 mmol) was dissolved in MeOH (130 mL) and THF (36 mL). KOH (3.57 g, 63.60 mmol) was added and heated to 60° C. and maintained for 12 hr. After completion of hydrolysis, reaction mass was diluted with water and pH of the solution was adjusted at 4 using 1.5 N HCl solutions. The product was extracted into EtOAc (3×100 mL). The combined organic layer was dried over $Na_2SO_4$ and concentrated under vacuum to get desired product as white solid (4.3 g, 88%). $^1$H NMR (400 MHz, DMSO) δ ppm: 0.94 (d, J=6.8 Hz, 3H), 0.97 (s, 3H), 1.03 (s, 3H), 1.38 (s, 9H), 3.83-3.89 (m, 1H), 6.53 (d, J=10 Hz, 1H).

Step 6: Methyl-2-(R)-3-((tert-butoxycarbonyl)amino)-2,2-dimethylbutanamido)-3-hydroxypropanoate

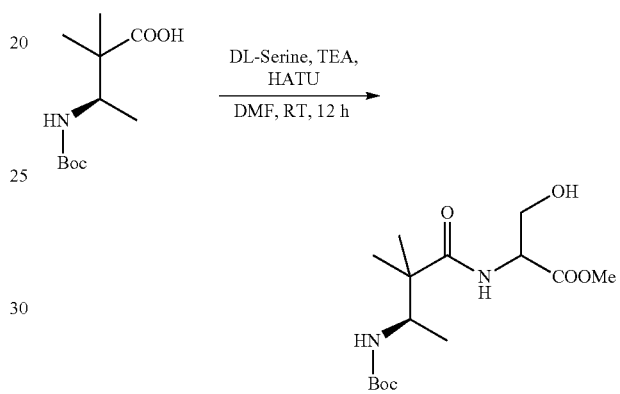

To a solution of (R)-3-((tert-butoxycarbonyl)amino)-2,2-dimethylbutanoic acid (4.3 g, 18.59 mmoles) in DMF (230 mL) were added methyl 2-amino-3-hydroxypropanoate hydrochloride (5.78 g, 37.2 mmol), HATU (21.21 g, 55.8 mmol), and TEA (25.9 mL, 186 mmol). The mixture was stirred overnight at RT. The reaction was quenched with ice cold water (500 mL) and extracted with EtOAc (3×150 mL). The combined organic layer was dried over $Na_2SO_4$ and the solvent was removed under vacuum. Crude product thus obtained was purified by ELSD combiflash (120 g silica column, 60% EtOAc: Pet-Ether) to afford a yellow oil (4.2 g, 68%). $^1$H NMR (400 MHz, DMSO) δ ppm: 0.91-0.94 (m, 3H), 1.02-1.06 (m, 6H), 1.40 (s, 9H), 3.62 (s, 3H), 3.66-3.84 (m, 3H), 4.29-4.30 (m, 1H), 4.96-5.03 (m, 1H), 6.48-6.54 (m, 1H), 7.42 (dd, J=30, 6.8 Hz, 1H).

Step 7: Methyl 2-((R)-3-((tert-butoxycarbonyl)amino)-2-methylbutan-2-yl)-4,5-dihydrooxazole-4-carboxylate

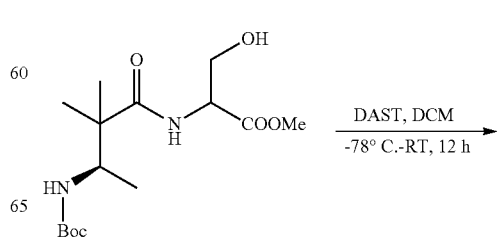

-continued

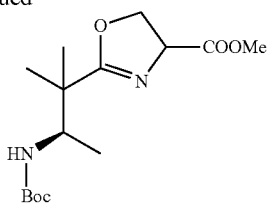

To a solution of methyl-2-(R)-3-((tert-butoxycarbonyl)amino)-2,2-dimethylbutanamido)-3-hydroxypropanoate (4.5 g, 13.54 mmol) in DCM (350 mL) was added DAST (7.15 mL, 54.02 mmol) at −78° C. The reaction mixture temperature was allowed to reach RT and stirring was continued at RT for overnight. It was then quenched with 10% aq. NaHCO₃ solution and treated with EtOAc (3×100 mL). The combined organic layers were dried over anhydrous Na₂SO₄ and concentrated under vacuum. Crude product obtained was purified by ELSD combiflash (120 g silica column, 50% EtOAc: Pet-Ether) to get desired product as a yellow oil (2.2 g, 50.7%). ¹HNMR (400 MHz, CDCl₃) δ ppm: 1.10-1.13 (m, 3H), 1.23 (s, 3H), 1.25 (s, 3H), 1.44 (s, 9H), 3.78 (m, 4H), 4.33-4.39 (m, 1H), 4.43-4.50 (m, 1H), 4.69-4.74 (m, 1H), 5.22 (m, 1H).

Step 8: (R)-methyl 2-(3-((tert-butoxycarbonyl)amino)-2-methylbutan-2-yl)oxazole-4-carboxylate

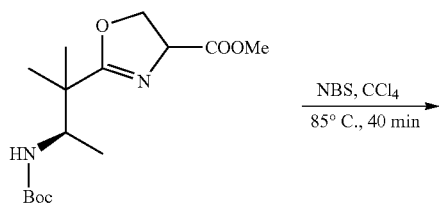

To a solution of methyl 2-((R)-3-((tert-butoxycarbonyl)amino)-2-methylbutan-2-yl)-4,5-dihydrooxazole-4-carboxylate (2.0 g, 6.36 mmol) in CCl₄ (180 mL) was added NBS (3.96 g, 22.27 mmol) at RT. The reaction mixture was heated to 85° C. and stirred for 30 min. It was then diluted with water and extracted with CCl₄ (3×50 mL). The combined organic layers were dried over anhydrous Na₂SO₄ and the solvent was removed under vacuum. Crude product was purified by ELSD combiflash (120 g silica column, 40% EtOAc: Pet-Ether) to afford a white solid (1.2 g, 60.4%). ¹HNMR (400 MHz, CDCl₃) δ ppm: 1.12 (d, J=6.8 Hz, 3H), 1.408 (s, 15H), 3.89-3.97 (m, 4H), 4.88-4.91 (d, J=10 Hz, 1H), 8.17 (s, 1H). LC retention time: 1.985 min (analytical HPLC Method N).

Step 9: (R)-methyl 2-(3-((tert-butoxycarbonyl)amino)-2-methylbutane-2-yl)oxazole-4-carboxylate

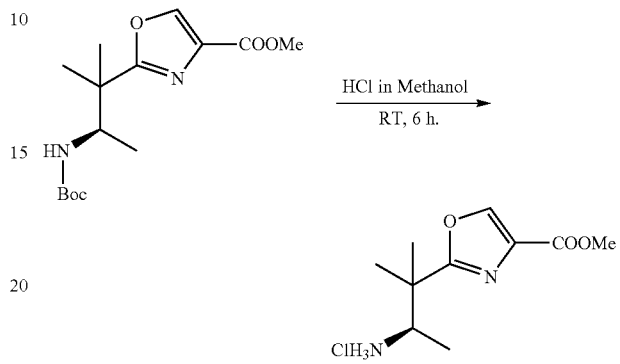

To a solution of (R)-methyl 2-(3-((tert-butoxycarbonyl)amino)-2-methylbutan-2-yl)oxazole-4-carboxylate (1.2 g, 3.84 mmol) in MeOH (100 mL) was added 4M-Methanolic-HCl (30 mL, 987 mmol). The reaction mixture was stirred overnight at RT. After deprotection was completed, methanol was stripped off concentrated under vacuum. Crude product obtained was triturated with acetone to afford a white solid (710 mg, 74.30%). ¹HNMR (400 MHz, DMSO) δ ppm: 1.16 (d, J=6.8 Hz, 3H), 1.38 (s, 3H), 1.40 (s, 3H), 3.58 (m, 1H), 3.81 (s, 3H), 8.19 (br-s, 3H), 8.86 (s, 1H). LC retention time: 1.319 min (analytical HPLC Method N).

Step 10: (R)- methyl 2-(3-((6-bromo-3-carbamoylpyrrolo[1,2-b]pyridazin-4-yl)amino) 2-methylbutane-2-yl)oxazole-4-carboxylate

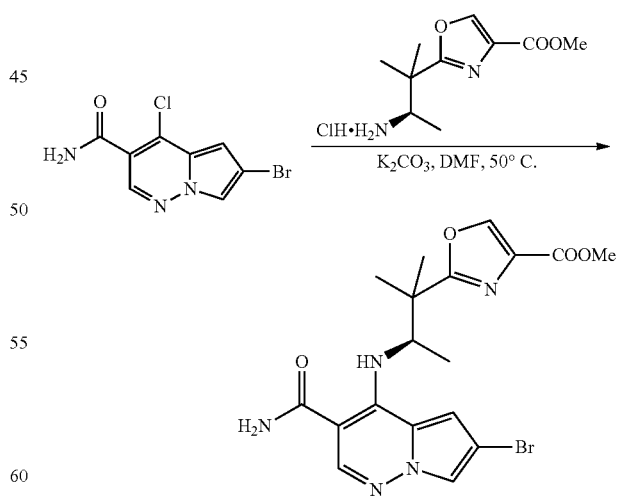

To a solution of 6-bromo-4-chloropyrrolo[1,2-b]pyridazine-3-carboxamide (200 mg, 0.729 mmol) in DMF (15 mL) was added (R)-methyl 2-(3-amino-2-methylbutan-2-yl)oxazole-4-carboxylate hydrochloride (217 mg, 0.874 mmol) and potassium carbonate (302 mg, 2.186 mmol) at RT and the reaction mixture was allowed to stir at 50° C. for 52 h. It was then quenched with water (150 ml) and extracted with EtOAc (3×100 mL). The combined organic layers were dried over anhydrous Na$_2$SO$_4$ and concentrated under vacuum. Crude product was purified by combiflash (12 g silica column, 60% EtOAc: Pet-Ether) to get desired product as yellow solid (85 mg, 25.9%). $^1$H NMR (400 MHz, DMSO) δ ppm: 1.23-1.25 (d, J=8.0 Hz, 3H), 1.42-1.44 (d, J=8.0 Hz, 6H), 3.79 (s, 3H), 4.61-4.62 (d, J=4.0 Hz, 1H), 7.09-7.10 (d, J=4.0 Hz, 1H), 7.892-7.896 (d, J=1.6 Hz, 1H), 8.22 (s, 1H), 8.75 (s, 1H), 10.91-10.95 (t, J=16.0 Hz, 1H). LC retention time: 1.680 min (analytical HPLC Method P).

Steps 11 and 12: (R)-2-(3-((6-bromo-3-carbamoylpyrrolo[1,2-b]pyridazin-4-yl)amino)-2-methylbutan-2-yl)oxazole-4-carboxamide

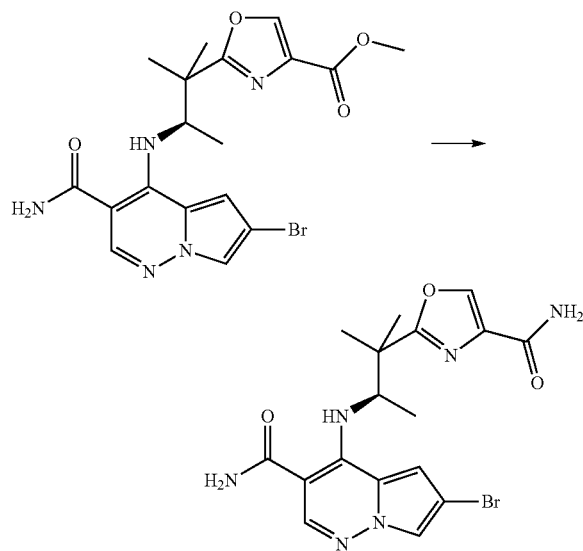

1N aqueous sodium hydroxide (5.69 ml, 5.69 mmol) was added in one portion to a solution of methyl 2-((2R,3R)-2-((tert-butoxycarbonyl)amino)pentan-3-yl)oxazole-4-carboxylate (100 mg, 0.32 mmol) in anhydrous THF (1.11 ml). The reaction mixture was allowed to stir at room temperature for 3.5 hours before evaporating the organic in vacuo. The remaining aqueous portion was cooled to 0° C. and acidified to pH 4 using 1N HCl. The aqueous phase was then extracted with ethyl acetate (3×3 mL). The aqueous pH was re-checked and judged to be ~pH 6-7. A small amount of 1N HCl was added to re-acidify the aqueous layer which was once again extracted with an additional portion of ethyl acetate (1×3 mL). The combined organics were dried (MgSO$_4$) and evaporated in vacuo to give crude 2-((2R,3R)-2-((tert-butoxycarbonyl)amino)pentan-3-yl)oxazole-4-carboxylic acid (95 mg, 0.32 mmol, 100% yield) as a white solid which was used immediately in the next reaction. EDC (86 mg, 0.45 mmol) was added in one portion to a mixture of 2-((2R,3R)-2-((tert-butoxycarbonyl)amino)pentan-3-yl)oxazole-4-carboxylic acid (95 mg, 0.32 mmol) and HOBT (69 mg, 0.45 mmol) in anhydrous dichloromethane (5.0 ml) and the reaction allowed to stir at room temperature under a nitrogen atmosphere for 30 minutes. Ammonia was then bubbled through for approximately 5 minutes and the resulting white suspension allowed to stir at room temperature overnight. The reaction was then evaporated in vacuo and the residue partitioned between ethyl acetate (10 mL) and water (10 mL). The organic layer was then dried (MgSO$_4$) and evaporated in vacuo to give tert-butyl ((2R,3R)-3-(4-carbamoyloxazol-2-yl)pentan-2-yl)carbamate (95 mg, 0.32 mmol, 100% yield) which was used immediately in the next step. LC/MS: M+H$^+$436.11, ret. time=1.89 min. Column: Phenomenex, 2.0×30 mm, 2.5-μm particles; Mobile Phase A: 10:90 methanol:water with 0.05% TFA; Mobile Phase B: 90:10 methanol:water with 0.05% TFA; Temperature: 50° C.; Gradient: 0-100% B over 3 minutes, then a 0.75-minute hold at 100% B; Flow: 1.11 mL/min. HPLC: ret. time=2.73 min. Column: YMC CombiScreen ODS-A, 4.6×50 mm; Mobile Phase A: 10:90 methanol:water with 0.2% H$_3$PO$_4$; Mobile Phase B: 90:10 methanol:water with 0.2% H$_3$PO$_4$; Temperature: 50° C.; Gradient: 0-100% B over 4 minutes, then a 0.75-minute hold at 100% B; Flow: 4 mL/min.

Step 13: (R)-2-(3-((3-carbamoyl-6-(6-methylpyridin-3-yl)pyrrolo[1,2-b]pyridazin-4-yl)amino)-2-methylbutan-2-yl)oxazole-4-carboxamide

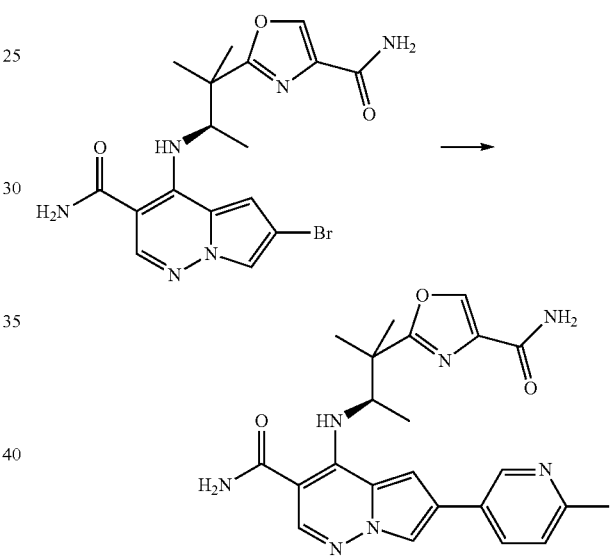

PdCl$_2$(dppf).CH$_2$Cl$_2$ adduct (1.8 mg, 2.3 μmol) was added in one portion to a solution of (R)-2-(3-((6-bromo-3-carbamoylpyrrolo[1,2-b]pyridazin-4-yl)amino)-2-methylbutan-2-yl)oxazole-4-carboxamide (10 mg, 0.023 mmol), (6-methylpyridin-3-yl) boronic acid (6.5 mg, 0.046 mmol) and potassium phosphate solution (2M aqueous solution, 35 μL, 0.069 mmol). The reaction was then heated in the CEM microwave at 120° C. for 20 min. The crude material was purified via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 15 minutes, then a 5-minute hold at 100% B; Flow: 20 mL/min. Fractions containing the desired product were combined and dried via centrifugal evaporation. The yield of the product was 7.7 mg, and its estimated purity by LCMS analysis was 100%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. Injection 2 conditions: Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. $^1$H NMR (500 MHz, CD$_3$OD) δ 8.68 (d, J=2.0 Hz, 1H), 8.20 (s, 1H), 8.09 (s, 1H), 7.93 (dd, J=8.2, 2.2 Hz, 1H), 7.89 (d, J=2.0 Hz, 1H), 7.29 (d, J=7.9 Hz, 1H), 7.13 (d, J=2.0 Hz, 1H), 4.39-4.18 (m, 1H), 1.56 (s, 3H), 1.52 (s, 3H), 1.35 (d, J=6.4 Hz, 3H).

TABLE 14

| Ex # | Structure | HPLC Rt (minutes) | LCMS [m/z (M + H)] |
|---|---|---|---|
| 219 | 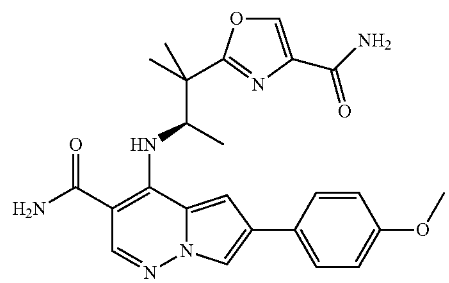 [SMILES: COc1ccc(-c2cc3c(N[C@H](C)C(C)(C)c4nc(C(N)=O)co4)c(C(N)=O)cnn3c2)cc1] | 2.04 | 463.15 |
| 220 | 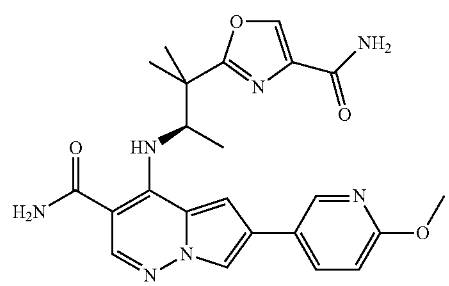 [SMILES: COc1ccc(-c2cc3c(N[C@H](C)C(C)(C)c4nc(C(N)=O)co4)c(C(N)=O)cnn3c2)cn1] | 1.96 | 464.15 |
| 221 | 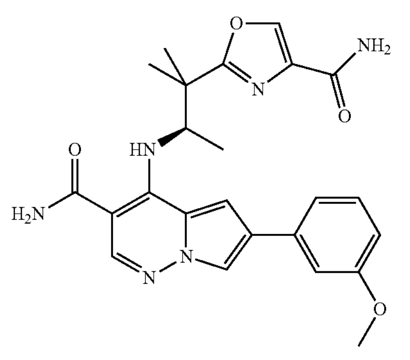 [SMILES: COc1cccc(-c2cc3c(N[C@H](C)C(C)(C)c4nc(C(N)=O)co4)c(C(N)=O)cnn3c2)c1] | 2.08 | 463.20 |
| 222 | 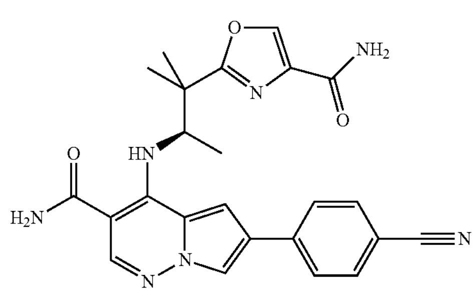 [SMILES: C[C@@H](Nc1c(C(N)=O)cnn2cc(-c3ccc(C#N)cc3)cc12)C(C)(C)c1nc(C(N)=O)co1] | 2.00 | 458.15 |

TABLE 14-continued

| Ex # | Structure | HPLC Rt (minutes) | LCMS [m/z (M + H)] |
|---|---|---|---|
| 223 | 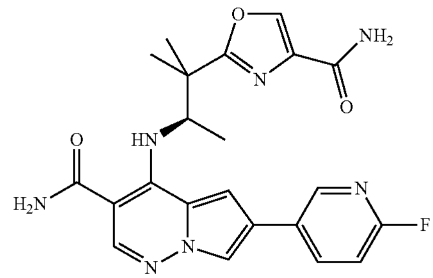 [SMILES: C[C@@H](Nc1c(C(N)=O)cnn2cc(-c3ccc(F)nc3)cc12)C(C)(C)c1nc(C(N)=O)co1] | 1.31 | 451.2 |

Example 224

2-((2R,3R)-2-((3-carbamoyl-6-(6-methoxypyridin-3-yl)pyrrolo[1,2-b]pyridazin-4-yl)amino)pentan-3-yl)oxazole-4-carboxamide

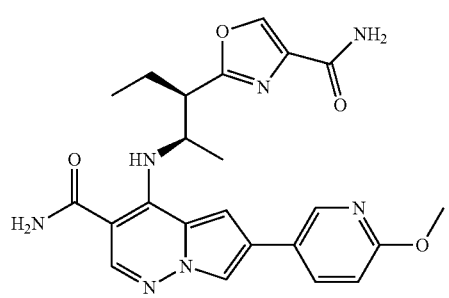

(224)

The amino acid utilized in Step 1 was synthesized according to the procedures contained within the reference: Sibi, M. P., Prabagaran, N., Ghorpade, S. G. and Jasperse, C. P., *J. Am. Chem. Soc.* 2003, 125, 11796-11797.

Step 1: (2R,3R)-3-((tert-butoxycarbonyl)amino)-2-ethylbutanoic acid

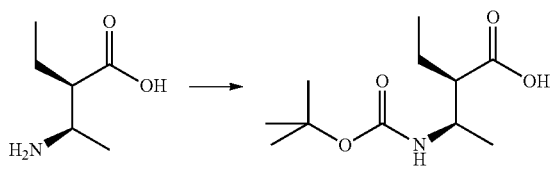

Triethylamine (1.77 mL, 12.69 mmol) was added in one portion to a mixture of (2R,3R)-3-amino-2-ethylbutanoic acid (1.11 g, 8.46 mmol) and (Boc)$_2$O (2.161 mL, 9.31 mmol) in 1,4-dioxane (25 mL) and water (25 mL). The reaction mixture was allowed to stir at room temperature under a nitrogen atmosphere for 2 days. The organic material was then evaporated in vacuo and the remaining aqueous layer extracted with ethyl acetate (3×30 mL). The combined organics were then dried (MgSO$_4$) and evaporated in vacuo to give the title compound (1.62 g, 83%) which was taken directly into the next reaction. $^1$H NMR (400 MHz, CCl$_3$D) δ 5.21 (br. s., 1H), 3.97 (br. s., 1H), 3.16 (dd, J=7.0, 2.6 Hz, 1H), 2.42 (br. s., 1H), 1.83-1.55 (m, 2H), 1.40 (s, 9H), 1.23-1.13 (m, 3H), 0.99 (t, J=7.4 Hz, 3H).

Step 2: Methyl 2-((2R,3R)-3-((tert-butoxycarbonyl)amino)-2-ethylbutanamido)-3-hydroxypropanoate

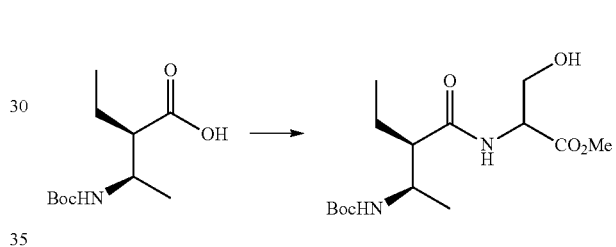

EDC (2.01 g, 10.51 mmol) was added in one portion to a solution of (2R,3R)-3-((tert-butoxycarbonyl)amino)-2-ethylbutanoic acid (1.62 g, 7.00 mmol), (S)-methyl 2-amino-3-hydroxypropanoate hydrochloride (1.64 g, 10.51 mmol), HOBT (1.61 g, 10.51 mmol) and triethylamine (3.42 ml, 24.51 mmol) in anhydrous dichloromethane (28.0 ml). The reaction mixture was allowed to stir at rt under a nitrogen atmosphere overnight before evaporating in vacuo. The residue was then taken up in ethyl acetate (50 mL) and washed with water (50 mL). The organic was then dried (MgSO$_4$) and evaporated in vacuo. The residue was treated with MeOH to precipitate title compound (1.71 g, 74%) which was used immediately in the next reaction. $^1$H NMR (400 MHz, CCl$_3$D) δ 6.56 (d, J=6.6 Hz, 1H), 4.68 (dt, J=7.2, 3.5 Hz, 1H), 4.09-3.98 (m, 2H), 3.98-3.91 (m, 1H), 3.86 (br. s., 1H), 3.81 (s, 3H), 1.83-1.67 (m, 1H), 1.67-1.52 (m, 1H), 1.44 (s, 9H), 1.18 (d, J=6.8 Hz, 3H), 0.96 (t, J=7.5 Hz, 3H).

Steps 3 and 4: Methyl 2-((2R,3R)-2-((tert-butoxycarbonyl)amino)pentan-3-yl)oxazole-4-carboxylate

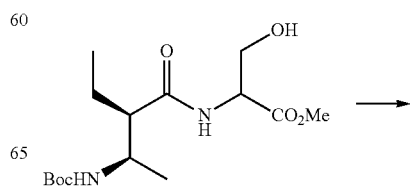

-continued

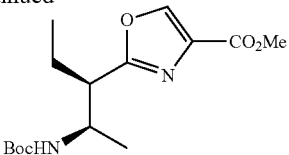

Burgess reagent (1.35 g, 5.66 mmol) was added in one portion to a solution of (S)-methyl 2-((2R,3R)-3-((tert-butoxycarbonyl)amino)-2-ethylbutanamido)-3-hydroxypropanoate (1.71 g, 5.14 mmol) in anhydrous THF (79 ml) under a nitrogen atmosphere. The reaction was then allowed to stir at 60° C. for about 4 hr. TLC indicated complete consumption of starting material and a less polar spot (1:1 hexane:ethyl acetate; $KMnO_4$ staining). After cooling to 0° C., saturated aqueous sodium bicarbonate solution (30 mL) was added and the mixture extracted with ethyl acetate (3×25 mL). The combined organics were then dried ($MgSO_4$) and evaporated in vacuo to give (S)-methyl 2-((2R,3R)-2-((tert-butoxycarbonyl)amino)pentan-3-yl)-4,5-dihydrooxazole-4-carboxylate (1.62 g, 5.14 mmol, 100% yield) as an oil which was used immediately in the next step.

A solution of (S)-methyl 2-((2R,3R)-2-((tert-butoxycarbonyl)amino)pentan-3-yl)-4,5-dihydrooxazole-4-carboxylate (1.62 g, 5.14 mmol) in anhydrous dichloromethane (15 mL+15 mL+6 mL washing) was added via a glass Pasteur pipette to a stirred suspension of copper(II) bromide (4.60 g, 20.61 mmol), hexamethylenetetramine (2.89 g, 20.61 mmol) and DBU (3.11 ml, 20.61 mmol) in anhydrous dichloromethane (20 mL). The thick suspension was stirred at room temperature for 1.5 hours-HPLC analysis (at 220 nm) indicated complete consumption of starting material and desired product formation. The reaction was partitioned between dichloromethane (20 mL) and a mixture of 10% $NH_4OH$ solution and saturated aqueous ammonium chloride solution (1:1, 30 mL). The aqueous phase was extracted with dichloromethane (3×25 mL). The combined organic phase was then washed with 10% $NH_4OH$ solution and saturated aqueous ammonium chloride solution (1:1, 30 mL), and a mixture of 1N HCl:brine (1:1, 30 mL). The organic layer was then dried ($MgSO_4$) and evaporated in vacuo to give the crude product which was purified by column chromatography using ethyl acetate-hexane as eluent to give methyl 2-((2R,3R)-2-((tert-butoxycarbonyl)amino)pentan-3-yl)oxazole-4-carboxylate (711 mg, 2.28 mmol, 44.2% yield) as an oil. $^1H$ NMR (400 MHz, $CCl_3D$) δ 8.20 (s, 1H), 5.00 (d, J=9.0 Hz, 1H), 4.17-3.99 (m, 1H), 3.92 (s, 3H), 2.94 (dt, J=9.6, 5.4 Hz, 1H), 1.95-1.70 (m, 2H), 1.42 (s, 9H), 1.10 (d, J=6.8 Hz, 3H), 0.88 (t, J=7.4 Hz, 3H). LC/MS: M+H$^+$313.08, ret. time=0.93 min. Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min.

Steps 5 and 6: tert-butyl((2R,3R)-3-(4-carbamoyloxazol-2-yl)pentan-2-yl)carbamate -continued

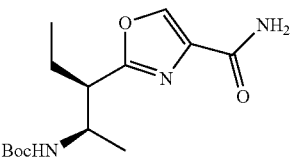

1N aqueous sodium hydroxide (5.69 ml, 5.69 mmol) was added in one portion to a solution of methyl 2-((2R,3R)-2-((tert-butoxycarbonyl)amino)pentan-3-yl)oxazole-4-carboxylate (711 mg, 2.28 mmol) in anhydrous THF (9.11 ml). The reaction was allowed to stir at room temperature for 3.5 hours before evaporating the organic in vacuo. The remaining aqueous was cooled to 0° C. and acidified to pH 4 using 1N HCl. The aqueous phase was then extracted with ethyl acetate (3×25 mL). The aqueous pH was re-checked and judged to be ~pH 6-7. A small amount of 1N HCl was added to re-acidify the aqueous layer which was once again extracted with an additional portion of ethyl acetate (1×25 mL). The combined organics were dried ($MgSO_4$) and evaporated in vacuo to give crude 2-((2R,3R)-2-((tert-butoxycarbonyl)amino)pentan-3-yl)oxazole-4-carboxylic acid (679 mg, 2.28 mmol, 100% yield) as a white solid which was used immediately in the next reaction. EDC (545 mg, 2.84 mmol) was added in one portion to a mixture of 2-((2R,3R)-2-((tert-butoxycarbonyl)amino)pentan-3-yl)oxazole-4-carboxylic acid (679 mg, 2.28 mmol) and HOBT (436 mg, 2.84 mmol) in anhydrous dichloromethane (23.0 ml) and the reaction allowed to stir at room temperature under a nitrogen atmosphere for 30 minutes. Ammonia was then bubbled through for approximately 5 minutes and the resulting white suspension allowed to stir at room temperature overnight. The reaction was then evaporated in vacuo and the residue partitioned between ethyl acetate (25 mL) and water (25 mL). The organic layer was then dried ($MgSO_4$) and evaporated in vacuo to give tert-butyl-((2R,3R)-3-(4-carbamoyloxazol-2-yl)pentan-2-yl)carbamate (677 mg, 2.28 mmol, 100% yield) which was used immediately in the next step. LC/MS: M+H$^+$320.15, ret. time=1.89 min. Column: Phenomenex, 2.0×30 mm, 2.5-μm particles; Mobile Phase A: 10:90 methanol:water with 0.05% TFA; Mobile Phase B: 90:10 methanol:water with 0.05% TFA; Temperature: 50° C.; Gradient: 0-100% B over 3 minutes, then a 0.75-minute hold at 100% B; Flow: 1.11 mL/min. HPLC: ret. time=2.73 min. Column: YMC CombiScreen ODS-A, 4.6×50 mm; Mobile Phase A: 10:90 methanol:water with 0.2% $H_3PO_4$; Mobile Phase B: 90:10 methanol:water with 0.2% $H_3PO_4$; Temperature: 50° C.; Gradient: 0-100% B over 4 minutes, then a 0.75-minute hold at 100% B; Flow: 4 mL/min.

Step 7: 2-((2R,3R)-2-aminopentan-3-yl)oxazole-4-carboxamide hydrochloride

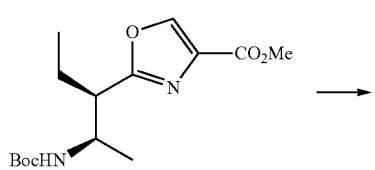

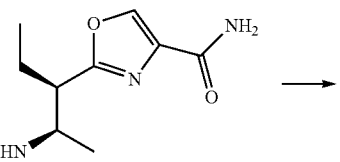

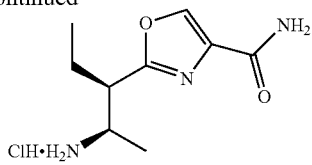

A solution of tert-butyl((2R,3R)-3-(4-carbamoyloxazol-2-yl)pentan-2-yl)carbamate (677 mg, 2.28 mmol) in anhydrous dichloromethane (6 mL) was treated with HCl (4M HCl in 1,4-dioxane, 12 mL, 48.0 mmol) and allowed to stir at room temperature overnight. The reaction was then evaporated in vacuo to give 2-((2R,3R)-2-aminopentan-3-yl)oxazole-4-carboxamide hydrochloride (532 mg, 2.28 mmol, 100% yield) which was used immediately in the next reaction.

Step 8: 2-((2R,3R)-2-((6-bromo-3-carbamoylpyrrolo[1,2-b]pyridazin-4-yl)amino)pentan-3-yl)oxazole-4-carboxamide

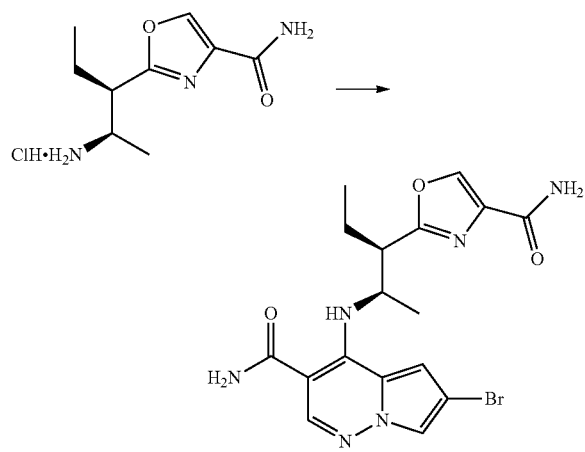

DIPEA (1.08 ml, 6.21 mmol) was added in one portion to a solution of 6-bromo-4-chloropyrrolo[1,2-b]pyridazine-3-carboxamide (568 mg, 2.07 mmol) and 2-((2R,3R)-2-aminopentan-3-yl)oxazole-4-carboxamide hydrochloride (532 mg, 2.28 mmol) in DMF (6.9 ml). The reaction was heated to 90° C. overnight before evaporating in vacuo and treating the residue with water to precipitate 2-((2R,3R)-2-((6-bromo-3-carbamoylpyrrolo[1,2-b]pyridazin-4-yl)amino)pentan-3-yl)oxazole-4-carboxamide (843 mg, 1.94 mmol, 94% yield) which was used immediately in the next reaction. $^1$H NMR (400 MHz, CCl$_3$D) δ 8.00 (s, 1H), 7.81 (s, 1H), 7.34 (d, J=1.5 Hz, 1H), 6.76 (d, J=1.5 Hz, 1H), 4.51-4.37 (m, 1H), 2.90 (dt, J=9.6, 4.9 Hz, 1H), 1.78-1.53 (m, 2H), 1.08 (d, J=6.4 Hz, 3H), 0.65 (t, J=7.4 Hz, 3H). LC/MS: M+H$^+$337.08, ret. time=0.84 min. Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min.

Step 9

Example 224

PdCl$_2$(dppf).CH$_2$Cl$_2$ adduct (1.8 mg, 2.3 mmol) was added in one portion to a solution of 2-((2R,3R)-2-((6-bromo-3-carbamoylpyrrolo[1,2-b]pyridazin-4-yl)amino)pentan-3-yl)oxazole-4-carboxamide (10 mg, 0.023 mmol), (6-methoxy-pyridin-3-yl) boronic acid (6.5 mg, 0.046 mmol) and potassium phosphate solution (2M aqueous solution, 35 μL, 0.069 mmol). The reaction was then heated in the CEM microwave at 120° C. for 20 min. The crude material was purified via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 15 minutes, then a 5-minute hold at 100% B; Flow: 20 mL/min. Fractions containing the desired product were combined and dried via centrifugal evaporation. The yield of the product was 6.0 mg, and its estimated purity by LCMS analysis was 100%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. Injection 2 conditions: Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. $^1$H NMR (500 MHz, DMSO-d$_6$) δ 10.98 (d, J=9.4 Hz, 1H), 8.73 (d, J=2.0 Hz, 1H), 8.55 (s, 1H), 8.44 (td, J=8.1, 2.2 Hz, 1H), 8.36-8.28 (m, 1H), 8.22 (s, 1H), 7.81-7.45 (m, 2H), 7.24 (dd, J=8.4, 2.5 Hz, 1H), 4.98-4.81 (m, 1H), 3.18 (dt, J=9.5, 4.9 Hz, 1H), 1.92-1.66 (m, 2H), 1.25 (d, J=6.4 Hz, 3H), 0.81 (t, J=7.4 Hz, 3H).

TABLE 15

| Ex # | Structure | HPLC Rt (minutes) | LCMS [m/z (M + H)] |
|---|---|---|---|
| 225 | 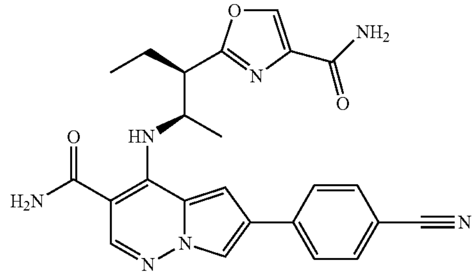 [SMILES: CC[C@@H](c1nc(C(N)=O)co1)[C@@H](C)Nc1c(C(N)=O)cnn2cc(-c3ccc(C#N)cc3)cc12] | 1.49 | 457.2 |

TABLE 15-continued

| Ex # | Structure | HPLC Rt (minutes) | LCMS [m/z (M + H)] |
|---|---|---|---|
| 226 | 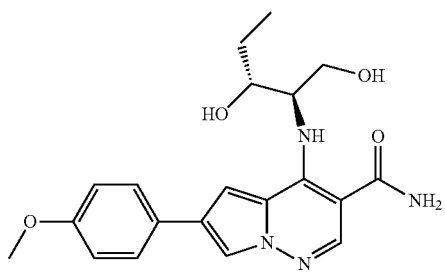 | 1.19 | 450.2 |

Example 227

4-(((2R,3R)-1,3-dihydroxypentan-2-yl)amino)-6-(4-methoxyphenyl)pyrrolo[1,2-b]pyridazine-3-carboxamide

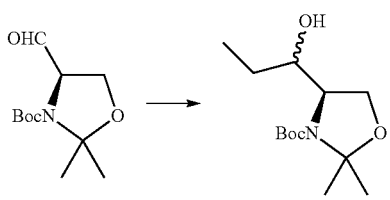 [SMILES: CC(C)(C)OC(=O)N1[C@@H](C=O)COC1(C)C ; CCC(O)[C@H]1COC(C)(C)N1C(=O)OC(C)(C)C]

(227)

Step 1: (4R)-tert-butyl 4-(1-hydroxypropyl)-2,2-dimethyloxazolidine-3-carboxylate

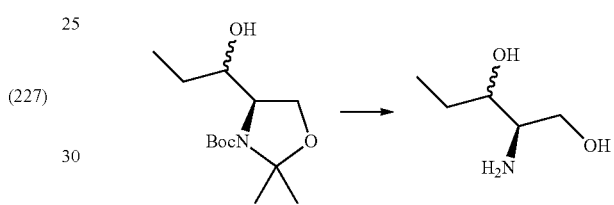

(R)-tert-butyl 4-formyl-2,2-dimethyloxazolidine-3-carboxylate (1.53 g, 6.67 mmol) was purged with nitrogen, and then was diluted with tetrahydrofuran (20 mL) and cooled to 0° C. in a ice-water bath. Ethylmagnesium bromide (3.34 mL, 10.01 mmol) was added slowly over 10 minutes. The reaction was stirred for 1 h in the ice water bath. After stirring 1 h, the reaction was slowly quenched with 30 mL sat. ammonium chloride. This was extracted with ethyl acetate (2×50 mL). The combined organic layers were washed 1× brine, then dried over sodium sulfate, filtered and concentrated to afford crude (4R)-tert-butyl 4-(1-hydroxypropyl)-2,2-dimethyloxazolidine-3-carboxylate as a colorless oil (1.65 g) which was carried on directly in the next step.

Step 2: (2R)-2-aminopentane-1,3-diol, HCl

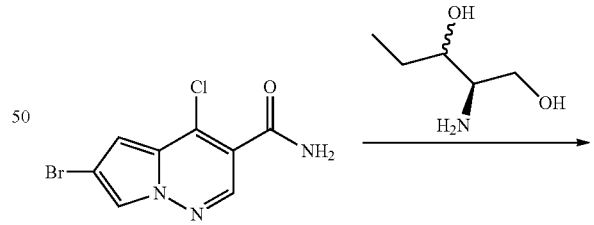

Crude (4R)-tert-butyl 4-(1-hydroxypropyl)-2,2-dimethyloxazolidine-3-carboxylate (1.65 g, 6.36 mmol) was dissolved in dichloromethane (20 mL) and then 4N HCl in 1,4-dioxane (15.91 mL, 63.6 mmol) was added. The reaction solution was stirred overnight at room temperature. The reaction was then concentrated to a brown oil, dried 1 h under high vacuum.

Step 3: 6-bromo-4-(((2R,3R)-1,3-dihydroxypentan-2-yl)amino)pyrrolo[1,2-b]pyridazine-3-carboxamide 6-bromo-4-chloropyrrolo[1,2-b]pyridazine-3-carboxamide (650 mg, 2.368 mmol) was weighed into the flask containing crude (2R)-2-aminopentane-1,3-diol, HCl (737 mg, 4.74 mmol). The flask was purged with nitrogen, and then dimethylacetamide (10 mL) and N,N-diisopropylethylamine (1.650 mL, 9.47 mmol) were added. The reaction solution was stirred at 120° C. for 3 hours. The reaction was then cooled to room temperature. Aqueous 10% LiCl (70 mL) was added. The mixture was then extracted with ethyl acetate (3×80 mL). The combined organic layers were washed 2× with brine, and then were dried over sodium sulfate. After filtration and concentration, the residue was purified by silica gel chromatography eluting with 0-10% methanol in dichloromethane, affording a cis/trans mixture comprised of the title compound and its diastereomer (225 mg, 53.2% yield) as an off-white solid. This material was then further purified via supercritical fluid chromatography with the following conditions: Column: ChiralPak OJ-H 0.46×25 cm; Mobile Phase: 15% methanol with 0.1% diethylamine in carbon dioxide; Flow: 3 mL/min; Temperature: 35° C.; Back Pressure: 100 bars; Detection Wavelength: 220 nm. Concentration of the pure fractions afforded the title compound as an off-white solid (95 mg, 22.5%). $^1$H NMR (400 MHz, DMSO-$d_6$) δ ppm 10.64 (d, J=8.8 Hz, 1H), 8.19 (s, 1H), 7.83 (d, J=1.8 Hz, 1H), 7.07 (d, J=1.8 Hz, 1H), 5.05 (d, J=4.2 Hz, 1H), 4.97 (t, J=5.3 Hz, 1H), 4.03-3.94 (m, 1H), 3.80-3.72 (m, 1H), 3.68-3.51 (m, 2H), 1.46-1.29 (m, 2H), 0.81 (t, J=7.5 Hz, 3H); MS (ES+) m/z: 357.0 359.0 (M+H); LC retention time: 2.14 min (analytical HPLC Method B).

Step 4

Example 227

6-bromo-4-(((2R,3R)-1,3-dihydroxypentan-2-yl)amino)pyrrolo[1,2-b]pyridazine-3-carboxamide (18 mg, 0.050 mmol), (4-methoxyphenyl)boronic acid (15.31 mg, 0.101 mmol) and 1,1'-bis(diphenylphosphino)ferrocene-palladium (II) dichloride (dichloromethane complex) (8.23 mg, 10.08 μmol) were weighed into a 2 dram vial, which was purged with nitrogen. Dimethylacetamide (0.5 mL) and 2M aqueous potassium phosphate tribasic (0.126 mL, 0.252 mmol) were added, and the reaction was stirred at 95° C. After 15 minutes, the reaction was complete. The solution was diluted with DMF and was then purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 25 minutes, then a 5-minute hold at 100% B; Flow: 20 mL/min. Fractions containing the desired product were combined and dried via centrifugal evaporation to give the title compound (13.6 mg, 69% yield). $^1$H NMR (500 MHz, DMSO-$d_6$) δ ppm 10.64 (d, J=8.4 Hz, 1H), 8.20-8.16 (m, 1H), 8.08 (d, J=1.5 Hz, 1H), 7.96 (s, 1H), 7.70 (d, J=8.9 Hz, 2H), 7.25 (d, J=1.5 Hz, 1H), 6.98 (d, J=8.4 Hz, 2H), 5.13-5.01 (m, 2H), 4.20 (q, J=6.9 Hz, 1H), 3.87-3.76 (m, 4H), 3.73-3.61 (m, 2H), 1.51-1.37 (m, 2H), 0.85 (t, J=7.4 Hz, 3H); MS (ES+) m/z: 385.2 (M+H); LC retention time: 2.367 min (analytical HPLC Method B).

TABLE 16

| Ex # | Structure | HPLC Rt (minutes) | LCMS [m/z (M + H)] |
|---|---|---|---|
| 228 | 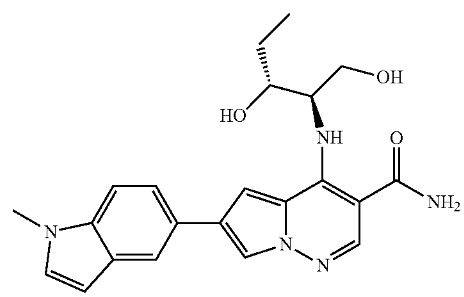 [SMILES: CC[C@@H](O)[C@@H](CO)Nc1c(C(N)=O)cnn2cc(-c3ccc4c(ccn4C)c3)cc12] | 1.38 | 408.17 |
| 229 | 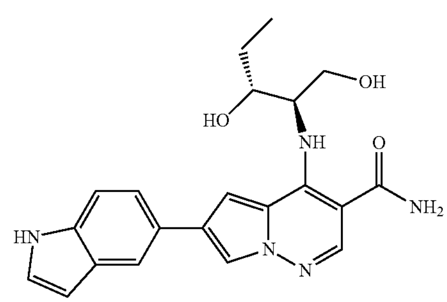 [SMILES: CC[C@@H](O)[C@@H](CO)Nc1c(C(N)=O)cnn2cc(-c3ccc4[nH]ccc4c3)cc12] | 1.15 | 394.13 |

TABLE 16-continued

| Ex # | Structure | HPLC Rt (minutes) | LCMS [m/z (M + H)] |
|---|---|---|---|
| 230 | 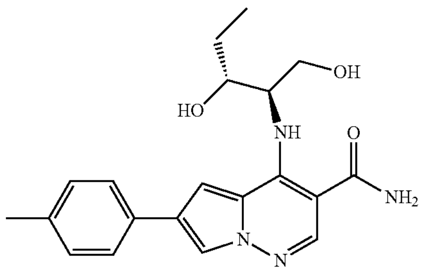 [SMILES: CC[C@@H](O)[C@@H](CO)Nc1c(C(N)=O)cnn2cc(-c3ccc(C)cc3)cc12] | 1.47 | 369.11 |

Example 231

4-(((2R,3R)-1,3-dihydroxybutan-2-yl)amino)-6-(1-methyl-1H-indol-5-yl)pyrrolo[1,2-b]pyridazine-3-carboxamide

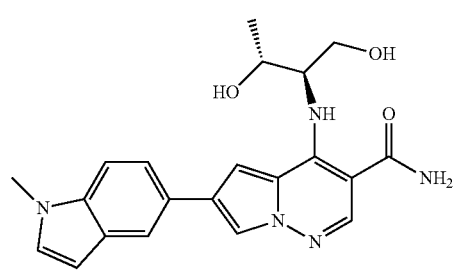

(231)

Step 1: 6-bromo-4-(((2R,3R)-1,3-dihydroxybutan-2-yl)amino)pyrrolo[1,2-b]pyridazine-3-carboxamide

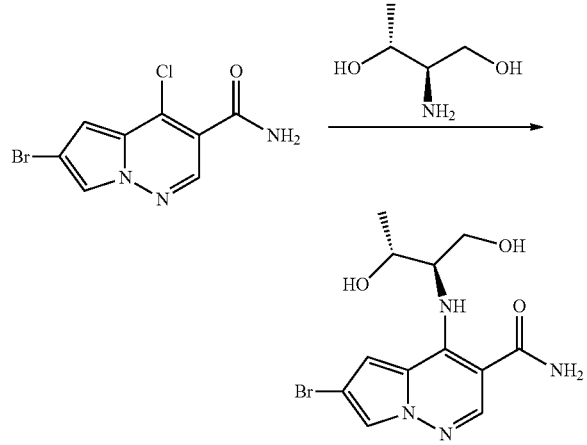

A mixture of 6-bromo-4-chloropyrrolo[1,2-b]pyridazine-3-carboxamide (686 mg, 2.5 mmol), (2R,3R)-2-aminobutane-1,3-diol (394 mg, 3.75 mmol) and diisopropylethylamine (0.873 mL, 5.00 mmol) in DMA (10 mL) was heated to 125° C. for 3 hr. After cooling to rt, the volatiles were removed under high vacuum to afford a red oil that was treated with ~25 ml of water. A gummy solid formed and the mixture was stirred at rt overnight. A few crystals of pure title compound from a previous batch were added at the beginning of the stirring. The suspension was filtered and dried to afford a yellow solid that was washed with 25 ml of Et$_2$O:EtOAc, 1:1. Drying afforded 6-bromo-4-(((2R,3R)-1,3-dihydroxybutan-2-yl)amino)pyrrolo[1,2-b]pyridazine-3-carboxamide (670 mg, 1.952 mmol, 78% yield) as a pale yellow solid. $^1$H NMR (400 MHz, CD$_3$OD) δ 8.13 (s, 1H), 7.62 (d, J=1.8 Hz, 1H), 7.09 (d, J=1.5 Hz, 1H), 4.21 (dd, J=6.4, 2.6 Hz, 1H), 4.15-4.06 (m, 1H), 3.90-3.74 (m, 2H), 1.23 (d, J=6.4 Hz, 3H); (ES+) m/z: 343.1, 345.1 (M+H); LC retention time: 1.957 min (analytical HPLC Method P).

Step 2: 4-(((2R,3R)-1,3-dihydroxybutan-2-yl)amino)-6-(1-methyl-1H-indol-5-yl)pyrrolo[1,2-b]pyridazine-3-carboxamide

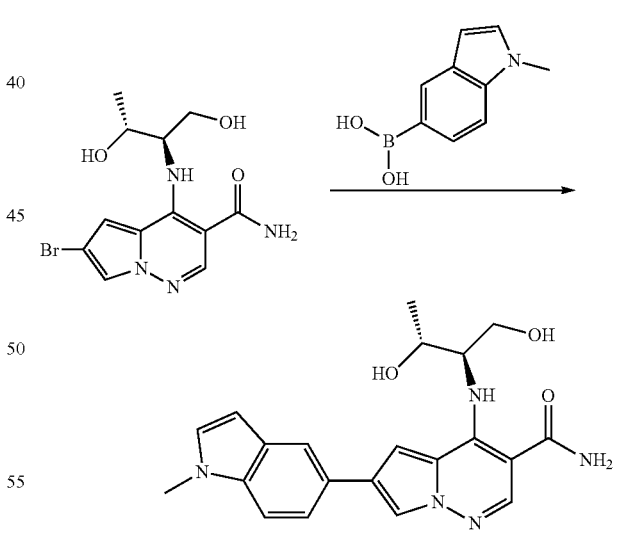

A mixture of 6-bromo-4-(((2R,3R)-1,3-dihydroxybutan-2-yl)amino) pyrrolo[1,2-b]pyridazine-3-carboxamide (25 mg, 0.073 mmol), (1-methyl-1H-indol-5-yl)boronic acid (38.2 mg, 0.219 mmol), PdCl$_2$(dppf)-CH$_2$Cl$_2$ adduct (11.90 mg, 0.015 mmol) and potassium phosphate, tribasic, 2M (0.182 mL, 0.364 mmol) in DMA (0.5 mL) was heated to 95° C. for 45 minutes. After cooling to rt, the reaction mixture was filtered and the filtrate was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-100% B over 25 minutes, then a 5-minute hold at 100% B; Flow: 20 mL/min. Fractions containing the desired product were combined and dried via centrifugal evaporation. $^1$H NMR (500 MHz, DMSO-$d_6$) δ 10.65 (d, J=8.4 Hz, 1H), 8.17 (s, 1H), 8.10 (d, J=1.5 Hz, 1H), 7.93 (d, J=1.0 Hz, 1H), 7.57 (dd, J=8.4, 1.5 Hz, 1H), 7.45 (d, J=8.4 Hz, 1H), 7.31 (dd, J=6.7, 2.2 Hz, 2H), 6.43 (d, J=3.0 Hz, 1H), 5.13-4.89 (m, 2H), 4.27-4.08 (m, 2H), 3.80 (s, 3H), 3.73-3.61 (m, 2H), 1.13 (d, J=6.4 Hz, 3H). to afford the title compound (24.6 mg, 85% yield). MS (ES+) m/z: 394.1 (M+H); LC retention time: 1.27 min (analytical HPLC Method P).

Example 232

(R)-4-((3,3-dimethyl-4-(methylsulfonamido)butan-2-yl)amino)-6-(6-methoxypyridin-3-yl)pyrrolo[1,2-b]pyridazine-3-carboxamide

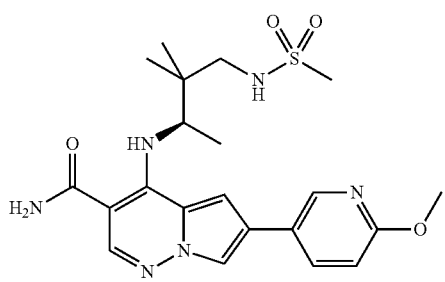

(232)

Step 1: (R)-methyl 3-(((benzyloxy)carbonyl)amino)-2,2-dimethylbutanoate

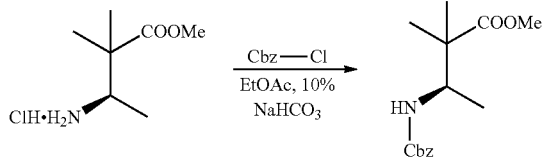

To a solution of (R)-methyl 3-amino-2,2-dimethylbutanoate hydrochloride (15.0 g, 83 mmol) in EtOAc (130 mL) and 10% NaHCO$_3$ (130 mL) was added Cbz-Cl (16.90 g, 99 mmol) at 0° C. and allowed to stir for 1 h at RT. The organic layer was separated, washed with brine solution and dried over Na$_2$SO$_4$ and concentrated under vacuum. Crude product was obtained and purified by prep-HPLC to yield a colorless oil (14.5 g, 60.7%). $^1$HNMR (400 MHz, CDCl$_3$) δ ppm: 1.12 (d, J=6.8 Hz, 3H), 1.21 (s, 6H), 3.67 (s, 3H), 3.82-3.86 (m, 1H), 5.10 (s, 2H), 5.32 (br-d, J=8.8 Hz, 1H), 7.31-7.37 (m, 5H). LCMS Purity: Column: Purospherstar RP-18 (4×55) mm, 3 μm. Buffer: 20 mM NH$_4$OAc in Water, Mobile Phase: A-Buffer+ACN (90+10); B-Buffer+ACN (10+90); Flow: 2.5 mL/min, Retention Time: 1.810 min. Purity: 89.46%. Chiral HPLC: Column: CHIRAL PAK IC (250×4.6) mm, 5 micron C.NO: SC\601. Mobile phase: 0.2% DEA n-Hexane:Ethanol (80:20). Flow: 1.0 mL\min Retention Time: 5.16 min. % of e.e: 100.

Step 2: (R)-3-(((benzyloxy)carbonyl)amino)-2,2-dimethylbutanoic acid

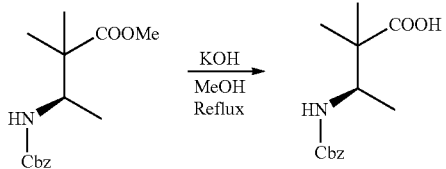 [SMILES: COC(=O)C(C)(C)[C@@H](C)NC(=O)OCc1ccccc1 ; "KOH" ; C[C@@H](NC(=O)OCc1ccccc1)C(C)(C)C(=O)O]

To a solution of (R)-methyl 3-(((benzyloxy)carbonyl)amino)-2,2-dimethylbutanoate (2.2 g, 7.88 mmol) in methanol (25 mL) was KOH (3.54 g, 63.0 mmol) solution and stirred at 65° C. for overnight. Reaction mass was concentrated under reduced pressure to remove methanol. The residue was diluted with water (50 mL) and acidified to pH 5 using 1.5N HCl solution and extracted with ethyl acetate (2×200 mL), the combined organic layer was dried over anhydrous sodium sulphate and concentrated under reduced pressure to yield (R)-3-(((benzyloxy) carbonyl)amino)-2,2-dimethylbutanoic acid (1.2 g, 56.9%) as colorless oil. $^1$HNMR (400 MHz, DMSO-$d_6$) δ ppm: 12.23 (bs, 1H), 7.30-7.39 (m, 5H), 5.03 (s, 2H), 3.92-3.98 (m, 1H), 0.98-1.09 (m, 9H). LCMS conditions: Column: Ascentis C18 (5×2.1 mm-2.7 μm); Mobile Phase A: 2% ACN-98% H$_2$O-10 mM NH$_4$COOH; Mobile Phase B: 98% CAN-2% H$_2$O-10 mM NH$_4$COOH, Flow: 1.0 mL/min, Retention Time: 1.639 min, Purity: 86.5% (m/z=266.2 M$^+$).

Step 3: (R)-benzyl (4-amino-3,3-dimethyl-4-oxobutan-2-yl)carbamate

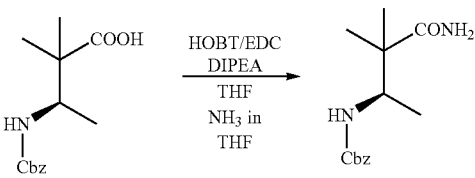 [SMILES: C[C@@H](NC(=O)OCc1ccccc1)C(C)(C)C(=O)O ; "HOBT/EDCDIPEA" ; C[C@@H](NC(=O)OCc1ccccc1)C(C)(C)C(N)=O]

To a solution of (R)-3-(((benzyloxy)carbonyl)amino)-2,2-dimethylbutanoic acid (9.0 g, 33.9 mmol) in THF (100 mL) under N$_2$ atmosphere DIPEA (17.77 mL, 102 mmol) was added followed by addition of HOBT (5.19 g, 33.9 mmol) and EDC (6.50 g, 33.9 mmol) at 25° C. The reaction mixture was stirred at 25° C. for 1 h. Then freshly prepared saturated ammonia in THF 50 mL (50 mL of THF, ammonia gas was purged at −40° C. for 20 min) was poured into the above reaction mixture at −20° C. and slowly allowed reaction mass temperature to 25° C. and stirred for further 12 h. Upon completion of the reaction, it was quenched with water (250 mL) and extracted into ethyl acetate (2×200 mL). The combined organic layer was washed with brine solution, dried over anhydrous sodium sulphate, concentrated under reduced pressure to obtain pale brown oil. This crude product was purified by column chromatography using 60-120 silica gel, by eluted with ethyl acetate:hexane (40:60) to yield (R)-benzyl (4-amino-3,3-dimethyl-4-oxobutan-2-yl)carbamate (4.8 g, 46.5%) as pale yellow oil. $^1$HNMR (400 MHz, CDCl$_3$) δ ppm: 7.36-7.35 (d, J=4.4 Hz, 5H), 5.104 (s, 2H), 3.75-3.67 (t, J=16, 18.4 Hz, 1H), 1.25-1.24 (d, J=5.2 Hz, 6H), 1.18-1.17 (d, J=6.8 Hz, 3H). HPLC purity: Column: Sunfire C18 (4.6× 150 mm, 3.5 μm), Buffer: 0.05% TFA in H$_2$O (pH 2.5, adjusted with ammonia), Solvent A: Buffer: CH$_3$CN (95:5). Solvent B: Buffer: CH$_3$CN (5:95). Time: 0-10, 12-100, 15-100 min, Flow: 1.0 mL/min Retention Time: 7.408: Purity: 93.74%. Chiral HPLC purity: Column: CHIRALPAK AD-H (250×4.6 mm) 5 micron, Mobile Phase: 0.2% DEA in hexane:ethanol (50:50). Flow: 1.0 mL/min: Retention Time: 6.036. Purity: 100%. LCMS Purity: Column: Ascentis C18 (5×2.1 mm-2.7 μm). Mobile Phase A: 2% ACN –98% H$_2$O-10 mM NH$_4$COOH. Mobile Phase B: 98% ACN –2% H$_2$O-10 mM NH$_4$COOH. Flow: 1.0 mL/min. Retention Time: 1.785 Min. Purity: 99.9% (m/z=265.2 M$^+$).

Step 4: (R)-benzyl (3-cyano-3-methylbutan-2-yl) carbamate

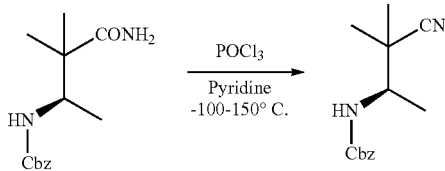 [SMILES: C[C@@H](NC(=O)OCc1ccccc1)C(C)(C)C(N)=O ; "POCl3" ; C[C@@H](NC(=O)OCc1ccccc1)C(C)(C)C#N]

To a solution of (R)-benzyl (4-amino-3,3-dimethyl-4-oxobutan-2-yl) carbamate (4.5 g, 17.02 mmol) in pyridine (90 mL) was added POCl$_3$ (3.97 mL, 42.6 mmol) at 0° C. The reaction mixture was stirred at 25° C. for 1 h. It was concentrated under reduced pressure to remove pyridine and excess POCl$_3$. The obtained residue was diluted with ice crushed water (250 mL) and treated with ethyl acetate (2×250 mL). The combined organic layer was dried over anhydrous sodium sulphate and concentrated under reduced pressure to yield (R)-benzyl (3-cyano-3-methylbutan-2-yl)carbamate (3.6 g, 86%) as pale brown oil. CHIRAL HPLC purity: Column: CHIRAL-PAK AD-H (250×4.6 mm) 5 micron, Mobile Phase: 0.2% DEA in Hexane: Ethanol (50:50). Flow: 1.0 mL/min Retention Time: 4.58 min Purity: 100%. LCMS Purity: Column: Ascentis C18 (5×2.1 mm), 2.7 μm. Mobile Phase A: 2% ACN –98% H$_2$O-10 mM NH$_4$COOH; Mobile Phase B: 98% ACN –2% H$_2$O-10 mM NH$_4$COOH, Flow: 1.0 mL/min, Retention Time: 1.987 Min, Purity: 92.55% (m/z=245.2 M).

Step 5: (R)-3-amino-2,2-dimethylbutanenitrile hydrochloride

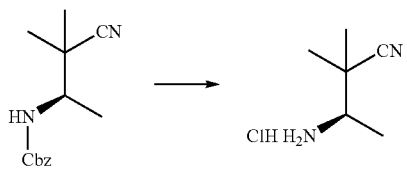

To a solution of (R)-benzyl (3-cyano-3-methylbutan-2-yl) carbamate (76 mg, 0.310 mmol) in ethyl acetate (25 mL) was added 10% Pd/C (330 mg, 0.310 mmol). The reaction mixture was stirred under hydrogen atmosphere at rt for 2 h. The reaction was monitored by LCMS. The reaction mixture was filtered through celite bed, given ethyl acetate. To the filtrate, HCl in ethyl acetate (10 mL, 2M solution) was added slowly at rt and stirred for 1 h. Then the reaction mass was concentrated as such to get (R)-3-amino-2,2-diethylbutanenitrile hydrochloride (40 mg, 0.270 mmol). LCMS Purity: Column: zorbax SB AQ (4.6×50 mm-3.5 nm). Mobile Phase A: 0.1% HCOOH; Mobile Phase B: ACN, Flow: 1.0 mL/min, Retention Time: 0.809 Min, Purity: 98.53% (m/z=113.2 M$^+$). $^1$HNMR (400 MHz, MeOD) δ ppm: 3.502-3.451 (q, J=6.8, 6.8 and 6.8 Hz, 1H), 1.519-1.468 (m, 9H).

Step 6: (R)-6-bromo-4-(3-cyano-3-methylbutan-2-ylamino)pyrrolo[1,2-b]pyridazine-3-carboxamide

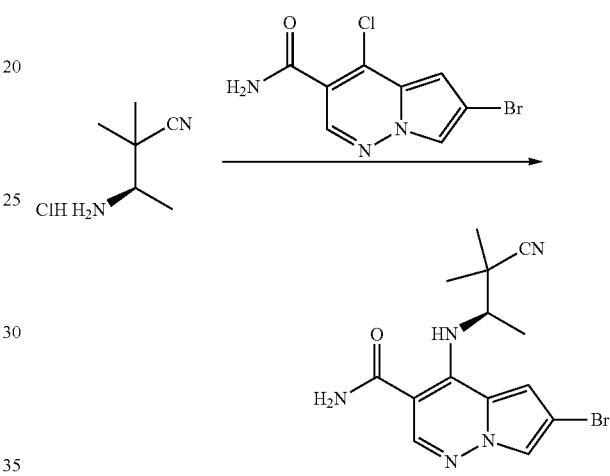

To a suspension of 6-bromo-4-chloropyrrolo[1,2-b]pyridazine-3-carboxamide (250 mg, 0.911 mmol) and (R)-3-amino-2,2-dimethylbutanenitrile hydrochloride (165 mg, 0.408 mmol) in DMF (10 mL) taken in a pressure tube (25 mL) was added DIPEA (0.477 mL, 2.73 mmol) at rt. The resulting reaction mixture was heated 100° C. and stirred for overnight. Reaction was monitored by LCMS. Reaction mass was quenched with water (50 mL) and extracted with ethyl acetate (3×30 mL). The combined organic layer was dried and concentrated under reduced pressure to get crude as brown colored oil. The crude was purified by combiflash using 24 g silicycle column eluted with 50% EA in hexane. The fractions were concentrated under reduced pressure to get (R)-6-bromo-4-((3-cyano-3-methylbutan-2-yl)amino)pyrrolo[1,2-b]pyridazine-3-carboxamide (165 mg, 0.408 mmol, 44.7% yield) as pale brown solid. $^1$HNMR (400 MHz, DMSO-d$_6$) δ ppm: 11.16-11.13 (d, J=9.6 Hz, 1H), 8.32 (s, 1H), 7.96-7.93 (d, J=13.2 Hz, 2H), 7.92 (bs, 2H), 7.22-7.21 (d, J=1.6 Hz, 2H), 4.43-4.39 (q, J=6.4, 3.6 and 6.4 Hz, 1H), 1.43-1.35 (m, 9H). HPLC purity: Column: Sunfire C18 (4.6×150 mm, 3.5μ, Buffer: 0.05% TFA in H$_2$O pH 2.5, Solvent A: Buffer: CH$_3$CN (95:5). Solvent B: Buffer: CH$_3$CN (5:95). Time: 0-10, 12-100, 15-100 min, Flow: 1.0 mL/min Retention Time: 9.68: Purity: 91.94%. LCMS Purity: Column: Purospher@star RP-18 (4×55) mm, 3 μm. Buffer: 20 mM NH$_4$OAc in water Mobile Phase A: Buffer: CH$_3$CN (90:10). Solvent B: Buffer: CH$_3$CN (10:90).Flow: 2.5 mL/min, Time:

0-0, 2-100, 2.5-100, 3.0-0 min. Retention Time: 1.688 min. Purity: 91.5% (m/z=348.2 M−2).

Step 7: (R)-4-(3-cyano-3-methylbutan-2-ylamino)-6-(6-methoxypyridin-3-yl)pyrrolo[1,2-b]pyridazine-3-carboxamide

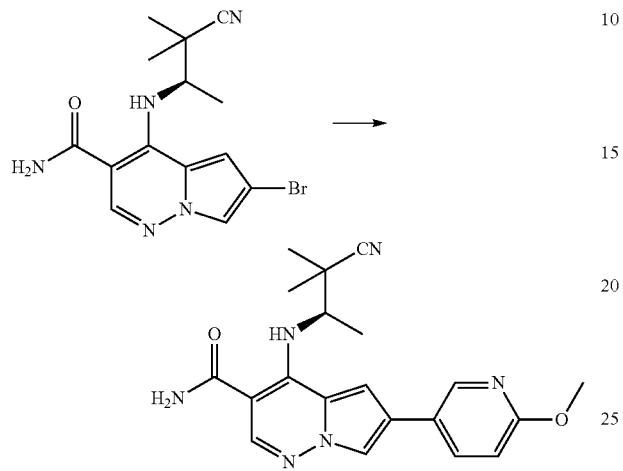

To a mixture of (R)-6-bromo-4-((3-cyano-3-methylbutan-2-yl)amino)pyrrolo[1,2-b]pyridazine-3-carboxamide (160 mg, 0.457 mmol), (6-methoxypyridin-3-yl) boronic acid (105 mg, 0.685 mmol), 2-(dicyclohexylphosphino)-2',4',6'-triisopropylbiphenyl (21.78 mg, 0.046 mmol), palladium(II) acetate (5.13 mg, 0.023 mmol) and phosphoric acid, potassium salt (291 mg, 1.371 mmol) taken in 1,4-dioxane (2 mL) and water (0.2 mL) in a pressure tube (15 mL). The reaction mixture was degassed using nitrogen and then heated to 135° C. for 45 min. Reaction was monitored by LCMS. Reaction mixture was quenched with water (40 mL) and extracted with ethyl acetate (3×30 mL). The combined organic layer was dried and concentrated under reduced pressure to get crude as brown colored oil. The crude was purified by combiflash using 24 g silicycle column eluted with 70% ethyl acetate in hexane. The fractions were concentrated under reduced pressure to get (R)-4-((3-cyano-3-methylbutan-2-yl)amino)-6-(6-methoxypyridin-3-yl)pyrrolo[1,2-b]pyridazine-3-carboxamide (120 mg, 0.313 mmol, 68.4% yield) as off white solid. $^1$H NMR (400 MHz, DMSO-d$_6$) δ ppm: 11.15-11.13 (d, J=9.6 Hz, 1H), 8.71-8.70 (d, J=2.4, 1H), 8.277-8.25 (t, J=8.8 and 1.2, 2H), 8.196-8.168 (dd, J=2.4 and 2.8 Hz, 1H), 7.41-7.40 (bs, 2H), 6.89-6.87 (d, J=8.4 Hz, 1H), 4.63-4.56 (m, 1H), 3.89 (s, 3H), 1.46-1.41 (m, 9H). HPLC purity: Column: Xbridge phenyl (4.6×150 mm, 3.5 μm), Buffer: 0.05% TFA in H$_2$O (pH 2.5, adjusted with dilute ammonia), Solvent A: Buffer: CH$_3$CN (95:5). Solvent B: Buffer: CH$_3$CN (5:95). Time: 0-10, 25-100, 30-100 min, Flow: 1.0 mL/min Retention Time: 11.88: Purity: 98.6%. CHIRAL HPLC purity: Column: CHIRALPAK IC (250×4 6 mm) 5 micron, Mobile Phase: 0.2% DEA in Hexane:Ethanol (70:30). Flow: 1.0 mL/min: Retention Time: 10.138. Purity: 95%. LCMS Purity: Column: Purospher@star RP-18 (4×55) mm, 3 μm. Buffer: 20 mM NH$_4$OAc in water Mobile Phase A: Buffer: CH$_3$CN (90:10). Solvent B: Buffer: CH$_3$CN (10:90). Flow: 2.5 mL/min, Time: 0-0, 2-100, 2.5-100, 3.0-0 min. Retention Time: 1.605 min. Purity: 99.14% (m/z=379.2 M+1).

Step 8: (R)-4-(4-amino-3,3-dimethylbutan-2-ylamino)-6-(6-methoxypyridin-3-yl)pyrrolo[1,2-b]pyridazine-3-carboxamide

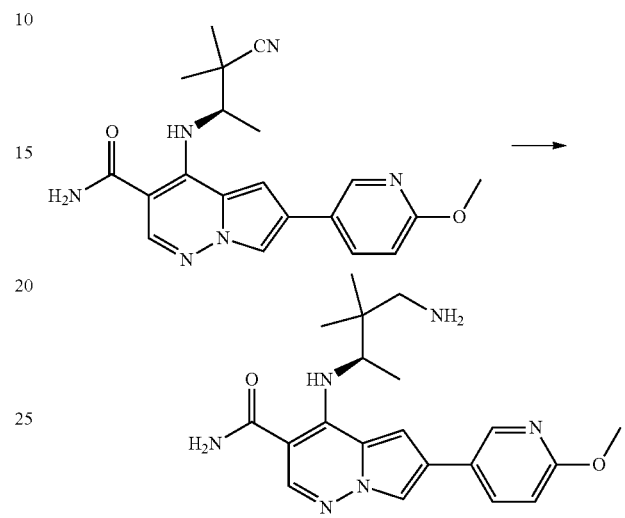

To a solution of (R)-4-((3-cyano-3-methylbutan-2-yl)amino)-6-(6-methoxypyridin-3-yl)pyrrolo[1,2-b]pyridazine-3-carboxamide (120 mg, 0.317 mmol) taken in THF (20 mL) under nitrogen atmosphere was added LAH (1M solution in THF) (12 mL, 12.00 mmol) at 0° C. slowly. The reaction mixture was stirred at 25° C. for overnight. Reaction was monitored by LCMS. Reaction mixture was quenched with saturated sodium sulfate and filtered through celite. The filtrate was taken and the two layers were separated. The organic layer was dried and concentrated under reduced pressure to get (R)-4-((4-amino-3,3-dimethylbutan-2-yl)amino)-6-(6-methoxypyridin-3-yl)pyrrolo[1,2-b]pyridazine-3-carboxamide (100 mg, 0.261 mmol, 82% yield) as yellow colored semi solid. LCMS Purity: Column: Purospher@star RP-18 (4×55) mm, 3 μm. Buffer: 20 mM NH$_4$OAc in water Mobile Phase A: Buffer: CH$_3$CN (90:10). Solvent B: Buffer: CH$_3$CN (10:90). Flow: 2.5 mL/min, Time: 0-0, 2-100, 2.5-100, 3.0-0 min. Retention Time: 1.173 min. Purity: 93.15% (m/z=383.2 M+1).

Step 9: (R)-4-(3,3-dimethyl-4-(methylsulfonamido)butan-2-ylamino)-6-(6-methoxypyridin-3-yl)pyrrolo[1,2-b]pyridazine-3-carboxamide

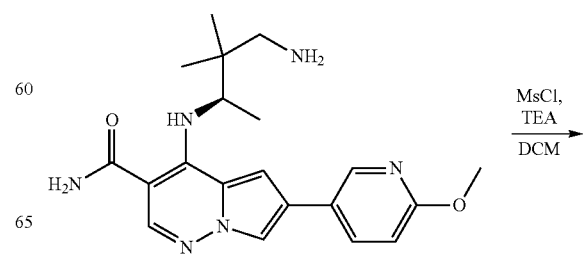

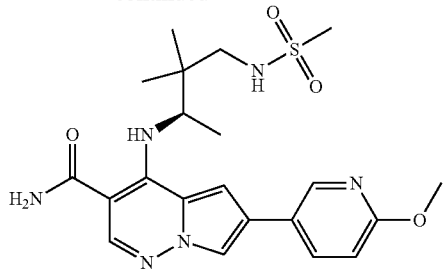

To a solution of (R)-4-((4-amino-3,3-dimethylbutan-2-yl)amino)-6-(6-methoxypyridin-3-yl)pyrrolo[1,2-b]pyridazine-3-carboxamide (60 mg, 0.157 mmol) taken in DCM (30 mL) under nitrogen atmosphere was added Mesyl-Cl (0.016 mL, 0.204 mmol) (the Mesyl-Cl was diluted with 3 mL of DCM slowly at 0° C.). The resulting reaction mixture was stirred at 0° C. for 30 min. Reaction was monitored by LCMS. Reaction mixture was quenched with 10% NaHCO$_3$ solution (25 mL) and extracted with ethyl acetate (3×20 mL), the combined organic layer was dried and concentrated under reduced pressure to get a crude compound as off white semi solid. The crude was purified by prep HPLC. The resulting fractions were concentrated under reduced pressure to remove ACN, further lyophilized to get (R)-4-((3,3-dimethyl-4-(methylsulfonamido)butan-2-yl)amino)-6-(6-methoxypyridin-3-yl)pyrrolo[1,2-b]pyridazine-3-carboxamide (23 mg, 0.049 mmol, 31.1% yield) as yellow solid. $^1$HNMR (400 MHz, DMSO-d$_6$) δ ppm: 11.013-10.99 (d, J=9.2 Hz, 1H), 8.65-8.64 (d, J=2.4 Hz, 1H), 8.22 (s, 1H), 8.188 (s, 1H), 8.11-8.10 (d, J=2.4 Hz, 1H), 7.31-7.30 (d, J=1.6 Hz, 1H), 7.15-7.13 (d, J=6.8 Hz, 1H), 6.87-6.85 (d, J=8.8 Hz, 1H), 4.37-4.34 (t, J=9.2, 6.4 Hz, 1H), 3.88 (s, 3H), 3.01-3.00 (m, 1H), 2.88 (s, 3H), 2.96-2.84 (m, 1H), 1.27-1.26 (d, J=6.4 Hz, 3H), 0.98-0.955 (d, J=10.4 Hz, 6H). HPLC purity: Column: Xbridge phenyl (4.6×150 mm, 3.5 µm), Buffer: 0.05% TFA in H$_2$O (pH 2.5, adjusted with dilute ammonia), Solvent A: Buffer: CH$_3$CN (95:5). Solvent B: Buffer: CH$_3$CN (5:95). Time: 0-10, 12-100, 15-100 min, Flow: 1.0 mL/min Retention Time: 7.578. Purity: 98.4%. HPLC purity: Column: Sunfire C18 (4.6×150 mm, 3.5µ, Buffer: 0.05% TFA in H$_2$O pH 2.5, Solvent A: Buffer: CH$_3$CN (95:5). Solvent B: Buffer: CH$_3$CN (5:95). Time: 0-10, 12-100, 15-100 min, Flow: 1.0 mL/min Retention Time: 8.318 Purity: 99.19% CHIRAL HPLC purity: Column: CHIRALCEL ODH (250×4.6 mm); 5 micron, Mobile Phase: 0.05% DEA in Hexane: Ethanol (60:40). Flow: 1.0 mL/min: Retention Time: 5.027. Purity: 100%. LCMS Purity: Column: Purospher@star RP-18 (4×55) mm, 3 µm. Buffer: 20 mM NH$_4$OAc in water Mobile Phase A: Buffer: CH$_3$CN (90:10). Solvent B: Buffer: CH$_3$CN (10:90). Flow: 2.5 mL/min, Time: 0-0, 2-100, 2.5-100, 3.0-0 min. Retention Time: 1.515 min. Purity: 99.63% (m/z=459.2 M+1). Optical rotation: [α]$_{d\ t=25.1}$=−17.6, Methanol.

TABLE 17

| Ex # | Structure | HPLC Rt (minutes) | LCMS [m/z (M + H)] |
|---|---|---|---|
| 233 | 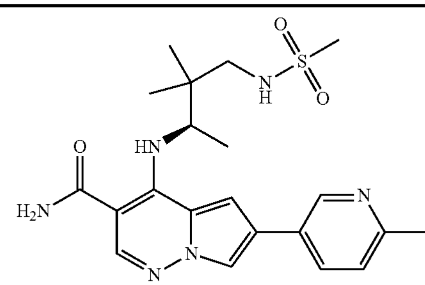 | 6.16 | 445.2 |
| 234 | 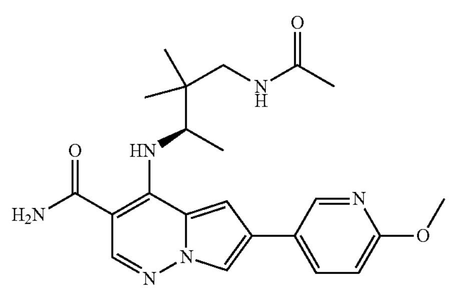 [SMILES: COc1ccc(-c2cc3c(N[C@H](C)C(C)(C)CNC(C)=O)c(C(N)=O)cnn3c2)cn1] | 7.66 | 423.4 |
| 235 | 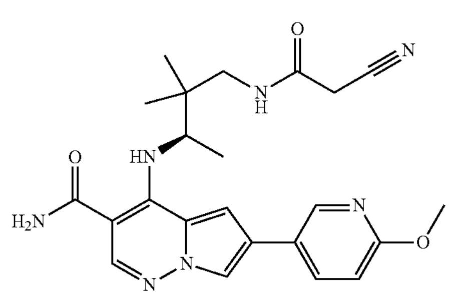 [SMILES: COc1ccc(-c2cc3c(N[C@H](C)C(C)(C)CNC(=O)CC#N)c(C(N)=O)cnn3c2)cn1] | 8.13 | 449.9 |

Example 236

(R)-4-((4-amino-3,3-dimethyl-4-oxobutan-2-yl)amino)-6-(4-methoxyphenyl)pyrrolo[1,2-b]pyridazine-3-carboxamide

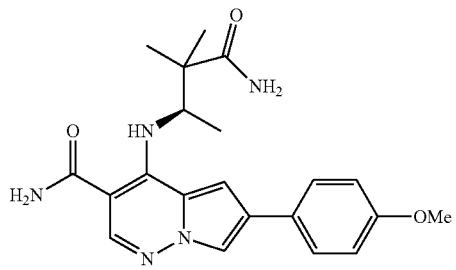

(236)

Step 1: (R)-benzyl (4-amino-3,3-dimethyl-4-oxobutane-2-yl)carbamate

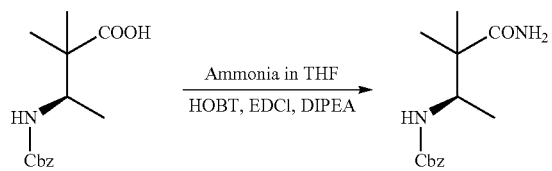 [SMILES: C[C@@H](NC(=O)OCc1ccccc1)C(C)(C)C(=O)O ; C[C@@H](NC(=O)OCc1ccccc1)C(C)(C)C(N)=O]

To a solution of (R)-3-(((benzyloxy)carbonyl)amino)-2,2-dimethylbutanoic acid (6.5 g, 23.27 mmol) in THF (60 mL) was added HOBT (3.00 g, 19.60 mmol), EDCI (3.76 g, 19.60 mmol) and DIPEA (10.27 ml, 58.8 mmol) and stirred at 0° C. for 30 min. 3M ammonia in THF (50 ml, 1848 mmol) was added to afford a white suspension. The reaction mixture was allowed to stir for 12 h at RT. Reaction mass was diluted with water (80 ml). The aqueous layer was treated with EtOAC (3×80 ml). The organic layer was dried over Na$_2$SO$_4$ and concentrated under vacuum to get desired crude product. Crude product was purified by column chromatography (60-120 mesh, 30% EtOAc: Pet-Ether) to get desired product as off white solid (2.7 g, 52%). $^1$HNMR (400 MHz, CDCl$_3$) δ ppm: 1.15-1.17 (d, J=6.8 Hz, 3H), 1.23-1.27 (m, 6H), 3.66-3.76 (m, 1H), 5.10-5.13 (s, 2H), 5.41-5.89 (m, 3H), 7.26-7.36 (m, 5H).

Step 2: (R)-3-amino-2,2-dimethylbutanamide hydrochloride

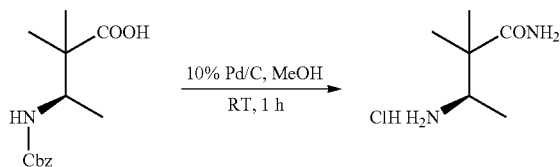

To a solution of (R)-benzyl (4-amino-3,3-dimethyl-4-oxobutane-2-yl)carbamate (1.0 g, 3.78 mmol) in MeOH (20 mL) was added 10% palladium carbon (0.101 g, 0.946 mmol) at RT under hydrogen atmosphere through bladder. The reaction mixture was stirred for 1 h at RT. It was filtered through celite and washed with methanol. Hydrochloric acid in methanol (10 mL) was added and stirred for overnight at RT. Reaction was concentrated to get desired product as hydrochloride salt (495 mg, 79%). $^1$H NMR (400 MHz, CDCl$_3$) δ ppm: 1.14 (m, 9H), 3.32 (s, 1H), 7.30-7.43 (d, 2H), 7.72 (br-s, 2H).

Step 3: (R)-4-((4-amino-3,3-dimethyl-4-oxobutane-2-yl)amino)-6-bromopyrrolo[1,2-b]pyridazine-3-carboxamide

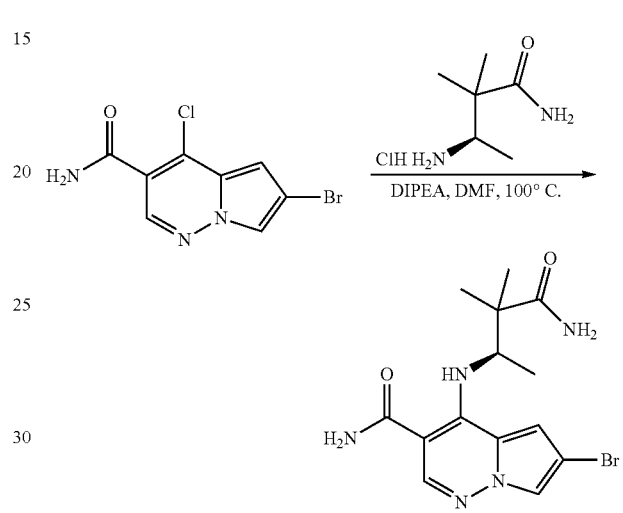

To a solution of 6-bromo-4-chloropyrrolo[1,2-b]pyridazine-3-carboxamide (400 mg, 1.457 mmol) in DMF (30 mL) was added (R)-3-amino-2,2 dimethylbutanamide hydrochloride (486 mg, 2.91 mmol) and DIPEA (1.273 ml, 7.29 mmol) at RT and the reaction mixture was allowed to stir at 100° C. for 12 h. It was then quenched with water (300 ml) and extracted with EtOAc (3×150 mL). The combined organic layers were dried over anhydrous Na$_2$SO$_4$ and concentrated under vacuum. Crude product was purified by combi-flash (12 g silica column, 85% EtOAc: Pet-Ether) to afford an off white solid (380 mg, 70.8% yield). $^1$HNMR (400 MHz, DMSO) δ ppm: 1.13-1.18 (m, 9H), 4.51-4.55 (d, J=16 Hz, 1H), 6.98 (s, 3H), 7.05-7.05 (d, J=1.6 Hz, 1H), 7.272 (s, 1H), 7.88-7.89 (d, J=4.0 Hz, 1H), 8.236 (s, 1H), 10.88-10.90 (d, J=8.0 Hz 1H).

Step 4: (R)-4-((4-amino-3,3-dimethyl-4-oxobutane-2-yl)amino)-6-(4-methoxyphenyl)pyrrolo[1,2-b]pyridazine-3-carboxamide

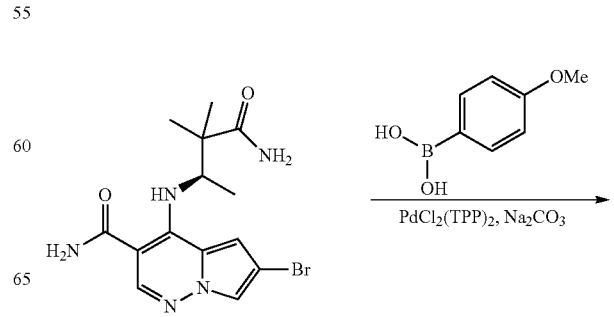

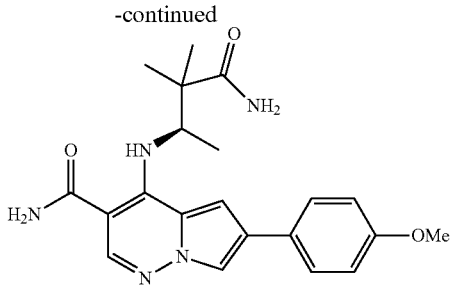

(R)-4-((4-amino-3,3-dimethyl-4-oxobutane-2-yl)amino)-6-bromopyrrolo[1,2-b]pyridazine-3-carboxamide (50 mg, 0.136 mmol) was taken in a sealed tube contained in acetonitrile (8 mL) and water (0.8 ml) mixture was added 4-methoxyphenylboronic acid (37.1 mg, 0.204 mmol), sodium carbonate (43.2 mg, 0.407 mmol). The reaction was degassed for 10 min. Next, PdCl$_2$(TPP)$_2$ (14.90 mg, 0.020 mmol) was added and the reaction mixture was heated to 100° C. and stirred for 30 min. After completion of reaction, it was then quenched with water (30 ml) and extracted into EtOAc (3×20 mL). The combined organic layers were dried over anhydrous Na$_2$SO$_4$ and solvent was removed under vacuum. Crude product was purified by prep HPLC purification to get desired product as an off white solid (16 mg, 29.8% yield). $^1$HNMR (400 MHz, DMSO) δ ppm: 1.16-1.19 (d, J=12 Hz, 6H), 1.23-1.24 (d, J=4.0 Hz, 3H), 3.79 (s, 3H), 4.69-4.73 (t, J=16 Hz, 1H), 6.95-7.01 (m, 3H), 7.214-7.263 (d, J=19.6 Hz, 4H), 7.67-7.70 (d, J=12 Hz, 2H), 8.08 (s, 1H), 8.198 (s, 1H), 10.827-10.851 (d, J=9.6 Hz, 1H). column: Puropsherstar RP-18 (4×55) mm, 3 µm. Buffer: 20 mM NH$_4$OAc in Water, Mobile Phase: A-Buffer+ACN (90+10), B-Buffer+ACN (10+90); Flow: 2.5 mL/min, Retention Time: 1.520 min, Purity: 99.46%. HPLC: Column: SUNFIRE C18 (4.6×150) mm, 3.5 micron Buffer: 0.05% TFA in water pH 2.5 Mobile phase: A: Buffer:Acetonitrile (95:5) B: Acetonitrile:buffer (95:5) Flow: 1.0 mL/min Retention Time: 8.269 min Enantioselectivity: 98.66%.

TABLE 18

| Ex # | Structure | HPLC Rt (minutes) | LCMS [m/z (M + H)] |
|---|---|---|---|
| 237 | 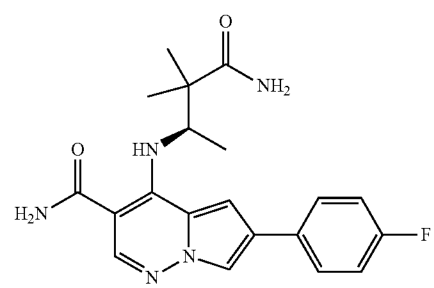 [SMILES: C[C@@H](Nc1c(C(N)=O)cnn2cc(-c3ccc(F)cc3)cc12)C(C)(C)C(N)=O] | 8.22 | 384.2 |
| 238 | 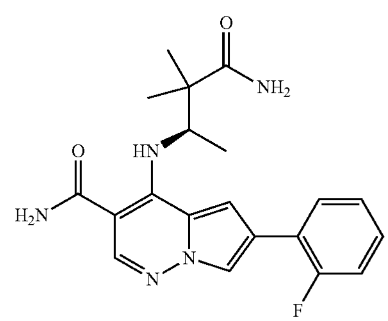 [SMILES: C[C@@H](Nc1c(C(N)=O)cnn2cc(-c3ccccc3F)cc12)C(C)(C)C(N)=O] | 8.12 | 384.2 |
| 239 | 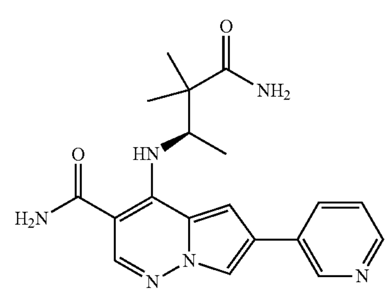 [SMILES: C[C@@H](Nc1c(C(N)=O)cnn2cc(-c3cccnc3)cc12)C(C)(C)C(N)=O] | 7.35 | 367.41 |

Example 240

(2R,3R)-2-((3-carbamoyl-6-phenylpyrrolo[1,2-b]pyridazin-4-yl)amino)-3-hydroxybutyl dihydrogen phosphate, disodium

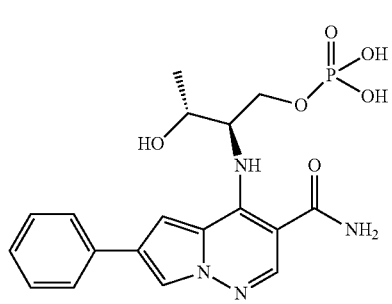
(240)

Step 1: tert-butyl((2R,3R)-3-(benzyloxy)-1-hydroxybutan-2-yl)carbamate

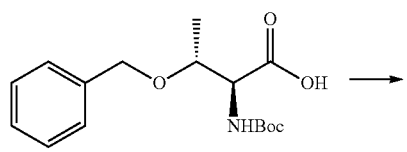

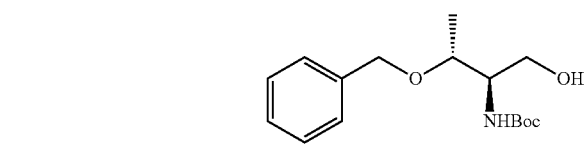

To a suspension of lithium aluminum hydride (2.94 g, 78 mmol) in 50 mL diethyl ether at 0° C. was slowly added a solution of (2S,3R)-3-(benzyloxy)-2-((tert-butoxycarbonyl)amino)butanoic acid (8.0 g, 25.9 mmol) in 25 mL diethyl ether. The reaction was allowed to warm to rt and stirred 1 hr. Water (3 ml) was added with caution, to the reaction mixture. This addition was followed by an addition of 15% NaOH (3 ml) and water (9 ml). These additions were made with extreme caution to control the rate of gas evolution. After stirring 1 hr at rt, MgSO$_4$ was added and the mixture was filtered. The filtrate was concentrated to afford an oil, which was chromatographed on a 120 gm Isco cartridge using an 0-75% EtOAc/Hex gradient. The pure fractions were concentrated to afford tert-butyl((2R,3R)-3-(benzyloxy)-1-hydroxybutan-2-yl)carbamate (5.44 g, 18.42 mmol, 71.2% yield) as a colorless oil. $^1$H NMR (400 MHz, CCl$_3$D) δ 7.32 (s, 5H), 5.07 (br. s., 1H), 4.64 (d, J=11.4 Hz, 1H), 4.38 (d, J=11.7 Hz, 1H), 3.83 (d, J=6.2 Hz, 1H), 3.79-3.71 (m, 1H), 3.70-3.59 (m, 2H), 2.60-2.38 (m, 1H), 1.48-1.42 (m, 9H), 1.27-1.25 (m, 3H).

Step 2: (2R,3R)-2-amino-3-(benzyloxy)butan-1-ol, HCl

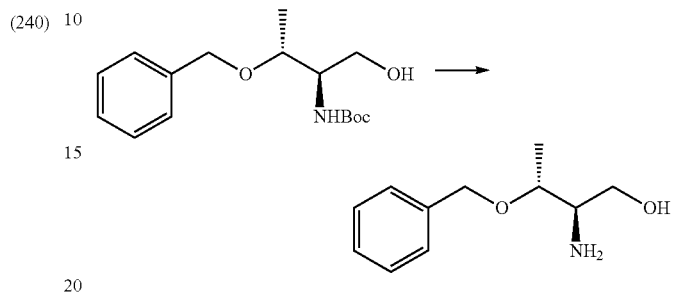

HCl, 4N in dioxane (28.3 mL, 113 mmol) was added to a solution of tert-butyl((2R,3R)-3-(benzyloxy)-1-hydroxybutan-2-yl)carbamate (2.79 g, 9.45 mmol) in DCM (30 mL) at rt. The reaction mixture was allowed to stand at rt for 18 hr. The volatiles were removed in vacuo and the residue was dried to afford (2R,3R)-2-amino-3-(benzyloxy)butan-1-ol, HCl (2.18 g, 9.41 mmol, 100% yield) as an off-white solid. $^1$H NMR (400 MHz, CD$_3$OD) δ 7.47-7.25 (m, 5H), 4.70 (d, J=11.7 Hz, 1H), 4.52 (d, J=11.4 Hz, 1H), 3.85-3.57 (m, 3H), 3.21-3.02 (m, 1H), 1.30 (d, J=6.2 Hz, 3H).

Step 3: 4-(((2R,3R)-3-(benzyloxy)-1-hydroxybutan-2-yl)amino)-6-bromopyrrolo[1,2-b]pyridazine-3-carboxamide

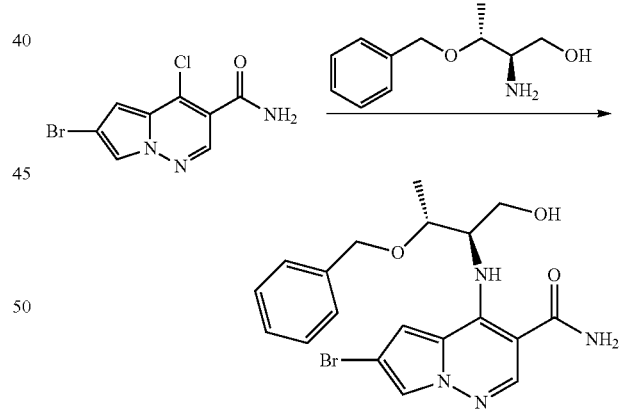

A mixture of 6-bromo-4-chloropyrrolo[1,2-b]pyridazine-3-carboxamide (1.9 g, 6.92 mmol), (2R,3R)-2-amino-3-(benzyloxy)butan-1-ol, HCl (2.18 g, 9.41 mmol) and diisopropylethylamine (4.84 mL, 27.7 mmol) in DMA (20 mL) was heated to 100° C. for 5 hr. After cooling to rt, the reaction mixture was partitioned between EtOAc (150 ml) and water (150 ml). The organic layer was washed with water (2×150 ml) and brine (150 ml). After drying (MgSO$_4$) and filtration, the organic layer was concentrated to afford 4-(((2R,3R)-3-(benzyloxy)-1-hydroxybutan-2-yl)amino)-6-bromopyrrolo[1,2-b]pyridazine-3-carboxamide (2.98 g, 6.88 mmol, 99% yield) as a brown solid. The material was used directly as is in the next step. MS (ES+) m/z: 433.0, 435.0 (M+H); LC retention time: 2.538 min (analytical HPLC Method B).

Step 4: 4-(((2R,3R)-3-(benzyloxy)-1-hydroxybutan-2-yl)amino)-6-phenylpyrrolo[1,2-b]pyridazine-3-carboxamide

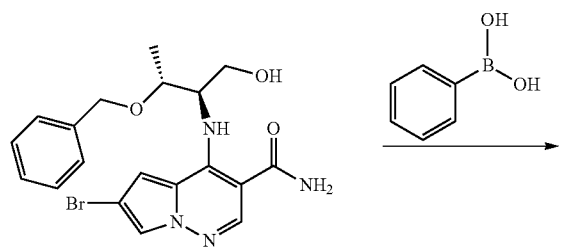

mL, 41.3 mmol) in dioxane (50 mL) was heated to 100° C. for 1 hr. After cooling to rt, the reaction mixture was filtered through a celite and the filtrate was partitioned between EtOAc (200 ml) and water (200 ml). The organic layer was washed with brine (150 ml), dried (MgSO$_4$) and concentrated to afford a brown solid that was triturated with ether. Filtration and drying afforded 4-(((2R,3R)-3-(benzyloxy)-1-hydroxybutan-2-yl)amino)-6-phenylpyrrolo[1,2-b]pyridazine-3-carboxamide (2.17 g, 5.04 mmol, 73.3% yield) as a tan solid. $^1$H NMR (400 MHz, CD$_3$OD) δ 8.16-8.11 (m, 1H), 7.94 (d, J=1.8 Hz, 1H), 7.73-7.67 (m, 2H), 7.45-7.21 (m, 9H), 4.76 (d, J=11.9 Hz, 1H), 4.56 (d, J=11.9 Hz, 1H), 4.44-4.33 (m, 1H), 4.09 (qd, J=6.3, 2.8 Hz, 1H), 3.96-3.83 (m, 2H), 1.31 (d, J=6.4 Hz, 3H). MS (ES+) m/z: 431.1 (M+H); LC retention time: 2.858 min (analytical HPLC Method B).

Step 5: dibenzyl((2R,3R)-3-(benzyloxy)-2-((3-carbamoyl-6-phenylpyrrolo[1,2-b]pyridazin-4-yl)amino)butyl)phosphate

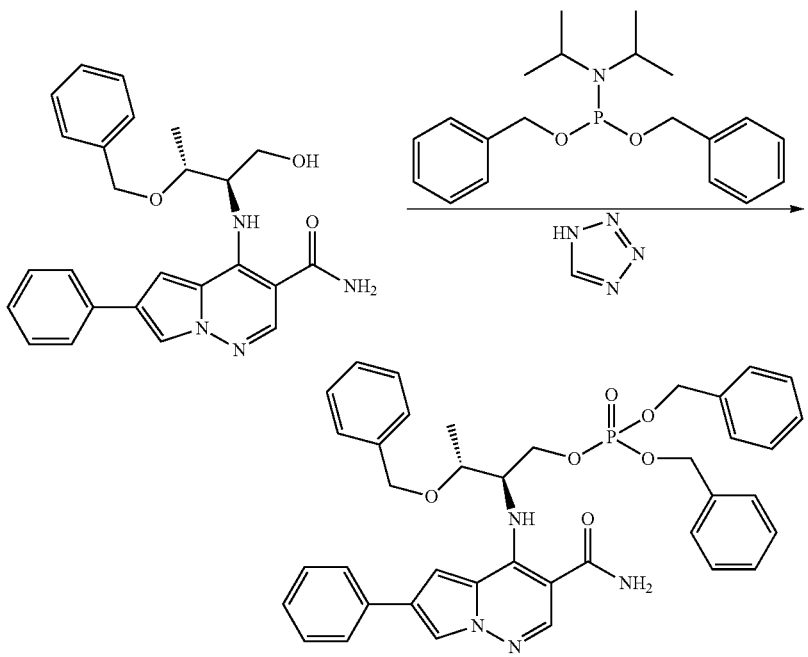

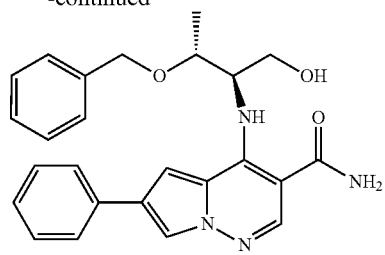
-continued

A mixture of 4-(((2R,3R)-3-(benzyloxy)-1-hydroxybutan-2-yl)amino)-6-bromopyrrolo[1,2-b]pyridazine-3-carboxamide (2.98 g, 6.88 mmol), phenylboronic acid (1.677 g, 13.75 mmol), palladium (II) acetate (0.309 g, 1.375 mmol), 2-(dicyclohexylphosphino)-2',4',6'-triisopropylbyphenyl (1.311 g, 2.75 mmol) and potassium phosphate, tribasic, 2M (20.63

To a solution of 4-((2R,3R)-3-(benzyloxy)-1-hydroxybutan-2-yl)amino)-6-phenylpyrrolo[1,2-b]pyridazine-3-carboxamide (2.15 g, 4.99 mmol) and dibenzyl diisopropylphosphoramidite (3.69 mL, 10.99 mmol) in DCM (10 mL) and THF (30 mL) at 0° C. was added 1H-tetrazole (0.770 g, 10.99 mmol). After stirring 1.5 hr at 0° C., hydrogen peroxide, 30% (4.08 mL, 40.0 mmol) was added and stirring was continued for 30 minutes. The reaction mixture was partitioned between EtOAc (300 ml) and 5% NaHSO$_3$ solution (250 ml). The organic layer was washed with 1N HCl (200 ml), saturated NaHCO$_3$ solution (200 ml) and brine (200 ml). After drying (MgSO$_4$) and filtration, the organic layer was concentrated to a yellow oil that was chromatographed on a gm ISCO silica gel column, eluting with a 0-3% MeOH/DCM gradient. The pure fractions were concentrated to afford 2.7 g of partially purified material that was re-chromatographed on a 120 gm ISCO column eluting with a 0-100% EtOAC/Hex gradient. The pure fractions were concentrated to afford dibenzyl((2R, 3R)-3-(benzyloxy)-2-((3-carbamoyl-6-phenylpyrrolo[1,2-b]pyridazin-4-yl)amino)butyl)phosphate (2.51 g, 3.63 mmol, 72.8% yield) as a light yellow foam. ¹H NMR (400 MHz, CCl₃D) δ 10.56 (d, J=8.8 Hz, 1H), 7.90 (d, J=1.8 Hz, 1H), 7.85 (s, 1H), 7.71-7.66 (m, 2H), 7.41-7.15 (m, 19H), 5.48 (s, 2H), 4.99-4.91 (m, 4H), 4.73 (d, J=12.1 Hz, 1H), 4.55-4.43 (m, 2H), 4.33-4.25 (m, 2H), 3.94 (qd, J=6.2, 2.0 Hz, 1H), 1.32-1.14 (m, 3H); (ES+) m/z: 691.3 (M+H); LC retention time: 3.445 min (analytical HPLC Method B).

Step 6: (2R,3R)-2-((3-carbamoyl-6-phenylpyrrolo[1,2-b]pyridazin-4-yl)amino)-3-hydroxybutyl dihydrogen phosphate

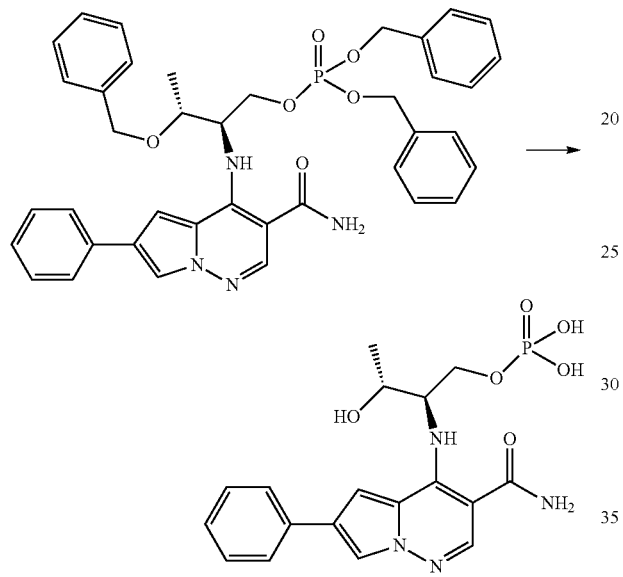

A mixture of dibenzyl((2R,3R)-3-(benzyloxy)-2-((3-carbamoyl-6-phenylpyrrolo[1,2-b]pyridazin-4-yl)amino)butyl) phosphate (2.50 g, 3.62 mmol) and Pearlman's catalyst (1.017 g, 1.448 mmol) in EtOH (100 mL) was stirred at rt under and atmosphere of hydrogen for 48 hr. The reaction mixture was filtered through celite and the celite filter cake was washed thoroughly with EtOH, followed by MeOH. The filtrate was concentrated and the residue (1.75 gm) was subjected to preparative HPLC; 6-injections of between 250 and 320 mg of crude (Phenominex 30×100 mm S-5 column; eluting with 40-90% aqueous methanol+0.1% TFA over an 12 minute gradient; Flow rate=40 ml/min; UV detection at 254 nM wavelength). The pure fractions of fully deprotected phosphate were concentrated to afford (2R,3R)-2-((3-carbamoyl-6-phenylpyrrolo[1,2-b]pyridazin-4-yl)amino)-3-hydroxybutyl dihydrogen phosphate (1.14 g, 2.71 mmol, 74.9% yield) as an off white solid. ¹H NMR (400 MHz, CD₃OD) δ 8.18-8.12 (m, 1H), 8.01-7.94 (m, 1H), 7.75 (d, J=7.3 Hz, 2H), 7.46-7.33 (m, 3H), 7.29-7.19 (m, 1H), 4.50 (d, J=5.5 Hz, 1H), 4.40-4.18 (m, 3H), 1.29-1.22 (m, 3H). (ES+) m/z: 421.1 (M+H); LC retention time: 2.477 min (analytical HPLC Method B).

Step 7: (2R,3R)-2-((3-carbamoyl-6-phenylpyrrolo[1,2-b]pyridazin-4-yl)amino)-3-hydroxybutyl dihydrogen phosphate, 2 Na+

(2R,3R)-2-((3-carbamoyl-6-phenylpyrrolo[1,2-b]pyridazin-4-yl)amino)-3-hydroxybutyl dihydrogen phosphate, 0.75-methanol (3.86 g, 8.69 mmol) was dissolved in MeOH (500 mL) and sodium bicarbonate (1.459 g, 17.37 mmol) was added as a solution in 40 ml of water. The solution was concentrated to an off-white solid that was dissolved in water and lyophilized to afford (2R,3R)-2-((3-carbamoyl-6-phenylpyrrolo[1,2-b]pyridazin-4-yl)amino)-3-hydroxybutyl dihydrogen phosphate, 2 Na+ (4.05 g, 8.68 mmol, 100% yield) as an off-white solid. ¹H NMR (400 MHz, CD₃OD) δ 8.11 (s, 1H), 7.91 (d, J=1.5 Hz, 1H), 7.78-7.59 (m, 2H), 7.40-7.32 (m, 3H), 7.26-7.20 (m, 1H), 4.58-4.47 (m, 1H), 4.43-4.31 (m, 1H), 4.22-4.03 (m, 2H), 1.23 (d, J=6.6 Hz, 3H). (ES+) m/z: 421.1 (M+H); LC retention time: 2.488 min (analytical HPLC Method B).

Example 241

(R)-4-((1-(1-methylcyclopropyl)ethyl)amino)-6-(5-(4-methylpiperazin-1-yl)-1,3,4-oxadiazol-2-yl)pyrrolo[1,2-b]pyridazine-3-carboxamide

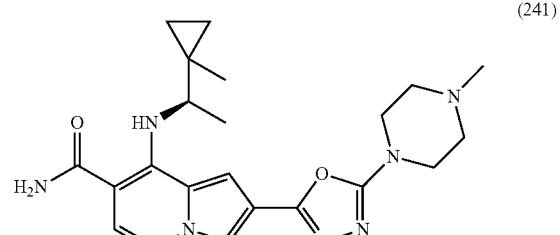

(241)

Step 1: (R)-ethyl 3-carbamoyl-4-((1-(1-methylcyclopropyl)ethyl)amino)pyrrolo[1,2-b]pyridazine-6-carboxylate

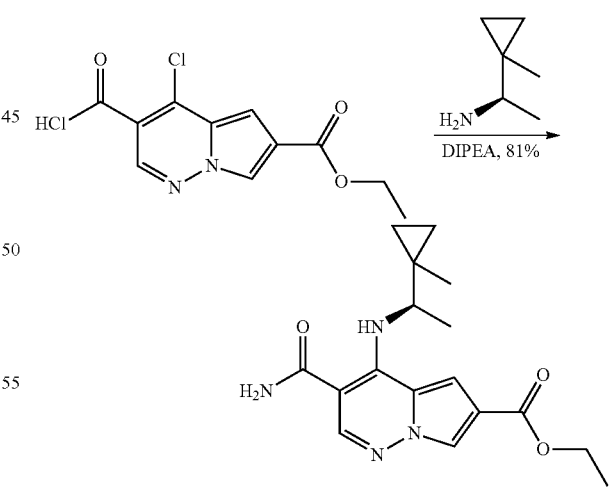

A solution of ethyl 3-carbamoyl-4-chloropyrrolo[1,2-b]pyridazine-6-carboxylate (1.25 g, 4.67 mmol) (R)-1-(1-methylcyclopropyl)ethanamine (0.697 g, 5.14 mmol) and DIPEA (2.039 mL, 11.67 mmol) in NMP (Volume: 5 mL) was heated to 100° C. for 4 hr. The reaction mixture was added 100 mL of EtOAc which was washed with 50 mL of water, 50 mL of 10% LiCl solution and 50 mL of brine, dried over Na₂SO₄.

Filtration and concentration to yield a crude product which was purified on silica gel column with hexanes/EtOAc(1/1) to yield the desired product (1.246 g, 81% yield). $^1$H NMR (400 MHz, CD$_3$OD) δ 8.23 (s, 1H), 8.03 (d, J=1.8 Hz, 1H), 7.32 (d, J=1.8 Hz, 1H), 4.38 (d, J=7.0 Hz, 2H), 4.04-3.93 (m, 1H), 1.46-1.36 (m, 6H), 1.27 (s, 3H), 0.65-0.51 (m, 2H), 0.48-0.37 (m, 2H). MS (ES+) m/z: 331.08 (M+H); HPLC: 96%, retention time: 3.260 min (analytical HPLC Method B).

Step 2: (R)-6-(hydrazinecarbonyl)-4-((1-(1-methyl-cyclopropyl)ethyl)amino)pyrrolo[1,2-b]pyridazine-3-carboxamide

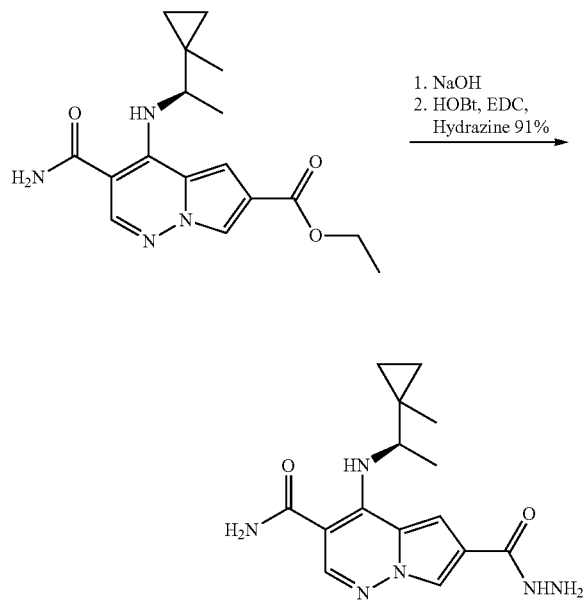

A solution of (R)-ethyl 3-carbamoyl-4-((1-(1-methylcyclopropyl)ethyl)amino)pyrrolo[1,2-b]pyridazine-6-carboxylate (1.246 g, 3.77 mmol) and NaOH 1N (5.66 mL, 5.66 mmol) in ethanol (Volume: 20 mL) was heated to 100° C. for 45 minutes. The reaction mixture was concentrated to yield a crude product which was added 20 mL of water. The mixture was acidified with 1N HCl solution until pH was about 4. The solid was collected and dried to yield (R)-3-carbamoyl-4-((1-(1-methylcyclopropyl)ethyl)aminopyrrolo[1,2-b]pyridazine-6-carboxylic acid (1.1 g, 97% yield). $^1$H NMR (400 MHz, CD$_3$OD) δ 8.22 (s, 1H), 8.03 (d, J=1.8 Hz, 1H), 7.33 (d, J=1.5 Hz, 1H), 4.03-3.93 (m, 1H), 1.42 (d, J=6.6 Hz, 3H), 1.27 (s, 3H), 0.64-0.52 (m, 2H), 0.48-0.37 (m, 2H). MS (ES+) m/z: 303.08 (M+H); HPLC: 99.5%, retention time: 2.650 min (analytical HPLC Method B).

A solution of (R)-3-carbamoyl-4-((1-(1-methylcyclopropyl)ethyl)amino)pyrrolo[1,2-b]pyridazine-6-carboxylic acid (1.11 g, 3.67 mmol) in DMF (Volume: 10 mL) was added HOBT (0.675 g, 4.41 mmol) and EDC (0.915 g, 4.77 mmol) which was stirred at 23° C. for 1 hr. To the reaction mixture was added hydrazine (0.576 mL, 18.36 mmol) dropwise and stirred for 30 minutes, followed by the addition of 50 mL of water and stirred for 20 minutes. The solid was collected as the desired product (1.54 g). MS (ES+) m/z: 317.08 (M+H); HPLC: 91%, retention time: 1.935 min (analytical HPLC Method B).

Step 3: (R)-4-((1-(1-methylcyclopropyl)ethyl)amino)-6-(5-(methylthio)-1,3,4-oxadiazol-2-yl)pyrrolo[1,2-b]pyridazine-3-carboxamide

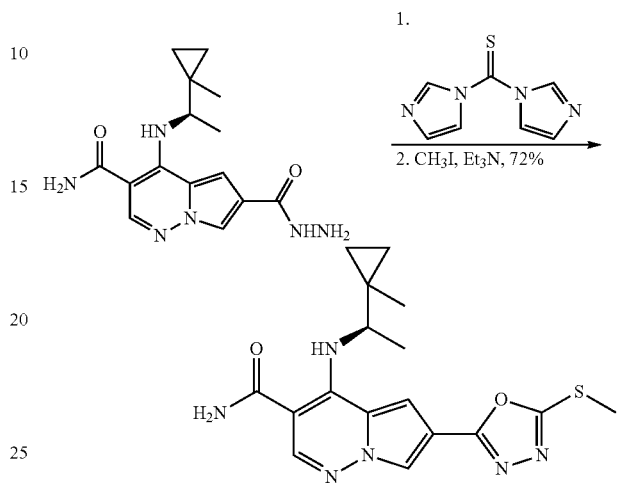

A solution of (R)-6-(hydrazinecarbonyl)-4-((1-(1-methylcyclopropyl)ethyl)amino)pyrrolo[1,2-b]pyridazine-3-carboxamide (1.54 g, 4.87 mmol) in THF (Volume: 40 mL) was added 1,1'-thiocarbonyldiimidazole (1.084 g, 6.08 mmol) which was heated to 70° C. for 3 hrs. The reaction mixture was concentrated to (R)-6-(5-mercapto-1,3,4-oxadiazol-2-yl)-4-((1-(1-methylcyclopropyl)ethyl)amino)pyrrolo[1,2-b]pyridazine-3-carboxamide. MS (ES+) m/z: 359.08 (M+H); HPLC retention time: 3.111 min (analytical HPLC Method B).

To a solution of (R)-6-(5-mercapto-1,3,4-oxadiazol-2-yl)-4-((1-(1-methylcyclopropyl)ethyl)amino)pyrrolo[1,2-b]pyridazine-3-carboxamide (4.87 mmol) and Et$_3$N (1.697 mL, 12.18 mmol) in ethanol (Volume: 20 mL) was added methyl iodide (0.381 mL, 6.09 mmol). The solution was stirred at 23° C. for 2 hrs. The reaction mixture was concentrated to yield a crude product which was added 50 mL of water and stirred for 20 minutes. The solid was collected as the desired product (1.30 g, 72% yield). $^1$H NMR (400 MHz, CD$_3$OD) δ 8.23 (s, 1H), 8.15 (d, J=1.8 Hz, 1H), 7.39 (d, J=1.5 Hz, 1H), 4.02-3.94 (m, 1H), 2.79 (s, 3H), 1.40 (d, J=6.6 Hz, 3H), 1.26 (s, 3H), 0.65-0.50 (m, 2H), 0.46-0.34 (m, 2H). MS (ES+) m/z: 373.08 (M+H); HPLC: 85%, retention time: 3.261 min (analytical HPLC Method B).

Step 4: 4-(((R)-1-(1-methylcyclopropyl)ethyl)amino)-6-(5-(methylsulfinyl)-1,3,4-oxadiazol-2-yl)pyrrolo[1,2-b]pyridazine-3-carboxamide

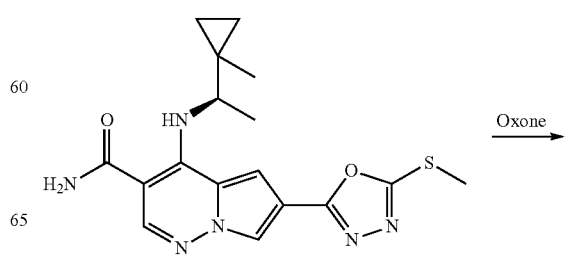

-continued

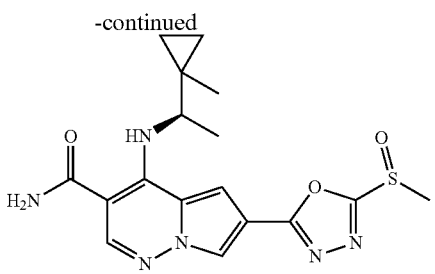

A solution of (R)-4-((1-(1-methylcyclopropyl)ethyl)amino)-6-(5-(methylthio)-1,3,4-oxadiazol-2-yl)pyrrolo[1,2-b]pyridazine-3-carboxamide (1.168 g, 3.14 mmol) in acetone (Ratio: 1.000, Volume: 30 mL) was added Oxone (4.24 g, 6.90 mmol) and stirred at 23° C. for 2 hrs, and the reaction mixture was diluted with 150 mL of EtOAc which was washed with 50 mL×2 of water, 50 mL of brine and dried over Na₂SO₄. The mixture was filtrated and then concentrated to yield a crude product which was triturated in MeOH. The solid was collected as the desired product (833 mg, 68% yield). ¹H NMR (400 MHz, CD₃OD) δ 8.31 (d, J=1.8 Hz, 1H), 8.27 (s, 1H), 7.52 (d, J=1.8 Hz, 1H), 4.08-3.97 (m, 1H), 3.34 (s, 3H), 1.45 (d, J=6.8 Hz, 3H), 1.29 (s, 3H), 0.69-0.54 (m, 2H), 0.49-0.39 (m, 2H). MS (ES+) m/z: 389.08 (M+H); HPLC: 88%, retention time: 2.628 min (analytical HPLC Method B).

Step 5: (R)-4-((1-(1-methylcyclopropyl)ethyl)amino)-6-(5-(4-methylpiperazin-1-yl)-1,3,4-oxadiazol-2-yl)pyrrolo[1,2-b]pyridazine-3-carboxamide

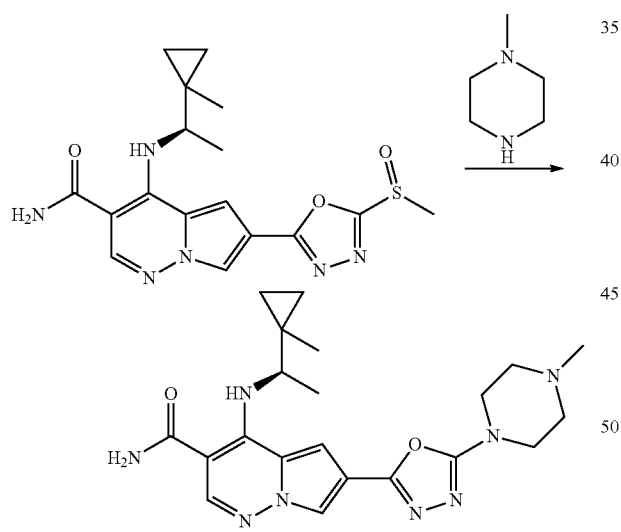

To a solution of 4-((R)-1-(1-methylcyclopropyl)ethylamino)-6-(5-(methylsulfinyl)-1,3,4-oxadiazol-2-yl)pyrrolo[1,2-b]pyridazine-3-carboxamide (16.00 mg, 0.041 mmol) in NMP (0.5 mL, 0.082M) was added 1-methylpiperazine (20.63 mg, 0.206 mmol) followed with DIPEA (0.029 mL, 0.165 mmol). The solution was stirred at 130° C. for 30 min in a Biotage Initiator microwave. The reaction mixture was dissolved in 1.5 mL of DMF and directly purified on Reverse Phase HPLC to yield desired product (2.65 mg, 15% yield). ¹H NMR (599 MHz), δ 8.33 (s, 1H), 8.27 (s, 1H), 7.20 (s, 1H), 3.96-3.89 (m, 1H), 3.63-3.53 (m, 4H), 2.72-2.23 (m, 7H), 1.37 (d, J=6.4 Hz, 3H), 1.23 (s, 3H), 0.68-0.58 (m, 1H), 0.55-0.49 (m, 1H), 0.39 (m, 2H). MS (ES+) m/z: 424.90 (M+H); HPLC: 97%, retention time: 1.70 min (analytical HPLC Method B).

Example 242

(R)-4-((1-(1-methylcyclopropyl)ethyl)amino)-6-(5-((2-morpholinoethyl)amino)-1,3,4-oxadiazol-2-yl)pyrrolo[1,2-b]pyridazine-3-carboxamide (242)

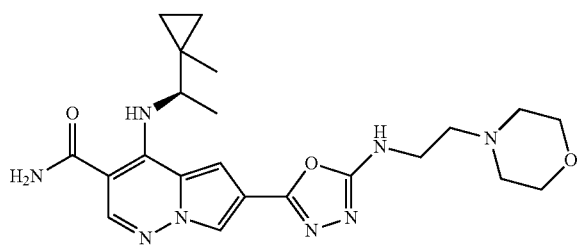

To a solution of 4-((R)-1-(1-methylcyclopropyl)ethylamino)-6-(5-(methylsulfinyl)-1,3,4-oxadiazol-2-yl)pyrrolo[1,2-b]pyridazine-3-carboxamide (16.00 mg, 0.041 mmol) in NMP (0.5 mL, 0.082M) was added 4-(2-aminoethyl)morpholine (26.80 mg, 0.206 mmol) followed with DIPEA (0.029 mL, 0.165 mmol) and stirred at 130° C. for 30 min in a Biotage Initiator microwave. The reaction mixture was dissolved in 1.5 mL of DMF and directly purified on Reverse Phase HPLC to yield desired product (2.23 mg, 12% yield). MS (ES+) m/z: 454.87 (M+H); HPLC: 92% retention time: 1.57 min (analytical HPLC Method B).

What is claimed is:

1. A compound of Formula (II):

(II)

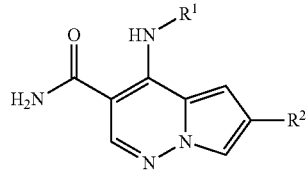

or stereoisomers or salts thereof, wherein:

$R^1$ is $C_{1-6}$ alkyl substituted with zero to 3 substituent groups independently selected from F, —OH, —CF₃, —NH₂, —C(O)OH, —C(O)OCH₃, —C(O)NH₂, —C(O)NHCH₂CN, —C(O)NH(phenyl), —NHC(O)CH₂CN, —NHS(O)₂CH₃, —OP(O)(OH)₂, phenyl, fluorophenyl, oxazolyl substituted with —C(O)NH₂; and/or two substituent groups along with the carbon atom to which they are attached, form a cyclopropyl ring;

$R^2$ is -L-$R^x$ or $R^y$;

L is —NHC(O)—, —NHC(O)O—, —NHS(O)₂—, —NHC(O)NH—, —NHC(O)O—, or —C(O)NH—;

$R^x$ is $C_{1-4}$ alkyl, $C_{3-6}$ cycloalkyl, $C_{1-3}$ fluoroalkyl, and a cyclic group selected from 5-membered heterocyclyl having 1 to 2 nitrogen heteroatoms, tetrahydrofuranyl, tetrahydropyranyl, or phenyl, each cyclic group substituted with zero to 2 substituents independently selected from F, Cl, —OH, —CN, —CH₃, —OCH₃, —C(O)OH, and/or —NH₂; and $R^y$ is:
a) phenyl substituted with zero to 2 substituents independently selected from
   i) F, Cl, —CN, $C_{1-4}$ alkyl, —O($C_{1-3}$ alkyl), —C(O)OH, —NH$_2$, —NH($C_{1-3}$ alkyl), —N($C_{1-3}$ alkyl)$_2$, $C_{3-6}$ cycloalkyl, and/or $C_{2-4}$ alkenyl;
   ii) $C_{1-4}$ alkyl substituted with —CN, —OH, —NH$_2$, —NH(CH$_3$), —N(CH$_3$)$_2$, $C_{3-6}$ cycloalkyl, morpholinyl, piperidinyl substituted with methoxyphenyl, —NHC(O)R$^m$, —NHC(O)NHR$^n$, —NHCH(=N—CN)NH($C_{1-3}$ alkyl), and/or —NHS(O)$_2$($C_{1-3}$ alkyl); wherein R$^m$ is $C_{1-4}$ alkyl, $C_{3-6}$ cycloalkyl, hydroxy($C_{3-6}$ cycloalkyl), $C_{1-3}$ cyanoalkyl, $C_{1-4}$ hydroxyalkyl, —CH$_2$NH$_2$, —CH$_2$H(CH$_3$), —CH$_2$N(CH$_3$)$_2$, phenyl, phenyl-S(O)$_2$NH$_2$, phenyl-NHC(O)CH$_3$, pyrrolidinyl, furanyl, pyridinyl, —CH$_2$OC(O)($C_{1-3}$ alkyl), —CH$_2$(morpholinyl), or CH$_2$NHS(O)$_2$(methylphenyl); and R$^n$ is H, $C_{1-3}$ alkyl, $C_{3-6}$ cycloalkyl, or $C_{1-4}$ hydroxyalkyl;
   iii) —C(O)NR$^i$R$^j$ wherein R$^i$ is H or —CH$_3$, and R$^j$ is $C_{1-3}$ alkyl, $C_{3-6}$ cycloalkyl, —CH$_2$C(O)NH$_2$, —H$_2$C(O)NH(CH$_3$), —CH$_2$C(O)N(CH$_3$)$_2$, or —CH$_2$CH$_2$N(CH$_3$)$_2$;
   iv) —OC(O)($C_{1-3}$ alkyl) and/or —C(O)(N-methyl morpholinyl);
   v) —NHC(O)R$^k$ wherein R$^k$ is H, $C_{1-3}$ alkyl, or $C_{3-6}$ cycloalkyl;
   vi) —S(O)$_2$($C_{1-3}$ alkyl), —NHS(O)$_2$($C_{1-3}$ alkyl), —S(O)$_2$NH$_2$, and/or —S(O)$_2$N(CH$_3$)$_2$;
   vii) thiophenyl, morpholinonyl, imidazolyl, oxazolyl, and/or imidazolidine-2,4-dionyl, each substituted with zero to 1 substituent selected from —CH$_3$, —C(O)O($C_{1-3}$ alkyl), and dimethylaminophenyl;
b) heterocycle selected from azetidinonyl, pyrrolidinonyl, morpholinonyl, pyridinonyl, imidazolidinonyl, oxazolidinonyl, propane-1,3-sultam, butane-1,4-sultam, 5-thioxo-4,5-dihydro-1,3,4-oxadiazoly-2-yl, and 5-methylthio-1,3,4-oxadiazoly-2-yl, wherein said heterocycle is substituted with zero to 1 substituent selected from $C_{1-4}$ alkyl, $C_{1-3}$ fluoroalkyl, —NHC(O)O($C_{1-4}$ alkyl), and phenyl; or
c) heteroaryl selected from pyrrolyl, pyrazolyl, thiazolyl, oxadiazolyl, pyridinyl, pyrimidinyl, pyrazinyl, indolyl, quinolinyl, 3,4-dihydroisoquinolin-1(2H)-onyl, benzo[d][1,3]dioxolyl, quinolin-2(1H)-onyl, benzothiazolyl, 1H-benzo[d]imidazol-2(3H)-onyl, wherein said heteroaryl is substituted with zero to 3 substituents independently selected from F, Cl, —OH, —CN, $C_{1-4}$ alkyl, $C_{1-3}$ fluoroalkyl, —O($C_{1-4}$ alkyl), —NH$_2$, —NH($C_{1-3}$ alkyl), —N($C_{1-3}$ alkyl)$_2$, —C(O)NH$_2$, —C(O)NH($C_{1-3}$ alkyl), —C(O)N($C_{1-3}$ alkyl)$_2$, —S(O)$_2$($C_{1-3}$ alkyl), —NHCH$_2$CH$_2$N($C_{1-2}$ alkyl)$_2$, —N(CH$_3$)CH$_2$CH$_2$N($C_{1-2}$ alkyl)$_2$, —NHCH$_2$CH$_2$(morpholinyl), piperidinyl, piperazinyl, phenyl, chlorophenyl, methoxyphenyl, dimethylaminophenyl, pyridinyl, morpholinyl, N-methyl piperazinyl, and/or piperazinyl(C(O)O(t-butyl)).

2. The compound according to claim 1 or stereoisomers or salts thereof, wherein:
   R$^1$ is $C_{1-6}$ alkyl substituted with zero to 3 substituent groups independently selected from F, —OH, —CF$_3$, —NH$_2$, —C(O)OH, —C(O)OCH$_3$, —C(O)NH$_2$, —C(O)NHCH$_2$CN, —C(O)NH(phenyl), —NHC(O)CH$_2$CN, —NHS(O)$_2$CH$_3$, —OP(O)(OH)$_2$, phenyl, fluorophenyl, oxazolyl substituted with —C(O)NH$_2$; and/or 2 substituents along with the carbon atom to which they are attached, form a cyclopropyl ring;
   L is —NHC(O)—, —NHC(O)O—, or —NHS(O)$_2$—;

$R^y$ is:
a) phenyl substituted with zero to 2 substituents independently selected from
   i) F, —CN, $C_{1-3}$ alkyl, —OCH$_3$, —C(O)OH, —N(CH$_3$)$_2$, cyclohexyl, and/or —CH=CH$_2$;
   ii) $C_{1-3}$ alkyl substituted with —CN, —OH, —NH$_2$, —N(CH$_3$)$_2$, cyclopentyl, morpholinyl, piperidinyl substituted with methoxyphenyl, —NHC(O)R$^m$, —NHC(O)NHR$^n$, —NHCH(=N—CN)NH($C_{1-3}$ alkyl), and/or —NHS(O)$_2$($C_{1-3}$ alkyl); wherein R$^m$ is $C_{1-4}$ alkyl, cyclopropyl, hydroxycyclopropyl, —CH$_2$CN, $C_{1-3}$ hydroxyalkyl, —CH$_2$N(CH$_3$)$_2$, phenyl, phenyl-S(O)$_2$NH$_2$, phenyl-NHC(O)CH$_3$, pyrrolidinyl, furanyl, pyridinyl, —CH$_2$OC(O)CH$_3$, —CH$_2$(morpholinyl), or —CH$_2$NHS(O)$_2$(methylphenyl); and R$^n$ is H, $C_{1-3}$ alkyl, cyclopropyl, or $C_{1-3}$ hydroxyalkyl;
   iii) —C(O)NR$^i$R$^j$ wherein R$^i$ is H or —CH$_3$, and R$^j$ is $C_{1-3}$ alkyl, cyclopropyl, —CH$_2$C(O)NH$_2$, or —CH$_2$CH$_2$N(CH$_3$)$_2$;
   iv) —OC(O)CH$_3$ and/or —C(O)(N-methyl morpholinyl);
   v) —NHC(O)R$^k$ wherein R$^k$ is H, —CH$_3$, or cyclopropyl;
   vi) —S(O)$_2$($C_{1-2}$ alkyl), —NHS(O)$_2$($C_{1-2}$ alkyl), —S(O)$_2$NH$_2$, and/or —S(O)$_2$N(CH$_3$)$_2$; and/or
   vii) thiophenyl, morpholinonyl, imidazolyl, oxazolyl, and/or imidazolidine-2,4-dionyl, each substituted with zero to 1 substituent selected from —CH$_3$, —C(O)O($C_{1-3}$ alkyl), and dimethylaminophenyl;
b) heterocycle selected from azetidinonyl, pyrrolidinonyl, morpholinonyl, pyridinonyl, imidazolidinonyl, oxazolidinonyl, propane-1,3-sultam, butane-1,4-sultam, 5-thioxo-4,5-dihydro-1,3,4-oxadiazoly-2-yl, and 5-methylthio-1,3,4-oxadiazoly-2-yl, wherein said heterocycle is substituted with zero to 1 substituent selected from $C_{1-3}$ alkyl, $C_{1-2}$ fluoroalkyl, —NHC(O)O($C_{1-2}$ alkyl), and phenyl; or
c) heteroaryl selected from pyrrolyl, pyrazolyl, thiazolyl, oxadiazolyl, pyridinyl, pyrimidinyl, pyrazinyl, indolyl, quinolinyl, 3,4-dihydroisoquinolin-1(2H)-onyl, benzo[d][1,3]dioxolyl, quinolin-2(1H)-onyl, benzothiazolyl, 1H-benzo[d]imidazol-2(3H)-onyl, wherein said heteroaryl is substituted with zero to 3 substituents independently selected from F, Cl, —OH, —CN, $C_{1-3}$ alkyl, $C_{1-2}$ fluoroalkyl, —O($C_{1-3}$ alkyl), —NH$_2$, —NH($C_{1-3}$ alkyl), —C(O)NH($C_{1-3}$ alkyl), —S(O)$_2$ ($C_{1-3}$ alkyl), —NHCH$_2$CH$_2$N($C_{1-2}$ alkyl)$_2$, —N(CH$_3$)CH$_2$CH$_2$N($C_{1-2}$ alkyl)$_2$, —NHCH$_2$CH$_2$(morpholinyl), piperidinyl, piperazinyl, phenyl, chlorophenyl, methoxyphenyl, dimethylaminophenyl, pyridinyl, morpholinyl, N-methyl piperazinyl, and/or piperazinyl(C(O)O(t-butyl)).

3. The compound according to claim 1 or stereoisomers or salts thereof, wherein:
   R$^1$ is: —CH$_3$, —CH$_2$CH$_2$CH$_3$, —CH(CH$_3$)$_2$,

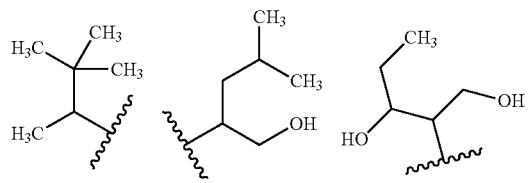

-continued

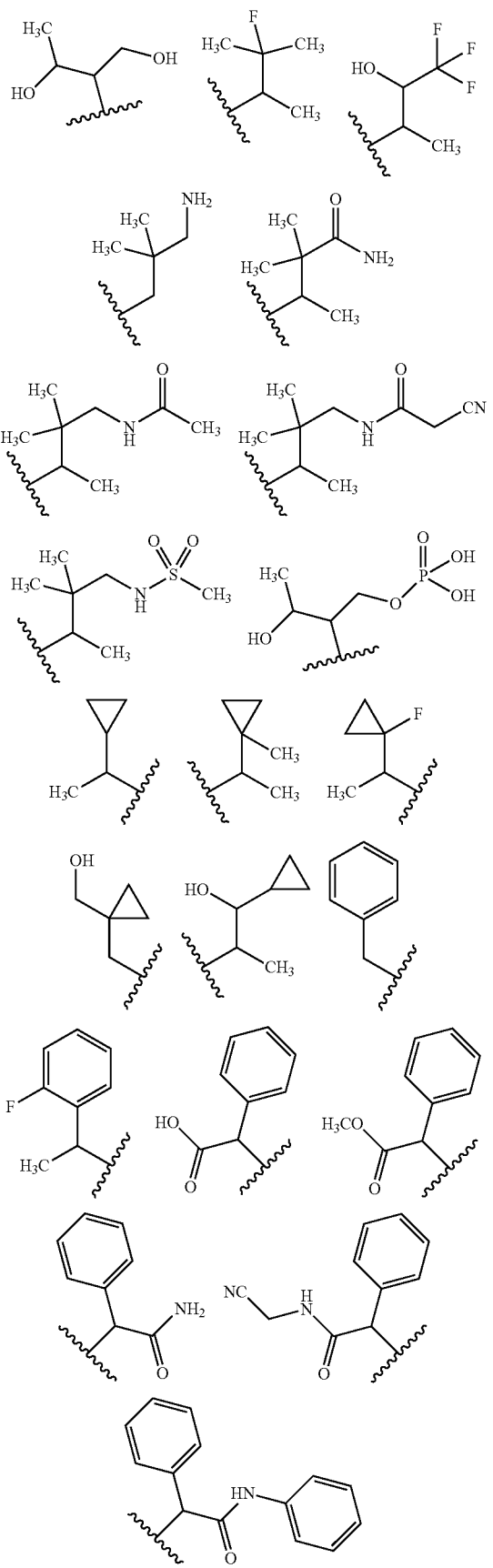

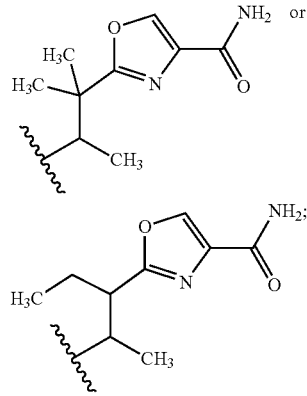

$R^x$ is $C_{1-4}$ alkyl, $C_{3-6}$ cycloalkyl, —$CHF_2$, —$CF_3$, tetrahydropyranyl, or methoxyphenyl; and $R^y$ is:

a) phenyl substituted with zero to 2 substituents independently selected from F, —CN, —$OCH_3$, —C(O)OH, cyclohexyl, —CH=$CH_2$, —$CH_2CN$, —$CH_2OH$, —$CH_2NH_2$, —$CH_2N(CH_3)_2$, —$CH_2$(morpholinyl), —$CH(OH)CH_2OH$, —$CH(CH_3)_2CN$, —$CH_2CH_2$(piperidinyl)-(methoxyphenyl), —$C(O)NH_2$, —C(O)NH(cyclopropyl), —$C(O)N(CH_3)_2$, —$C(O)NHCH(CH_3)_2$, —$C(O)NHCH_2C(O)NH_2$, —$C(O)N(CH_3)CH_2C(O)NH_2$, —$C(O)NHCH_2CH_2N(CH_3)_2$, —$OC(O)CH_3$, —C(O)(N-methyl morpholinyl), —$N(CH_3)_2$, —NHC(O)H, —$NHC(O)CH_3$, —NHC(O)(cyclopropyl), —CH($NH_2$)$CH_3$, —CH(cyclopentyl)NH(C(O)$CH_3$), —$CH_2NHC(O)CH_3$, —$CH_2NHC(O)CH(CH_3)_2$, —$CH_2NHC(O)$(t-butyl), —$CH_2NHC(O)$(cyclopropyl), —$CH_2NHC(O)$(hydroxycyclopropyl), —$CH_2NHC(O)CH_2CN$, —$CH_2NHC(O)CH_2OH$, —$CH_2NHC(O)C(CH_3)_2OH$, —$CH_2NHC(O)$(phenyl), —$CH_2NHC(O)$(phenyl-$S(O)_2NH_2$), —$CH_2NHC(O)$(phenyl-NHC(O)$CH_3$), —$CH_2NHC(O)$(pyrrolidinyl), —$CH_2NHC(O)$(furanyl), —$CH_2NHC(O)$(pyridinyl), —$CH_2NHC(O)CH_2OC(O)CH_3$, —$CH_2NHC(O)CH_2$(morpholinyl), —$CH_2NHC(O)NH_2$, —$CH_2NHC(O)NHCH(CH_3)_2$, —$CH_2NHC(O)NH$(cyclopropyl), —$CH_2NHC(O)NH(CH_2CH_2OH)$, —$CH_2NHCH$(=N—CN)$NHCH(CH_3)_2$, —$CH_2NHS(O)_2CH_3$, —$CH_2NHC(O)CH_2N(CH_3)_2$, —$CH_2NHC(O)CH_2NHS(O)_2$(methylphenyl), —$S(O)_2CH_3$, —$NHS(O)_2CH_3$, —$S(O)_2NH_2$, —$S(O)_2N(CH_3)_2$, thiophenyl, methylthiophenyl, morpholinonyl, imidazolyl substituted with methyl and —C(O)O(ethyl), oxazolyl substituted with dimethylaminophenyl, and/or imidazolidine-2,4-dionyl;

b) heterocycle selected from azetidinonyl, pyrrolidinonyl, morpholinonyl, pyridinonyl, imidazolidinonyl, oxazolidinonyl, propane-1,3-sultam, butane-1,4-sultam, 5-thioxo-4,5-dihydro-1,3,4-oxadiazoly-2-yl, and 5-methylthio-1,3,4-oxadiazoly-2-yl, wherein said heterocycle is substituted with zero to 1 substituent selected from —$CH_3$, —$CH(CH_3)_2$, —$CF_3$, —NHC(O)O(t-butyl), and phenyl; or c) heteroaryl selected from pyrrolyl, pyrazolyl, thiazolyl, oxadiazolyl, pyridinyl, pyrimidinyl, pyrazinyl, indolyl, quinolinyl, 3,4-dihydroisoquinolin-1(2H)-onyl, benzo[d][1,3]dioxolyl, quinolin-2(1H)-onyl, benzothiazolyl, 1H-benzo[d]imidazol-2(3H)-onyl, wherein said heteroaryl is substituted with zero to 3 substituents independently selected from F, Cl, —OH, —CN, $C_{1-2}$ alkyl, —CF₃, —OCH₃, —NH₂, —NH(CH₃), —C(O)NH(CH₃), —S(O)₂CH₃, —NHCH₂CH₂N(CH₃)₂, —N(CH₃)CH₂CH₂N(CH₃)₂, —NHCH₂CH₂(morpholinyl), piperidinyl, piperazinyl, phenyl, chlorophenyl, methoxyphenyl, dimethylaminophenyl, pyridinyl, morpholinyl, N-methyl piperazinyl, and/or piperazinyl (C(O)O(t-butyl)).

4. The compound according to claim 3 or stereoisomers or salts thereof, wherein:

R¹ is: —CH₃, —CH₂CH₂CH₃, —CH(CH₃)₂,

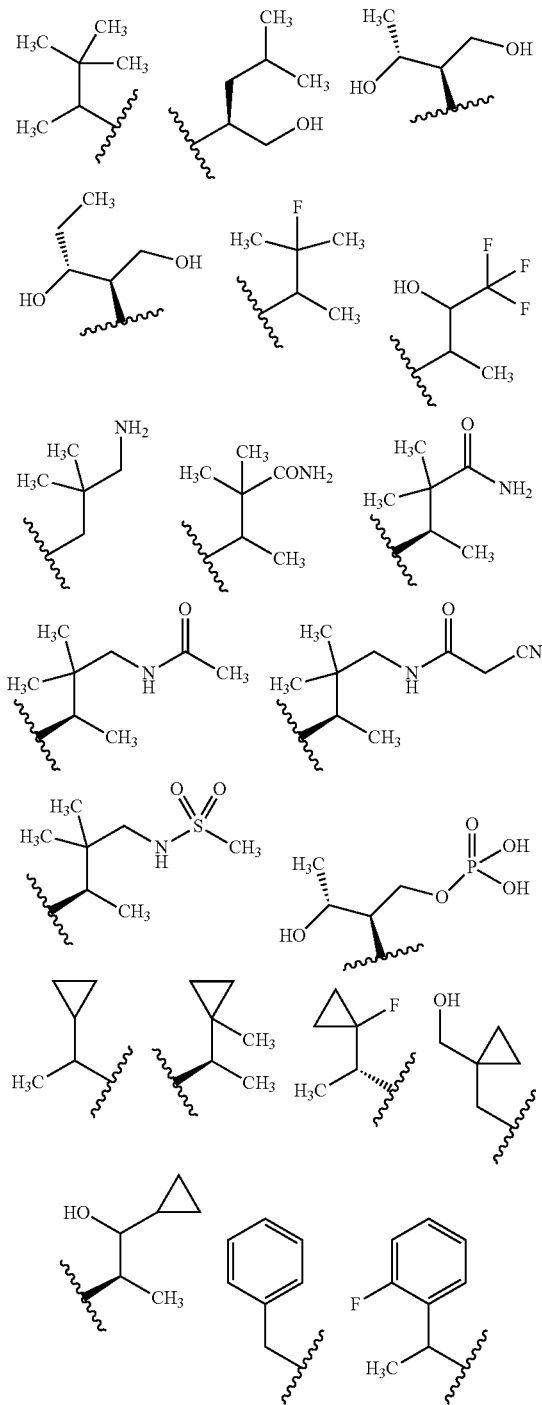

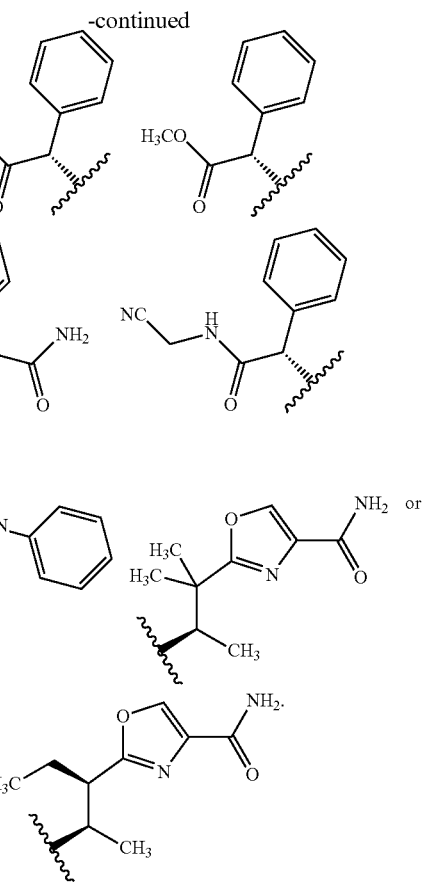

5. The compound according to claim 3 or salts thereof, wherein:
R² is -L-Rˣ; and
Rˣ is C₁₋₄ alkyl, C₃₋₆ cycloalkyl, —CHF₂, —CF₃, tetrahydropyranyl, or methoxyphenyl.

6. The compound according to claim 3 or stereoisomers or salts thereof, wherein:
R² is Rʸ; and
Rʸ is phenyl substituted with zero to 2 substituents independently selected from F, —CN, —OCH₃, —C(O)OH, cyclohexyl, —CH═CH₂, —CH₂CN, —CH₂OH, —CH₂NH₂, —CH₂N(CH₃)₂, —CH₂(morpholinyl), —CH(OH)CH₂OH, —CH(CH₃)₂CN, —CH₂CH₂(piperidinyl)-(methoxyphenyl), —C(O)NH₂, —C(O)NH(cyclopropyl), —C(O)N(CH₃)₂, —C(O)NHCH(CH₃)₂, —C(O)NHCH₂C(O)NH₂, —C(O)N(CH₃)CH₂C(O)NH₂, —C(O)NHCH₂CH₂N(CH₃)₂, —OC(O)CH₃, —C(O)(N-methyl morpholinyl), —N(CH₃)₂, —NHC(O)H, —NHC(O)CH₃, —NHC(O)(cyclopropyl), —CH(NH₂)CH₃, —CH(cyclopentyl)NH(C(O)CH₃, —CH₂NHC(O)CH₃, —CH₂NHC(O)CH(CH₃)₂, —CH₂NHC(O)(t-butyl), —CH₂NHC(O)(cyclopropyl), —CH₂NHC(O)(hydroxycyclopropyl), —CH₂NHC(O)CH₂CN, —CH₂NHC(O)CH₂OH, —CH₂NHC(O)C(CH₃)₂OH, —CH₂NHC(O)(phenyl), —CH₂NHC(O)(phenyl-S(O)₂NH₂), —CH₂NHC(O)(phenyl-NHC(O)CH₃), —CH₂NHC(O)(pyrrolidinyl), —CH₂NHC(O)(furanyl), —CH₂NHC(O)(pyridinyl), —CH₂NHC(O)CH₂OC(O)CH₃, —CH₂NHC(O)CH₂(morpholinyl), —CH₂NHC(O)NH₂, —CH₂NHC(O)NHCH(CH₃)₂, —CH₂NHC(O)NH(cyclopropyl), —CH₂NHC(O)NH(CH₂CH₂OH), —CH₂NHCH(═N—CN)NHCH (CH₃)₂, —CH₂NHS(O)₂CH₃, —CH₂NHC(O)CH₂N (CH₃)₂, —CH₂NHC(O)CH₂NHS(O)₂(methylphenyl), —S(O)₂CH₃, —NHS(O)₂CH₃, —S(O)₂NH₂, —S(O)₂N(CH₃)₂, thiophenyl, methylthiophenyl, morpholinonyl, imidazolyl substituted with methyl and —C(O)O(ethyl), oxazolyl substituted with dimethylaminophenyl, and/or imidazolidine-2,4-dionyl.

7. The compound according to claim 3 or stereoisomers or salts thereof, wherein:

R² is Rʸ; and

Rʸ is heterocycle selected from azetidinonyl, pyrrolidinonyl, morpholinonyl, pyridinonyl, imidazolidinonyl, oxazolidinonyl, propane-1,3-sultam, butane-1,4-sultam, 5-thioxo-4,5-dihydro-1,3,4-oxadiazoly-2-yl, and 5-methylthio-1,3,4-oxadiazoly-2-yl, wherein said heterocycle is substituted with zero to 1 substituent selected from —CH₃, —CH(CH₃)₂, —CF₃, —NHC(O)O(t-butyl), and phenyl.

8. The compound according to claim 3 or stereoisomers or salts thereof, wherein:

R² is Rʸ; and

Rʸ is heteroaryl selected from pyrrolyl, pyrazolyl, thiazolyl, oxadiazolyl, pyridinyl, pyrimidinyl, pyrazinyl, indolyl, quinolinyl, 3,4-dihydroisoquinolin-1(2H)-onyl, benzo[d][1,3]dioxolyl, quinolin-2(1H)-onyl, benzothiazolyl, 1H-benzo[d]imidazol-2(3H)-onyl, wherein said heteroaryl is substituted with zero to 3 substituents independently selected from F, Cl, —OH, —CN, $C_{1-2}$ alkyl —CF₃, —OCH₃, —NH₂, —NH(CH₃), —C(O)NH (CH₃), —S(O)₂CH₃, —NHCH₂CH₂N(CH₃)₂, —N(CH₃)CH₂CH₂N(CH₃)₂, —NHCH₂CH₂(morpholinyl), piperidinyl, piperazinyl, phenyl, chlorophenyl, methoxyphenyl, dimethylaminophenyl, pyridinyl, morpholinyl, N-methyl piperazinyl, and/or piperazinyl (C(O)O(t-butyl)).

9. A pharmaceutical composition comprising a pharmaceutically acceptable carrier and at least one of the compounds according to claim 1 or a stereoisomer or pharmaceutically acceptable salt thereof.

10. A method of treating an inflammatory and/or autoimmune disease comprising administering an effective amount of a compound of claim 1 to a patient in need thereof, wherein said inflammatory and/or autoimmune disease is selected from Crohn's Disease, ulcerative colitis, rheumatoid arthritis, psoriasis, and solid organ transplant rejection.

* * * * *